United States Patent
Coe et al.

(10) Patent No.: US 9,617,275 B2
(45) Date of Patent: *Apr. 11, 2017

(54) HETEROAROMATIC COMPOUNDS AND THEIR USE AS DOPAMINE D1 LIGANDS

(71) Applicant: PFIZER INC., New York, NY (US)

(72) Inventors: Jotham Wadsworth Coe, Niantic, CT (US); John Arthur Allen, Billerica, MA (US); Jennifer Elizabeth Davoren, Cambridge, MA (US); Amy Beth Dounay, Colorado Springs, CO (US); Ivan Viktorovich Efremov, Brookline, MA (US); David Lawrence Firman Gray, Groton, MA (US); Edward Raymond Guilmette, Franklin, MA (US); Anthony Richard Harris, Narragansett, RI (US); Chris John Helal, Mystic, CT (US); Jaclyn Louise Henderson, Cambridge, MA (US); Scot Richard Mente, Arlington, MA (US); Deane Milford Nason, Norwich, CT (US); Steven Victor O'Neil, East Lyme, CT (US); Chakrapani Subramanyam, South Glastonbury, CT (US); Wenjian Xu, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/820,611

(22) Filed: Aug. 7, 2015

(65) Prior Publication Data

US 2015/0344490 A1    Dec. 3, 2015

Related U.S. Application Data

(63) Continuation of application No. 14/435,954, filed as application No. PCT/IB2013/059754 on Oct. 29, 2013.

(60) Provisional application No. 61/881,218, filed on Sep. 23, 2013, provisional application No. 61/723,966, filed on Nov. 8, 2012.

(51) Int. Cl.
| | |
|---|---|
| *C07D 491/048* | (2006.01) |
| *C07D 491/04* | (2006.01) |
| *C07D 495/04* | (2006.01) |
| *C07D 519/04* | (2006.01) |
| *C07D 519/00* | (2006.01) |

(52) U.S. Cl.
CPC ....... *C07D 491/048* (2013.01); *C07D 491/04* (2013.01); *C07D 495/04* (2013.01); *C07D 519/00* (2013.01); *C07D 519/04* (2013.01)

(58) Field of Classification Search
None
See application file for complete search history.

(56) References Cited

U.S. PATENT DOCUMENTS

| | | | |
|---|---|---|---|
| 6,106,864 A | 8/2000 | Dolan et al. | |
| 6,232,320 B1 | 5/2001 | Stewart et al. | |
| 6,689,883 B1 | 2/2004 | Dumas et al. | |
| 7,138,240 B2 | 11/2006 | Barak et al. | |
| 7,572,888 B2 | 8/2009 | Barak et al. | |
| 7,763,731 B2 | 7/2010 | Rockway et al. | |
| 8,664,401 B2 * | 3/2014 | Brown ............ | C07D 213/64 546/268.1 |

(Continued)

FOREIGN PATENT DOCUMENTS

| | | |
|---|---|---|
| WO | 9111172 | 8/1991 |
| WO | 94/02518 | 2/1994 |

(Continued)

OTHER PUBLICATIONS

Allen JA, et al., "Discovery of beta-arrestin-biased dopamine D2 ligands for probing signal transduction pathways essential for antipsychotic efficacy," Proceedings of the National Academy of Sciences of the United States of America. 2011;108(45):18488-93.

(Continued)

*Primary Examiner* — David K O'Dell
(74) *Attorney, Agent, or Firm* — Feng Shao

(57) ABSTRACT

The present invention provides, in part, compounds of Formula I:

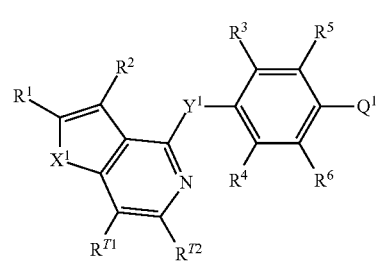

and pharmaceutically acceptable salts thereof and N-oxides thereof; processes and intermediates for preparation of; and compositions and uses thereof. The present invention further provides D1 agonists with reduced D1R desensitization, D1 agonists with a reduced β-arrestin recruitment activity relative to Dopamine, D1 agonists interacting significantly with the Ser188 but not significantly with the Ser202 of a D1R when binding to the D1R, D1 agonists interacting less strongly with the Asp103 and interacting less strongly with the Ser198 of a D1R when binding to the D1R, and their uses.

18 Claims, No Drawings

(56) References Cited

U.S. PATENT DOCUMENTS

| | | |
|---|---|---|
| 8,822,494 B2 | 9/2014 | Davoren et al. |
| 2008/0032972 A1 | 2/2008 | Dorsey |
| 2008/0194557 A1 | 8/2008 | Barbosa |
| 2008/0200458 A1 | 8/2008 | Barbosa |
| 2008/0280925 A1 | 11/2008 | Wahhab |
| 2009/0111987 A1 | 4/2009 | Tzeng |
| 2010/0063047 A1 | 3/2010 | Borchardt |
| 2010/0113452 A1 | 5/2010 | Klein |
| 2011/0015190 A1 | 1/2011 | Huang |
| 2011/0027264 A1 | 2/2011 | Huang |
| 2014/0336176 A1 | 11/2014 | Davoren |
| 2015/0005313 A1 | 1/2015 | Brodney |
| 2015/0175573 A1 | 6/2015 | Brodney |
| 2015/0196561 A1 | 7/2015 | Brodney |

FOREIGN PATENT DOCUMENTS

| | | |
|---|---|---|
| WO | 98/55148 | 12/1998 |
| WO | 0035298 | 6/2000 |
| WO | 2004/009557 | 1/2004 |
| WO | 2008/020306 | 2/2008 |
| WO | 2008/037607 | 4/2008 |
| WO | 2010131147 | 11/2010 |
| WO | 2010/144586 | 12/2010 |

OTHER PUBLICATIONS

Almarsson, O. and Zaworotko, M. J. , Chem. Commun. 2004, 17, 1889-1896.
Bina KG et al., "Dopaminergic agonists normalize elevated hypothalamic neuropeptide Y and corticotropin-releasing hormone, body weight gain, and hyperglycemia in ob/ob mice", Neuroendocrinology 71(1):68-78 (2000).
Bringmann, G. et al. Atroposelective Synthesis of Axially Chiral Biaryl Compounds. Angew. Chem., Int. Ed. 2005, 44: 5384-5427.
Buchwald, S. L., et al., J. Am. Chem. Soc. 2010, 132, 14073-14075.
Castner SA, Williams GV "Tuning the engine of cognition: a focus on NMDA/D1 receptor interactions in prefrontal cortex", Brain Cognition 63(2):94-122 (2007).
Chen, P, et al., Bioorg. Med. Chem. Lett. 2003, 13, 1345-1348.
Dyck et al., J. Med. Chem. 2006, 49, 3753-3756.
Elman, B., Tetrahedron 1985, 41, 4941-4948.
Erdik, E., Tetrahedron 1992, 48, 9577-9648.
Finnin and Morgan, J. Pharm. Sci. 1999, 88, 955-958.
Freedman, T. B. et al. Absolute Configuration Determination of Chiral Molecules in the Solution State Using Vibrational Circular Dichroism. Chirality 2003, 15, 743-758.
Goldman-Rakic PS, Castner SA, Svensson TH, Siever LJ, Williams GV "Targeting the dopamine D1 receptor in schizophrenia: insights for cognitive dysfunction", Psychopharmacology 174(1):3-16 (2004).
Goulet M, Madras BK "D(1) dopamine receptor agonists are more effective in alleviating advanced than mild parkinsonism in 1-methyl-4-phenyl-1,2,3,6-tetrahydropyridine treated monkeys", Journal of Pharmacology and Experimental Therapy 292(2):714-24 (2000).
Haleblian, J. K., J. Pharm. Sci. 1975, 64, 1269-1288.
Harris, A. R., et al., Tetrahedron 2011, 67, 9063-9066.
Jose PA, et. al., "Dopamine D1 receptor regulation of phospholipase C", Hypertension Research 18 Suppl 1:S39-42 (1995).
Kaiser, F., et al., J. Org. Chem. 2002, 67, 9248-9256.
Kalaitzakis, D., et al.,Tetrahedron: Asymmetry 2007, 18, 2418-2426.
Kido, F., et al., Tetrahedron 1987, 43, 5467-5474.
Lewis M. M. et. al, "Homologous Desensitization of the D1A Dopamine Receptor: Efficacy in Causing Desensitization Dissociates from Both Receptor Occupancy and Functional Potency"; JPET 286: 345-353, 1998.
Liang and Chen, Expert Opinion in Therapeutic Patents 2001, 11, 981-986.
Littke, A.F., et al., J. Am. Chem. Soc. 2000, 122, 4020-4028.
Luttrell Louis M et. al., "The role of β-arrestins in the termination and transduction of G-protein-coupled receptor signals"; J. Cell Sci., 115, 455-465 (2002).
Missale C, Nash SR, Robinson SW, Jaber M, Caron MG "Dopamine receptors: from structure to function", Physiological Reviews 78:189-225 (1998).
Miyaura, N. and Suzuki, A., Chem. Rev. 1995, 95, 2457-2483.
Miyazaki, Y., et al., Bioorg. Med. Chem. Lett. 2007, 17, 250-254.
Nikhil M Urs, et. al, "A Dopamine D1 Receptor-Dependent β-Arrestin Signaling Complex Potentially Regulates Morphine-Induced Psychomotor Activation but not Reward in Mice," Neuropsychopharmacology (2011) 36, 551-558.
Ohta, A., et al., J. Het. Chem. 1985, 19, 465-473.
Pierre, C., and Baudoin, O., Org. Lett. 2011, 13,1816-1819.
Pollock, et.al, "Serine mutations in transmembrane V of the dopamine D1 receptor affect ligand interactions and receptor activation." J. Biol. Chem. 1992, 267 [25], 17780-17786.
Reiter E, et.al, "Molecular mechanism of beta-arrestin-biased agonism at seven-transmembrane receptors," Annual review of pharmacology and toxicology, 2012;52:179-97.
Ryman-Rasmussen et al., "Differential activation of adenylate cyclase and receptor internalization by novel dopamine D1 receptor agonists", Molecular Pharmacology 68(4):1039-1048, 2005.
Sakamoto, T., et al., Chem. Pharm. Bull. 1985, 33, 565-571.
Schneider CA, Rasband WS, Eliceiri KW. "NIH Image to ImageJ: 25 years of image analysis". Nature Methods. 2012;9(7):671-5.
Surmeier DJ, et. al, "The role of dopamine in modulating the structure and function of striatal circuits", Prog. Brain Research 183:149-67 (2010).
Suzuki, A. , Organomet, . J, Chem. 1999, 576, 147-168.
Umrani DN, Goyal RK "Fenoldopam treatment improves peripheral insulin sensitivity and renal function in STZ-induced type2 diabetic rats", Clin. Exp. Hypertension 25(4):221-233 (2003).
Verma et al., Pharmaceutical Technology On-line, 25(2), 1-14 (2001).
Wang, Z., et al., Synthesis 2011, 1529-1531.
Yudowski GA, von Zastrow M. ""; Methods in Molecular Biology. 2011;756:325-32.
International Search Report—WO 2014/072881—May 15, 2014.
Sato, J. Heterocycl. Chem. 1980, 171, 143-147.

\* cited by examiner

HETEROAROMATIC COMPOUNDS AND THEIR USE AS DOPAMINE D1 LIGANDS

This application is a continuation of U.S. patent application Ser. No. 14/435,954, filed Apr. 15, 2015, which in turn is a national phase filing under 35 U.S.C. §371 of international patent application number PCT/IB2013/059754 filed Oct. 29, 2013, which in turn claims the benefit of priority to U.S. Provisional Patent Application Ser. No. 61/723,966 filed Nov. 8, 2012, and to U.S. Provisional Patent Application Ser. No. 61/881,218 filed Sep. 23, 2013, the disclosure of each of the foregoing applications is hereby incorporated by reference in its entirety.

FIELD OF THE INVENTION

The present invention generally relates to heteroaromatic compounds, which are dopamine D1 ligands, for example dopamine D1 agonists or partial agonists.

BACKGROUND OF THE INVENTION

Dopamine acts upon neurons through two families of dopamine receptors, D1-like receptors (D1Rs) and D2-like receptors (D2Rs). The D1-like receptor family consists of D1 and D5 receptors (D1), which are highly expressed in many regions of the brain. D1 mRNA has been found in the striatum and nucleus accumbens. See e.g., Missale C, Nash S R, Robinson S W, Jaber M, Caron M G "Dopamine receptors: from structure to function", *Physiological Reviews* 78:189-225 (1998).

Pharmacological studies have reported that D1 and D5 receptors (D1/D5), namely D1-like receptors, are linked to stimulation of adenylyl cyclase, whereas D2, D3, and D4 receptors, namely D2-like receptors, are linked to inhibition of cAMP production See, e.g., Jose P A, et. al, "Dopamine D1 receptor regulation of phospholipase C", *Hypertension Research* 18 Suppl 1:S39-42 (1995).

Dopamine D1 receptors are implicated in numerous neuropharmacological and neurobiological functions. For example, D1 receptors are involved in different types of memory function and synaptic plasticity. See e.g., Goldman-Rakic P S, Castner S A, Svensson T H, Siever L J, Williams G V "Targeting the dopamine D1 receptor in schizophrenia: insights for cognitive dysfunction", *Psychopharmacology* 174(1):3-16 (2004); Castner S A, Williams G V "Tuning the engine of cognition: a focus on NMDA/D1 receptor interactions in prefrontal cortex", *Brain Cognition* 63(2):94-122 (2007). In addition, D1 receptors have been implicated in a variety of psychiatric, neurological, neurodevelopmental, neurodegenerative, mood, motivational, metabolic, cardiovascular, renal, ophthalmic, endocrine, and/or other disorders described herein including schizophrenia (e.g., cognitive and negative symptoms in schizophrenia), cognitive impairment associated with D2 antagonist therapy, ADHD, impulsivity, autism spectrum disorder, Mild cognitive impairment (MCI), age-related cognitive decline, Alzheimer's dementia, Parkinson's disease, Huntington's chorea, depression, anxiety, treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, Tourette's syndrome, tardive dyskinesia, drowsiness, sexual dysfunction, migraine, systemic lupus erythematosus (SLE), hyperglycemia, dislipidemia, obesity, diabetes, sepsis, post-ischemic tubular necrosis, renal failure, resistant edema, narcolepsy, hypertension, congestive heart failure, postoperative ocular hypotonia, sleep disorders, pain, and other disorders in a mammal. See e.g., Goulet M, Madras B K "D(1) dopamine receptor agonists are more effective in alleviating advanced than mild parkinsonism in 1-methyl-4-phenyl-1,2,3,6-tetrahydropyridine-treated monkeys", *Journal of Pharmacology and Experimental Therapy* 292 (2):714-24 (2000); Surmeier D J, et. al, "The role of dopamine in modulating the structure and function of striatal circuits", *Prog. Brain Research* 183:149-67 (2010); Umrani D N, Goyal R K "Fenoldopam treatment improves peripheral insulin sensitivity and renal function in STZ-induced type2 diabetic rats", *Clin. Exp. Hypertension* 25(4):221-233 (2003); Bina K G et al., "Dopaminergic agonists normalize elevated hypothalamic neuropeptide Y and corticotropin-releasing hormone, body weight gain, and hyperglycemia in ob/ob mice", *Neuroendocrinology* 71(1):68-78 (2000).

G protein-coupled receptors (GPCRs, including D1Rs) desensitize via a common mechanism involving G protein-coupled receptor kinase (GRK) phosphorylation followed by β-arrestin binding which prevents G protein-coupling (and thus G protein activation). See Louis M. Luttrell et. al., "*The role of β-arrestins in the termination and transduction of G-protein-coupled receptor signals*"; *J. Cell Sci.*, 115, 455-465 (2002). For example, D1 receptor desensitization involves agonist-induced phosphorylation of the receptor (i.e., preferential phosphorylation of the receptor that are in the agonist-occupied conformation) and β-arrestin recruitment (β-arrestin-receptor binding) that prevents G protein coupling and in turn leads to desensitization of D1 receptor's canonical G protein pathway/activation signaling [which can be measured, for example, by cyclic adenosine monophosphate (cAMP) accumulation/production]. See M. M. Lewis et. al, "*Homologous Desensitization of the D1A Dopamine Receptor: Efficacy in Causing Desensitization Dissociates from Both Receptor Occupancy and Functional Potency*"; *JPET* 286: 345-353, 1998.

In addition to their well-established role in GPCR desensitization, β-arrestins may also enable GPCR-mediated "arrestinergic" signaling by functioning as scaffolds for downstream effector molecules such as the extracellular regulated kinases (ERKs). See; Nikhil M Urs, et. al, "*A Dopamine D1 Receptor-Dependent β-Arrestin Signaling Complex Potentially Regulates Morphine-Induced Psychomotor Activation but not Reward in Mice,*" *Neuropsychopharmacology*(2011) 36, 551-558; Reiter E, et. al, "*Molecular mechanism of beta-arrestin-biased agonism at seven-transmembrane receptors,*" *Annual review of pharmacology and toxicology.* 2012; 52:179-97; and Allen J A, et al. "*Discovery of beta-arrestin-biased dopamine D2 ligands for probing signal transduction pathways essential for antipsychotic efficacy,*" *Proceedings of the National Academy of Sciences of the United States of America.* 2011; 108(45): 18488-93.

New or improved agents that modulate (such as agonize or partially agonize) D1 are needed for developing new and more effective pharmaceuticals to treat diseases or conditions associated with dysregulated activation of D1, such as those described herein.

SUMMARY OF THE INVENTION

The present invention provides, in part, a compound of Formula I:

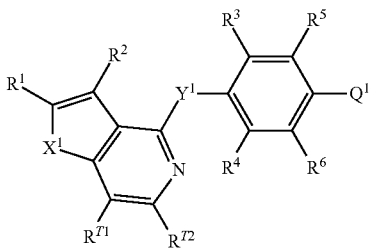

or an N-oxide thereof, or a pharmaceutically acceptable salt of said compound or said N-oxide, wherein:

$X^1$ is O or S;

$Y^1$ is O, S, or $NR^N$;

$Q^1$ is an N-containing 5- to 10-membered heterocycloalkyl, an N-containing 5- to 10-membered heteroaryl, or phenyl, wherein the heterocycloalkyl or heteroaryl is optionally substituted with 1, 2, 3, 4, or 5 independently selected $R^7$; and the phenyl is optionally substituted with 1, 2, 3, 4, or 5 independently selected $R^{7a}$;

$R^{T1}$ and $R^{T2}$ are each independently selected from the group consisting of H, $C_{1-3}$ alkyl, $C_{1-3}$ fluoroalkyl, cyclopropyl, fluorocyclopropyl, $C_{1-3}$ alkoxy, $C_{1-3}$ haloalkoxy, —C(=O)—O—($C_{1-3}$ alkyl), and —C(=O)OH;

$R^1$ is selected from the group consisting of H, F, —C(=O)OH, —C(=O)—O—($C_{1-3}$ alkyl), $C_{1-3}$ alkyl, $C_{1-3}$ fluoroalkyl, $C_{3-6}$ cycloalkyl, and $C_{3-6}$ fluorocycloalkyl, wherein said $C_{3-6}$ cycloalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy;

$R^2$ is selected from the group consisting of H, halogen (e.g., F, Cl, Br, or I), —CN, —OH, C(=O)OH, C(=O)—O—($C_{1-3}$ alkyl), $C_{1-3}$ alkoxy, $C_{1-3}$ haloalkoxy, —N($R^8$)($R^9$), $C_{1-3}$ alkyl, $C_{1-3}$ fluoroalkyl, $C_{3-6}$ cycloalkyl, $C_{3-6}$ fluorocycloalkyl, $C_{2-6}$ alkenyl, and $C_{2-6}$ alkynyl, wherein said $C_{3-6}$ cycloalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy;

$R^3$ and $R^4$ are each independently selected from the group consisting of H, $C_{1-6}$ alkyl, $C_{1-6}$ haloalkyl, $C_{1-6}$ alkoxy, $C_{1-6}$ haloalkoxy, —CN, $C_{3-6}$ cycloalkyl, —C(=O)OH, C(=O)—O—($C_{1-4}$ alkyl), and halogen, wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;

$R^5$ and $R^6$ are each independently selected from the group consisting of H, halogen, —OH, —NO$_2$, —CN, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —N($R^8$)($R^9$), —N($R^{10}$)(C(=O)$R^{11}$), —C(=O)—N($R^8$)($R^9$), —C(=O)—$R^{12}$, —C(=O)—$OR^{12}$, and —$OR^{13}$, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-3}$ alkyl, $C_{1-3}$ alkoxy, $C_{1-3}$ haloalkyl, $C_{1-3}$ haloalkoxy, $C_{3-6}$ cycloalkyl, —N($R^{14}$)($R^{15}$), —N($R^{16}$)(C(=O)$R^{17}$), —C(=O)—$OR^{18}$, —C(=O)H, —C(=O)$R^{18}$, —C(=O)N($R^{14}$)($R^{15}$), and —$OR^{19}$;

or $R^5$ and $R^3$ together with the two carbon atoms to which they are attached form a fused N-containing 5- or 6-membered heteroaryl, a fused N-containing 5- or 6-membered heterocycloalkyl, a fused 5- or 6-membered cycloalkyl, or a fused benzene ring, each optionally substituted with 1, 2, or 3 substituents each independently selected from the group consisting of halo, —CN, —OH, $C_{1-3}$ alkyl, $C_{1-3}$ alkoxy, $C_{1-3}$ haloalkyl, and $C_{1-3}$ haloalkoxy;

$R^7$ and $R^{7a}$ are each independently selected from the group consisting of halogen, —OH, —CN, —NO$_2$, oxo, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, cycloalkylalkyl, heterocycloalkylalkyl, arylalkyl, heteroarylalkyl, heteroarylalkenyl, —CH=N—O—($C_{1-3}$ alkyl), —N($R^{14}$)($R^{15}$), —N($R^{16}$)(C(=O)$R^{17}$), —S(=O)$_2$N($R^{14}$)($R^{15}$), —C(=O)N($R^{14}$)($R^{15}$), —C(=O)—$R^{12}$, —C(=O)—$OR^{18}$, and —$OR^{19}$, wherein each of said $C_{1-6}$ alkyl, $C_{3-7}$ cycloalkyl, cycloalkylalkyl, heterocycloalkylalkyl, arylalkyl, heteroarylalkyl, heteroarylalkenyl, $C_{6-10}$ aryl, heterocycloalkyl and heteroaryl is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N($R^{14}$)($R^{15}$), —S—($C_{1-3}$ alkyl), —S(=O)$_2$—($C_{1-4}$ alkyl), aryloxy, arylalkyloxy optionally substituted with 1 or 2 $C_{1-4}$ alkyl, oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or two adjacent $R^{7a}$ together with the two carbon atoms to which they are attached form a fused 5- or 6-membered cycloalkyl, a fused 5- or 6-membered heterocycloalkyl, or a fused benzene ring, each optionally substituted with 1, 2, 3, or 4 $R^{7b}$, wherein each $R^{7b}$ is independently selected from the group consisting of halo, —CN, —NO$_2$, —NH$_2$, —NH($C_{1-4}$ alkyl), —N($C_{1-4}$ alkyl)$_2$, azetidin-1-yl, pyrrolidin-1-yl, pyridin-1-yl, OH, oxo, $C_{1-4}$ alkyl, $C_{1-4}$ alkoxy, $C_{1-4}$ hydroxylalkyl, $C_{1-4}$ haloalkyl, and $C_{1-4}$ haloalkoxy;

$R^8$ and $R^9$ are each independently selected from the group consisting of H, $C_{1-6}$ alkyl, $C_{1-6}$ haloalkyl, $C_{3-10}$ cycloalkyl, a 4- to 10-membered heterocycloalkyl, cycloalkylalkyl, heterocycloalkylalkyl, arylalkyl, and heteroarylalkyl, wherein each of said $C_{1-6}$ alkyl, $C_{3-10}$ cycloalkyl, 4- to 10-membered heterocycloalkyl, cycloalkylalkyl, arylalkyl, and heteroarylalkyl is optionally substituted with 1, 2, 3, or 4 substituents each independently selected from the group consisting of —OH, —CN, $C_{1-3}$ alkyl, $C_{3-7}$ cycloalkyl, $C_{1-3}$ hydroxylalkyl, —S—$C_{1-3}$ alkyl, —C(=O)H, —C(=O)—$C_{1-3}$ alkyl, —C(=O)—O—$C_{1-3}$ alkyl, —C(=O)—NH$_2$, —C(=O)—N($C_{1-3}$ alkyl)$_2$, $C_{1-3}$ haloalkyl, $C_{1-3}$ alkoxy, and $C_{1-3}$ haloalkoxy;

or $R^8$ and $R^9$ together with the N atom to which they are attached form a 4- to 10-membered heterocycloalkyl or heteroaryl optionally substituted with 1, 2, 3, or 4 substituents each independently selected from the group consisting of halogen, —OH, oxo, —C(=O)H, —C(=O)OH, —C(=O)—$C_{1-3}$ alkyl, —C(=O)—NH$_2$, —C(=O)—N($C_{1-3}$ alkyl)$_2$, —CN, $C_{1-3}$ alkyl, $C_{1-3}$ alkoxy, $C_{1-3}$ hydroxylalkyl, $C_{1-3}$ haloalkyl, and $C_{1-3}$ haloalkoxy;

$R^{10}$ is selected from the group consisting of H, $C_{1-3}$ alkyl, and $C_{3-7}$ cycloalkyl;

$R^{11}$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, oxo, —S—$C_{1-3}$ alkyl, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{12}$ is H or is selected from the group consisting of $C_{1-10}$ alkyl, $C_{3-7}$ cycloalkyl, a 4-14 membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, —C(=O)OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{13}$ is selected from the group consisting of $C_{1-10}$ alkyl, $C_{1-6}$ haloalkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, 3, or 4 substituents each independently selected from the group consisting of halogen, —$N(R^{14})(R^{15})$, —C(=O)$N(R^{14})(R^{15})$, —$N(R^{16})(C(=O)R^{17})$, —C(=O)H, —C(=O)N($R^{16}$)($OR^{18}$), —C(=O)—$R^{18}$, —C(=O)—$OR^{18}$, —O—C(=O)$R^{18}$, —$CF_3$, —CN, —OH, —O—($C_{1-6}$ hydroxylalkyl), $C_{1-6}$ alkyl, oxo, $C_{1-6}$ hydroxylalkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{14}$ and $R^{15}$ are each independently selected from the group consisting of H, $C_{1-6}$ alkyl, $C_{2-6}$ alkenyl, $C_{3-10}$ cycloalkyl, a 4- to 14-membered heterocycloalkyl, cycloalkylalkyl, heterocycloalkylalkyl, arylalkyl, and heteroarylalkyl, wherein each of said $C_{1-6}$ alkyl, $C_{3-7}$ cycloalkyl, cycloalkylalkyl, arylalkyl, and heteroarylalkyl is optionally substituted with 1, 2, or 3 substituents each independently selected from the group consisting of —OH, —CN, oxo, —NHC(=O)—($C_{1-3}$ alkyl), —C(=O)N($C_{1-3}$ alkyl)$_2$, —O—($C_{1-6}$ hydroxylalkyl), —S(=O)$_2$—$C_{1-3}$ alkyl, —S—$C_{1-3}$ alkyl, $C_{1-3}$ alkyl, $C_{3-7}$ cycloalkyl, $C_{1-3}$ hydroxylalkyl, a 5- to 10-membered heteroaryl, $C_{1-3}$ alkoxy, $C_{1-3}$ haloalkyl, and $C_{1-3}$ haloalkoxy;

or $R^{14}$ and $R^{15}$ together with the N atom to which they are attached form a 4- to 10-membered heterocycloalkyl or 5- to 10-membered heteroaryl optionally substituted with 1, 2, or 3 substituents each independently selected from the group consisting of halogen, oxo, —OH, $C_{1-3}$ alkyl, $C_{1-3}$ alkoxy, $C_{1-3}$ haloalkyl, $C_{1-3}$ haloalkoxy, $C_{1-3}$ hydroxylalkyl, $C_{2-4}$ alkoxyalkyl, oxo, a 5- to 6-membered heteroaryl, —$NH_2$, —N($C_{1-3}$ alkyl)$_2$, —S(=O)$_2$—$C_{1-3}$ alkyl, —S—$C_{1-3}$ alkyl, —C(=O)H, —C(=O)OH, —C(=O)$NH_2$, and —C(=O)—$C_{1-3}$ alkyl;

$R^{16}$ is selected from the group consisting of H, $C_{1-3}$ alkyl, and $C_{3-7}$ cycloalkyl;

$R^{17}$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{18}$ is H or is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{19}$ is selected from the group consisting of $C_{1-6}$ alkyl, $C_{1-6}$ haloalkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$N(R^{14})(R^{15})$, —C(=O)$N(R^{14})(R^{15})$, —$N(R^{16})(C(=O)R^{17})$, —C(=O)—$R^{18}$, —C(=O)—$OR^{18}$, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy; and $R^N$ is selected from the group consisting of H, $C_{1-6}$ alkyl, $C_{3-6}$ cycloalkyl, $C_{3-6}$ fluorocycloalkyl, heteroarylalkyl, and arylalkyl, wherein each of said $C_{3-6}$ cycloalkyl, heteroarylalkyl, and arylalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy.

As used herein, the term "adjacent" in describing the relative positions of two substituent groups on a ring structure refers to two substituent groups that are respectively attached to two ring-forming atoms of the same ring, wherein the two-ring forming atoms are directly connected through a chemical bond. For example, in each of the following structures:

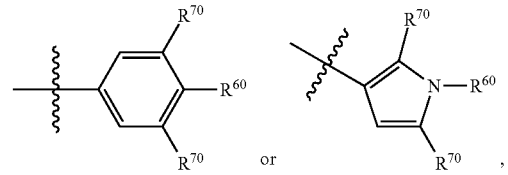

either of the two $R^{70}$ groups is an adjacent group of $R^{60}$.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include methyl, ethyl, $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 10, e.g., 1 to 6, carbon atoms. For example, as used herein, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl), optionally substituted by 1 or more (such as 1 to 5) suitable substituents. The term "$C_{1-4}$ alkyl" refers to linear or branched aliphatic hydrocarbons chains of 1 to 4 carbon atoms (i.e. methyl, ethyl, n-propyl, isopropyl, n-butyl, isobutyl, sec-butyl, tert-butyl). The term "$C_{1-3}$ alkyl" refers to linear or branched aliphatic hydrocarbons chains of 1 to 3 carbon atoms As used herein, the term "alkenyl" refers to aliphatic hydrocarbons having at least one carbon-carbon double bond, including straight chains and branched chains having at least one carbon-carbon double bond. In some embodiments, the alkenyl group has 2 to 6 carbon atoms. In some embodiments, the alkenyl group has 2 to 4 carbon atoms. For example, as used herein, the term "$C_{2-6}$ alkenyl" means straight or branched chain unsaturated radicals of 2 to 6 carbon atoms, including, but not limited to, ethenyl, 1-propenyl, 2-propenyl (allyl), isopropenyl, 2-methyl-1-propenyl, 1-butenyl, 2-butenyl, and the like, optionally substituted by 1 to 5 suitable substituents. When the compounds of Formula I contain an alkenyl group, the alkenyl group may exist as the pure E form, the pure Z form, or any mixture thereof.

As used herein, the term "alkynyl" refers to aliphatic hydrocarbons having at least one carbon-carbon triple bond, including straight chains and branched chains having at least one carbon-carbon triple bond. In some embodiments, the alkynyl group has 2 to 6 carbon atoms. For example, as used herein, the term "$C_{2-6}$ alkynyl" is used herein to mean straight or branched hydrocarbon chain alkynyl radicals as defined above, having 2 to 6 carbon atoms and one triple bond, optionally substituted by 1 or more (such as 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.), optionally substituted by 1 or more (such as 1 to 5) suitable substituents. The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 15 carbon atoms. For example, the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, or bicyclo[1.1.1]pentanyl). The term "$C_{3-6}$ cycloalkyl" refers to saturated or unsaturated, non-aromatic, monocyclic or polycyclic (such as bicyclic) hydrocarbon rings of 3 to 6 ring-forming carbon atoms. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group is optionally substituted by 1 or more (such as 1 to 5) suitable substituents.

As used herein, the term "aryl" refers to all-carbon monocyclic or fused-ring polycyclic aromatic groups having a conjugated pi-electron system. The aryl group has 6, 8, or 10 carbon atoms in the ring(s). More commonly, the aryl group has 6 or 10 carbon atoms in the ring(s). Most commonly, the aryl group has 6 carbon atoms in the ring. For example, as used herein, the term "$C_{6-10}$ aryl" means aromatic radicals containing from 6 to 10 carbon atoms such as phenyl, naphthyl, tetrahydronaphthyl, indanyl and the like. The aryl group is optionally substituted by 1 or more (such as 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo groups. In some embodiments, the heteroaryl group has 5 to 8 ring-forming atoms including one, two or three heteroatoms. Examples of monocyclic heteroaryls include those with 5 ring-forming atoms including one to three heteroatoms or those with 6 ring-forming atoms including one or two nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, pyridone, pyrimidone, pyrazinone, pyrimidinone, 1H-imidazol-2(3H)-one, 1H-pyrrole-2,5-dione, and the like. The heteroaryl group is optionally substituted by 1 or more (such as 1 to 5) suitable substituents.

As used herein, the term "N-containing" when used in connection with a heteroaryl or heterocycloalkyl means that the heteroaryl or heterocycloalkyl comprises at least one ring-forming nitrogen (N) atom and optionally one or more (e.g. 1, 2, 3, or 4) ring-forming heteroatoms each independently selected from O, S and N. The term "N-containing 5- to 10-membered heteroaryl" refers to a 5- to 10-membered heteroaryl group (including monocyclic or bi-cyclic) comprising at least one ring-forming nitrogen (N) atom and optionally one or more (e.g. 1, 2, 3, or 4) ring-forming heteroatoms each independently selected from O, S and N. The term "N-containing 5- or 6-membered heteroaryl" refers to a 5- or 6-membered heteroaryl group comprising at least one ring-forming nitrogen (N) atom and optionally one or more (e.g. 1, 2, 3, or 4) ring-forming heteroatoms each independently selected from O, S and N. Examples of N-containing 5- to 10-membered heteroaryl groups include pyridinyl, pyrazinyl, pyrimidinyl, pyridazinyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, pyridone, pyrimidone, pyrazinone, pyrimidinone, 1H-imidazol-2(3H)-one, 1H-pyrrole-2,5-dione, and the like. Examples of N-containing 5- or 6-membered heteroaryl groups include pyridinyl, pyrazinyl, pyrimidinyl, pyridazinyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), and thiadiazolyl (e.g., 1,3,4-thiadiazolyl), The N-containing 5- to 10-membered heteroaryl group or the N-containing 5- or 6-membered heteroaryl is optionally substituted by 1 or more (such as 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 3- to 15-membered ring system (such as a 4- to 14-membered ring system, 4- to 10-membered ring system, or 5- to 10-membered ring system), including 1 to 14 ring-forming carbon atoms and 1 to 10 ring-forming heteroatoms each independently selected from O, S and N. The heterocycloalkyl group can also include one to three oxo groups. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, and the like. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of heterocycles such as indolene, isoindolene, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (such as 1 to 5) suitable substituents. Examples of heterocycloalkyl groups include 5- or 6-membered monocyclic rings and 9- or 10-membered fused bicyclic rings.

As used herein, the term "N-containing 5- to 10-membered heterocycloalkyl" refers to a 5- to 10-membered heterocycloalkyl group comprising at least one ring-forming nitrogen (N) atom and optionally one or more ring-forming heteroatoms each independently selected from O, S and N. The term "N-containing 5- or 6-membered heterocycloalkyl" refers to a 5- or 6-membered heterocycloalkyl group comprising at least one ring-forming nitrogen (N) atom and optionally one or more ring-forming heteroatoms each independently selected from O, S and N. Examples of N-containing 5- to 10-membered heterocycloalkyl groups include piperidin-1-yl, piperidin-4-yl, piperazin-1-yl, 1,3-thiazinan-3-yl, 1,4,5,6-tetrahydropyrrolo[3,4-c]pyrazol-5-yl, and 3,4-dihydroisoquinolin-1(2H)-one-3-yl. Examples of N-containing 5- or 6-membered heterocycloalkyl groups include piperidin-1-yl, piperidin-4-yl, piperazin-1-yl, 1,3-thiazinan-3-yl, and morpholino. The N-containing 5- to 10-membered heterocycloalkyl or the N-containing 5- or 6-membered heterocycloalkyl is optionally substituted by 1 or more (such as 1 to 5) suitable substituents.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). The term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom). The term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom). Examples of haloalkyl groups include $CF_3$, $C_2F_5$, $CHF_2$, $CH_2F$, $CH_2CF_3$, $CH_2Cl$ and the like.

As used herein, the term "alkoxy" or "alkyloxy" refers to an —O-alkyl group. The term "$C_{1-6}$ alkoxy" or "$C_{1-6}$ alkyloxy" refers to an —O—($C_{1-6}$ alkyl) group. The term "$C_{1-4}$ alkoxy" or "$C_{1-4}$ alkyloxy" refers to an —O—($C_{1-4}$ alkyl) group. The term "$C_{1-3}$ alkoxy" or "$C_{1-3}$ alkyloxy" refers to an —O—($C_{1-3}$ alkyl) group. Examples of alkoxy include methoxy, ethoxy, propoxy (e.g., n-propoxy and isopropoxy), tert-butoxy, and the like.

As used here, the term "haloalkoxy" refers to an —O-haloalkyl group. The term "$C_{1-6}$ haloalkoxy" refers to an —O—($C_{1-6}$ haloalkyl) group. The term "$C_{1-4}$ haloalkoxy" refers to an —O—($C_{1-4}$ haloalkyl) group. The term "$C_{1-3}$ haloalkoxy" refers to an —O—($C_{1-3}$ haloalkyl) group. An example of a haloalkoxy group is —OCF$_3$.

As used here, the term "aryloxy" refers to an —O—($C_{6-10}$ aryl) group. An example of an aryloxy group is —O-phenyl [i.e., phenoxy].

As used here, the term "arylalkyloxy" or "arylalkoxy" refers to an O—$C_{1-6}$ alkyl-$C_{6-10}$ aryl group. Examples of arylalkyloxy groups include O—$C_{1-4}$ alkyl-$C_{6-10}$ aryl, O—$C_{1-2}$ alkyl-$C_6$ aryl, or —O—CH$_2$-phenyl [i.e., benzyloxy].

As used herein, the term "fluoroalkyl" refers to an alkyl group having one or more fluorine substituents (up to perfluoroalkyl, i.e., every hydrogen atom of the alkyl group has been replaced by fluorine). For example, the term "$C_{1-6}$ fluoroalkyl" refers to a $C_{1-6}$ alkyl group having one or more fluorine substituents (up to perfluoroalkyl, i.e., every hydrogen atom of the $C_{1-6}$ alkyl group has been replaced by fluorine). The term "$C_{1-4}$ fluoroalkyl" refers to a $C_{1-4}$ alkyl group having one or more fluorine substituents (up to perfluoroalkyl, i.e., every hydrogen atom of the $C_{1-4}$ alkyl group has been replaced by fluorine). The term "$C_{1-3}$ fluoroalkyl" refers to a $C_{1-3}$ alkyl group having one or more fluorine substituents (up to perfluoroalkyl, i.e., every hydrogen atom of the $C_{1-3}$ alkyl group has been replaced by fluorine). The term "$C_1$ fluoroalkyl" refers to a $C_1$ alkyl group (i.e., methyl) having one or more fluorine substituents (up to perfluoromethyl, i.e., CF$_3$). Examples of fluoroalkyl groups include $CF_3$, $C_2F_5$, $CH_2CF_3$, $CHF_2$, $CH_2F$, and the like.

As used herein, the term "fluorocycloalkyl" refers to a cycloalkyl group having one or more fluorine substituents (up to perfluorocycloalkyl, i.e., every hydrogen atom of the cycloalkyl group has been replaced by fluorine). For example, the term "$C_{3-6}$ fluorocycloalkyl" refers to a $C_{3-6}$ cycloalkyl group having one or more fluorine substituents (up to $C_{3-6}$ perfluorocycloalkyl, i.e., every hydrogen atom of the $C_{3-6}$ cycloalkyl group has been replaced by fluorine). Examples of fluorocycloalkyl groups include fluorocyclopropyl [i.e., a cyclopropyl group having one or more fluorine substituents (up to perfluorocyclopropyl, i.e., every hydrogen atom of the cyclopropyl group has been replaced by fluorine), for example, 2-fluoro-cyclopropan-1-yl or 2,3-difluorocyclopropan-1-y] and fluorocyclobutyl [i.e., a cyclobutyl group having one or more fluorine substituents (up to perfluorocyclobutyl, i.e., every hydrogen atom of the cyclobutyl group has been replaced by fluorine)], As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents. Examples of hydroxylalkyl groups are —CH$_2$OH and —CH$_2$CH$_2$OH.

As used herein, the term "alkoxyalkyl" refers to an alkyl group having one or more alkoxy (e.g., 1, 2, or 3) substituents. The term "$C_{2-4}$ alkoxyalkyl" refers to a $C_{1-3}$ alkyl group substituted by a $C_{1-3}$ alkoxy group wherein the total carbon numbers of the akyl and alkoxy moieties of the alkoxyalkyl is 2, 3, or 4. One example of a hydroxylalkyl group is —CH$_2$OCH$_3$.

As used herein, the term "cyanoalkyl" refers to an alkyl group having one or more (e.g., 1, 2, or 3) cyano substituents. The term "$C_{1-6}$ cyanoalkyl" refers to a $C_{1-6}$ alkyl group having one or more (e.g., 1, 2, or 3) CN substituents. The term "$C_{1-3}$ cyanoalkyl" refers to a $C_{1-3}$ alkyl group having one or more (e.g., 1, 2, or 3) CN substituents. One example of a cyanoalkyl group is —CH$_2$CN.

As used herein, the term "heteroarylalkenyl" refers to a —$C_{2-6}$ alkenyl-(heteroaryl) group. Examples of such a heteroarylalkenyl group include 2-(thiophen-2-yl)-ethen-1-yl and 1-(pyridin-2-yl)-prop-1-en-3-yl.

As used herein, the term "arylalkyl" refers to —$C_{1-6}$ alkyl-$C_{6-10}$ aryl and "cycloalkylalkyl" refers to —$C_{1-6}$ alkyl-$C_{3-14}$ cycloalkyl. Examples of arylalkyl groups include —$C_{1-4}$ alkyl-$C_{6-10}$ aryl, —$C_{1-2}$ alkyl-$C_{6-10}$ aryl, and benzyl. Examples of cycloalkylalkyl groups include —$C_{1-4}$ alkyl-$C_{3-7}$, cycloalkyl, —$C_{1-2}$ alkyl-$C_{3-6}$ cycloalkyl, and cyclopropylmethyl-.

As used herein, the term "heteroarylalkyl" refers to —$C_{1-6}$ alkyl-(a 5- to 14-membered heteroaryl) and the term "heterocycloalkylalkyl" refers to —$C_{1-6}$ alkyl-(a 3- to 14-membered heterocycloalkyl). Examples of heteroarylalkyl groups include —$C_{1-4}$ alkyl-(a 5- to 14-membered heteroaryl), —$C_{1-2}$ alkyl-(a 5- to 10-membered heteroaryl), —$C_{1-2}$ alkyl-(a 5- or 6-membered heteroaryl), and (pyridin-2-yl)-methyl-. Examples of heterocycloalkylalkyl groups include-$C_{1-4}$ alkyl-(a 3- to 14-membered heterocycloalkyl), —$C_{1-2}$ alkyl-(a 3- to 10-membered heterocycloalkyl), and 2-(piperidin-4-yl)-ethyl-.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., CH$_3$) is optionally substituted, then up to 3 hydrogen atoms on the carbon atom can be replaced with substituent groups.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms that are substitutable (i.e., linking to one or more hydrogen atoms). For example, as shown in formula a-101 below, $R^7$ may be bonded to the amide nitrogen atom or one of the two ring carbon atoms each of which links to a hydrogen atom. For another example, as shown in formula a-102 below (when a bond to a substituent is shown to cross a bond in each of the two rings in a bicyclic ring system), $R^7$ may be bonded to any ring-forming atom that is substitutable (i.e., linking to one or more hydrogen atoms) either in the benzene ring or the pyrazole ring of the indazole. For yet another example, as shown I formula a-103 below, substitution of $R^{7a}$ is on the benzene ring and substitution $R^{7b}$ is on the 5-membered ring.

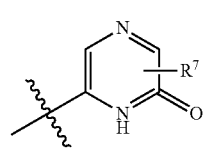

a-101

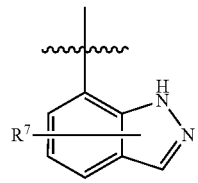

a-102

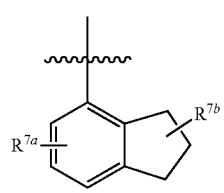

a-103

When a substituent is listed without indicating the atom via which such substituent is bonded to the rest of the compound of a given formula, then such substituent may be bonded via any atom in such substituent. For example, a substituent on an arylalkyl can be bonded to any atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as, e.g., acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I", "Formula I or pharmaceutically acceptable salts thereof", "pharmaceutically acceptable salts of the compound or the salt [of Formula I]" are defined to include all forms of the compound of Formula I, including hydrates, solvates, isomers (including for example rotational stereoisomers), crystalline and non-crystalline forms, isomorphs, polymorphs, metabolites, and prodrugs thereof.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together ether forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

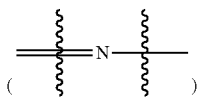

atom [such as a nitrogen atom in pyridine, pyridazine, or pyrazine], can be N-oxidized to form the N-oxide comprising the group

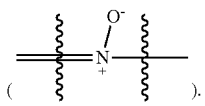

Thus, a compound according to the present invention comprising one or more nitrogen atoms (e.g., an imine nitrogen atom), for example, as a part of $Q^1$ of Formula I, may be capable of forming an N-oxide thereof (e.g., mono-N-oxides, bis-N-oxides or multi-N-oxides, or mixtures thereof depending on the number of nitrogen atoms suitable to form stable N-oxides). As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono N-oxide) or multi-N-oxides (e.g., bis-N-oxides), or mixtures thereof in any ratio.

The compounds of Formula I can be converted, optionally, into N-oxides thereof, for example, in the presence of a suitable oxidizing reagent in a suitable solvent, for example in the presence of hydrogen peroxide in methanol or in the presence of m-chloroperoxybenzoic acid in dichloromethane. One skilled in the art would readily recognize the reaction conditions suitable for carrying out the N-oxidation reactions.

Compounds of Formula I described herein (compounds of the invention) include N-oxides thereof and pharmaceutically acceptable salts of the compounds or the N-oxides.

Compounds of Formula I may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components which may be in stoichiometric or non-stoichiometric amounts. The resulting complexes may be ionized, partially ionized, or non-ionized. For a review of such complexes, see J. K. Haleblian, *J. Pharm. Sci.* 1975, 64, 1269-1288. Co-crystals are typically defined as crystalline complexes of neutral molecular constituents which are bound together through non-covalent interactions, but could also be a complex of a neutral molecule with a salt. Co-crystals may be prepared by melt crystallization, by recrystallisation from solvents, or by physically grinding the components together—see O. Almarsson and M. J. Zaworotko, *Chem. Commun.* 2004, 17, 1889-1896. For a general review of multi-component complexes, see Haleblian, *J. Pharm. Sci.* 1975, 64, 1269-1288.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see Crystals and the *Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some non-limiting examples of prodrugs in accordance with the invention include:

(i) where the compound of Formula I contains a carboxylic acid functionality that is functionalized into a suitably metabolically labile group (esters, carbamates, etc.);

(ii) where the compound of Formula I contains an alcohol functionality that is functionalized into a suitably metabolically labile group (ethers, esters, phosphonates, sulfonates, carbamates, acetals, ketals, etc.); and (iii) where the compound of Formula I contains a primary or secondary amino functionality, or an amide, that is functionalized into a suitably metabolically labile group, e.g., a hydrolyzable group (amides, carbamates, ureas, etc.).

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug.

In some embodiments, the compounds of Formula I include N-oxides thereof and pharmaceutically acceptable salts of the compounds or the N-oxides.

The compounds of Formula I include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I may have asymmetric carbon atoms. The carbon-carbon bonds of the compounds of Formula I may be depicted herein using a solid line (——), a solid wedge (———) or a dotted wedge (........). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al. Absolute Configuration Determination of Chiral Molecules in the Solution State Using Vibrational Circular Dichroism. *Chirality* 2003, 15, 743-758; and Bringmann, G. et al. Atroposelective Synthesis of Axially Chiral Biaryl Compounds. *Angew. Chem., Int. Ed.* 2005, 44: 5384-5427.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers of the invention is disclosed in the experimental section herein, those skilled in the art would readily recognize that the invention also includes the other.

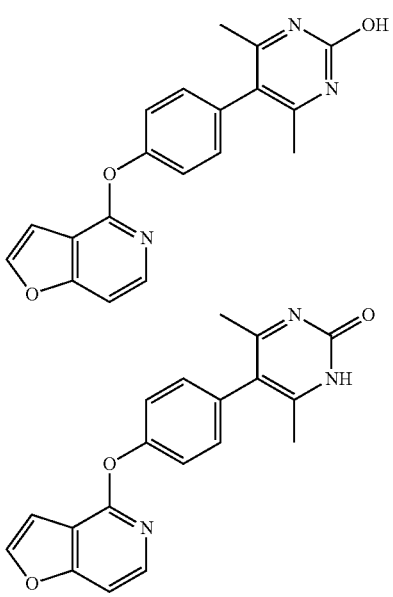

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and a N, can be useful in Positron Emission Topography (PET) studies for examining substrate receptor occupancy.

Isotopically-labeled compounds of Formula I (or pharmaceutically acceptable salts thereof or N-oxides of the compounds or salts) can generally be prepared by conventional techniques known to those skilled in the art or by processes analogous to those described in the accompanying Examples and Preparations using an appropriate isotopically-labeled reagent in place of the non-labeled reagent previously employed.

Specific embodiments of the compounds of Formula I include N-oxides thereof and pharmaceutically acceptable salts of the compounds or the N-oxides.

An embodiment of the present invention is a compound of Formula I wherein $Y^1$ is O.

An embodiment of the present invention is a compound of Formula I wherein $Y^1$ is S.

An embodiment of the present invention is a compound of Formula wherein $Y^1$ is NH or N(CH$_3$). In a further embodiment, $Y^1$ is NH. In another further embodiment, $Y^1$ is N(CH$_3$).

An embodiment of the present invention is a compound of Formula I wherein $X^1$ is O.

An embodiment of the present invention is a compound of Formula I wherein $X^1$ is S.

An embodiment of the present invention is a compound of Formula I wherein $Q^1$ is an N-containing 5- to 10-membered heterocycloalkyl or N-containing 5- to 10-membered heteroaryl, wherein each of the ring-forming atoms of the heterocycloalkyl or heteroaryl is independently selected from N and C; and the heterocycloalkyl or heteroaryl is optionally substituted with 1, 2, 3, or 4 independently selected $R^7$. In a further embodiment, $Q^1$ is an N-containing 5- to 10-membered heterocycloalkyl optionally substituted with 1, 2, 3, or 4 independently selected $R^7$, and wherein each of the ring-forming atoms of the heterocycloalkyl is independently selected from N and C.

An embodiment of the present invention is a compound of Formula I wherein $Q^1$ is an N-containing 5- to 10-membered heteroaryl optionally substituted with 1, 2, 3, or 4 independently selected $R^7$, and wherein each of the ring-forming atoms of the heteroaryl is independently selected from N and C. In a further specific embodiment, $Q^1$ is selected from quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, pyrimidinyl, pyrazinyl, pyridinyl, pyridazinyl, 1H-pyrazolyl, 1H-pyrrolyl, 4H-pyrazolyl, 4H-imidazolyl, imidazo[1,2-a]pyrimidinyl, [1,2,4]triazolo[1,5-a]pyrimidinyl, [1,2,4]triazolo[4,3-b]pyridazinyl, 1H-imidazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each optionally substituted with 1, 2, 3, or 4 independently selected $R^7$.

An embodiment of the present invention is a compound of Formula I wherein $Q^1$ is selected from 1H-pyrazolyl, 1H-imidazolyl, pyridinyl, pyrimidinyl, pyridazinyl, pyrazinyl, 3-oxo-2H-pyridazinyl, 1H-2-oxo-pyrimidinyl, 1H-2-oxo-pyrazinyl, 2,4(1H,3H)-dioxo-pyrimidinyl, 1H-2-oxo-pyridinyl, isoquinolinyl, 1H-imidazo[4,5-c]pyridinyl, imidazo[1,2-a]pyridinyl, imidazo[1,2-a]pyrimidinyl, [1,2,4]triazolo[4,3-b]pyridazinyl, and imidazo[1,2-a]pyrazinyl, each optionally substituted with 1, 2, 3, or 4 independently selected $R^7$.

An embodiment of the present invention is a compound of Formula I wherein $Q^1$ is selected from:

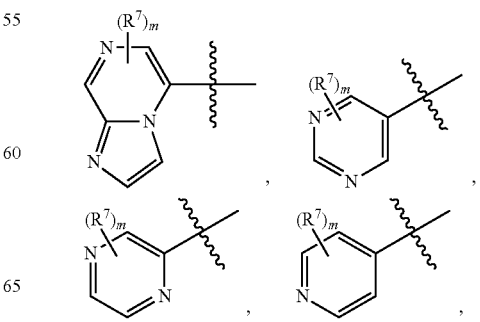

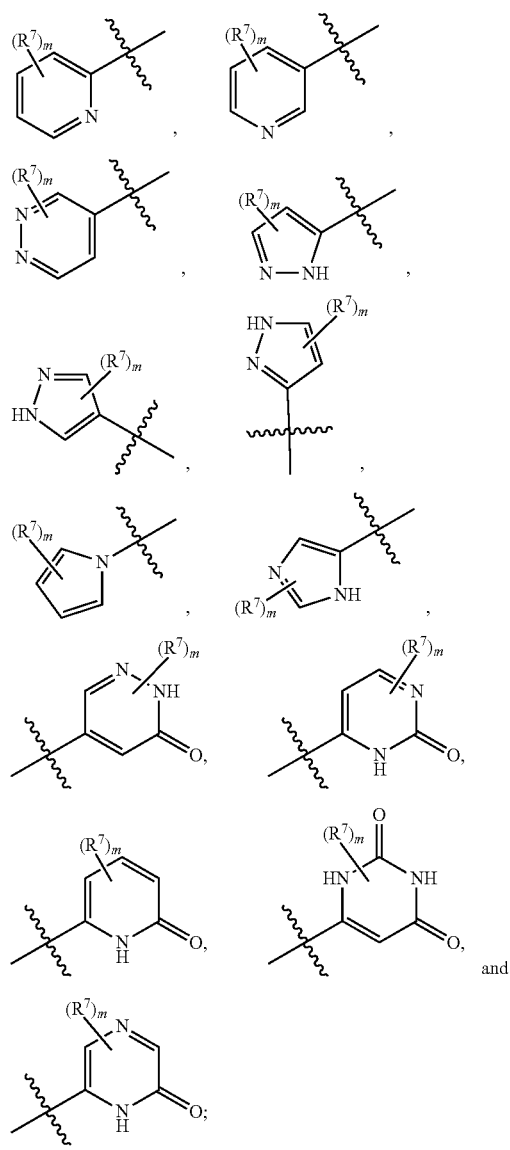
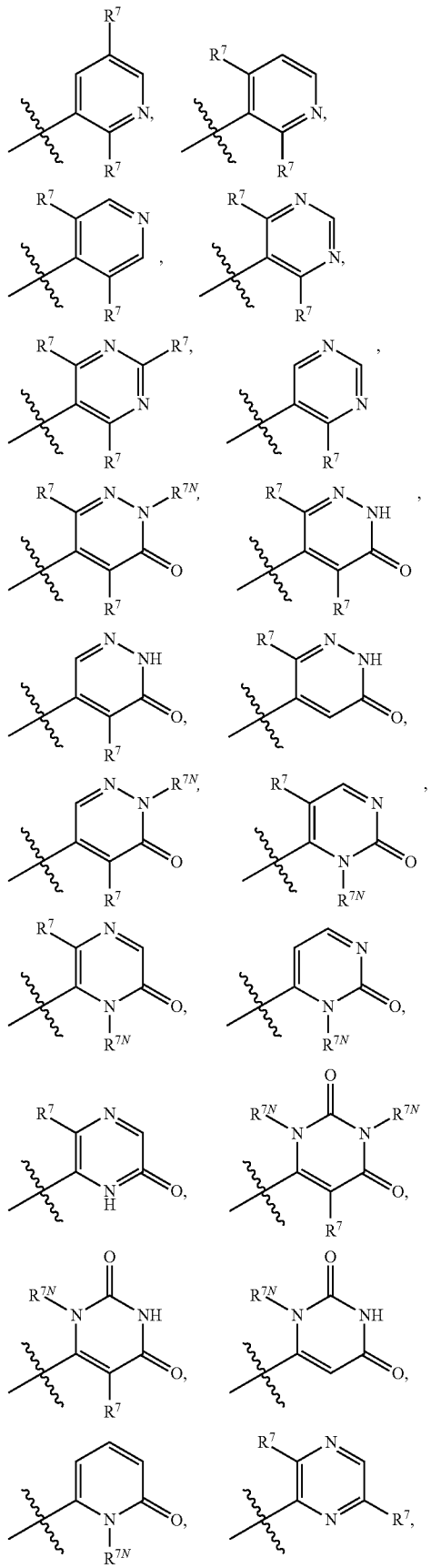
and
each m is independently 0, 1, 2, or 3.
An embodiment of the present invention is a compound of Formula I wherein $Q^1$ is selected from:
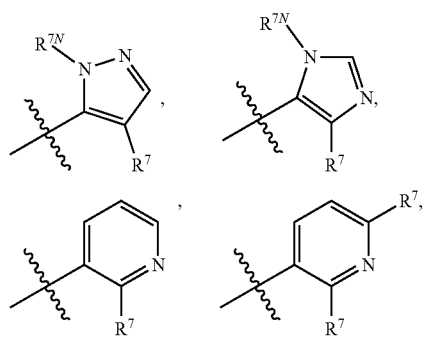

-continued

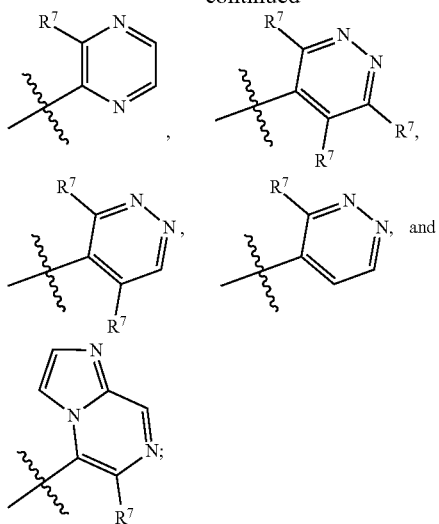

and each $R^{7N}$ is H or $C_{1-3}$ alkyl, wherein the $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, and —$N(R^{14})(R^{15})$; and wherein $R^{14}$ and $R^{15}$ together with the N atom to which they are attached form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a further embodiment, each $R^{7N}$ is H or $C_{1-3}$ alkyl, wherein the $C_{1-3}$ alkyl is optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, azetidin-1-yl, pyrrolidin-1-yl, and pyridin-1-yl.

An embodiment of the present invention is a compound of Formula I wherein $Q^1$ is pyrimidinyl, pyrazinyl, 3-oxo-2H-pyridazinyl, 1H-2-oxo-pyrazinyl, 2,4(1H,3H)-dioxo-pyrimidinyl, 1H-2-oxo-pyrimidinyl, or imidazo[1,2-a]pyrazinyl, each optionally substituted with 1, 2, or 3 independently selected $R^7$. In a further embodiment, each $R^7$ is independently $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, and —$N(R^{14})(R^{15})$; wherein $R^{14}$ and $R^{15}$ together with the N atom to which they are attached form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a yet further embodiment, each $R^7$ is independently $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, azetidin-1-yl, pyrrolidin-1-yl, and pyridin-1-yl. In a still further embodiment, each $R^7$ is methyl.

An embodiment of the present invention is a compound of Formula I wherein $Q^1$ is selected from:

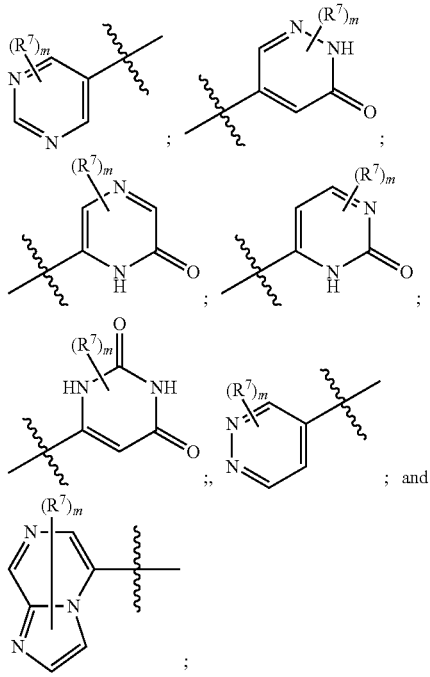

and m is 1, 2, or 3. In a further embodiment, each $R^7$ is independently $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, and —$N(R^{14})(R^{15})$; wherein $R^{14}$ and $R^{15}$ together with the N atom to which they are attached form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a yet further embodiment, each $R^7$ is independently $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl$)_2$, azetidin-1-yl, pyrrolidin-1-yl, and pyridin-1-yl. In a still further embodiment, m is 1 or 2. In a yet still further embodiment, each $R^7$ is methyl.

An embodiment of the present invention is a compound of Formula I wherein $Q^1$ is selected from:

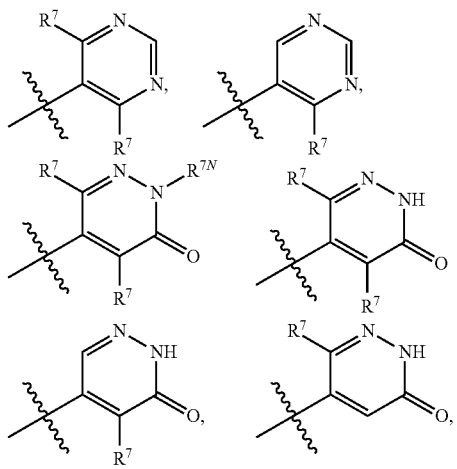

-continued

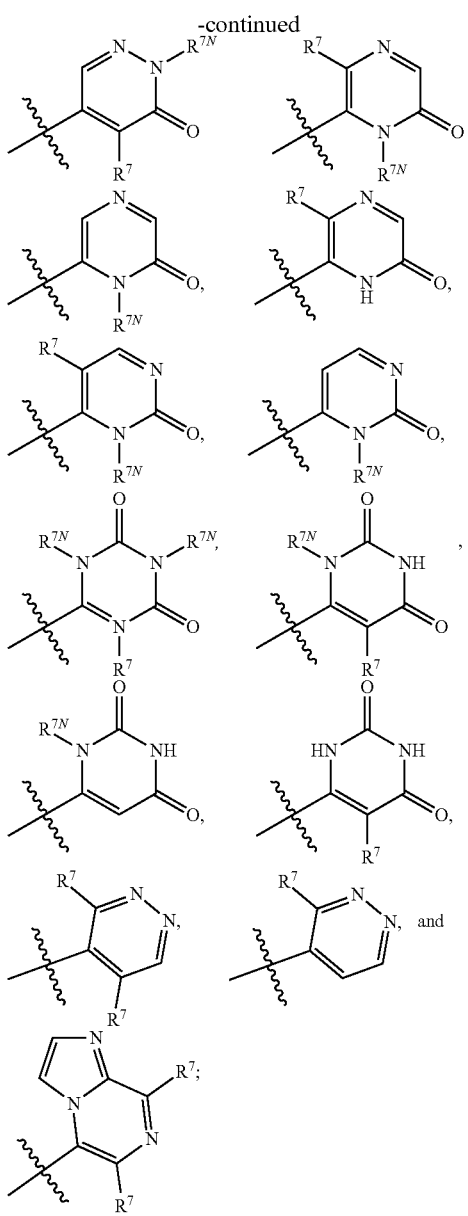

each R[7] is independently H or $C_{1-3}$ alkyl (e.g. methyl or ethyl); and each R[7N] is H or $C_{1-3}$ alkyl, wherein the $C_{1-3}$ alkyl is optionally substituted with 1, 2, 3, 4, or 5 substituents each independent selected from halogen (e.g., F), OH, $C_{1-4}$ alkoxy, —NH$_2$, —NH($C_{1-4}$ alkyl), —N($C_{1-4}$ alkyl)$_2$, and —N(R[14])(R[15]), and wherein R[14] and R[15] together with the N atom to which they are attached form a 4- to 10-membered heterocycloalkyl optionally substituted with 1, 2, or 3 substituents each independently selected from the group consisting of halogen (e.g., F), oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a further embodiment, each R[7] is independently H, methyl, or ethyl; and each R[7N] is $C_{1-3}$ alkyl optionally substituted with 1, 2, 3, 4, or 5 substituents each independent selected from halogen (e.g., F), OH, $C_{1-4}$ alkoxy, —NH$_2$, —NH($C_{1-4}$ alkyl), —N($C_{1-4}$ alkyl)$_2$, azetidin-1-yl, pyrrolidin-1-yl, and pyridin-1-yl. In a further embodiment, each R[7] is methyl or ethyl; and each R[7N] is $C_{1-3}$ alkyl optionally substituted with 1, 2, 3, 4, or 5 substituents each independent selected from halogen (e.g., F), OH, $C_{1-4}$ alkoxy, —NH$_2$, —NH($C_{1-4}$ alkyl), —N($C_{1-4}$ alkyl)$_2$, azetidin-1-yl, pyrrolidin-1-yl, and pyridin-1-yl. In a yet further embodiment, each R[7] is methyl and each R[7N] is methyl.

An embodiment of the invention is a compound of Formula I wherein $Q^1$ is selected from:

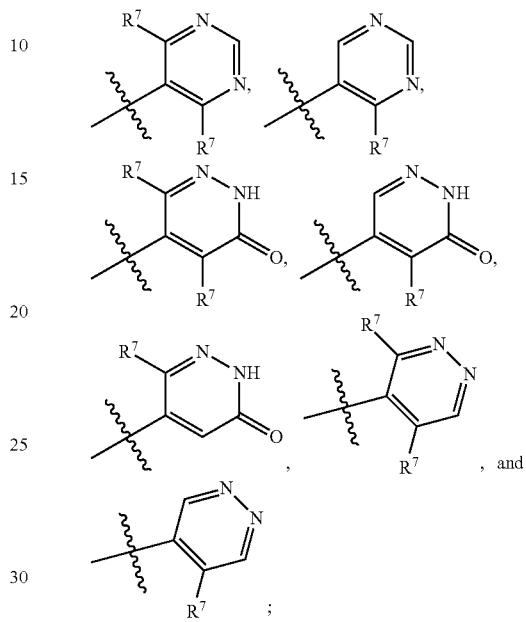

and each R[7] is independently $C_{1-3}$ alkyl (e.g. methyl or ethyl). In a further embodiment, each R[7] is independently methyl or ethyl. In a yet further embodiment, each R[7] is methyl.

An embodiment of the present invention is a compound of Formula I wherein $Q^1$ is

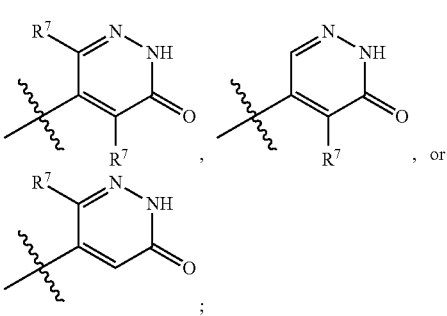

and each R[7] is independently $C_{1-3}$ alkyl (e.g. methyl or ethyl). In a further embodiment, each R[7] is methyl.

An embodiment of the present invention is a compound of Formula I wherein $Q^1$ is

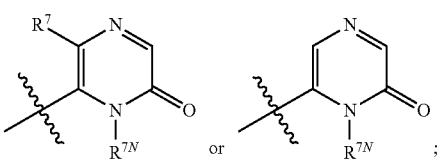

$R^7$ is H or $C_{1-3}$ alkyl (e.g. methyl or ethyl); and $R^{7N}$ is $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl)$_2$, and —$N(R^{14})(R^{15})$; and wherein $R^{14}$ and $R^{15}$ together with the N atom to which they are attached form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a further embodiment, $R^7$ is methyl or ethyl; and $R^{7N}$ is $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl)$_2$, azetidin-1-yl, pyrrolidin-1-yl, and pyridin-1-yl. In a yet further embodiment, $R^7$ is methyl and $R^{7N}$ is methyl.

An embodiment of the present invention is a compound of Formula I wherein $Q^1$ is

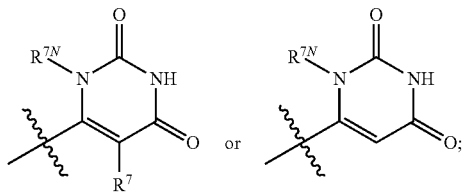

$R^7$ is H or $C_{1-3}$ alkyl (e.g. methyl or ethyl); $R^{7N}$ is $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl)$_2$, and —$N(R^{14})(R^{15})$; and $R^{14}$ and $R^{15}$ together with the N atom to which they are attached form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl. In a further embodiment, $R^7$ is methyl or ethyl; and $R^{7N}$ is $C_{1-3}$ alkyl optionally substituted with 1, 2, 3, 4, or 5 substituents each independent selected from halogen (e.g., F), OH, $C_{1-4}$ alkoxy, —$NH_2$, —$NH(C_{1-4}$ alkyl), —$N(C_{1-4}$ alkyl)$_2$, azetidin-1-yl, pyrrolidin-1-yl, and pyridin-1-yl. In a yet further embodiment, $R^7$ is methyl and $R^{7N}$ is methyl.

An embodiment of the present invention is a compound of Formula I wherein $Q^1$ is phenyl optionally substituted with 1, 2, 3, 4, or 5 independently selected $R^{7a}$.

An embodiment of the present invention is a compound of Formula I wherein:

$Q^1$ is a moiety of

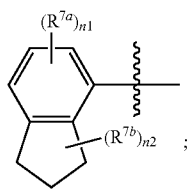

n1 is 0, 1, or 2; and n2 is 0, 1, 2, or 3.

An embodiment of the present invention is a compound of Formula I (wherein $R^{T1}$ and $R^{T2}$ are each independently selected from the group consisting of H, $C_{1-3}$ alkyl, and $C_{1-3}$ fluoroalkyl. In a further embodiment, $R^{T1}$ and $R^{T2}$ are each independently selected from the group consisting of H, methyl, and $C_1$ fluoroalkyl. In a yet further embodiment, $R^{T1}$ and $R^{T2}$ are each independently selected from the group consisting of H and methyl. In a still further embodiment, $R^{T1}$ and $R^{T2}$ are both H.

An embodiment of the present invention is a compound of Formula I wherein $R^1$ is H or $C_{1-3}$ alkyl (e.g., methyl). In a further embodiment, $R^1$ is H.

An embodiment of the present invention is a compound of Formula I wherein $R^2$ is H, —CN, Br, $C_{1-3}$ alkyl (e.g., methyl), or cyclopropyl. In a further embodiment, $R^2$ is H, —CN, or Br. In a yet further embodiment, $R^2$ is H or —CN. In a still further embodiment, $R^2$ is H. In another further embodiment, $R^2$ is —CN. In another further embodiment, $R^2$ is Br.

An embodiment of the present invention is a compound of Formula I wherein $R^3$ and $R^4$ are each independently selected from the group consisting of H, F, Cl, and $C_{1-3}$ alkyl. In a further embodiment, $R^3$ and $R^4$ are each independently selected from the group consisting of H, methyl, and F. In a yet further embodiment, one of $R^3$ and $R^4$ is H; and the other of $R^3$ and $R^4$ is selected from the group consisting of H, methyl, and F. In a still further embodiment, $R^3$ and $R^4$ are both H.

An embodiment of the present invention is a compound of Formula I wherein $R^3$ and $R^4$ are each independently H or F. In a further embodiment, one of $R^3$ and $R^4$ is H; and the other of $R^3$ and $R^4$ is H or F.

An embodiment of the present invention is a compound of Formula I wherein $R^5$ and $R^6$ are each independently selected from the group consisting of H, halogen, OH, —CN, $C_{1-6}$ alkyl, $C_{1-6}$ haloalkyl, a 4- to 10-membered heterocycloalkyl, —$N(R^8)(R^9)$, —$N(R^{10})(C(=O)R^{11})$, —$C(=O)$—$N(R^8)(R^9)$, —$C(=O)$—$OR^{12}$, and —$OR^{13}$, wherein each of said $C_{1-6}$ alkyl and 4- to 10-membered heterocycloalkyl is optionally substituted with 1, 2, or 3 substituents each independently 14)($R^{15}$), —$N(R^{16})(C(=O)R^{17})$, selected from the group consisting of halogen, —CN, —OH, —$N(R^{14})(R^{15})$, —$N(R^{16})(C(=O)R^{17})$, —$C(=O)$—$OR^{18}$, —$C(=O)H$, —$C(=O)R^{18}$, and —$C(=O)N(R^{14})(R^{15})$. In a further embodiment, $R^5$ and $R^6$ are each independently selected from the group consisting of H, OH, —CN, Cl, F, methyl, ethyl, $C_1$ fluoroalkyl, $C_{1-3}$ cyanoalkyl, —$OCH_3$, $C_1$ fluoroalkoxy, —$N(R^8)(R^9)$, and —$OR^{13}$, wherein each of said methyl or ethyl is optionally substituted with —$N(R^{14})(R^{15})$. In a yet further embodiment, one of $R^5$ and $R^6$ is H, F, or methyl; and the other of $R^5$ and $R^6$ is selected from the group consisting of H, —OH, —CN, Cl, F, methyl, ethyl, $C_1$ fluoroalkyl, $C_{1-3}$ cyanoalkyl, —$OCH_3$, $C_1$ fluoroalkoxy, —$N(R^8)(R^9)$, and —$OR^{13}$, wherein each of said methyl or ethyl is optionally substituted with —$N(R^{14})(R^{15})$.

An embodiment of the present invention is a compound of Formula I wherein one of $R^5$ and $R^6$ is H, F, or methyl; and the other of $R^5$ and $R^6$ is selected from the group consisting of H, OH, —CN, Cl, F, methyl, ethyl, $C_1$ fluoroalkyl (e.g., $CF_3$ or $CH_2F$), $C_{1-3}$ cyanoalkyl, —$OCH_3$, $C_1$ fluoroalkoxy (e.g., —$OCF_3$), and $NH_2$. In a further embodiment, one of $R^5$ and $R^6$ is H, F, or methyl; and the other of $R^5$ and $R^6$ is selected from the group consisting of H, —OH, —CN, Cl, F, methyl, ethyl, $CF_3$, $CH_2F$, and —$OCH_3$. In a yet further embodiment, one of $R^5$ and $R^6$ is H; and the other of $R^5$ and $R^6$ is selected from the group consisting of H, —OH, —CN, Cl, F, methyl, ethyl, $CF_3$, $CH_2F$, and —$OCH_3$.

An embodiment of the present invention is a compound of Formula I wherein one of $R^5$ and $R^6$ is H, F, or methyl; and the other of $R^5$ and $R^6$ is selected from the group consisting of H, —CN, F, methyl, and —$OCH_3$. In a further embodiment, one of $R^5$ and $R^6$ is H or F; and the other of $R^5$ and $R^6$ is selected from the group consisting of H, —CN, F, methyl, and —OCH$_3$. In a yet further embodiment, one of $R^5$ and $R^6$ is H; and the other of $R^5$ and $R^6$ is selected from the group consisting of H, —CN, F, methyl, and —OCH$_3$. In a still further embodiment, one of $R^5$ and $R^6$ is H; and the other of $R^5$ and $R^6$ is —CN.

An embodiment of the present invention is a compound of Formula I wherein one of $R^5$ and $R^6$ is H; and the other of $R^5$ and $R^6$ is —OR$^{13}$.

An embodiment of the present invention is a compound of Formula I wherein one of $R^5$ and $R^6$ is H; and the other of $R^5$ and $R^6$ is selected from the group consisting of —N(R$^8$)(R$^9$) and CH$_2$—N(R$^{14}$)(R$^{15}$).

An embodiment of the present invention is a compound of Formula I wherein $R^4$ and $R^6$ are each independently selected from the group consisting of H, F, and C$_{1-3}$ alkyl; and $R^5$ and $R^3$ together with the two carbon atoms to which they are attached form a fused N-containing 5- or 6-membered heteroaryl, a fused N-containing 5- or 6-membered heterocycloalkyl, or a fused benzene ring; wherein each of the fused heteroaryl, the fused heterocycloalkyl, and the fused benzene ring is optionally substituted with 1, 2, or 3 substituents each independently selected from the group consisting of C$_{1-3}$ alkyl, C$_{1-3}$ alkoxy, C$_{1-3}$ haloalkyl, and C$_{1-3}$ haloalkoxy.

An embodiment of the present invention is a compound of Formula I wherein $R^6$ and $R^4$ are both H; and $R^5$ and $R^3$ together with the two carbon atoms to which they are attached form a fused benzene ring; wherein the fused benzene ring is optionally substituted with 1, 2, or 3 substituents each independently selected from the group consisting of halo, C$_{1-3}$ alkyl, C$_{1-3}$ alkoxy, C$_{1-3}$ haloalkyl, and C$_{1-3}$ haloalkoxy.

An embodiment of the present invention is a compound of Formula I wherein $R^6$ and $R^4$ are both H; and $R^5$ and $R^3$ together with the two carbon atoms to which they are attached form a fused N-containing 5- or 6-membered heteroaryl; wherein the fused heteroaryl is optionally substituted with 1, 2, or 3 substituents each independently selected from the group consisting of C$_{1-3}$ alkyl, C$_{1-3}$ alkoxy, C$_{1-3}$ haloalkyl, and C$_{1-3}$ haloalkoxy.

An embodiment of the present invention is a compound of Formula I wherein $R^6$ and $R^4$ are both H; and $R^5$ and $R^3$ together with the two carbon atoms to which they are attached form a fused N-containing 5- or 6-membered heterocycloalkyl; wherein the fused heterocycloalkyl is optionally substituted with 1 to 2 substituents each independently selected from the group consisting of C$_{1-3}$ alkyl.

An embodiment of the present invention is a compound of Formula I wherein each of $R^7$ and $R^{7a}$ is independently selected from the group consisting of halogen, oxo, —OH, —CN, C$_{1-6}$ alkyl, C$_{1-6}$ haloalkyl, C$_{1-6}$ alkoxy, C$_{3-7}$ cycloalkyl, a 4- to 10-membered heterocycloalkyl, a 5- to 10-membered heteroaryl, arylalkyl, heteroarylalkyl, and —N(R$^{14}$)(R$^{15}$), wherein the C$_{1-6}$ alkyl is optionally substituted with 1, 2, 3, 4, or 5 substituents each independently selected from halogen (e.g., F), OH, C$_{1-4}$ alkoxy, and —N(R$^{14}$)(R$^{15}$); and wherein each of said C$_{3-7}$ cycloalkyl, heterocycloalkyl, heteroaryl, arylalkyl, and heteroarylalkyl is optionally substituted with 1, 2, or 3 substituents each independently selected from the group consisting of halogen, —OH, C$_{1-4}$ alkyl, and C$_{1-4}$ alkoxy.

An embodiment of the present invention is a compound of Formula I wherein each of $R^7$ and $R^{7a}$ is independently selected from the group consisting of halogen, oxo, —OH, —CN, C$_{1-6}$ alkyl, C$_{1-6}$ haloalkyl, C$_{1-6}$ alkoxy, C$_{3-7}$ cycloalkyl, a 4- to 10-membered heterocycloalkyl, a 5- to 10-membered heteroaryl, arylalkyl, heteroarylalkyl, and —N(R$^{14}$)(R$^{15}$), wherein the C$_{1-6}$ alkyl is optionally substituted with 1, 2, 3, 4 or 5 substituents each independently selected from the group consisting of halogen (e.g., F), OH, C$_{1-4}$ alkoxy, —NH$_2$, —NH(C$_{1-4}$ alkyl), —N(C$_{1-4}$ alkyl)$_2$, azetidin-1-yl, pyrrolidin-1-yl, and pyridin-1-yl; and wherein each of said C$_{3-7}$ cycloalkyl, heterocycloalkyl, heteroaryl, arylalkyl, and heteroarylalkyl is optionally substituted with 1, 2, or 3 substituents each independently selected from the group consisting of halogen, —OH, C$_{1-4}$ alkyl, and C$_{1-4}$ alkoxy. In a further embodiment, each of $R^7$ and $R^{7a}$ is independently selected from the group consisting of halogen, —OH, —CN, C$_{1-6}$ alkyl, C$_{1-6}$ haloalkyl, C$_{1-6}$ alkoxy, C$_{3-7}$ cycloalkyl, a 4- to 10-membered heterocycloalkyl, a 5- to 10-membered heteroaryl, arylalkyl, heteroarylalkyl, and —N(R$^{14}$)(R$^{15}$), wherein the C$_{1-6}$ alkyl is optionally substituted 1 with 1, 2, 3, 4 or 5 substituents each independently selected from the group consisting of halogen (e.g., F), OH, C$_{1-4}$ alkoxy, —NH$_2$, —NH(C$_{1-4}$ alkyl), —N(C$_{1-4}$ alkyl)$_2$, azetidin-1-yl, pyrrolidin-1-yl, and pyridin-1-yl; and wherein each of said C$_{3-7}$ cycloalkyl, heterocycloalkyl, heteroaryl, arylalkyl, and heteroarylalkyl is optionally substituted with 1, 2, or 3 substituents each independently selected from the group consisting of halogen, —OH, C$_{1-4}$ alkyl, and C$_{1-4}$ alkoxy.

An embodiment of the present invention is a compound of Formula I wherein each of $R^7$ and $R^{7a}$ is independently selected from the group consisting of C$_{1-4}$ alkyl, C$_{1-4}$ haloalkyl, oxo, —OH, C$_{1-4}$ alkoxy, C$_{1-4}$ haloalkoxy, halogen, —CN, —NH$_2$, —NH(C$_{1-4}$ alkyl), —N(C$_{1-4}$ alkyl)$_2$, and —N(R$^{14}$)(R$^{15}$); wherein the C$_{1-4}$ alkyl is optionally substituted with 1, 2, 3, 4 or 5 substituents each independently selected from the group consisting of halogen (e.g., F), OH, C$_{1-4}$ alkoxy, —NH$_2$, —NH(C$_{1-4}$ alkyl), —N(C$_{1-4}$ alkyl)$_2$, azetidin-1-yl, pyrrolidin-1-yl, and pyridin-1-yl; where R$^{14}$ and R$^{15}$ together with the N atom to which they are attached form a 4- to 10-membered heterocycloalkyl or a 5- to 10-membered heteroaryl optionally substituted with 1, 2, or 3 substituents each independently selected from the group consisting of halogen, oxo, —OH, —CN, —NH$_2$, —NH(C$_{1-4}$ alkyl), —N(C$_{1-4}$ alkyl)$_2$, C$_{1-4}$ alkyl, C$_{1-4}$ alkoxy, C$_{1-4}$ haloalkyl, C$_{1-4}$ haloalkoxy, and C$_{1-4}$ hydroxylalkyl. In a further embodiment, R$^{14}$ and R$^{15}$ together with the N atom to which they are attached form a 4- to 10-membered heterocycloalkyl optionally substituted with 1, 2, or 3 substituents each independently selected from the group consisting of halogen, oxo, —OH, C$_{1-4}$ alkyl, C$_{1-4}$ alkoxy, C$_{1-4}$ haloalkyl, C$_{1-4}$ haloalkoxy, and C$_{1-4}$ hydroxylalkyl.

An embodiment of the present invention is a compound of Formula I wherein each of $R^7$ and $R^{7a}$ is independently selected from the group consisting of C$_{1-4}$ alkyl, C$_{1-4}$ fluoroalkyl, oxo, —OH, C$_{1-4}$ alkoxy, and C$_{1-4}$ haloalkoxy; wherein the C$_{1-4}$ alkyl is optionally substituted with 1, 2, 3, 4 or 5 substituents each independently selected from the group consisting of halogen (e.g., F), OH, C$_{1-4}$ alkoxy, —NH$_2$, —NH(C$_{1-4}$ alkyl), —N(C$_{1-4}$ alkyl)$_2$, azetidin-1-yl, pyrrolidin-1-yl, and pyridin-1-yl.

An embodiment of the present invention is a compound of Formula I wherein each $R^7$ is independently selected from the group consisting of C$_{1-4}$ alkyl, C$_{1-4}$ fluoroalkyl, oxo, OH, C$_{1-4}$ alkoxy, C$_{1-4}$ haloalkoxy, halogen, —CN, —NH$_2$, —NH(C$_{1-4}$ alkyl), —N(C$_{1-4}$ alkyl)$_2$, and azetidinyl, wherein the C$_{1-4}$ alkyl of $R^7$ is optionally substituted with 1, 2, 3, 4 or 5 substituents each independently selected from the group consisting of halogen (e.g., F), OH, C$_{1-4}$ alkoxy, —NH$_2$, —NH(C$_{1-4}$ alkyl), —N(C$_{1-4}$ alkyl)$_2$, azetidin-1-yl, pyrrolidin-1-yl, and pyridin-1-yl; and wherein said azetidinyl of $R^7$ is optionally substituted with 1, 2, or 3 substituents each independently selected from the group consisting of F, $C_{1-4}$ alkyl, $C_{1-4}$ hydroxylalkyl, and oxo.

An embodiment of the present invention is a compound of Formula I wherein each $R^7$ is independently selected from the group consisting of $C_{1-4}$ alkyl, $C_{1-4}$ fluoroalkyl, oxo, OH, $C_{1-4}$ alkoxy, and $C_{1-4}$ haloalkoxy, wherein the $C_{1-4}$ alkyl is optionally substituted with 1, 2, 3, 4 or 5 substituents each independently selected from the group consisting of halogen (e.g., F), OH, $C_{1-4}$ alkoxy, —$NH_2$, —$NH(C_{1-4}$ alkyl), —$N(C_{1-4}$ alkyl)$_2$, azetidin-1-yl, pyrrolidin-1-yl, and pyridin-1-yl. In a further embodiment, each $R^7$ is independently selected from the group consisting of $C_{1-4}$ alkyl, $C_{1-4}$ fluoroalkyl, and oxo; wherein the $C_{1-4}$ alkyl is optionally substituted with 1, 2, 3, 4 or 5 substituents each independently selected from the group consisting of halogen (e.g., F), OH, $C_1$-4 alkoxy, —$NH_2$, —$NH(C_{1-4}$ alkyl), —$N(C_{1-4}$ alkyl)$_2$, azetidin-1-yl, pyrrolidin-1-yl, and pyridin-1-yl. In a yet further embodiment, each $R^7$ is independently selected from the group consisting of $C_{1-4}$ alkyl (e.g., methyl) and oxo; wherein the $C_{1-4}$ alkyl is optionally substituted with 1, 2, 3, 4 or 5 substituents each independently selected from the group consisting of halogen (e.g., F), OH, $C_{1-4}$ alkoxy, —$NH_2$, —$NH(C_{1-4}$ alkyl), —$N(C_{1-4}$ alkyl)$_2$, azetidin-1-yl, pyrrolidin-1-yl, and pyridin-1-yl.

An embodiment of the present invention is a compound of Formula I wherein each $R^{7a}$ is independently selected from the group consisting of $C_{1-4}$ alkyl, $C_{1-4}$ fluoroalkyl, OH, $C_{1-4}$ alkoxy, $C_{1-4}$ haloalkoxy, halogen, —CN, —$NH_2$, —NH($C_{1-4}$ alkyl), —N($C_{1-4}$ alkyl)$_2$, azetidinyl, pyrrolidinyl, 1,4,5,6-tetrahydropyrrolo[3,4-c]pyrazolyl, 2,5-dihydro-1H-pyrrolyl, thiomorpholino, piperidinyl, and piperazinyl, wherein each of said azetidinyl, pyrrolidinyl, 1,4,5,6-tetrahydropyrrolo[3,4-c]pyrazolyl, 2,5-dihydro-1H-pyrrolyl, thiomorpholino, piperidinyl, and piperazinyl is optionally substituted with 1, 2, or 3 substituents each independently selected from the group consisting of F, $C_{1-4}$ alkyl, $C_{1-4}$ hydroxylalkyl, and oxo.

An embodiment of the present invention is a compound of Formula I wherein $Y^1$ is O and $X^1$ is O. An embodiment of the present invention is a compound of Formula I wherein $Y^1$ is O; $X^1$ is O; each of $R^{T1}$, $R^{T2}$, and $R^1$ is H; and $R^2$ is H or —CN. An embodiment of the present invention is a compound of Formula I wherein $Y^1$ is O; $X^1$ is O; each of $R^{T1}$, $R^{T2}$, and $R^1$ is H; $R^2$ is H or —CN; and $R^3$ and $R^4$ are each independently H or F. In a further embodiment, one of $R^3$ and $R^4$ is H; and the other of $R^3$ and $R^4$ is H or F. In a still further embodiment, $R^2$ is H; in another still further embodiment, $R^2$ is —CN.

An embodiment of the present invention is a compound of Formula I wherein $Y^1$ is O; $X^1$ is O; each of $R^{T1}$, $R^{T2}$, and $R^1$ is H; $R^2$ is H or —CN; one of $R^3$ and $R^4$ is H, and the other of $R^3$ and $R^4$ is H or F; and one of $R^5$ and $R^6$ is H or F, and the other of $R^5$ and $R^6$ is selected from the group consisting of H, —CN, F, methyl, and —$OCH_3$. In a further embodiment, one of $R^5$ and $R^6$ is H. In a still further embodiment, $R^2$ is H; in another still further embodiment, $R^2$ is —CN.

An embodiment of the present invention is a compound of Formula I wherein $Y^1$ is O; $X^1$ is O; each of $R^{T1}$, $R^{T2}$, and $R^1$ is H; $R^2$ is H or —CN; one of $R^3$ and $R^4$ is H, and the other of $R^3$ and $R^4$ is H or F; one of $R^5$ and $R^6$ is H or F, and the other of $R^5$ and $R^6$ is selected from the group consisting of H, —CN, F, methyl, and —$OCH_3$; and $Q^1$ is pyrimidinyl, pyrazinyl, 3-oxo-2H-pyridazinyl, 1H-2-oxo-pyrazinyl, 1H-2-oxo-pyrimidinyl, or imidazo[1,2-a]pyrazinyl, each optionally substituted with 1, 2, or 3 independently selected $R^7$. In a still further embodiment, $R^2$ is H; in another still further embodiment, $R^2$ is —CN.

An embodiment of the present invention is a compound of Formula I wherein $Y^1$ is O; $X^1$ is O; each of $R^{T1}$, $R^{T2}$, and $R^1$ is H; $R^2$ is H or —CN; one of $R^3$ and $R^4$ is H, and the other of $R^3$ and $R^4$ is H or F; one of $R^5$ and $R^6$ is H or F, and the other of $R^5$ and $R^6$ is selected from the group consisting of H, —CN, F, methyl, and —$OCH_3$; and $Q^1$ is pyrimidinyl, pyrazinyl, 3-oxo-2H-pyridazinyl, 1H-2-oxo-pyrazinyl, 1H-2-oxo-pyrimidinyl, or imidazo[1,2-a]pyrazinyl, each optionally substituted with 1, 2, or 3 $C_{1-3}$ alkyl. In a further embodiment, $Q^1$ is pyrimidinyl, pyrazinyl, 3-oxo-2H-pyridazinyl, 1H-2-oxo-pyrazinyl, 1H-2-oxo-pyrimidinyl, or imidazo[1,2-a]pyrazinyl, each optionally substituted with 1, 2, or 3 methyl.

An embodiment of the present invention is a compound of Formula I wherein $Y^1$ is O; $X^1$ is O; each of $R^{T1}$, $R^{T2}$, and $R^1$ is H; $R^2$ is H or —CN; one of $R^3$ and $R^4$ is H, and the other of $R^3$ and $R^4$ is H or F; one of $R^5$ and $R^6$ is H or F, and the other of $R^5$ and $R^6$ is selected from the group consisting of H, —CN, F, methyl, and —$OCH_3$; and $Q^1$ is selected from:

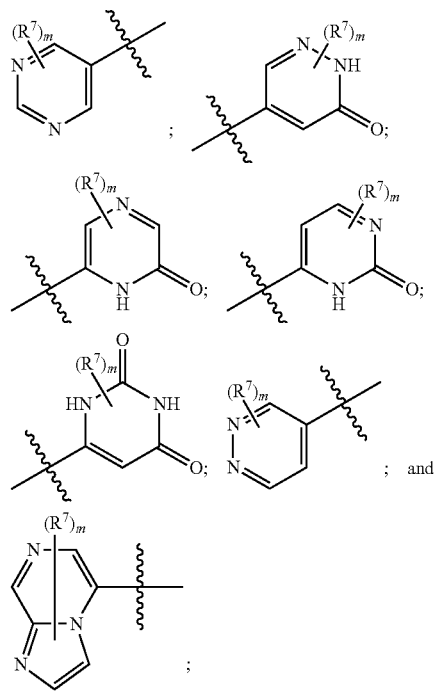

and m is 1, 2, or 3. In a further embodiment, each $R^7$ is independently $C_{1-3}$ alkyl optionally substituted with 1, 2, 3, 4 or 5 substituents each independently selected from the group consisting of halogen (e.g., F), OH, $C_{1-4}$ alkoxy, —$NH_2$, —$NH(C_{1-4}$ alkyl), —$N(C_{1-4}$ alkyl)$_2$, pyrrolidin-1-yl, and pyridin-1-yl. In a yet further embodiment, each $R^7$ is methyl. In a still further embodiment, $R^2$ is H; in another still further embodiment, $R^2$ is —CN.

An embodiment of the present invention is a compound of Formula I wherein $Y^1$ is O; $X^1$ is O; each of $R^{T1}$, $R^{T2}$, and $R^1$ is H; $R^2$ is H or —CN; one of $R^3$ and $R^4$ is H, and the other of $R^3$ and $R^4$ is H or F; one of $R^5$ and $R^6$ is H or F, and the other of $R^5$ and $R^6$ is selected from the group consisting of H, —CN, F, methyl, and —$OCH_3$; and $Q^1$ is selected from:

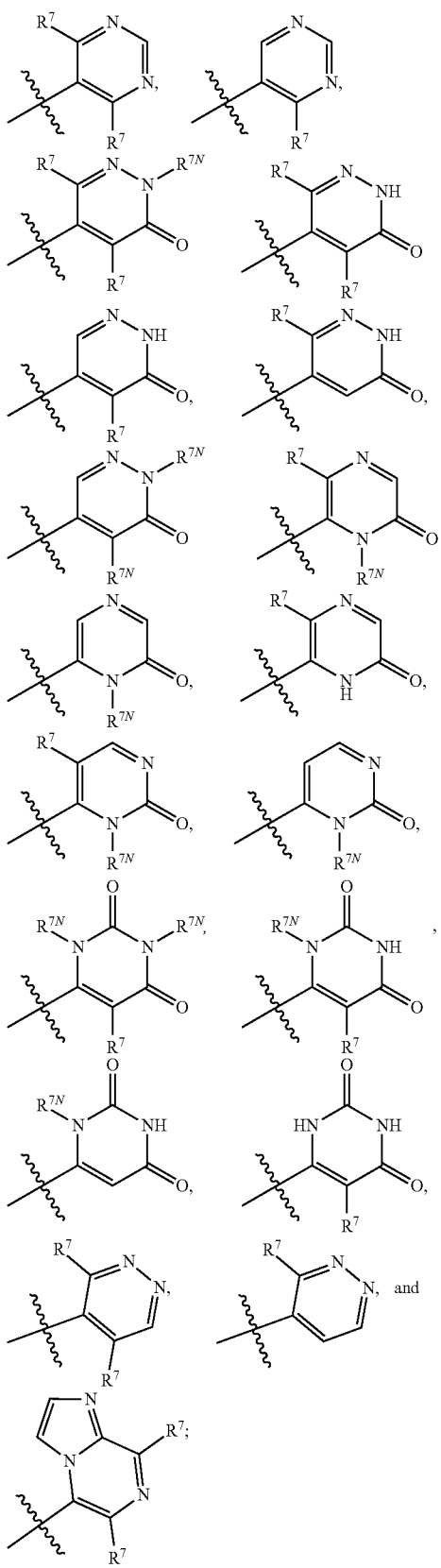

each R⁷ is independently H or C₁₋₃ alkyl (e.g. methyl or ethyl); and each R⁷ᴺ is H or C₁₋₃ alkyl, wherein the C₁₋₃ alkyl is optionally substituted with 1, 2, 3, 4, or 5 substituents each independently selected from halogen (e.g., F), OH, C₁₋₄ alkoxy, —NH₂, —NH(C₁₋₄ alkyl), —N(C₁₋₄ alkyl)₂, azetidin-1-yl, pyrrolidin-1-yl, and pyridin-1-yl. In a further embodiment, each R⁷ is methyl or ethyl and each R⁷ᴺ is C₁₋₃ alkyl optionally substituted with 1, 2, 3, 4, or 5 substituents each independently selected from halogen (e.g., F), OH, C₁₋₄ alkoxy, —NH₂, —NH(C₁₋₄ alkyl), —N(C₁₋₄ alkyl)₂, pyrrolidin-1-yl, and pyridin-1-yl. In a yet further embodiment, each R⁷ is methyl and each R⁷ᴺ is methyl. In a still further embodiment, R² is H; in another still further embodiment, R² is —CN.

In one embodiment, the invention also provides one or more of the compounds described as Examples 1-216 in the Examples section of the subject application, N-oxides thereof, and pharmaceutically acceptable salts of the compounds or the N-oxides.

In another embodiment the invention relates to a compound of Formula I selected from the group consisting of:
4-[4-(4,6-dimethylpyrimidin-5-yl)-3-methylphenoxy]furo[3,2-c]pyridine;
2-(4,6-dimethylpyrimidin-5-yl)-5-(furo[3,2-c]pyridin-4-yloxy)benzonitrile;
5-[2-fluoro-4-(furo[3,2-c]pyridin-4-yloxy)phenyl]-4,6-dimethylpyridazin-3(2H)-one;
5-[4-(furo[3,2-c]pyridin-4-yloxy)phenyl]-4,6-dimethylpyridazin-3(2H)-one;
(+)-5-[4-(furo[3,2-c]pyridin-4-yloxy)-2-methylphenyl]-4,6-dimethylpyridazin-3(2H)-one;
(−)-5-[4-(furo[3,2-c]pyridin-4-yloxy)-2-methylphenyl]-4,6-dimethylpyridazin-3(2H)-one;
5-[4-(furo[3,2-c]pyridin-4-yloxy)-2-methylphenyl]-4,6-dimethylpyridazin-3(2H)-one;
(+)-5-[4-(furo[3,2-c]pyridin-4-yloxy)-2-methylphenyl]-6-methylimidazo[1,2-a]pyrazine;
(−)-5-[4-(furo[3,2-c]pyridin-4-yloxy)-2-methylphenyl]-6-methylimidazo[1,2-a]pyrazine;
5-[4-(furo[3,2-c]pyridin-4-yloxy)-2-methylphenyl]-6-methylimidazo[1,2-a]pyrazine;
4-[4-(4,6-dimethylpyrimidin-5-yl)-3-fluorophenoxy]furo[3,2-c]pyridine;
4-[4-(4,6-dimethylpyrimidin-5-yl)phenoxy]furo[3,2-c]pyridine;
(−)-6-[4-(furo[3,2-c]pyridin-4-yloxy)-2-methylphenyl]-1,5-dimethylpyrazin-2(1H)-one;
(+)-6-[4-(furo[3,2-c]pyridin-4-yloxy)-2-methylphenyl]-1,5-dimethylpyrazin-2(1H)-one;
6-[4-(furo[3,2-c]pyridin-4-yloxy)-2-methylphenyl]-1,5-dimethylpyrazin-2(1H)-one;
6-[4-(furo[3,2-c]pyridin-4-yloxy)-2-methylphenyl]-1,5-dimethylpyrimidin-2(1H)-one;
4-[4-(4,6-dimethylpyrimidin-5-yl)-2-fluorophenoxy]furo[3,2-c]pyridine;
5-[4-(furo[3,2-c]pyridin-4-yloxy)-2-methylphenyl]-2,4,6-trimethylpyridazin-3(2H)-one;
5-[4-(furo[3,2-c]pyridin-4-yloxy)-2-methylphenyl]-4-methylpyridazin-3(2H)-one;
(+)-4-[4-(3,5-dimethylpyridazin-4-yl)-3-methylphenoxy]furo[3,2-c]pyridine;
(−)-4-[4-(3,5-dimethylpyridazin-4-yl)-3-methylphenoxy]furo[3,2-c]pyridine;
4-[4-(3,5-dimethylpyridazin-4-yl)-3-methylphenoxy]furo[3,2-c]pyridine;
4-[4-(3,5-dimethyl-6-oxo-1,6-dihydropyridazin-4-yl)phenoxy]furo[3,2-c]pyridine-3-carbonitrile;
(−)-4-[4-(3,5-dimethylpyridazin-4-yl)-3-methoxyphenoxy]furo[3,2-c]pyridine;

(+)-4-[4-(3,5-dimethylpyridazin-4-yl)-3-methoxyphenoxy]furo[3,2-c]pyridine;

4-[4-(3,5-dimethylpyridazin-4-yl)-3-methoxyphenoxy]furo[3,2-c]pyridine;

6-[4-(furo[3,2-c]pyridin-4-yloxy)-2-methylphenyl]-1,5-dimethylpyrimidine-2,4(1H,3H)-dione;

(−)-6-[4-(furo[3,2-c]pyridin-4-yloxy)-2-methylphenyl]-1,5-dimethylpyrimidine-2,4(1H,3H)-dione;

(+)-6-[4-(furo[3,2-c]pyridin-4-yloxy)-2-methylphenyl]-1,5-dimethylpyrimidine-2,4(1H,3H)-dione; and 6-[4-(furo[3,2-c]pyridin-4-yloxy)phenyl]-1,5-dimethylpyrimidine-2,4(1H,3H)-dione, or an N-oxide thereof or a pharmaceutically acceptable salt of the compound or the N-oxide.

The present invention also provides compositions (e.g., pharmaceutical compositions) comprising a compound of Formula I (including an N-oxide thereof or a pharmaceutically acceptable salt of the compound or the N-oxide). Accordingly, in one embodiment, the invention provides a pharmaceutical composition comprising (a therapeutically effective amount of) a compound of Formula I (an N-oxide thereof or a pharmaceutically acceptable salt of the compound or the N-oxide) and optionally comprising a pharmaceutically acceptable carrier. In one further embodiment, the invention provides a pharmaceutical composition comprising (a therapeutically effective amount of) a compound of Formula I (an N-oxide thereof or a pharmaceutically acceptable salt of the compound or the N-oxide), optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or an N-oxide thereof or a pharmaceutically acceptable salt of the compound or the N-oxide) and a pharmaceutically acceptable carrier.

Compounds of Formula I (including N-oxides thereof and pharmaceutically acceptable salts of the compounds or the N-oxides) are D1 modulators. In some embodiments, a compound of Formula I is a D1 agonist [i.e., binding (having affinity for) and activating D1 receptors]. In some embodiments, using dopamine as a reference full D1 agonist, a compound of Formula I is a super agonist (i.e., a compound that is capable of producing a greater maximal response than the endogenous D1 agonist, dopamine, for a D1 receptor, and thus exhibiting an efficacy of more than about 100%, for example 120%). In some embodiments, using dopamine as a reference full agonist, a compound of Formula I is a full D1 agonist (i.e., having an efficacy of about 100%, for example, 90%-100%, compared to that of dopamine). In some embodiments, using dopamine as a reference full D1 agonist, a compound of Formula I is a partial agonist [i.e., a compound having only partial efficacy (i.e., less than 100%, for example 10%-80% or 50%-70%) at a D1 receptor relative to the full agonist, dopamine, although it binds and activates a D1 receptor]. A D1 agonist (including superagonist, full agonist, and partial agonist) can agonize or partially agonize an activity of D1. In some embodiments, the $EC_{50}$ of a compound of Formula I with respect to D1 is less than about 10 µM, 5 µM, 2 µM, 1 µM, 500 nM, 200 nM, 100 nM, 50, 40, 30, 20, 10, 5, 2, or 1 nM.

As used herein, when referencing to a compound, the term "D1 modulator" or "D1 agonist" (including a super D1 agonist, a full D1 agonist, or a partial D1 agonist) refers to a compound that is a D1-like receptor modulator or a D1-like receptor agonist respectively (i.e., not necessarily selective between/among subtypes of D1-like receptors). See Lewis, *JPET* 286:345-353, 1998. D1Rs include, for example, D1 and D5 in humans and D1A and D1B in rodents.

The present invention further provides a method for modulating (such as agonizing or partially agonizing) an activity of D1 receptor (either in vitro or in vivo), comprising contacting (including incubating) the D1 receptor with a compound of Formula I (such as one selected from Examples 1-216), or an N-oxide thereof or a pharmaceutically acceptable salt of the compound or the N-oxide.

Another embodiment of the invention includes a method for treating a D1-mediated (or D1-associated) disorder, comprising administering to a mammal (e.g., a human) in need thereof an amount of a compound of Formula I (including a pharmaceutically acceptable salt thereof or an N-oxide of the compound or salt) effective in modulating (e.g., agonizing or partially agonizing) D1.

The compounds of Formula I used for treatment of a D1-mediated disorder include N-oxides thereof or pharmaceutically acceptable salts of the compounds or the N-oxides.

D1-mediated (or D1-associated) disorders include neurological disorders [such as Tourette's syndrome; tardive dyskinesia; Parkinson's disease; cognitive disorders {including amnesia, senile dementia, age-related cognitive decline, HIV-associated dementia, Alzheimer's-associated dementia, Huntington's-associated dementia, Lewy body dementia, vascular dementia, drug-related dementia (for example, cognitive impairment associated with D2 antagonist therapy), delirium, and mild cognitive impairment}; Huntington's chorea/disease], psychiatric disorders [such as anxiety (including acute stress disorder, generalized anxiety disorder, social anxiety disorder, panic disorder, post-traumatic stress disorder, and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, depression including major depression, chronic depression, seasonal depression, psychotic depression, postpartum depression, and treatment resistant depression (TRD)); psychomotor disorders; psychotic disorders [including schizophrenia (including, for example, cognitive and negative symptoms in schizophrenia), schizoaffective disorder, schizophreniform, and delusional disorder]; substance abuse and drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); autism spectrum disorder (e.g., autism); chronic apathy, anhedonia, chronic fatigue, seasonal affective disorder, and pediatric psychiatric disorders (including attention deficit disorder, attention deficit hyperactive disorder (ADHD), conduct disorder, and autism)], endocrine disorders (such as hyperprolactinemia), or other disorders including drowsiness, sexual dysfunction, pain, migraine, systemic lupus erythematosus (SLE), hyperglycemia, dislipidemia, obesity, diabetes, sepsis, post-ischemic tubular necrosis, renal failure, resistant edema, narcolepsy, cardiovascular disease (e.g., hypertension), congestive heart failure, postoperative ocula hypotonia, sleep disorders, serotonin syndrome.

Another embodiment of the invention provides a method for treating neurological disorders [such as Tourette's syndrome; tardive dyskinesia; Parkinson's disease; cognitive disorders {including amnesia, senile dementia, HIV-associated dementia, Alzheimer's-associated dementia, Huntington's-associated dementia, Lewy body dementia, vascular dementia, drug-related dementia (for example, cognitive impairment associated with D2 antagonist therapy), delirium, and mild cognitive impairment)}; and Huntington's chorea/disease], psychiatric disorders [such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism)], or endocrine disorders (such as hyperprolactinemia) in a mammal, for example a human, comprising administering to said mammal a therapeutically effective amount of a compound of Formula I.

Another embodiment of the invention includes a method for treating a disorder in a mammal (e.g., a human), which method comprises administering to said mammal a therapeutically effective amount of a compound of Formula I, wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy)], attention deficit hyperactivity disorder (ADHD), impulsivity, compulsive gambling, overeating, autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, a movement disorder [e.g., dyskinesia (e.g., Chorea, Levodopa-induced dyskinesia, or tardive dyskinesia) a Tic disorder (e.g., Tourette's syndrome), or Tremor], a therapy-induced movement disorder [e.g., therapy-related dyskinesia (e.g., Levodopa-induced dyskinesia ("LID")) or therapy-related dyskinesia tremor (SSRI-induced postural tremor)], sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

Another embodiment of the invention includes a method for treating a disorder in a mammal (e.g., a human), which method comprises administering to said mammal a therapeutically effective amount of a compound of Formula I, wherein the disorder is selected from schizophrenia (e.g., cognitive and negative symptoms in schizophrenia or cognitive impairment associated with schizophrenia), cognitive impairment associated with D2 antagonist therapy, attention deficit hyperactivity disorder (ADHD), impulsivity, compulsive gambling, autism spectrum disorder, Mild cognitive impairment (MCI), age-related cognitive decline, Alzheimer's dementia, Lewy body dementia, vascular dementia, Parkinson's disease, Huntington's chorea, depression, anxiety, treatment resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, Tourette's syndrome, tardive dyskinesia, drowsiness, sexual dysfunction, migraine, systemic lupus erythematosus (SLE), hyperglycemia, dislipidemia, obesity, diabetes, sepsis, post-ischemic tubular necrosis, renal failure, resistant edema, narcolepsy, hypertension, congestive heart failure, postoperative ocular hypotonia, sleep disorders, and pain.

Another embodiment of the invention includes a method for treating depression in a mammal, for example a human, comprising administering to said mammal (e.g., a human) a therapeutically effective amount of a compound of Formula I.

Another embodiment of the invention includes a method for treating Parkinson's disease in a mammal, for example a human, comprising administering to said mammal (e.g., a human) a therapeutically effective amount of a compound of Formula I.

Another embodiment of the invention includes a method for treating schizophrenia (e.g., cognitive and negative symptoms in schizophrenia or cognitive impairment associated with schizophrenia) or psychosis in a mammal, for example a human, comprising administering to said mammal (e.g., a human) a therapeutically effective amount of a compound of Formula I.

Another embodiment of the invention includes a method for treating schizophrenia (e.g., cognitive and negative symptoms in schizophrenia or cognitive impairment associated with schizophrenia) in a mammal, for example a human, comprising administering to said mammal a therapeutically effective amount of a compound of Formula I.

Another embodiment of the invention includes a method for the treatment of cognitive impairment associated with schizophrenia in a mammal, for example a human, comprising administering to said mammal a therapeutically effective amount of a compound of Formula I.

The term "therapeutically effective amount" as used herein refers to that amount of the compound (including a pharmaceutically acceptable salt thereof or an N-oxide of the compound or salt) being administered which will relieve to some extent one or more of the symptoms of the disorder being treated. In reference to the treatment of a D1-mediated disorder (e.g., schizophrenia), a therapeutically effective amount refers to that amount which has the effect of relieving to some extent (or, for example, eliminating) one or more symptoms associated with a D1-mediated disorder (e.g., schizophrenia, or cognitive and negative symptoms in schizophrenia, or cognitive impairment associated with schizophrenia).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

Administration of the compounds of Formula I may be effected by any method that enables delivery of the compounds to the site of action. These methods include, for example, enteral routes (e.g., oral routes, buccal routes, sublabial routes, sublingual routes), intranasal routes, inhaled routes, intraduodenal routes, parenteral injection (including intravenous, subcutaneous, intramuscular, intravascular or infusion), intrathecal routes, epidural routes, intracerebral routes, intracerbroventricular routes, topical, and rectal administration.

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.0001 to about 50 mg per kg body weight per day, for example about 0.01 to about 5 mg/kg/day, in single or divided doses. For a 70 kg human, this would amount to about 0.7 mg to about 3500 mg/day, for example about 5 mg to about 2000 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I together with an at least one additional pharmaceutical or medicinal agent (e.g., an anti-schizophrenia agent), either sequentially or simultaneously.

The present invention includes the use of a combination of a compound of Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including an N-oxide thereof or a pharmaceutically acceptable salt of the compound or the N-oxide); (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $Aβ_{1-15}$ conjugated to pan HLA DR-binding epitope (PADRE) and ACC-001 (Elan/Wyeth;

(iii) antibodies to amyloid-β (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) PDE9 inhibitors such as BAY 73-6691 (Bayer AG);

(xxx) phosphodiesterase (PDE) inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));

(xxxi) quinolines such as quinine (including its hydrochloride, dihydrochloride, sulfate, bisulfate and gluconate salts);

(xxxii) β-secretase inhibitors such as WY-25105;

(xxxiii) γ-secretase inhibitors such as LY-411575 (Lilly);

(xxxiv) serotonin (5-hydroxytryptamine) 1A ($5-HT_{1A}$) receptor antagonists such as spiperone;

(xxxv) serotonin (5-hydroxytryptamine) 4 ($5-HT_4$) receptor agonists such as PRX-03140 (Epix);

(xxxvi) serotonin (5-hydroxytryptamine) 6 ($5-HT_6$) receptor antagonists such as mianserin (TORVOL, BOLVIDON, NORVAL);

(xxxvii) serotonin (5-HT) reuptake inhibitors such as alaproclate, citalopram (CELEXA, CIPRAMIL);

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;

and the like.

The compound of Formula I is optionally used in combination with another active agent. Such an active agent may be, for example, an atypical antipsychotic or an anti-Parkinson's disease agent or an anti-Alzheimer's agent. Accordingly, another embodiment of the invention provides methods of treating a D1-mediated disorder (e.g., a neurological and psychiatric disorder associated with D1), comprising administering to a mammal an effective amount of a compound of Formula I (including an N-oxide thereof or a pharmaceutically acceptable salt of the compound or the N-oxide) and further comprising administering another active agent.

As used herein, the term "another active agent" refers to any therapeutic agent, other than the compound of Formula I (including an N-oxide thereof or a pharmaceutically acceptable salt of the compound or the N-oxide) that is useful for the treatment of a subject disorder. Examples of additional therapeutic agents include antidepressants, antipsychotics (such as anti-schizophrenia), anti-pain, anti-Parkinson's disease agents, anti-LID, anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcypromine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine. milnacipran, guanfacine, bupropion, and atomoxetine.

As noted above, the compounds of Formula I (including N-oxides thereof and pharmaceutically acceptable salts thereof the compounds or salts) may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of Formula I (or an N-oxide thereof or a pharmaceutically acceptable salt of the foregoing), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

It will be understood that the compounds of Formula I depicted above are not limited to the particular enantiomer shown, but also include all stereoisomers and mixtures thereof.

In a second aspect, the invention provides a D1 agonist with reduced D1R desensitization. The D1 agonist with reduced D1R desensitization desensitizes D1R cAMP signaling less than about 25% relative to Control as measured by an assay similar to (or same as) example EE as provided herein. In some embodiments, the D1 agonist with reduced D1R desensitization desensitizes D1R cAMP signaling less than about 20%, about 18%, about 15%, about 10%, or about 5%) relative to Control as measured by an assay similar to (or same as) example EE as provided herein. In a further embodiment, the D1 agonist with reduced D1R desensitization is not a catechol derivative. In a yet further embodiment, the D1 agonist with reduced D1R desensitization is not a dopamine derivative.

As used herein, the D1R desensitization in connection with the D1 agonists of the present invention referred herein is homologous desensitization.

D1R receptor homologous desensitization refers to a loss (partial or total) of responsiveness after agonist exposure. See *JPET* 286: 345-353, 1998. The D1 agonists with reduced D1R desensitization of the present invention provide prolonged and/or less-reduced level of potency/effects of the D1 agonists (i.e., drug effect) after exposure to a D1R for a certain period of time, comparing to those D1 agonists without reduced desensitization (e.g., catechol derivative D1 agonists such as Dopamine, SKF-38393, Dihydrexidine, and SKF-81297). In this respect, the D1 agonist with reduced D1R desensitization of the present invention may maintain a therapeutic effect for a more sustained period of time and avoid loss of efficacy caused by desensitization (known as tachyphylaxsis), and thus may require a less amount and/or a less frequent dosage for its therapeutic application in the treatment of a D1-mediated/associated disorder. It may also reduce or eliminate drug abuse/dependence.

In some embodiments, the D1 agonist with reduced D1R desensitization is a full D1 agonist or a super D1 agonist. In a further embodiment, the D1 agonist with reduced D1R desensitization is a full D1 agonist.

In some embodiments, the D1 agonist with reduced D1R desensitization is a partial D1 agonist.

As used here, a catechol derivative refers to a compound or a salt thereof, wherein the structure of the compound includes the following moiety DD-1:

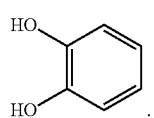

(DD-1)

In a catechol derivative, the phenyl ring of DD-1 can be further optionally substituted or embedded in a poly-cyclic ring (which can also be optionally substituted). Some examples of catechol derivative include dopamine, SKF-38393, SKF-77434, dihydrexidine, and SKF-81297:

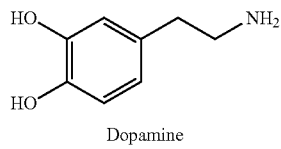

Dopamine

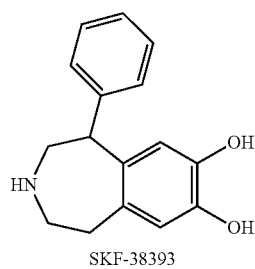

SKF-38393

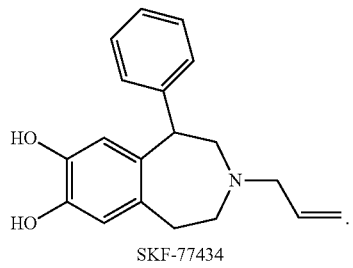

SKF-77434

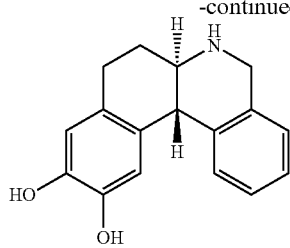

dihydrexidine

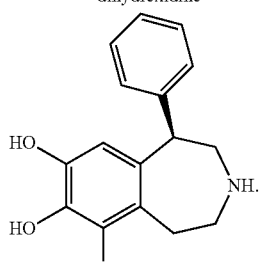

SKF-81297

As used here, a dopamine derivative refers to a compound or a salt thereof, wherein the structure of the compound includes the following moiety DD-2:

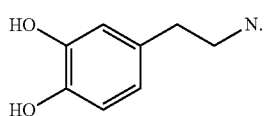

(DD-2)

In a dopamine derivative, the phenyl ring of DD-2 can be further optionally substituted or embedded in a poly-cyclic ring (which can also be optionally substituted), and/or each of the carbon atoms of ethylene group and the N atom of DD-2 can be further optionally substituted or embedded in a poly-cyclic ring (which can also be optionally substituted). Some examples of dopamine derivative include SKF-38393, SKF-77434, dihydrexidine, and SKF-81297.

In a third aspect, the invention provides a method for treating a disorder in a human, which method comprises administering to said human a therapeutically effective amount of a compound or salt thereof wherein the compound or salt thereof is a D1 agonist with reduced D1R desensitization in the second aspect, and wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy)], attention deficit hyperactivity disorder (ADHD), impulsivity, compulsive gambling, overeating, autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, a movement disorder [e.g., dyskinesia (e.g., Chorea, Levodopa-induced dyskinesia, or tardive dyskinesia) a Tic disorder (e.g., Tourette's syndrome), or Tremor], a therapy-induced movement disorder [e.g., therapy-related dyskinesia (e.g., LID) or therapy-related dyskinesia tremor (SSRI-induced postural tremor)], sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

In a fourth aspect, the invention provides a D1 agonist with a reduced β-arrestin recruitment activity relative to Dopamine. A D1R, after binding to the D1 agonist with a reduced β-arrestin recruitment activity, recruits less than about 60% of β-arrestin relative to the D1R binding to Dopamine, as measured by an assay similar to (or the same as) Example CC as provided herein (either using Total Intensity/cell or Total Area/cell). In some embodiments, a D1R, after binding to the D1 agonist with a reduced β-arrestin recruitment activity, recruits less than about 55%, about 50%, about 45%, about 40%, 35%, or about 30% of β-arrestin relative to the D1R binding to Dopamine. In a further embodiment, the D1 agonist with a reduced β-arrestin recruitment activity is not a catechol derivative. In a yet further embodiment, the D1 agonist with a reduced β-arrestin recruitment activity is not a dopamine derivative.

Under the D1R homologous desensitization mechanism, a reduced β-arrestin recruitment activity leads to reduced D1R desensitization. Accordingly, the D1 agonist with a reduced β-arrestin recruitment activity is also a D1 agonist with reduced D1R desensitization, and thus provides prolonged and/or less-reduced level of potency effects of the D1 agonist (i.e., drug effect) after exposure to a D1R, for a certain period of time comparing to those D1 agonists without reduced desensitization. Moreover, the D1 agonist with a reduced β-arrestin recruitment activity may provide other benefits or unique properties. For example, a β-arr2/pERK signaling complex mediated by the activation of the D1 receptor may potentially have a role in regulating morphine-induced locomotion. See Nikhil M Urs, et. al, "*A Dopamine D1 Receptor-Dependent β-Arrestin Signaling Complex Potentially Regulates Morphine-Induced Psychomotor Activation but not Reward in Mice,*" *Neuropsychopharmacology* (2011) 36, 551-558. A reduced β-arrestin recruitment activity of the D1 agonist of the present invention may affect a D1 mediated "arrestinergic" signaling (such as β-arr2/pERK signaling complex mediated by the activation of the D1 receptor) that may be utilized for further therapeutic benefits relative to a D1 agonist that does not have reduced β-arrestin recruitment activity.

In some embodiments, the D1 agonist with a reduced β-arrestin recruitment activity desensitizes D1R cAMP signaling less than about 25% (e.g., about 20%, about 18%, about 15%, about 10%, or about 5%) relative to Control.

In some embodiments, the D1 agonist with reduced D1R desensitization is a full D1 agonist or a super D1 agonist. In some further embodiment, the D1 agonist with reduced D1R desensitization is a full D1 agonist.

In some embodiments, the D1 agonist with reduced D1R desensitization is a partial D1 agonist.

In a fifth aspect, the invention provides a method for treating a disorder in a human, which method comprises administering to said human a therapeutically effective amount of a compound or salt thereof wherein the compound or salt thereof is a D1 agonist with a reduced β-arrestin recruitment activity in the fourth aspect, and wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy)], attention deficit hyperactivity disorder (ADHD), impulsivity, compulsive gambling, overeating, autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, a movement disorder [e.g., dyskinesia (e.g., Chorea, Levodopa-induced dyskinesia, or tardive dyskinesia) a Tic disorder (e.g., Tourette's syndrome), or Tremor], a therapy-induced movement disorder [e.g., therapy-related dyskinesia (e.g., LID) or therapy-related dyskinesia tremor (SSRI-induced postural tremor)], sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

In a sixth aspect, the invention provides a D1 agonist that interacts significantly with the Ser188 of a D1R when binding to the D1R. In a further embodiment, the D1 agonist interacting significantly with the Ser188 of a D1R is not a catechol derivative. In a yet further embodiment the D1 agonist interacting significantly with the Ser188 of a D1R is not a dopamine derivative.

As used herein, "interacting significantly with the Ser188" refers to an $EC_{50}$ fold shift being greater than about 7.0 as measured by a S188I mutant study similar to the one provided herein. In some embodiments, the D1 agonist that interacts significantly with the Ser188 of a D1R when binding to the D1R has an $EC_{50}$ fold shift greater than about 8.0 or 9.0 as measured by a S188I mutant study similar to the one provided herein.

In a further embodiment, the invention provides a D1 agonist that interacts significantly with the Ser188 but not significantly with the Ser202 of a D1R when binding to the D1R. In a further embodiment, the D1 agonist interacting significantly with the Ser188 but not significantly with the Ser202 of a D1R is not a catechol derivative. In a yet further embodiment the D1 agonist interacting significantly with the Ser188 but not significantly with the Ser202 of a D1R is not a dopamine derivative.

As used herein, "interacting significantly with the Ser202" refers to an $EC_{50}$ fold shift being greater than about 7.0 as measured by a S202A mutant study similar to the one provided herein. In some embodiments, the D1 agonist that does not interact significantly with the Ser202 of a D1R when binding to the D1R has an $EC_{50}$ fold shift less than about 7.0, 6.0, 5.0, or 4.0 as measured by a S202A mutant study similar to the one provided herein.

In some embodiments, the D1 agonist interacting significantly with the Ser188 of a D1R is a full D1 agonist or a super D1 agonist. In some embodiments, the D1 agonist interacting significantly with the Ser188 but not significantly with the Ser202 of a D1R is a full D1 agonist or a super D1 agonist.

In some embodiments, the D1 agonist interacting significantly with the Ser188 of a D1R is a partial D1 agonist. In some embodiments, the D1 agonist interacting significantly with the Ser188 but not significantly with the Ser202 of a D1R is a partial D1 agonist.

In some embodiments, the D1 agonist interacting significantly with the Ser188 but not significantly with the Ser202 of a D1R is also a D1 agonist with reduced D1R desensitization in the second aspect.

In some embodiments, the D1 agonist interacting significantly with the Ser188 but not significantly with the Ser202 of a D1R is a D1 agonist with a reduced β-arrestin recruitment activity in the fourth aspect.

In some embodiments, the D1 agonist interacting significantly with the Ser188 but not significantly with the Ser202 of a D1R is also a D1 agonist with reduced D1R desensitization in the second aspect and a D1 agonist with a reduced β-arrestin recruitment activity in the fourth aspect.

In some embodiments, the present invention provides a D1 agonist that interacts less strongly with the Asp103 of the D1R. In some embodiments, the present invention provides a D1 agonist that interacts significantly with the Ser188 but not significantly with the Ser202 of a D1R, wherein the D1 agonist interacts less strongly with the Asp103 of the D1R.

As used herein, "interact less strongly with the Asp103" refers to an $EC_{50}$ fold shift being less than about 100 as measured by a D103A mutant study similar to (or same as) the one provided herein. In some embodiments, the D1 agonist that interacts less strongly with the Asp103 of a D1R when binding to the D1R has an $EC_{50}$ fold shift less than about 95, 90, 85, or 80 as measured by a D103A mutant study similar to the one provided herein.

In some embodiments, the present invention provides a full D1 agonist or a super D1 agonist that interacts less strongly with the Ser198 of the D1R. In some further embodiments, the present invention provides a full D1 agonist or a super D1 agonist that interacts less strongly with the Ser198 of the D1R and interacts less strongly with the Asp103 of the D1R.

In some embodiments, the present invention provides a full D1 agonist or a super D1 agonist that interacts significantly with the Ser188 but not significantly with the Ser202 of a D1R wherein the full D1 agonist interacts less strongly with the Ser198 of the D1R. In a further embodiment, the full D1 agonist or a super D1 agonist interacts less strongly the Asp103 of the D1R. In a yet further embodiment, the D1 agonist interacting significantly with the Ser188 but not significantly with the Ser202, interacting less strongly with the Ser198, and interacting less strongly with the Asp103 of a D1R is also a D1 agonist with reduced D1R desensitization in the second aspect. In another yet further embodiment, the D1 agonist interacting significantly with the Ser188 but not significantly with the Ser202, interacting less strongly with the Ser198, and interacting less strongly with the Asp103 of a D1R is a D1 agonist with a reduced β-arrestin recruitment activity in the fourth aspect.

As used herein, "interact less strongly with the Ser198" refers to an $EC_{50}$ fold shift being less than about 25 as measured by a S198A mutant study similar to (or same as) the one provided herein. In some embodiments, the D1 agonist that interacts less strongly with the Ser198 of a D1R when binding to the D1R has an $EC_{50}$ fold shift less than about 22, 20, 18, or 15 as measured by a S198A mutant study similar to (or same as) the one provided herein.

In a seventh aspect, the invention provides a method for treating a disorder in a human, which method comprises administering to said human a therapeutically effective amount of a compound or salt thereof wherein the compound or salt thereof is a D1 agonist interacting significantly with the Ser188 (optionally but not significantly with the Ser202) of a D1R in the sixth aspect, and wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy)], attention deficit hyperactivity disorder (ADHD), impulsivity, compulsive gambling, overeating, autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, a movement disorder [e.g., dyskinesia (e.g., Chorea, Levodopa-induced dyskinesia, or tardive dyskinesia) a Tic disorder (e.g., Tourette's syndrome), or Tremor], a therapy-induced movement disorder [e.g., therapy-related dyskinesia (e.g., LID) or therapy-related dyskinesia tremor (SSRI-induced postural tremor)], sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

DETAILED DESCRIPTION OF THE INVENTION

Compounds of the invention, including N-oxides and salts of the compounds or N-oxides, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$, $R^5$, $R^6$, $R^7$, $R^{T1}$, $R^{T2}$, $Q^1$, $X^1$, and $Y^1$, and structural Formula I in the reaction schemes and discussion that follow are as defined above. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1 refers to preparation of compounds of Formula I. Referring to Scheme 1, compounds of Formula 1-1 [where Lg$^1$ is a suitable leaving group such as triazolyl or halo (e.g., Cl or Br)] or 1-2 [wherein $Z^1$ is a halogen (Cl, Br, or I)] are commercially available or can be made by methods described herein or other methods well known to those skilled in the art. A compound of Formula 1-3 can be prepared by coupling a compound of Formula 1-1 with a compound of Formula 1-2, for example, by heating a mixture of a compound of Formula 1-1 with a compound of Formula 1-2 in the presence of a base, such as Cs$_2$CO$_3$, in an appropriate solvent, such as DMSO at temperatures between 50° C. and 120° C. for about 20 minutes to 48 hours. Alternatively, a metal-catalyzed (such as a palladium or copper catalyst) coupling may be employed to accomplish the aforesaid coupling. In this variant of the coupling, a mixture of a compound of Formula 1-1 and a compound of Formula 1-2 can be heated at temperatures ranging between 50° C. and 120° C. in the presence of a base [such as Cs$_2$CC$_3$], a metal catalyst [such as a palladium catalyst, e.g., Pd(OAc)$_2$], and a ligand [such as BINAP] in an appropriate solvent, such as 1,4-dioxane, for about 30 minutes to 48 hours. A compound of Formula 1-3 can subsequently be reacted with a compound of Formula $Q^1$-$Z^2$ [wherein $Z^2$ can be Br; B(OH)$_2$; B(OR)$_2$ wherein each R is independently H or C$_{1-6}$ alkyl, or wherein two (OR) groups, together with the B atom to which they are attached, form a 5- to 10-membered heterocycloalkyl or heteroaryl optionally substituted with one or more C$_{1-6}$ alkyl; a trialkyltin moiety; or the like] by a metal-catalyzed (such as palladium-) coupling reaction to obtain a compound of Formula I. Compounds of Formula $Q^1$-$Z^2$ are commercially available or can be prepared by methods analogous to those described in the chemical art.

Alternatively, a compound of Formula 1-3 can be converted to a compound of Formula 1-4 [wherein $Z^2$ is defined as above]. For example, a compound of Formula 1-3 (wherein $Z^1$ is halogen such as Br) can be converted to a compound of Formula 1-4 [wherein $Z^2$ is B(OH)$_2$; B(OR)$_2$ wherein each R is independently H or C$_{1-6}$ alkyl, or wherein two (OR) groups, together with the B atom to which they are attached, form a 5- to 10-membered heterocycloalkyl or heteroaryl optionally substituted with one or more C$_{1-6}$ alkyl] by methods described herein or other methods well known to those skilled in the art. In this example, the reaction can be accomplished, for example, by reacting a compound of Formula 1-3 (wherein $Z^1$ is halogen such as Br) with 4,4,4',4',5,5,5',5'-octamethyl-2,2'-bi-1,3,2-dioxaborolane, a suitable base [such as potassium acetate], and a palladium catalyst [such as [1,1'-bis(diphenylphosphino)ferrocene]dichloropalladium(II)] in a suitable solvent such as 1,4-dioxane. In another example, a compound of Formula 1-3 (wherein $Z^1$ is halogen such as Br) can be converted to a compound of Formula 1-4 [wherein $Z^2$ is a trialkyltin moiety] by alternate methods described herein or other methods well known to those skilled in the art. In this example, the reaction can be accomplished, for example, by reacting a compound of Formula 1-3 (wherein $Z^1$ is halogen such as Br) with a hexaalkyldistannane [such as hexamethyldistannane] and a palladium catalyst [such as tetrakis(triphenylphosphine)palladium(0)] in a suitable solvent such as 1,4-dioxane. A compound of Formula 1-4 can then be reacted with a compound of Formula $Q^1$-$Z^1$ [wherein $Z^1$ is defined as above] by a metal-catalyzed (such as palladium-) coupling reaction to obtain a compound of Formula I.

Compounds of Formula $Q^1$-$Z^1$ are commercially available or can be prepared by methods analogous to those described in the chemical art. The type of reaction employed depends on the selection of $Z^1$ and $Z^2$. For example, when $Z^1$ is halogen or triflate and the $Q^1$-$Z^2$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. In some specific embodiments, an aromatic iodide, bromide, or triflate of Formula 1-3 is combined with 1 to 3 equivalents of an aryl or heteroaryl boronic acid or boronic ester of Formula $Q^1$-$Z^2$ and a suitable base, such as 2 to 5 equivalents of potassium phosphate, in a suitable organic solvent such as THF. A palladium catalyst is added, such as 0.01 equivalents of S-Phos precatalyst {also known as chloro(2-dicyclohexylphosphino-2',6'-dinnethoxy-1,1'-biphenyl)[2-(2-anninoethylphenyl)]palladium(II) tert-butyl methyl ether adduct}, and the reaction mixture is heated to temperatures ranging from 60 to 100° C. for 1 to 24 hours. Alternatively, when $Z^1$ is halogen or triflate and $Z^2$ is trialkyltin, a Stille coupling may be employed [V. Farina et al., *Organic Reactions* 1997, 50, 1-652]. More specifically, a compound of Formula 1-3 [wherein $Z^1$ is bromide, iodide, or triflate] may be combined with 1.5 to 3 equivalents of a compound of Formula $Q^1$-$Z^2$

[wherein the $Q^1$-$Z^2$ compound is an $Q^1$ stannane compound] in the presence of a palladium catalyst, such as 0.05 equivalents of dichlorobis(triphenylphosphine)palladium(II), in a suitable organic solvent such as toluene, and the reaction may be heated to temperatures ranging from 100° C. to 130° C. for 12 to 36 hours. Where $Z^1$ is Br, I or, triflate and $Z^2$ is Br or I, a Negishi coupling may be used [E. Erdik, *Tetrahedron* 1992, 48, 9577-9648]. More specifically, a compound of Formula 1-3 [wherein $Z^1$ is bromide, iodide, or triflate] may be transmetallated by treatment with 1 to 1.1 equivalents of an alkyllithium reagent followed by a solution of 1.2 to 1.4 equivalents of zinc chloride in an appropriate solvent such as tetrahydrofuran at a temperature ranging from −80° C. to −65° C. After warming to a temperature between 10° C. and 30° C., the reaction mixture may be treated with a compound of Formula $Q^1$-$Z^2$ (wherein $Z^2$ is Br or I), and heated at 50 to 70° C. with addition of a catalyst such as tetrakis(triphenylphosphine)palladium(0). The reaction may be carried out for times ranging from 1 to 24 hours. None of these reactions are limited to the employment of the solvent, base, or catalyst described above, as many other conditions may be used.

Scheme 2 also refers to preparation of compounds of Formula I. Referring to Scheme 2, compounds of Formula I may be prepared utilizing analogous chemical transformations to those described in Scheme 1, but with a different ordering of steps. Compounds of Formula 2-1 [wherein Pg is a suitable protecting group such as Boc or Cbz when $Y^1$ is NH or methyl, or Pg is benzyl when $Y^1$ is O] are commercially available or can be made by methods described herein or other methods well known to those skilled in the art. A compound of Formula 2-1 can be converted to a compound of Formula 2-2 either directly or after conversion to a compound of Formula 2-3 using methods analogous to those described in Scheme 1. A compound of Formula 2-2 may then be deprotected, using appropriate conditions depending on the selection of the Pg group, to obtain a compound of Formula 2-4, which in turn can be coupled with a compound of Formula 1-1 in Scheme 1 to afford a compound of Formula I. The coupling conditions employed may be analogous to those described for the preparation of a compound of Formula 1-3 in Scheme 1.

Scheme 1

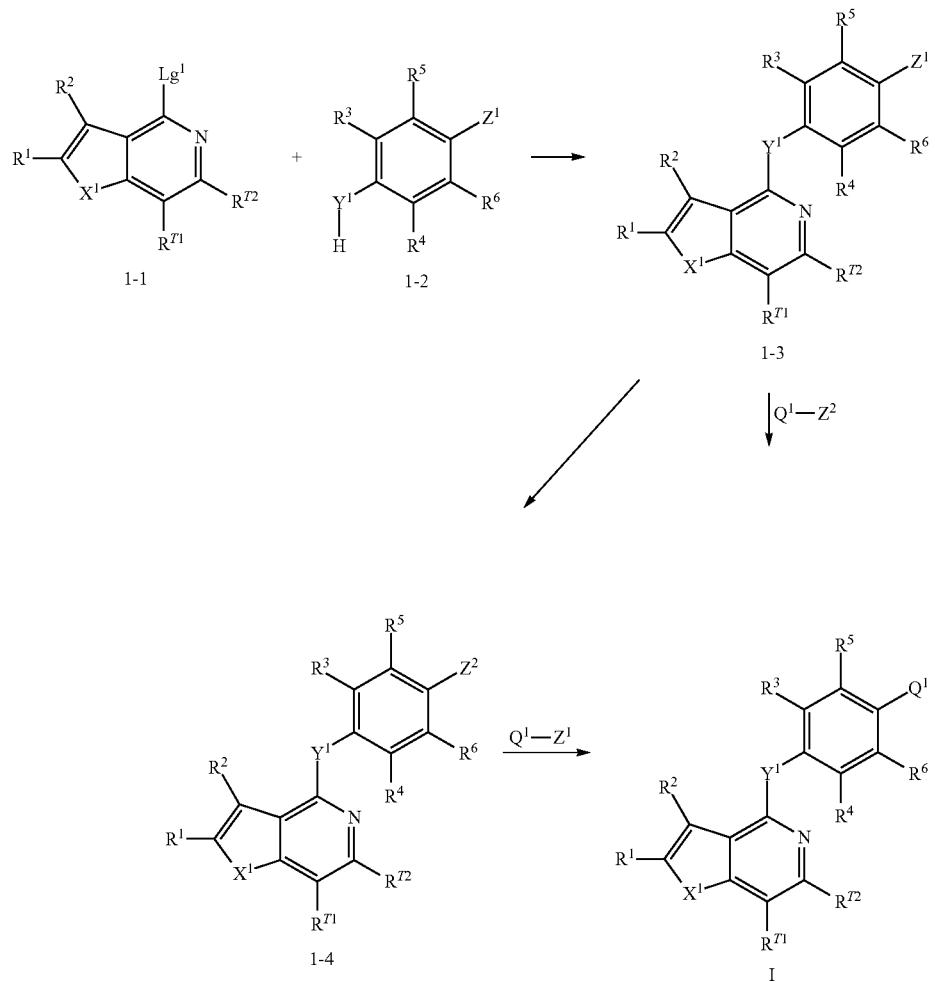

Scheme 2

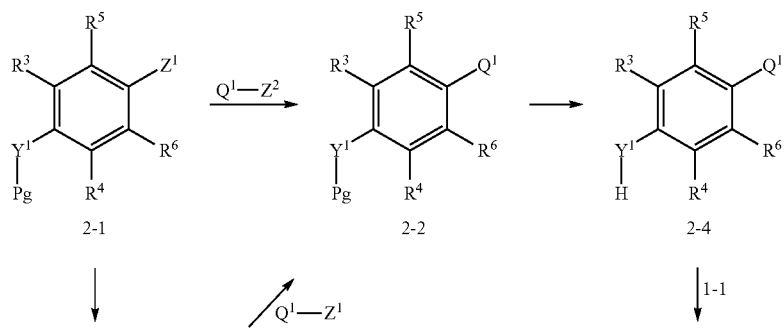

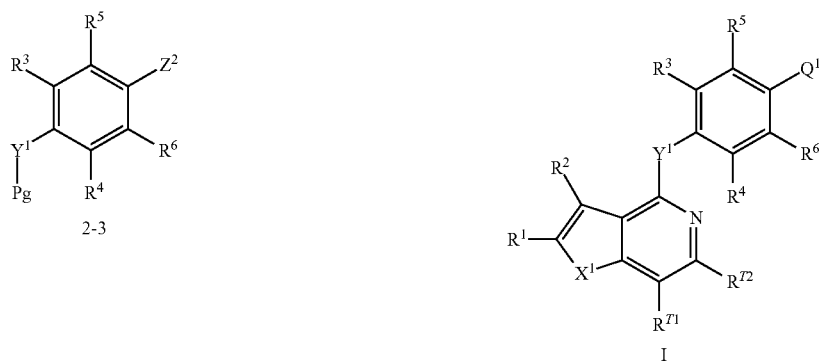

Scheme 3 refers to a preparation of a compound of Formula 3-3 [wherein $A^1$ is either Pg as defined above or a moiety of Formula $A^{1a}$]. When $A^1$ is Pg, the compound of Formula 3-3 is an example of a compound of Formula 2-2. When $A^1$ is $A^{1a}$, the compound of Formula 3-3 is an example of a compound of Formula I. Referring to Scheme 3, compounds of Formula 3-1 are commercially available or can be made by methods described herein or other methods well known to those skilled in the art. A compound of Formula 3-1 can be reacted with 4-chloro-3-nitropyridine and the initial product can be subsequently reduced to obtain a compound of Formula 3-2. Examples of suitable reaction conditions for the coupling of a compound of Formula 3-1 with 4-chloro-3-nitropyridine include mixing the two reactants with a suitable base, such as triethylamine, in a suitable reaction solvent such as ethanol, at temperatures typically between 0° C. and 100° C. for about 20 minutes to 48 hours. The subsequent reduction of the nitro group to afford a compound of Formula 3-2 can be achieved by, for example, hydrogenation in the presence of a catalyst such as palladium on carbon in a suitable solvent such as methanol under hydrogen pressures typically between 1 atm and 4 atm. A compound of Formula 3-2 can then be reacted with acetic anhydride and triethyl orthoformate at temperatures between about 100° C. and 150° C. for about 1 hour to 48 hours to obtain a compound of Formula 3-3.

Scheme 3

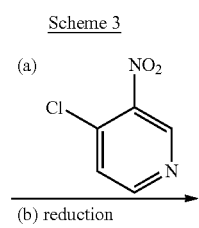

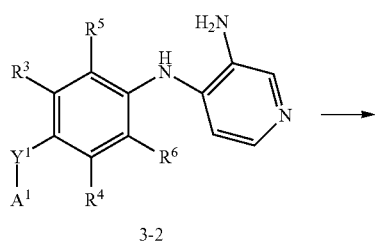

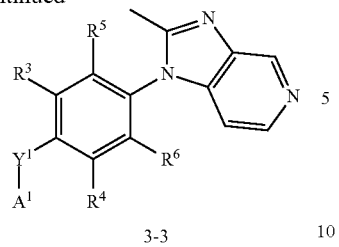

3-3

$A^1$ is Pg or a moiety of $A^{1a}$:

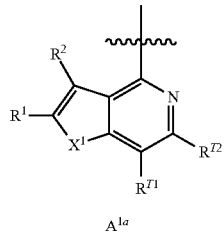

$A^{1a}$

Scheme 4 refers to a preparation of a compound of Formula 4-3 [wherein each $R^{77}$ is independently H or $R^7$ (such as $C_{1-3}$ alkyl, for example methyl)]. When $A^1$ is Pg, the compound of Formula 4-3 is an example of a compound of Formula 2-2. When $A^1$ is $A^{1a}$, the compound of Formula 4-3 is an example of a compound of Formula I. Referring to Scheme 4, compounds of Formula 4-1 are commercially available or can be made by methods described herein or other methods well known to those skilled in the art. A compound of Formula 4-2 can be prepared by reacting an aryl ketone of Formula 4-1 with N,N-dimethylformamide dimethylacetal (DMF-DMA) in a suitable solvent such as N,N-dimethylformamide (DMF, which is also a reagent), at temperatures typically between 0° C. and 160° C., for about 1 hour to 24 hours. A pyrazole of Formula 4-3 can be prepared by reacting a compound of Formula 4-2 with a hydrazine of formula $R^{77}$—NH—NH$_2$ in a suitable solvent such as DMF or 1,4-dioxane, at temperatures typically between 0° C. and 100° C., for about 1 hour to 24 hours.

Scheme 4

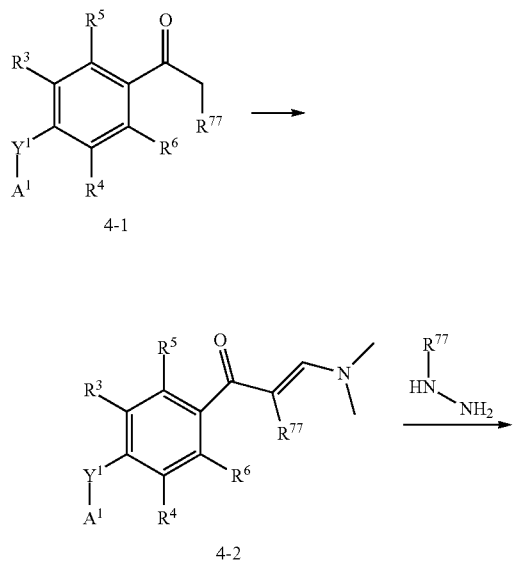

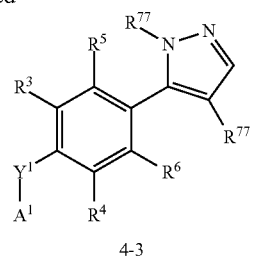

4-3

Scheme 5 refers to a preparation of a compound of Formula 5-4 or 5-5 [wherein $R^{77}$ is H or $R^7$ (such as $C_{1-3}$ alkyl, for example methyl)]. When $A^1$ is Pg, the compound of Formula 5-4 or 5-5 is an example of a compound of Formula 2-2. When $A^1$ is $A^{1a}$, the compound of Formula 5-4 or 5-5 is an example of a compound of Formula I. Referring to Scheme 5, compounds of Formula 5-1 are commercially available or can be made by methods described herein or other methods well known to those skilled in the art. A compound of Formula 5-2 can be prepared by reacting an arylketone of Formula 5-1 with an alkyl nitrite (e.g., isoamyl nitrite) in the presence of an acid (such as hydrochloric acid) at temperatures typically between 0° C. and 100° C. for about 1 hour to 24 hours. The resulting oxime of Formula 5-2 can be converted to the diketone of Formula 5-3 upon treatment with formaldehyde (or its equivalent such as metaformaldehyde or polyformaldehyde) in the presence of an acid (such as an aqueous hydrochloric acid solution) at temperatures typically between 0° C. and 50° C. for about 1 hour to 24 hours. Diketones of Formula 5-3 can be reacted with glycinamide or a salt thereof [such as an acetic acid salt] in the presence of a base such as sodium hydroxide to obtain pyrazinones of Formula 5-4. Alkylation of the pyrazinone nitrogen to obtain a compound of Formula 5-5 can be achieved by treatment of a compound of Formula 5-4 with a base [such as LDA, LHMDS, and the like] and a compound of the formula of $R^7Z^3$ (wherein $Z^3$ is an acceptable leaving group such as Cl, Br, I, methanesulfonate, and the like), in a suitable solvent such as DMF, 1,4-dioxane, or THF, at temperatures typically between 0° C. and 50° C., for about 1 hour to 24 hours.

Scheme 5

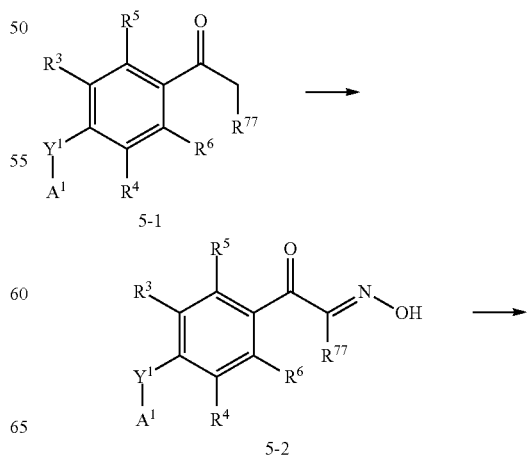

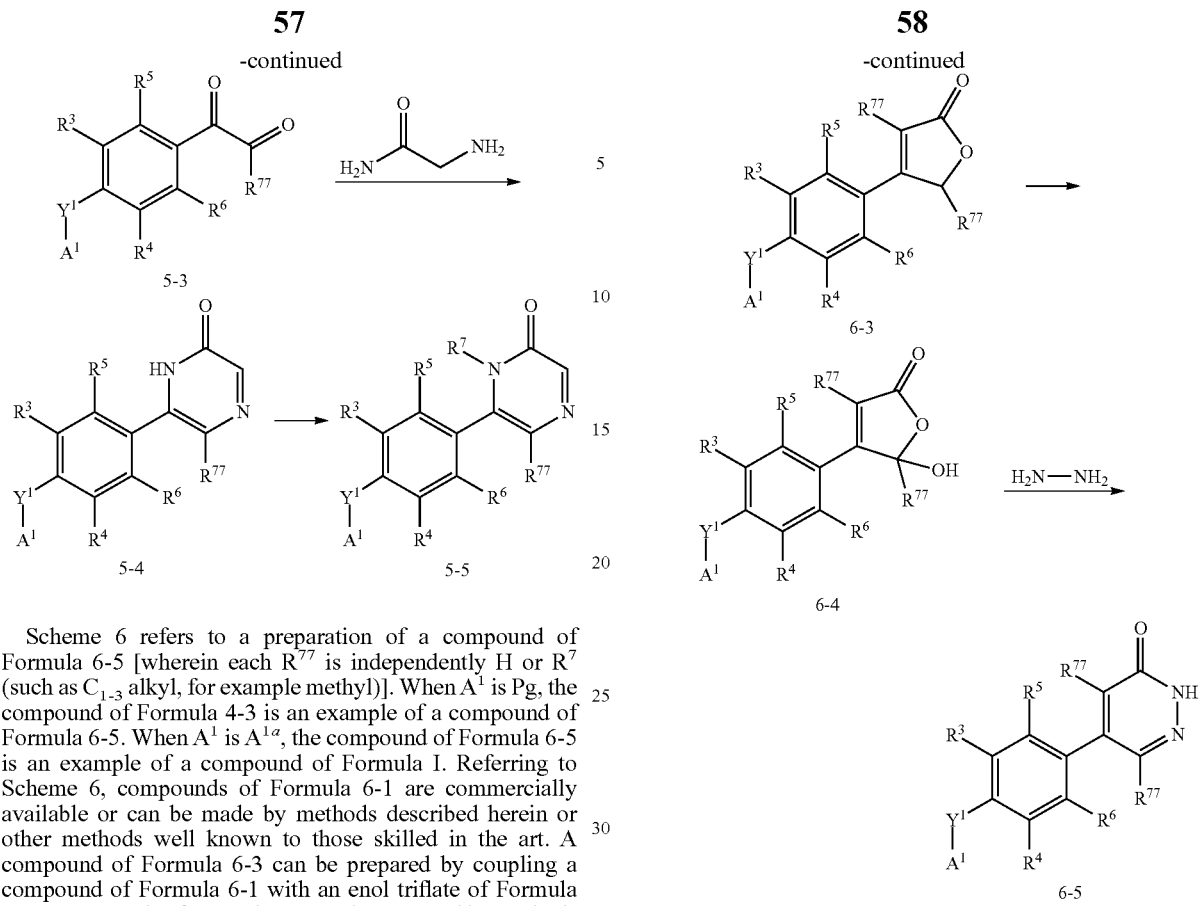

Scheme 6 refers to a preparation of a compound of Formula 6-5 [wherein each $R^{77}$ is independently H or $R^7$ (such as $C_{1-3}$ alkyl, for example methyl)]. When $A^1$ is Pg, the compound of Formula 4-3 is an example of a compound of Formula 6-5. When $A^1$ is $A^{1a}$, the compound of Formula 6-5 is an example of a compound of Formula I. Referring to Scheme 6, compounds of Formula 6-1 are commercially available or can be made by methods described herein or other methods well known to those skilled in the art. A compound of Formula 6-3 can be prepared by coupling a compound of Formula 6-1 with an enol triflate of Formula 6-2. Compounds of Formula 6-2 can be prepared by methods described herein or other methods well known to those skilled in the art. The aforesaid coupling may be accomplished by reacting a compound of Formula 6-1 with 1 to 3 equivalents of a triflate of Formula 6-2 in the presence of a suitable base [such as potassium carbonate], a suitable catalyst [such as palladium(II) acetate], a suitable ligand [such as tricyclohexylphosphine], and optionally a suitable phase transfer catalyst such as tetrabutylammonium chloride, in a suitable solvent such as a polar aprotic solvent (e.g., 1,4-dioxane or THF), at temperatures typically between 20° C. and 80° C., for about 1 hour to 24 hours. A compound of Formula 6-3 can be reacted with 1 to 5 equivalents of a suitable base [such as DBU] under an oxygen atmosphere to obtain a compound of Formula 6-4, in a suitable solvent such as a polar aprotic solvent (e.g., DMF, 1,4-dioxane or THF), at temperatures typically between 20° C. and 80° C., for about 12 hours to 48 hours. A compound of Formula 6-5 can be obtained by reacting a compound of Formula 6-4 with hydrazine in a suitable solvent such as 1-butanol, at temperatures typically between 20° C. and 120° C., for about 1 hour to 24 hours.

Scheme 6

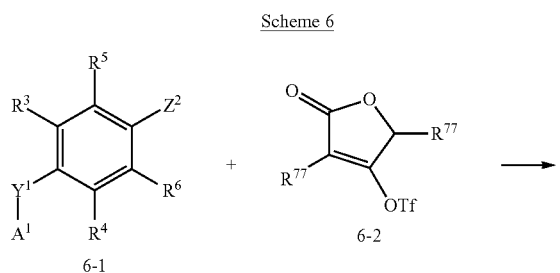

Scheme 7 refers to a preparation of a compound of Formula 7-6 [wherein $R^{77}$ is H or $R^7$ (such as $C_{1-3}$ alkyl, e.g., methyl)]. When $A^1$ is Pg, the compound of Formula 7-6 is an example of a compound of Formula 2-2. When $A^1$ is $A^{1a}$, the compound of Formula 7-6 is an example of a compound of Formula I. Referring to Scheme 7, compounds of Formula 7-1 are commercially available or can be made by methods described herein or other methods well known to those skilled in the art. A compound of Formula 7-3 can be prepared by coupling a compound of Formula 7-1 with a compound of Formula 7-2 [wherein $Pg^3$ is a suitable protecting group such as 2-tetrahydropyranyl (THP)]. A compound of Formula 7-2 can be prepared by methods described herein or other methods well known to those skilled in the art. The aforesaid coupling may be accomplished by reacting a compound of Formula 7-1 with 1 to 3 equivalents of a compound of Formula 7-2 in the presence of a suitable base [such as cesium carbonate] and a suitable catalyst [such as [1,1'-bis(diphenylphosphino)ferrocene]dichloropalladium (II)], in a suitable solvent such as a polar aprotic solvent (e.g., 1,4-dioxane or THF), at temperatures typically between 50° C. and 120° C., for about 1 hour to 24 hours. A compound of Formula 7-4 can be obtained by removing the protecting $Pg^3$ group, for example, by treating a compound of Formula 7-3 (wherein $Pg^3$ is, for example, THP) with HCl in an alcoholic solvent [such as 2-propanol] at temperatures ranging from 20° C. to 80° C. Treatment of a compound of Formula 7-4 with phosphorous oxychloride can provide a compound of Formula 7-5, at temperatures typically between 50° C. and 120° C., for about 20 minutes to 24 hours. A compound of Formula 7-5 can be a reactive intermediate in numerous chemical transformations to obtain a compound of Formula 7-6. For example, a compound of Formula 7-5 can be reacted with 1 to 3 equivalents of trimethylaluminum and 0.05 to 0.1 equivalents of a suitable palladium catalyst [such as tetrakis(triphenylphosphine)palladium(0)] in 1,4-dioxane to afford a compound of Formula 7-6 [wherein the newly introduced $R^7$ is methyl], at temperatures typically between 50° C. and 120° C., for about 30 minutes to 12 hours.

Formula 8-4 in a suitable solvent such as a polar aprotic solvent (e.g., 1,4-dioxane, DMF, or dimethyl sulfoxide), at temperatures typically between 50° C. and 150° C., for about 1 hour to 24 hours.

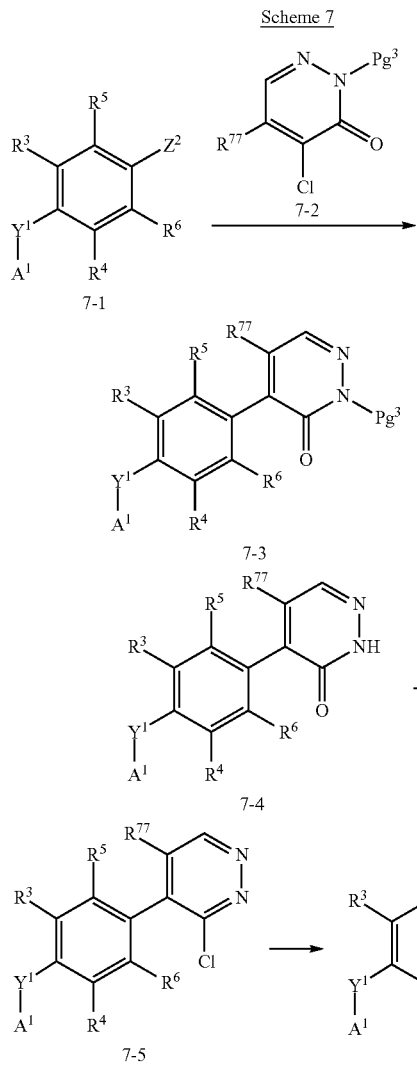

Scheme 7

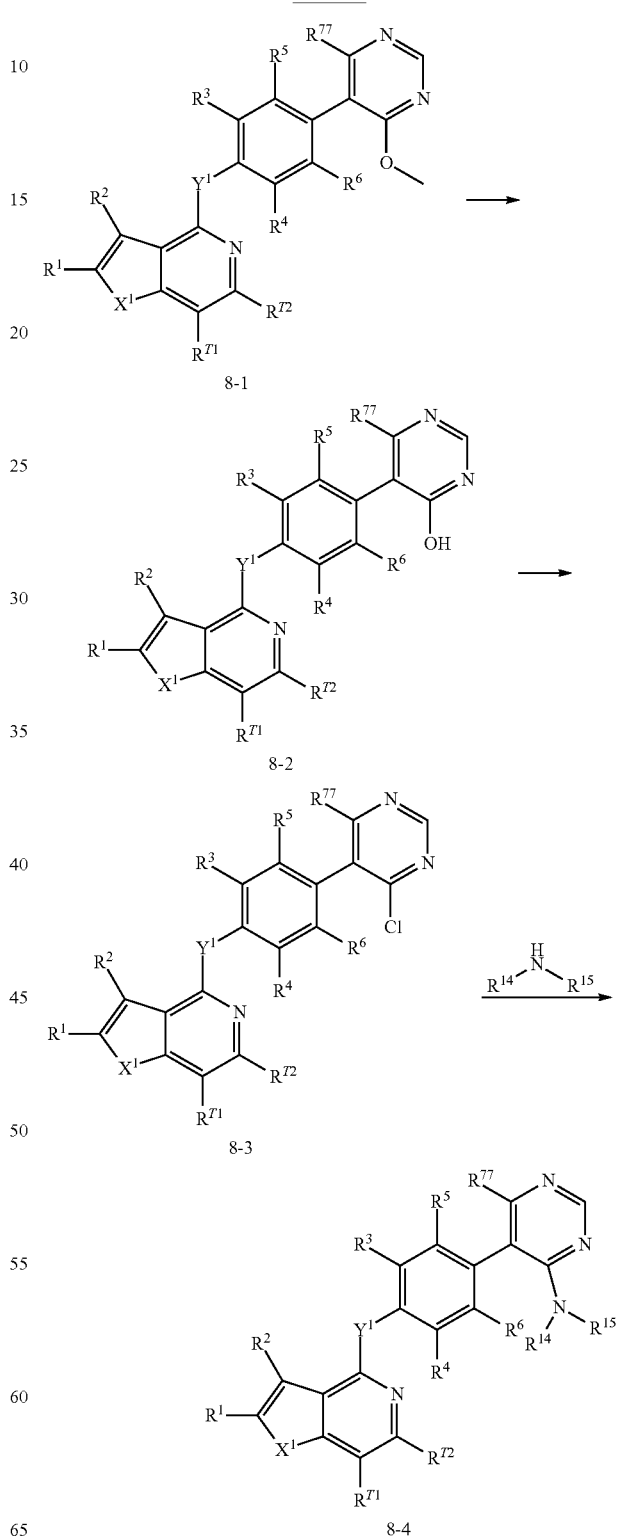

Scheme 8

Scheme 8 refers to a preparation of a compound of Formula 8-4 [wherein $R^{77}$ is H or $R^7$ (such as $C_{1-3}$ alkyl, e.g., methyl)], which is an example of a compound of Formula I. Referring to Scheme 8, compounds of Formula 8-1 can be prepared according to methods described in Scheme 1. A compound of Formula 8-2 can be prepared by reacting a compound of Formula 8-1 with boron tribromide at temperatures typically between −50° C. and 50° C. for about 1 hour to 24 hours. A compound of Formula 8-3 can be obtained by treating a compound of Formula 8-2 with phosphorous oxychloride at temperatures typically from 50° C. to 120° C. for about 20 minutes to 24 hours. A compound of Formula 8-3 can be reacted with 1 to 3 equivalents of a suitable amine $HNR^{14}R^{15}$, 1 to 5 equivalents of a base [such as triethylamine, diisopropylethylamine, and the like] and a catalytic amount of cesium fluoride to obtain a compound of Scheme 9 refers to a preparation of a compound of Formula 9-3 and/or 9-4, which can be used in Schemes 1 and/or 2. For example, when $A^1$ is Pg, the compound of Formula 9-3 or 9-4 is an example of a compound of Formula 2-1. When $A^1$ is $A^{1a}$, the compound of Formula 9-3 or 9-4 is an example of a compound of Formula 1-3. Referring to Scheme 9, compounds of Formula 9-1 are commercially available or can be made by methods described herein or other methods well known to those skilled in the art. A compound of Formula 9-2 can be prepared by treating a compound of Formula 9-1 with a suitable base [such as lithium diisopropylamide] and then reacting the resulting anion with N,N-dimethylformamide in a suitable solvent such as a polar aprotic solvent (e.g., 1,4-dioxane or THF), at temperatures typically between −78° C. and 0° C. for about 1 hour to 24 hours. A compound of Formula 9-2 can be reacted with methyl hydrazine to obtain a mixture of compounds of Formula 9-3 and Formula 9-4 in a suitable solvent such as 1,4-dioxane at temperatures typically between 50° C. and 150° C., for about 1 hour to 24 hours.

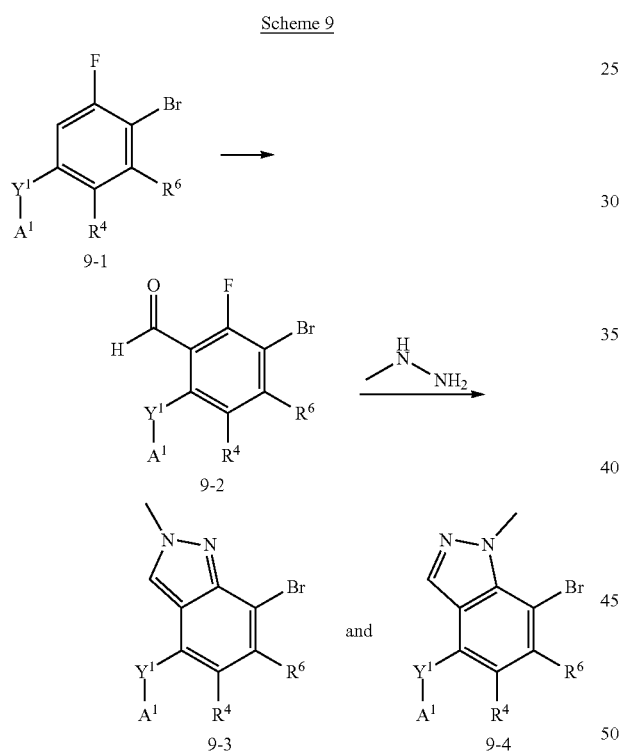

Scheme 9

Scheme 10 refers to a preparation of a compound of Formula 10-3, which can be used in Schemes 1 and/or 2. For example, when $A^1$ is Pg, the compound of Formula 10-3 is an example of a compound of Formula 2-1. When $A^1$ is $A^{1a}$, the compound of Formula 10-3 is an example of a compound of Formula 1-3. Referring to Scheme 10, compounds of Formula 10-1 are commercially available or can be made by methods described herein or other methods well known to those skilled in the art. A compound of Formula 10-2 can be prepared by treating a compound of Formula 10-1 with N-bromosuccinimide in a suitable solvent [such acetonitrile] at temperatures typically between 0° C. and 20° C. for about 30 minutes to 6 hours. A compound of Formula 10-2 can be reacted with diiodomethane and a suitable base [such as cesium carbonate] to obtain a compound of Formula 10-3.

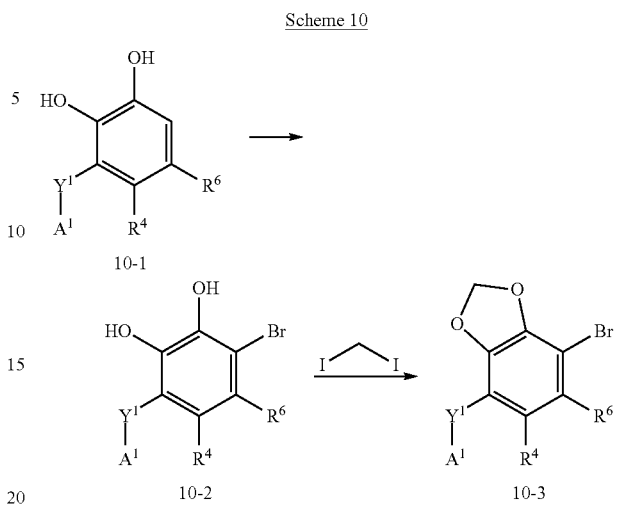

Scheme 10

Scheme 11 refers to a preparation of a compound of Formula 11-2. When $A^1$ is Pg, the compound of Formula 11-2 is an example of a compound of Formula 2-2. When $A^1$ is $A^{1a}$, the compound of Formula 11-2 is an example of a compound of Formula I. Referring to Scheme 11, compounds of Formula 11-1 can be prepared according to methods described in Scheme 5. A compound of Formula 11-1 can be reacted with 2-hydrazinyl-1H-imidazole in a suitable solvent such as DMF to obtain a compound of Formula 11-2 at temperatures between about 80° C. and 120° C.

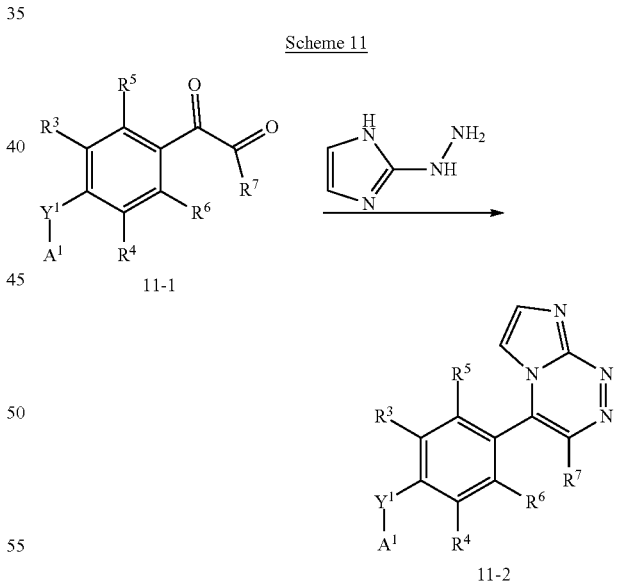

Scheme 11

Scheme 12 refers to a preparation of a compound of Formula 12-2 [wherein each $R^{77}$ is independently H or $R^7$ (such as $C_{1-3}$ alkyl, for example methyl)], which is an example of a compound of Formula I. Referring to Scheme 12, a compound of Formula 12-1 can be prepared by methods described in Scheme 1. A compound of Formula 12-1 can be reacted with chloroacetaldehyde to obtain a compound of Formula 12-2 at temperatures typically between 80° C. and 120° C. for about 1 hour to 24 hours.

Scheme 12

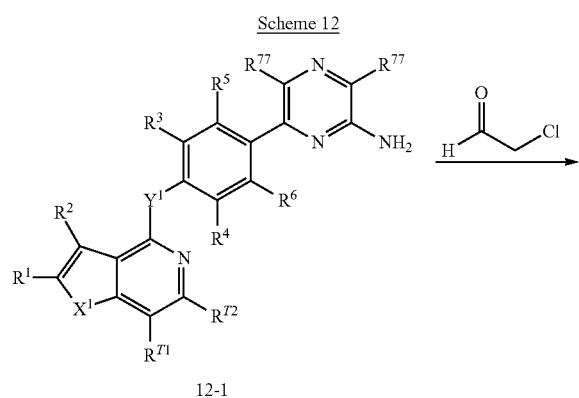

12-1

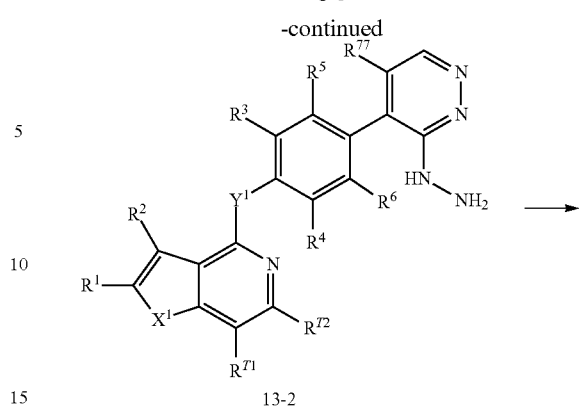

13-2

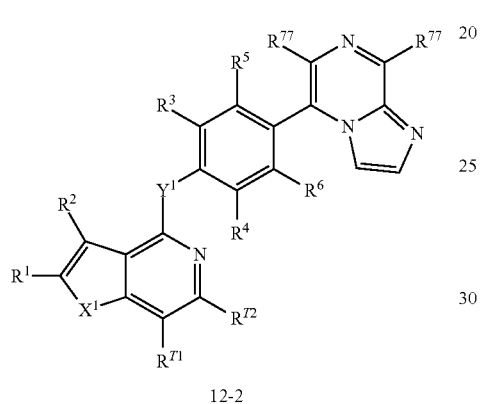

12-2

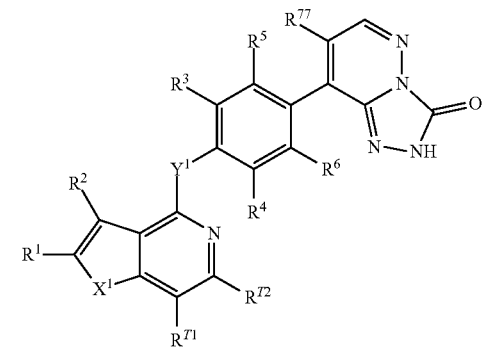

13-3

Scheme 13 refers to a preparation of a compound of Formula 13-3 [wherein $R^{77}$ is H or $R^7$ (such as $C_{1-3}$ alkyl, for example methyl)], which is an example of a compound of Formula I. Referring to Scheme 13, a compound of Formula 13-1 can be prepared according to methods described in Scheme 7. A compound of Formula 13-2 can be prepared by reacting a compound of Formula 13-1 with hydrazine in a suitable solvent such as ethanol at temperatures typically between 60° C. and 100° C. for about 12 to 24 hours. A compound of Formula 13-2 can be reacted with 1,1'-carbonyldiimidazole in a solvent such as acetonitrile to obtain a compound of Formula 13-3.

Additionally, a compound of Formula I may also be prepared by enzymatic modification [such as a microbial oxidation] of a related compound of Formula I. For example, as shown in Scheme 14, incubation of a compound of Formula I [for example, wherein $Q^1$ is a moiety that can be oxidized such as an optionally substituted pyridazinyl in a compound of Formula 14-1 (wherein each $R^{77}$ is independently H or $R^7$ (such as $C_{1-3}$ alkyl, for example methyl))] with *Pseudomonas putida* for a reaction time between 24 and 96 hours in a suitable buffer can provide an alternate compound of Formula I (for example, wherein $Q^1$ is an optionally substituted pyridazinonyl in a compound of Formula 14-2).

Scheme 13

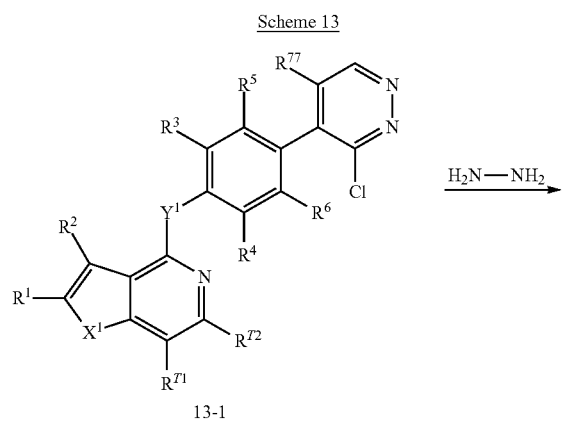

13-1

Scheme 14

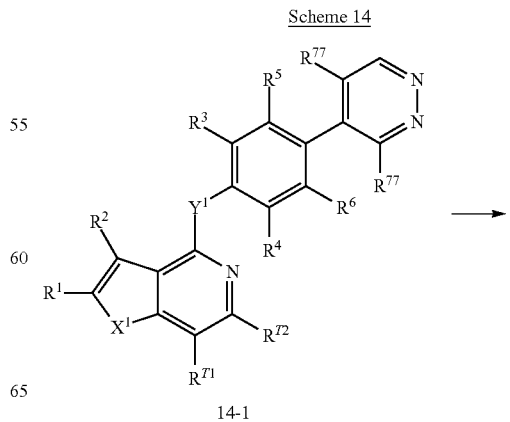

14-1

-continued

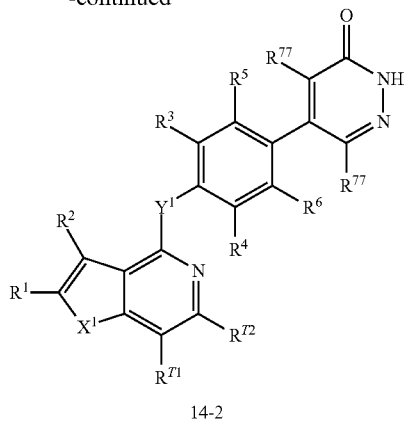

14-2

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, $R^4$, $R^5$, $R^6$, $R^7$, $X^1$, $Y^1$, $Q^1$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a mesylate, which in turn is suitable for nucleophilic substitution, such as by a cyanide ion (CN⁻). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^2$, $R^5$, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^3$, $R^5$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Boc) group, which can be deprotected and converted back to the $NH_2$ group in a later stage of the synthetic process.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I described herein include compounds of Formula I, N-oxides thereof, and salts of the compounds and the N-oxides.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well-known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 1,1'-methylene-bis-(2-hydroxy-3-naphthoate)] acids, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula Ia or Ib) may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxide thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention (or pharmaceutically acceptable salts thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxide thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (or pharmaceutically acceptable salts thereof or N-oxide thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (or pharmaceutically acceptable salts thereof or N-oxide thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™ etc.) injection.

Formulations for topical administration may be formulated to be immediate and/or modified release. Modified release formulations include delayed-, sustained-, pulsed-, controlled-, targeted and programmed release.

The compounds of the invention (or pharmaceutically acceptable salts thereof) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 µg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . ." etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memoryaid, so as to further facilitate compliance with the regimen. An example of such a memoryaid is a mechanical counter which indicates the number of daily doses that has been dispensed. Another example of such a memoryaid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXAMPLES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate atropisomers (or atropenantiomers) of certain compounds of the invention. The optical rotation of an atropisomer was measured using a polarimeter. According to its observed rotation data (or its specific rotation data), an atropisomer (or atropenantiomer) with a clockwise rotation was designated as the (+)-atropisomer [or the (+) atropenantiomer] and an atropisomer (or atropenantiomer) with a counter-clockwise rotation was designated as the (−)-atropisomer [or the (−) atropenantiomer].

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

4-[4-(4,6-Dimethylpyrimidin-5-yl)-3-methylphenoxy]furo[3,2-c]pyridine (1)

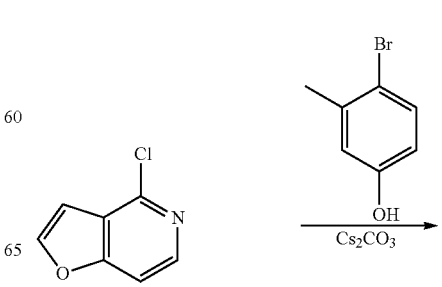

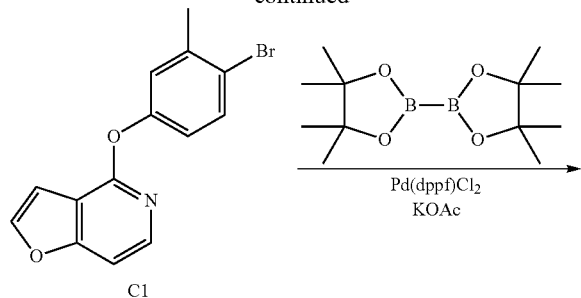

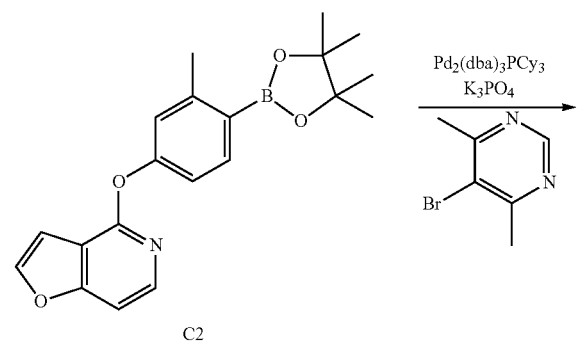

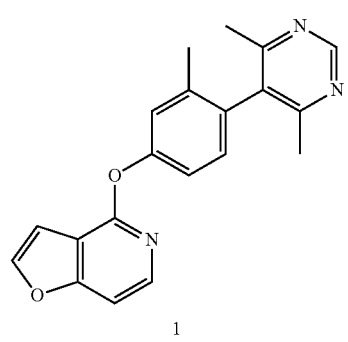

Step 1. Synthesis of 4-(4-bromo-3-methylphenoxy)furo-[3,2-c]pyridine (C1)

To a solution of 4-chlorofuro[3,2-c]pyridine (120 g, 781 mmol) in dimethyl sulfoxide (1.56 L) was added cesium carbonate (509 g, 1.56 mol) and 4-bromo-3-methylphenol (161 g, 861 mmol), and the reaction was heated to 125° C. for 16 hours. At this point, the reaction mixture was cooled to room temperature, poured into water (5 L), and extracted with ethyl acetate (2×2.5 L). The combined organic extracts were washed with water (2.5 L), washed with saturated aqueous sodium chloride solution (2.5 L), dried over anhydrous sodium sulfate, filtered and concentrated in vacuo. Purification by chromatography on silica gel (Eluent: 2% ethyl acetate in petroleum ether) afforded the product as a pale yellow solid. Yield: 205 g, 674 mmol, 86%. LCMS m/z 304.0, 306.0 (M+H). $^1$H NMR (400 MHz, CDCl$_3$) δ 8.00 (d, J=6.2 Hz, 1H), 7.64 (d, J=2.1 Hz, 1H), 7.55 (d, J=8.3 Hz, 1H), 7.20 (dd, J=5.8, 0.8 Hz, 1H), 7.12 (d, J=2.9 Hz, 1H), 6.93 (dd, J=8.5, 2.7 Hz, 1H), 6.88 (dd, J=2.5, 0.8 Hz, 1H), 2.41 (s, 3H).

Step 2. Synthesis of 4-[3-methyl-4-(4,4,5,5-tetramethyl-1,3,2-dioxaborolan-2-yl) phenoxy]furo-[3,2-c]pyridine (C2)

To a stirred solution of 4-(4-bromo-3-methylphenoxy)furo[3,2-c]pyridine (C1) (50.0 g, 164 mmol) in 1,4-dioxane (1.02 L) was added 4,4,4',4',5,5,5',5'-octamethyl-2,2'-bi-1,3,2-dioxaborolane (41.76 g, 164.4 mmol), potassium acetate (64.6 g, 658 mmol) and [1,1'-bis(diphenylphosphino)ferrocene]dichloropalladium(II) (6.0 g, 8.2 mmol), and the reaction mixture was heated at 85° C. for 16 hours. After cooling to room temperature, it was filtered through a pad of Celite, and the pad was washed with ethyl acetate. The combined filtrates were concentrated in vacuo and the residue was purified by silica gel chromatography (Eluent: 2% ethyl acetate in petroleum ether) to provide the product as a white solid. Yield: 40.0 g, 114 mmol, 70%. LCMS m/z 352.2 (M+H). $^1$H NMR (400 MHz, CDCl$_3$) δ 8.02 (d, J=5.8 Hz, 1H), 7.84 (d, J=7.5 Hz, 1H), 7.61 (d, J=2.1 Hz, 1H), 7.19 (d, J=5.8 Hz, 1H), 7.00 (m, 2H), 6.80 (m, 1H), 2.56 (s, 3H), 1.34 (s, 12H).

Step 3. Synthesis of 4-[4-(4,6-dimethylpyrimidin-5-yl)-3-methylphenoxy]furo-[3,2-c]pyridine (1)

4-[3-Methyl-4-(4,4,5,5-tetramethyl-1,3,2-dioxaborolan-2-yl)phenoxy]furo[3,2-c]pyridine (C2) (250 mg, 0.712 mmol), 5-bromo-4,6-dimethylpyrimidine (160 mg, 0.855 mmol), tris(dibenzylideneacetone)dipalladium(0) (95%, 26.9 mg, 0.142 mmol), tricyclohexylphosphine (79.9 mg, 0.285 mmol) and potassium phosphate (302 mg, 1.42 mmol) were combined in a 3:1 mixture of 1,4-dioxane and water (12 mL), and subjected to irradiation in a microwave reactor at 120° C. for 5 hours. The reaction mixture was filtered through Celite; the filtrate was concentrated under reduced pressure, taken up in ethyl acetate, filtered through silica gel (1 g), and concentrated in vacuo. Purification via silica gel chromatography (Gradient: 0% to 100% ethyl acetate in heptane) afforded the product as a colorless oil. Yield: 123 mg, 0.371 mmol, 52%. LCMS m/z 332.1 (M+H). $^1$H NMR (500 MHz, CDCl$_3$) δ 8.98 (s, 1H), 8.07 (d, J=5.9 Hz, 1H), 7.67 (d, J=2.2 Hz, 1H), 7.25-7.27 (m, 1H, assumed; partially obscured by solvent peak), 7.24 (br d, J=2.4 Hz, 1H), 7.19 (br dd, J=8.3, 2.4 Hz, 1H), 7.08 (d, J=8.3 Hz, 1H), 6.90 (dd, J=2.2, 1.0 Hz, 1H), 2.27 (s, 6H), 2.04 (s, 3H).

Example 2

5-[4-(Furo[3,2-c]pyridin-4-yloxy)-2-methylphenyl]-6-methyl-[8-²H]-imidazo[1,2-a]pyrazine (2)

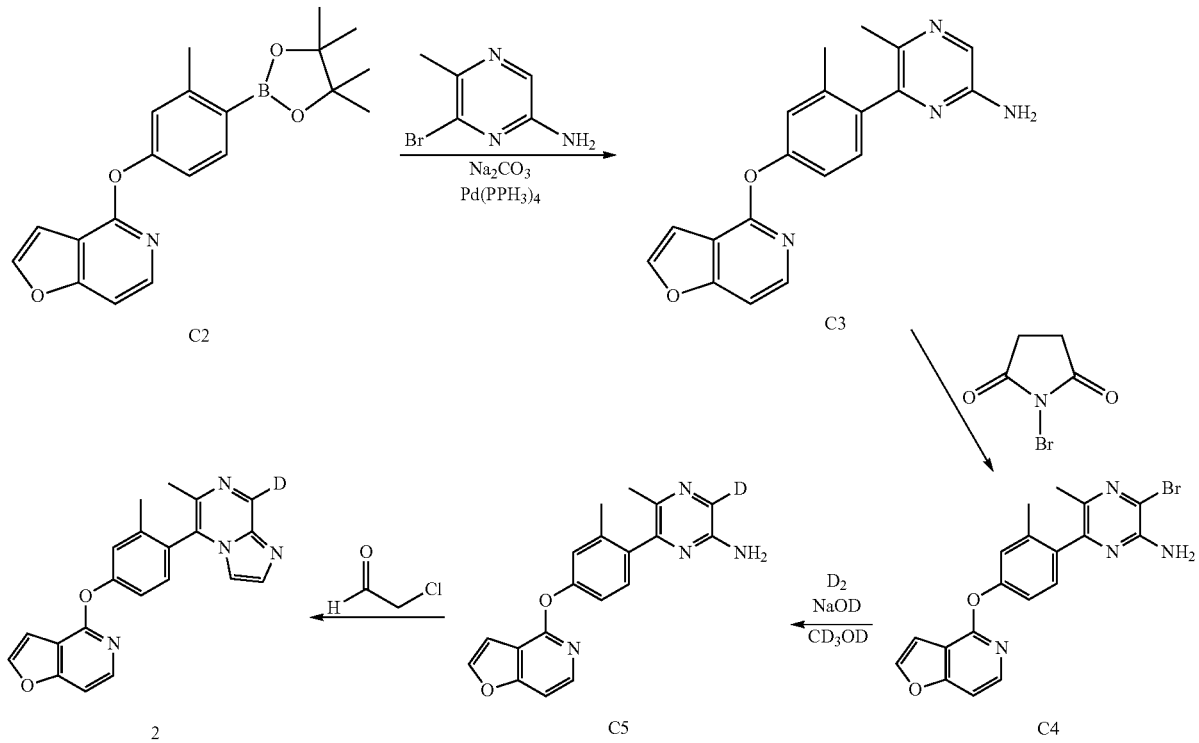

Step 1. Synthesis of 6-[4-(furo[3,2-c]pyridin-4-yloxy)-2-methylphenyl]-5-methylpyrazin-2-amine (C3)

6-Bromo-5-methylpyrazin-2-amine (which may be prepared according to the method of N. Sato, *J. Heterocycl. Chem.* 1980, 171, 143-147) (2.40 g, 12.8 mmol), 4-[3-methyl-4-(4,4,5,5-tetramethyl-1,3,2-dioxaborolan-2-yl)phenoxy]furo[3,2-c]pyridine (C2) (4.48 g, 12.8 mmol), and tetrakis(triphenylphosphine)palladium(0) (95%, 466 mg, 0.383 mmol) were combined in a pressure tube and dissolved in 1,4-dioxane (60 mL) and ethanol (20 mL). A solution of sodium carbonate (2.0 M in water, 19.1 mL, 38.2 mmol) was added, and argon was bubbled through the reaction mixture for 15 minutes. The tube was sealed, and then heated at 140° C. for 16 hours. The reaction mixture was combined with a second, identical, reaction mixture for workup. The combined reaction mixtures were filtered; solids remaining in the reaction vessels were slurried in water and filtered, and the filter cake was washed with ethanol. All of the organic filtrates were passed through a pad of Celite, and the Celite pad was washed with ethanol. These filtrates were concentrated in vacuo, and the resulting solid was slurried in water, filtered and washed with water. The solid was then slurried in 1:1 heptane/diethyl ether, filtered and washed with diethyl ether to afford the product as a light yellow solid. Yield: 6.774 g, 20.38 mmol, 80%. $^1$H NMR (500 MHz, DMSO-$d_6$) δ 8.14 (d, J=2.2 Hz, 1H), 8.01 (d, J=5.7 Hz, 1H), 7.82 (s, 1H), 7.47 (dd, J=5.8, 0.9 Hz, 1H), 7.21 (d, J=8.3 Hz, 1H), 7.15 (br d, J=2.4 Hz, 1H), 7.09 (br dd, J=8.2, 2.4 Hz, 1H), 7.06 (dd, J=2.2, 0.7 Hz, 1H), 6.18 (br s, 2H), 2.12 (s, 3H), 2.07 (br s, 3H).

Step 2. Synthesis of 3-bromo-6-[4-(furo-[3,2-c]pyridin-4-yloxy)-2-methylphenyl]-5-methylpyrazin-2-amine (C4)

N-Bromosuccinimide (95%, 609 mg, 3.25 mmol) was added to a solution of 6-[4-(furo[3,2-c]pyridin-4-yloxy)-2-methylphenyl]-5-methylpyrazin-2-amine (C3) (900 mg, 2.71 mmol) in N,N-dimethylformamide (15 mL), and the reaction mixture was heated to 60° C. for 45 minutes. The reaction mixture was cooled to room temperature, diluted with ethyl acetate and quenched with a small amount of water. After adsorption onto silica gel, the product was purified via silica gel chromatography (Gradient: 0% to 50% ethyl acetate in heptane). The purified material was taken up in ethyl acetate and washed with 1:1 water/saturated aqueous sodium bicarbonate solution, with water, and with saturated aqueous sodium chloride solution to remove residual N,N-dimethylformamide. The organic layer was dried over sodium sulfate and concentrated in vacuo to provide the product as a yellow solid. Yield: 700 mg, 1.71 mmol, 63%. LCMS m/z 412.9 (M+H). $^1$H NMR (400 MHz, DMSO-$d_6$) δ 8.14 (d, J=2.2 Hz, 1H), 8.01 (d, J=5.9 Hz, 1H), 7.48 (dd, J=5.9, 1.0 Hz, 1H), 7.26 (d, J=8.2 Hz, 1H), 7.17 (br d, J=2.3 Hz, 1H), 7.11 (br dd, J=8.3, 2.4 Hz, 1H), 7.07 (dd, J=2.2, 0.9 Hz, 1H), 6.51 (br s, 2H), 2.13 (s, 3H), 2.09 (br s, 3H).

Step 3. Synthesis of 6-[4-(furo-[3,2-c]pyridin-4-yloxy)-2-methylphenyl]-5-methyl-[3-$^2$H]-pyrazin-2-amine (C5)

3-Bromo-6-[4-(furo[3,2-c]pyridin-4-yloxy)-2-methylphenyl]-5-methylpyrazin-2-amine (C4) (575 mg, 1.40 mmol) was dissolved in a mixture of $^2H_4$-methanol and $^2H_6$-acetone under gentle warming. The solution was allowed to stand for 10 minutes, then was concentrated in vacuo. The residue was dissolved in 1:1 tetrahydrofuran/$^2H_4$-methanol (30 mL) and a solution of sodium deuteroxide in $^2H_4$-methanol (3 mM, 1.5 equivalents), and hydrogenated under 5 psi $^2H_2$ for 2.5 hours at room temperature, using 10% palladium on carbon catalyst (5% load). The reaction mixture was then filtered to remove catalyst and concentrated under reduced pressure, to provide a yellow solid. This solid was slurried in a small amount of ethyl acetate, filtered and rinsed with ethyl acetate to afford the product as a yellow solid. The filtrate was found to contain additional product via LCMS analysis. The filtrate was concentrated in vacuo to afford a yellow solid, which was washed with ethyl acetate; the resulting white precipitate was removed by filtration and discarded. The filtrate was combined with the initially collected yellow solid, diluted with additional ethyl acetate and washed with water, with saturated aqueous ammonium chloride solution, with saturated aqueous sodium chloride solution, dried over sodium sulfate and filtered. Concentration of the filtrate under reduced pressure provided a yellow solid, which was purified by silica gel chromatography (Gradient: 20% to 100% ethyl acetate in heptane). A yellow solid was obtained; upon attempted dissolution in ethyl acetate, a white solid formed, which was filtered to provide the product as a white solid. Yield: 207 mg, 0.621 mmol, 44%. LCMS m/z 334.1 (M+H). $^1$H NMR (400 MHz, DMSO-$d_6$) δ 8.14 (d, J=2.2 Hz, 1H), 8.01 (d, J=5.9 Hz, 1H), 7.47 (dd, J=5.9, 1.0 Hz, 1H), 7.21 (d, J=8.2 Hz, 1H), 7.15 (br d, J=2.4 Hz, 1H), 7.07-7.11 (m, 1H), 7.06 (dd, J=2.2, 1.1 Hz, 1H), 6.18 (br s, 2H), 2.11 (s, 3H), 2.07 (br s, 3H).

Step 4. Synthesis of 5-[4-(furo-[3,2-c]pyridin-4-yloxy)-2-methylphenyl]-6-methyl-[8-$^2$H]-imidazol[1,2-a]pyrazine (2)

Chloroacetaldehyde (55% solution in water, 1.28 mL, 10.9 mmol) was added to a mixture of 6-[4-(furo[3,2-c]pyridin-4-yloxy)-2-methylphenyl]-5-methyl-[3-$^2$H]-pyrazin-2-amine (C5) (182 mg, 0.546 mmol) in water (2.5 mL), and the reaction mixture was heated to 100° C. for 1 hour. After cooling to room temperature, the reaction mixture was diluted with water (15 mL) and ethyl acetate (15 mL), then treated with saturated aqueous sodium bicarbonate solution (5 to 10 mL). The aqueous layer was extracted with ethyl acetate, and the combined organic layers were washed with water, washed with saturated aqueous sodium chloride solution, dried over sodium sulfate, filtered, and concentrated in vacuo. Silica gel chromatography (Gradient: 0% to 5% methanol in dichloromethane) afforded the product as a solid. Yield: 158 mg, 0.442 mmol, 81%. LCMS m/z 358.0 (M+H). NMR (400 MHz, DMSO-$d_6$) δ 8.18 (d, J=2.2 Hz, 1H), 8.08 (d, J=5.9 Hz, 1H), 7.77 (d, J=1.0 Hz, 1H), 7.54 (dd, J=5.8, 0.9 Hz, 1H), 7.46 (d, J=8.4 Hz, 1H), 7.40 (br d, J=2.4 Hz, 1H), 7.30 (br dd, J=8.3, 2.4 Hz, 1H), 7.26 (d, J=1.0 Hz, 1H), 7.12 (dd, J=2.2, 1.0 Hz, 1H), 2.27 (s, 3H), 2.00 (br s, 3H).

Examples 3 and 4

(+)-5-[4-(Furo[3,2-c]pyridin-4-yloxy)-2-methylphenyl]-6-methyl-[8-$^2$H]-imidazo[1,2-a]pyrazine (3) and (+5-[4-(Furo[3,2-c]pyridin-4-yloxy)-2-methylphenyl]-6-methyl-[8-$^2$H]-imidazo[1,2-a]pyrazine (4)

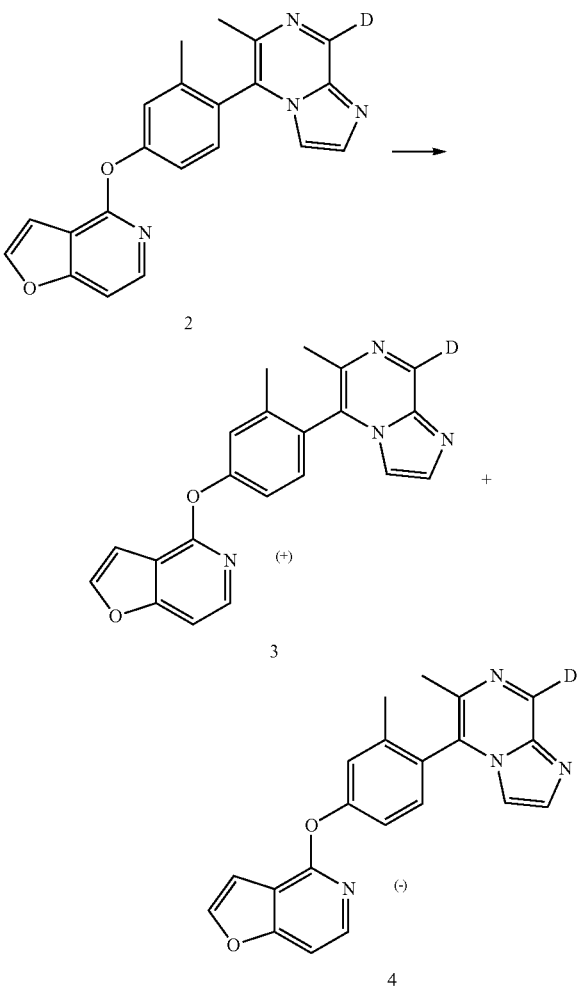

Chiral separation of 5-[4-(furo[3,2-c]pyridin-4-yloxy)-2-methylphenyl]-6-methyl-[8-$^2$H]-imidazo[1,2-a]pyrazine (2) (0.158 g) was carried out using supercritical fluid chromatography (Column: Chiralpak AD-H, 5 μm; Eluent: 3:1 carbon dioxide/methanol) to afford 3 [first-eluting peak, designated as the (+)-atropisomer according to its observed rotation data, 50 mg, 32%] and 4 [second-eluting peak, designated as the (−)-atropisomer according to its observed rotation data, 55 mg, 34%]. Compound 3: $^1$H NMR (400 MHz, CDCl$_3$) δ 8.09 (d, J=5.7 Hz, 1H), 7.78-7.86 (br m, 1H), 7.71 (d, J=2.4 Hz, 1H), 7.35-7.37 (m, 1H), 7.29-7.34 (m, 3H), 7.23-7.27 (m, 1H, assumed; partially obscured by solvent peak), 6.96 (dd, J=2.2, 1.0 Hz, 1H), 2.44 (s, 3H), 2.08 (s, 3H). Compound 4: $^1$H NMR (500 MHz, DMSO-$d_6$) δ 8.18 (d, J=2.3 Hz, 1H), 8.08 (d, J=5.7 Hz, 1H), 7.77 (d, J=1.0 Hz, 1H), 7.53 (dd, J=5.8, 0.9 Hz, 1H), 7.46 (d, J=8.3 Hz, 1H), 7.40 (d, J=2.4 Hz, 1H), 7.30 (dd, J=8.2, 2.6 Hz, 1H), 7.26 (d, J=1.0 Hz, 1H), 7.12 (dd, J=2.2, 0.8 Hz, 1H), 2.27 (s, 3H), 2.00 (s, 3H).

Example 5

1-[4-(Furo[3,2-c]pyridin-4-yloxy)-2-methylphenyl]-2-methyl-1H-imidazo[4,5-c]pyridine (5)

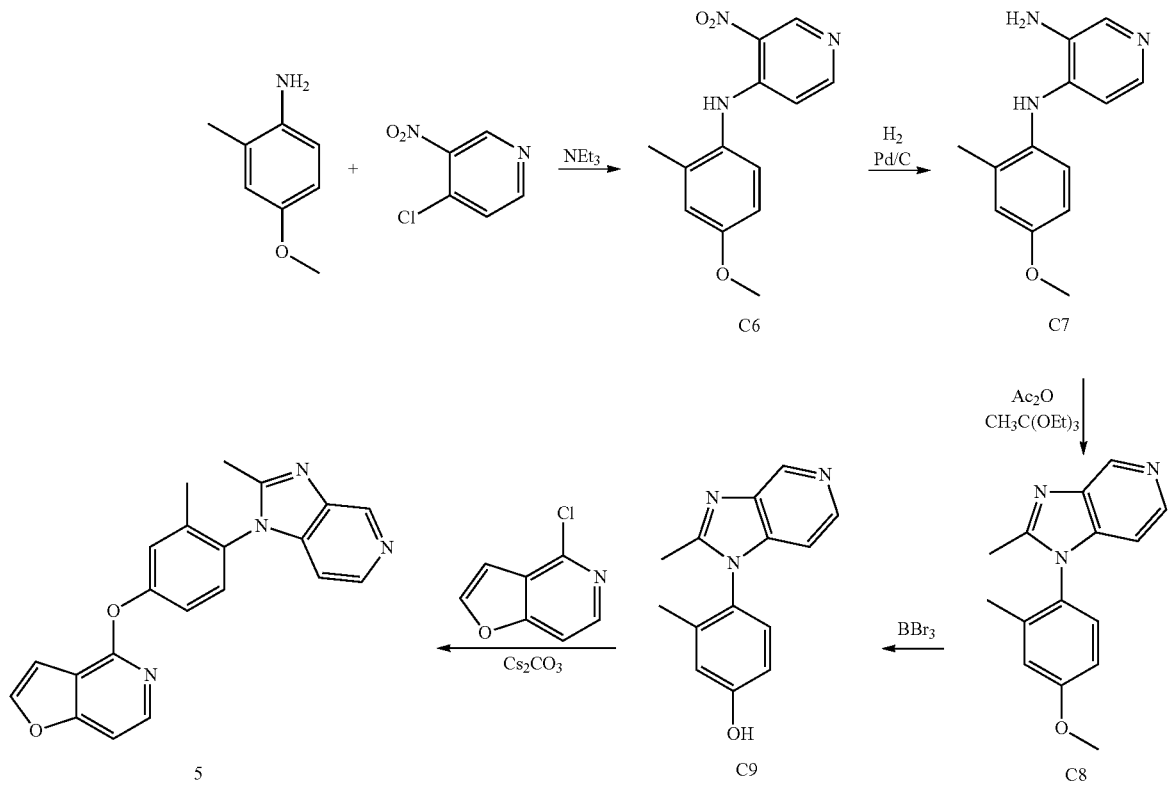

Step 1. Synthesis of N-(4-methoxy-2-methylphenyl)-3-nitropyridin-4-amine (C6)

A solution of 4-methoxy-2-methylaniline (23.8 g, 173 mmol), 4-chloro-3-nitropyridine (25 g, 160 mmol), and triethylamine (33.0 mL, 237 mmol) in ethanol (250 mL) was stirred at room temperature for 16 hours, then concentrated under reduced pressure. The residue was dissolved in ethyl acetate (200 mL) and filtered through a thick pad of silica gel (Eluent: ethyl acetate, 1 L). The filtrate was concentrated in vacuo to provide the product as a purple oil, which solidified on standing. This material was used without further purification. Yield: 41 g, 160 mmol, 100%. LCMS m/z 260.1 (M+H).

Step 2. Synthesis of $N^4$-(4-methoxy-2-methylphenyl)pyridine-3,4-diamine (C7)

Palladium on carbon (10%, 3×2.12 g) was added to each of three batches of N-(4-methoxy-2-methylphenyl)-3-nitropyridin-4-amine (C6) (each approximately 10 g; total 31 g, 120 mmol) in methanol (3×100 mL). The three suspensions were independently hydrogenated under 45 psi hydrogen at room temperature on a Parr shaker for 24 hours. The three reaction mixtures were combined, filtered through a pad of Celite, and concentrated in vacuo. Purification by silica gel chromatography [Gradient: 2% to 10% (1.7 M ammonia in methanol) in dichloromethane] afforded the product as a light brown solid. Yield: 24.0 g, 105 mmol, 88%. LCMS m/z 230.1 (M+H). $^1$H NMR (400 MHz, CDCl$_3$) δ 8.01 (s, 1H), 7.88 (d, J=5.5 Hz, 1H), 7.08 (d, J=8.6 Hz, 1H), 6.84 (br d, J=2.8 Hz, 1H), 6.78 (br dd, J=8.6, 3.0 Hz, 1H), 6.34 (d, J=5.5 Hz, 1H), 5.66 (br s, 1H), 3.82 (s, 3H), 2.20 (br s, 3H).

Step 3. Synthesis of 1-(4-methoxy-2-methylphenyl)-2-methyl-1H-imidazo[4,5-c]pyridine (C8)

A mixture of $N^4$-(4-methoxy-2-methylphenyl)pyridine-3,4-diamine (C7) (3.95 g, 17.2 mmol), acetic anhydride (1.96 mL, 20.7 mmol), and triethyl orthoacetate (99%, 15.9 mL, 86.4 mmol) was heated at 145° C. for 1 hour, then at 100° C. for 48 hours. After being cooled to room temperature, the reaction mixture was diluted with ethyl acetate (100 mL), washed with saturated aqueous sodium bicarbonate solution (30 mL), washed with water, dried over sodium sulfate, filtered, and concentrated under reduced pressure. Purification by silica gel chromatography (Gradient: 2% to 5% methanol in dichloromethane) provided the product as a light pink oil. Yield: 4.10 g, 16.2 mmol, 94%. LCMS m/z 254.1 (M+H). $^1$H NMR (400 MHz, CDCl$_3$) δ 9.07 (br d, J=0.8 Hz, 1H), 8.36 (d, J=5.5 Hz, 1H), 7.15 (d, J=8.6 Hz, 1H), 6.89-6.97 (m, 3H), 3.90 (s, 3H), 2.42 (s, 3H), 1.94 (br s, 3H).

Step 4. Synthesis of 3-methyl-4-(2-methyl-1H-imidazo[4,5-c]pyridin-1-yl)phenol (C9)

Boron tribromide (1 M solution in dichloromethane, 44.1 mL, 44.1 mmol) was added drop-wise to a solution of 1-(4-methoxy-2-methylphenyl)-2-methyl-1H-imidazo[4,5- c]pyridine (C8) (3.72 g, 14.7 mmol) in dichloromethane (150 mL) at −78° C. The reaction mixture was stirred at −78° C. for 15 minutes, then the cooling bath was removed and the reaction mixture was allowed to gradually warm to room temperature. After 20 hours at room temperature, the reaction mixture was recooled to −78° C. and slowly quenched with methanol (20 mL). At this point, the cooling bath was removed; the mixture was allowed to reach ambient temperature and then stir for 15 minutes. Volatiles were removed in vacuo, methanol (100 mL) was added, and the mixture was heated at reflux for 30 minutes. After concentration under reduced pressure, the resulting solid was taken directly to the next step. LCMS m/z 240.1 (M+H).

Step 5. Synthesis of 1-[4-(furo-[3,2-c]pyridin-4-yloxy)-2-methylphenyl]-2-methyl-1H-imidazo[4,5-c]pyridine (5)

A mixture of 3-methyl-4-(2-methyl-1H-imidazo[4,5-c]pyridin-1-yl)phenol (C9) (from the preceding step, <14.7 mmol), 4-chlorofuro[3,2-c]pyridine (2.37 g, 15.4 mmol) and cesium carbonate (99%, 19.3 g, 58.6 mmol) in dimethyl sulfoxide (100 mL) was heated to 140° C. for 16 hours. After cooling to room temperature, the reaction mixture was diluted with ethyl acetate (400 mL) and filtered through a pad of Celite. The filtrate was washed with water, with a 1:1 mixture of water and saturated aqueous sodium chloride solution (4×100 mL), dried over sodium sulfate, filtered, and concentrated in vacuo. The residue was purified by silica gel chromatography (Gradient: 2% to 10% methanol in ethyl acetate) to afford a yellow solid, which was dissolved in tert-butyl methyl ether (500 mL), treated with activated carbon (5 g) and heated to 40° C. The mixture was filtered to provide a colorless solution, which was concentrated at reflux until it became cloudy (~150 mL tert-butyl methyl ether remaining). Upon gradual cooling to room temperature, a precipitate formed. Filtration and washing with diethyl ether afforded the product as a free-flowing white solid. Yield: 2.02 g, 5.67 mmol, 39% over 2 steps. LCMS m/z 357.1 (M+H). $^1$H NMR (500 MHz, CDCl$_3$) δ 9.08 (d, J=1.0 Hz, 1H), 8.39 (d, J=5.5 Hz, 1H), 8.08 (d, J=5.9 Hz, 1H), 7.71 (d, J=2.2 Hz, 1H), 7.34-7.36 (m, 1H), 7.30 (dd, J=5.9, 1.0 Hz, 1H), 7.28-7.29 (m, 2H), 7.00 (dd, J=5.5, 1.1 Hz, 1H), 6.97 (dd, J=2.2, 1.0 Hz, 1H), 2.48 (s, 3H), 1.99 (br s, 3H).

Example 6

4-[3-Methoxy-4-(3-methylpyrazin-2-yl)phenoxy]furo[3,2-c]pyridine (6)

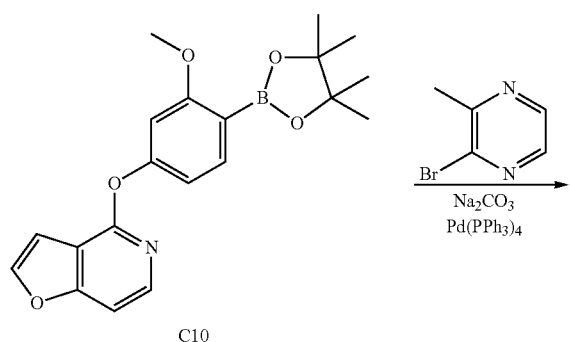

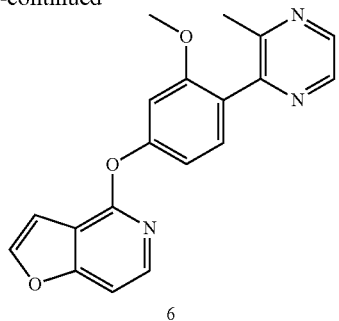

6

2-Bromo-3-methylpyrazine (104 mg, 0.600 mmol), tetrakis(triphenylphosphine)palladium(0) (95%, 133 mg, 0.109 mmol) and sodium carbonate (175 mg, 1.64 mmol) were combined with 4-[3-methoxy-4-(4,4,5,5-tetramethyl-1,3,2-dioxaborolan-2-yl)phenoxy]furo[3,2-c]pyridine [C10, which was prepared in analogous fashion to 4-[3-methyl-4-(4,4,5,5-tetramethyl-1,3,2-dioxaborolan-2-yl)phenoxy]furo[3,2-c]pyridine (C2) in Example 1] (200 mg, 0.545 mmol) in 1,4-dioxane (3 mL) and water (1 mL). The reaction mixture was heated to 130° C. in a microwave reactor for 1 hour. The mixture was cooled to room temperature, and the supernatant was decanted into another flask. The remaining solids were washed with ethyl acetate (3×10 mL) and the combined organic portions were concentrated in vacuo. Purification was carried out twice using silica gel chromatography (First column: Eluent: 2% methanol in dichloromethane; Second column: Gradient: 0% to 100% ethyl acetate in heptane). The colorless fractions were combined and concentrated under reduced pressure to provide the product as a white solid. Yield: 85 mg, 0.25 mmol, 46%. LCMS m/z 334.0 (M+H). $^1$H NMR (400 MHz, CDCl$_3$) δ 8.47 (AB quartet, downfield doublet is broadened, J$_{AB}$=2.5 Hz, Δν$_{AB}$=14 Hz, 2H), 8.08 (d, J=5.9 Hz, 1H), 7.66 (d, J=2.3 Hz, 1H), 7.36 (d, J=8.0 Hz, 1H), 7.25-7.28 (m, 1H, assumed; partially obscured by solvent peak), 6.90-6.96 (m, 2H), 6.88 (dd, J=2.2, 0.8 Hz, 1H), 3.79 (s, 3H), 2.50 (s, 3H). Yellow fractions were repurified to provide additional product: 55 mg, overall yield: 75%.

Example 7

4-[4-(1-Methyl-1H-pyrazol-5-yl)phenoxy]thieno[3,2-c]pyridine (7)

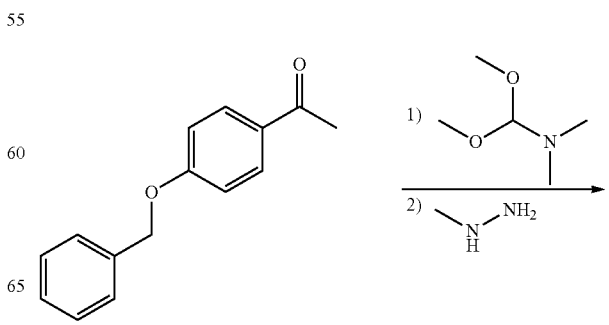

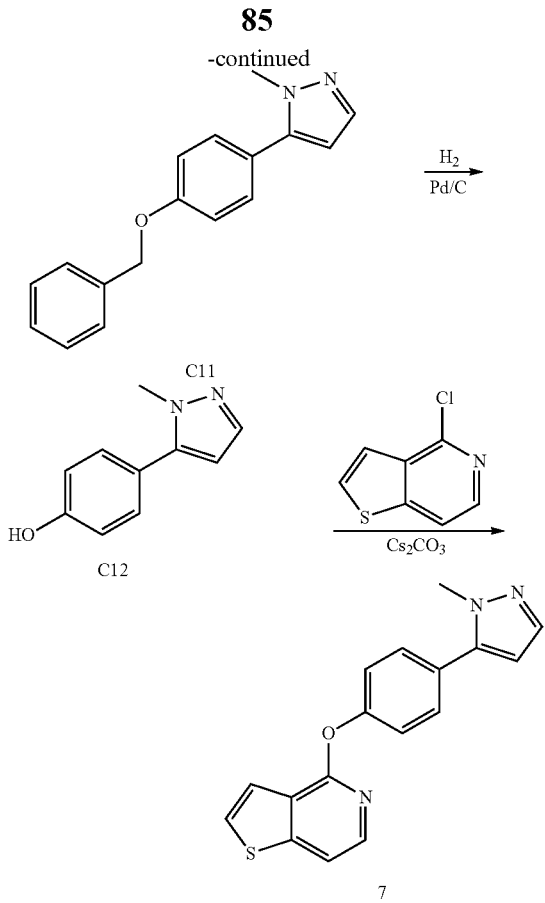

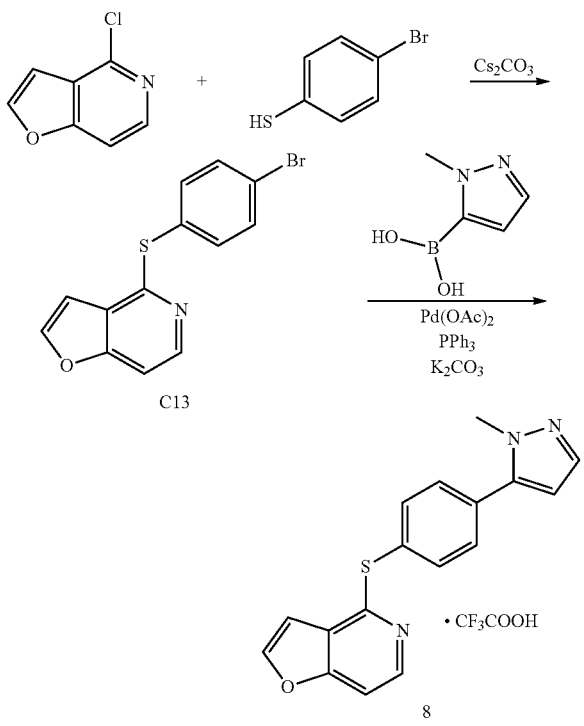

Step 1. Synthesis of 5-[4-(benzyloxy)phenyl]-1-methyl-1H-pyrazole (C11)

N,N-Dimethylformamide dimethyl acetal (94%, 19.0 mL, 134 mmol) was added to a solution of 1-[4-(benzyloxy)phenyl]ethanone (15.32 g, 67.71 mmol) in N,N-dimethylformamide (30 mL) and the reaction mixture was heated at reflux for 18 hours. At this point, the reflux condenser was replaced with a distillation head, and distillation was carried out until the temperature of the distillate reached 140° C. The material in the reaction pot was cooled to room temperature, treated with methylhydrazine (98%, 7.4 mL, 136 mmol) and heated at 75° C. for 3 hours. The reaction mixture was cooled, diluted with ethyl acetate, washed four times with aqueous 5% sodium chloride solution, dried over magnesium sulfate, filtered, and concentrated in vacuo. Purification via silica gel chromatography (Gradient: 2% to 10% ethyl acetate in dichloromethane) afforded the product as a light yellow solid. Yield: 13.79 g, 52.17 mmol, 77%. LCMS m/z 265.1 (M+H). $^1$H NMR (400 MHz, DMSO-$d_6$) characteristic peaks, δ 3.81 (s, 3H), 5.17 (s, 2H), 6.31 (d, J=1.5 Hz, 1H), 7.12 (d, J=8.8 Hz, 2H).

Step 2. Synthesis of 4-(1-methyl-1H-pyrazol-5-yl)phenol (C12)

5-[4-(Benzyloxy)phenyl]-1-methyl-1H-pyrazole (C11) (13.49 g, 51.04 mmol) was mixed with 10% palladium on carbon (~50% in water, 1.46 g) and dissolved in ethanol (125 mL). The reaction mixture was hydrogenated at room temperature and 1 atmosphere hydrogen for 18 hours, then filtered and concentrated in vacuo. The residue was triturated with heptane to afford the product as a colorless solid. Yield: 8.74 g, 50.2 mmol, 98%. LCMS m/z 175.1 (M+H). $^1$H NMR (400 MHz, DMSO-$d_6$) δ 9.73 (br s, 1H), 7.40 (d, J=1.9 Hz, 1H), 7.31 (br d, J=8.7 Hz, 2H), 6.86 (br d, J=8.7 Hz, 2H), 6.26 (d, J=1.9 Hz, 1H), 3.79 (s, 3H).

Step 3. Synthesis of 4-[4-(1-methyl-1H-pyrazol-5-yl)phenoxy]thieno[3,2-c]pyridine (7)

4-(1-Methyl-1H-pyrazol-5-yl)phenol (C12) (123 mg, 0.706 mmol) and 4-chlorothieno[3,2-c]pyridine (100 mg, 0.590 mmol) were combined in 1-methylpyrrolidin-2-one (2 mL). Cesium carbonate (99%, 388 mg, 1.18 mmol) was added and the reaction mixture was heated to 135° C. for 24 hours. After addition of water (30 mL), the layers were separated and the aqueous layer was extracted with 1:1 diethyl ether/hexanes (4×30 mL). The combined organic layers were washed with aqueous sodium hydroxide solution (1 N, 2×20 mL) and with saturated aqueous sodium chloride solution (20 mL), then dried over sodium sulfate. After filtration and concentration under reduced pressure, purification using silica gel chromatography (Eluent: 30% ethyl acetate in heptane) provided the product as a white solid. Yield: 78 mg, 0.25 mmol, 42%. LCMS m/z 308.3 (M+H). $^1$H NMR (500 MHz, CD$_3$OD) δ 7.90 (d, J=5.6 Hz, 1H), 7.74 (d, J=5.5 Hz, 1H), 7.69 (dd, J=5.7, 0.7 Hz, 1H), 7.65 (dd, J=5.5, 0.8 Hz, 1H), 7.55 (br d, J=8.7 Hz, 2H), 7.51 (d, J=2.0 Hz, 1H), 7.32 (br d, J=8.7 Hz, 2H), 6.39 (d, J=2.0 Hz, 1H), 3.91 (s, 3H).

Example 8

4-{[4-(1-Methyl-1H-pyrazol-5-yl)phenyl]sulfanyl}furo[3,2-c]pyridine, trifluoroacetate salt (8)

Step 1. Synthesis of 4-[(4-bromophenyl)sulfanyl]furo[3,2-c]pyridine (C13)

Cesium carbonate (99%, 522 mg, 1.59 mmol) was added to a mixture of 4-chlorofuro[3,2-c]pyridine (146 mg, 0.951 mmol) and 4-bromobenzenethiol (150 mg, 0.793 mmol) in dimethyl sulfoxide (3 mL); the reaction mixture was degassed, and then heated at 80° C. for 16 hours. Water (30 mL) was added and extraction was carried out with 1:1 ethyl acetate/hexanes (4×30 mL). The combined organic layers were dried over sodium sulfate, filtered, and concentrated in vacuo. Purification via silica gel chromatography (Gradient: 5% to 10% ethyl acetate in heptane) provided a colorless oil (220 mg); this was dissolved in diethyl ether (20 mL) and washed with aqueous sodium hydroxide solution (1 N, 3×15 mL). The organic layer was concentrated under reduced pressure to provide the product, determined by $^1$H NMR analysis to be contaminated with extraneous furo[3,2-c]pyridyl activity. This was taken to the following step without further purification. LCMS m/z 308.3 (M+H). $^1$H NMR (400 MHz, CDCl$_3$) product peaks only, δ 8.32 (d, J=5.7 Hz, 1H), 7.60 (d, J=2.2 Hz, 1H), 7.47 (br AB quartet, $J_{AB}$=8.7 Hz, $\Delta v_{AB}$=31.2 Hz, 4H), 7.29 (dd, J=5.8, 1.0 Hz, 1H), 6.58 (dd, J=2.3, 1.0 Hz, 1H).

Step 2. Synthesis of 4-{[4-(1-methyl-1H-pyrazol-5-yl)phenyl]sulfanyl}furo[3,2-c]pyridine, trifluoroacetate salt (8)

4-[(4-Bromophenyl)sulfanyl]furo[3,2-c]pyridine (C13) (210 mg from the previous step), (1-methyl-1H-pyrazol-5-yl)boronic acid (104 mg, 0.826 mmol), triphenylphosphine (21.5 mg, 0.0819 mmol) and potassium carbonate (190 mg, 1.37 mmol) were combined in N,N-dimethylformamide (6 mL) and water (2 mL), and the mixture was degassed with nitrogen for 20 minutes. Palladium(II) acetate (98%, 4.8 mg, 0.021 mmol) was added, and the reaction mixture was heated at 80° C. for 18 hours. After cooling to room temperature, the reaction mixture was diluted with water (15 mL) and extracted with 1:1 ethyl acetate/hexanes (3×15 mL). The combined organic layers were dried over sodium sulfate, filtered, and concentrated in vacuo. Purification was effected first via silica gel chromatography (Eluent: 80% ethyl acetate in heptane), followed by HPLC (Column: Waters XBridge C18, 5 win; Mobile phase A: water with trifluoroacetic acid modifier; Mobile phase B: acetonitrile with trifluoroacetic acid modifier; Gradient: 40% to 100% B), to afford the product as a white solid. Yield: 30 mg, 0.071 mmol, 9% over two steps. LCMS m/z 308.0 (M+H). $^1$H NMR (400 MHz, CD$_3$OD) δ 8.29 (d, J=5.8 Hz, 1H), 7.87 (d, J=2.2 Hz, 1H), 7.61 (br d, J=8.6 Hz, 2H), 7.53 (br d, J=8.7 Hz, 2H), 7.51 (d, J=2.1 Hz, 1H), 7.49 (dd, J=5.8, 1.0 Hz, 1H), 6.66 (dd, J=2.3, 1.1 Hz, 1H), 6.42 (d, J=2.0 Hz, 1H), 3.90 (s, 3H).

Example 9

2-(4,6-Dimethylpyrimidin-5-yl)-5-(furo[3,2-c]pyridin-4-yloxy)benzonitrile (9)

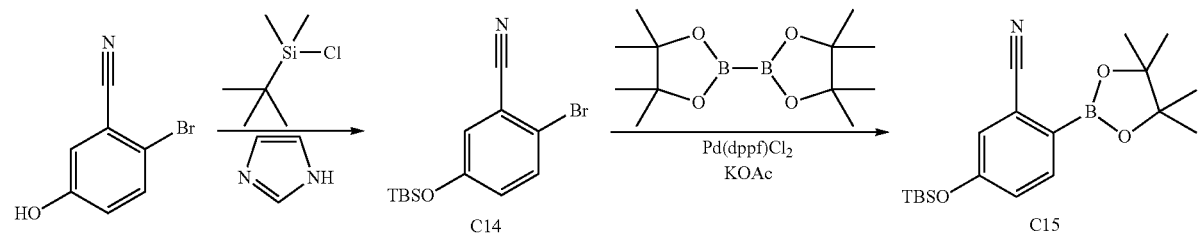

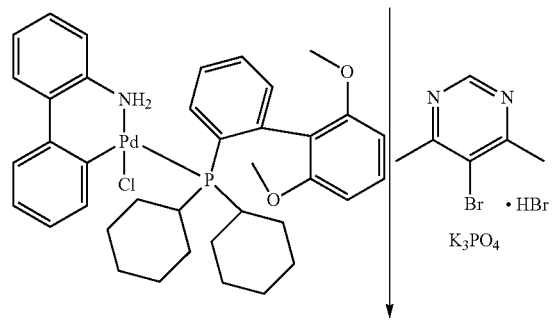

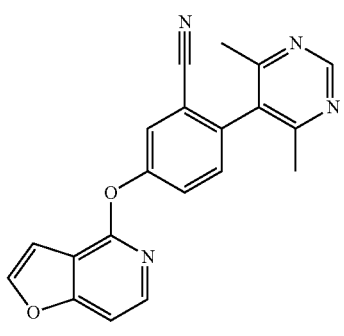

9

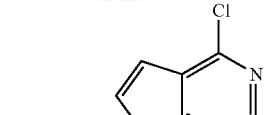

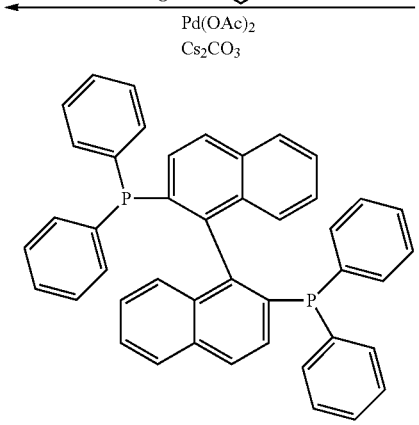

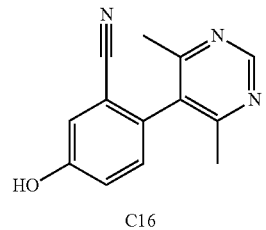

C16

Step 1. Synthesis of 2-bromo-5-{[tert-butyl(dimethyl)silyl]oxy}benzonitrile (C14)

1H-Imidazole (2.14 g, 31.4 mmol) was added portionwise to a 0° C. solution of 2-bromo-5-hydroxybenzonitrile (5.65 g, 28.5 mmol) and tert-butyldimethylsilyl chloride (4.52 g, 30.0 mmol) in tetrahydrofuran (56.5 mL). The reaction mixture was allowed to stir at room temperature for 2 hours, and was then filtered. The filtrate was washed with water and with saturated aqueous sodium chloride solution. The aqueous layer was extracted with diethyl ether, and the combined organic layers were concentrated in vacuo to afford the product as an orange oil. Yield: 8.87 g, 28.4 mmol, 99.6%. $^1$H NMR (400 MHz, CDCl$_3$) δ 7.50 (d, J=8.8 Hz, 1H), 7.08-7.12 (m, 1H), 6.90-6.95 (m, 1H), 0.98 (s, 9H), 0.22 (s, 6H).

Step 2. Synthesis of 5-{[tert-butyl(dimethyl)silyl]oxy}-2-(4,4,5,5-tetramethyl-1,3,2-dioxaborolan-2-yl)benzonitrile (C15)

2-Bromo-5-{[tert-butyl(dimethyl)silyl]oxy}benzonitrile (C14) (8.00 g, 25.6 mmol), 4,4,4',4',5,5,5',5'-octamethyl-2,2'-bi-1,3,2-dioxaborolane (6.83 g, 26.9 mmol) and potassium acetate (10.06 g, 102.5 mmol) were combined in degassed 1,4-dioxane (160 mL). After addition of [1,1'-bis(diphenylphosphino)ferrocene]dichloropalladium(II) (1.05 g, 1.28 mmol), the reaction mixture was heated to 80° C. for 4 hours. After cooling, it was filtered through Celite, and the filter pad was rinsed with ethyl acetate. The filtrate was concentrated in vacuo and purified via silica gel chromatography (Gradient: 20% to 50% ethyl acetate in heptane) to provide the product as a colorless, viscous oil. Yield: 5.60 g, 15.6 mmol, 61%. $^1$H NMR (400 MHz, CDCl$_3$) δ 7.76 (br d, J=8.3 Hz, 1H), 7.15 (dd, J=2.4, 0.3 Hz, 1H), 7.02 (dd, J=8.3, 2.3 Hz, 1H), 1.38 (s, 12H), 0.98 (s, 9H), 0.22 (s, 6H).

Step 3. Synthesis of 2-(4,6-dimethylpyrimidin-5-yl)-5-hydroxybenzonitrile (C16)

5-{[tert-Butyl(dimethyl)silyl]oxy}-2-(4,4,5,5-tetramethyl-1,3,2-dioxaborolan-2-yl)benzonitrile (C15) (4.05 g, 11.3 mmol) was combined with 5-bromo-4,6-dimethylpyrimidine hydrobromide (7.16 g, 26.7 mmol) and potassium phosphate (7.03 g, 33.1 mmol) in 2-methyltetrahydrofuran (20.2 mL) and water (16.2 mL). [2'-(Azanidyl-κN)biphenyl-2-yl-κC$_2$](chloro)[dicyclohexyl(2',6'-dimethoxybiphenyl-2-yl)-λ$^5$-phosphanyl]palladium (prepared from biphenyl-2-amine and dicyclohexyl(2',6'-dimethoxybiphenyl-2-yl)phosphane (S-Phos) according to the procedure of S. L. Buchwald et al., J. Am. Chem. Soc. 2010, 132, 14073-14075) (0.20 g, 0.28 mmol) was added, and the reaction mixture was heated to reflux for 18 hours. It was then cooled to room temperature, and the organic layer was extracted with aqueous hydrochloric acid (2 N, 2×20 mL). The combined extracts were adjusted to a pH of roughly 6-7 with 2 M aqueous sodium hydroxide solution, and then extracted with ethyl acetate. These combined organic layers were dried over magnesium sulfate, filtered, and concentrated in vacuo. The resulting solids were triturated with hot heptane to afford the product as a tan solid. Yield: 1.86 g, 8.26 mmol, 73%. $^1$H NMR (400 MHz, DMSO-d$_6$) δ 10.48 (s, 1H), 8.94 (s, 1H), 7.36 (d, J=8.4 Hz, 1H), 7.31 (d, J=2.5 Hz, 1H), 7.23 (dd, J=8.5, 2.6 Hz, 1H), 2.18 (s, 6H).

Step 4. Synthesis of 2-(4,6-dimethylpyrimidin-5-yl)-5-(furo-[3,2-c]pyridin-4-yloxy)benzonitrile (9)

2-(4,6-Dimethylpyrimidin-5-yl)-5-hydroxybenzonitrile (C16) (1.00 g, 4.44 mmol), 4-chlorofuro[3,2-c]pyridine (750 mg, 4.88 mmol), palladium(II) acetate (49.8 mg, 0.222 mmol), 1,1'-binaphthalene-2,2'-diylbis(diphenylphosphane) (96%, 288 mg, 0.444 mmol) and cesium carbonate (99%, 2.92 g, 8.87 mmol) were combined in 1,4-dioxane (25 mL) and nitrogen was bubbled through the mixture for 15 minutes. The reaction mixture was then heated at 100° C. for 18 hours, cooled to room temperature and filtered through Celite. The filtrate was partitioned between ethyl acetate and water, and the aqueous layer was extracted with ethyl acetate. The combined organic layers were washed with saturated aqueous sodium chloride solution, dried over magnesium sulfate, filtered, and concentrated in vacuo. Purification using silica gel chromatography (Gradient: 75% to 100% ethyl acetate in heptane) provided the product as a viscous yellow oil, which slowly solidified on standing. Further purification was effected using supercritical fluid chromatography (Column: Princeton 2-ethylpyridine, 5 μm; Eluent: 4:1 carbon dioxide/methanol). Yield: 1.5 g, 4.4 mmol, 99%. LCMS m/z 343.1 (M+H). $^1$H NMR (400 MHz, CDCl$_3$) δ 9.04 (s, 1H), 8.06 (d, J=5.9 Hz, 1H), 7.78 (br d, J=2.5 Hz, 1H), 7.72 (d, J=2.2 Hz, 1H), 7.66 (dd, J=8.4, 2.5 Hz, 1H), 7.36 (dd, J=8.4, 0.4 Hz, 1H), 7.33 (dd, J=5.7, 1.0 Hz, 1H) 6.97 (dd, J=2.2, 1.0 Hz, 1H), 2.36 (s, 6H).

Example 10

4-[4-(Furo[3,2-c]pyridin-4-yloxy)-2-methylphenyl]-5-methylpyridazin-3(2H)-one, bis-hydrochloride salt (10)

(Gradient: 3% to 5% ethyl acetate in petroleum ether) to afford the product as a white solid. Yield: 42 g, 170 mmol, 68%. $^1$H NMR (400 MHz, CDCl$_3$) δ 7.84 (s, 1H), 6.01 (br d, J=11 Hz, 1H), 4.10-4.16 (m, 1H), 3.70-3.79 (m, 1H), 1.99-2.19 (m, 2H), 1.50-1.80 (m, 4H).

Step 2. Synthesis of 4-chloro-5-methyl-2-(tetrahydro-2H-pyran-2-yl)pyridazin-3(2H)-one (C18) and 5-chloro-4-methyl-2-(tetrahydro-2H-pyran-2-yl)pyridazin-3(2H)-one (C19)

To a mixture of 4,5-dichloro-2-(tetrahydro-2H-pyran-2-yl)pyridazin-3(2H)-one (C17) (40 g, 0.16 mol), methylboronic acid (9.6 g, 0.16 mol) and cesium carbonate (155 g, 0.476 mol) in a mixture of 1,4-dioxane (500 mL) and water (50 mL) was added [1,1'-bis(diphenylphosphino)ferrocene]

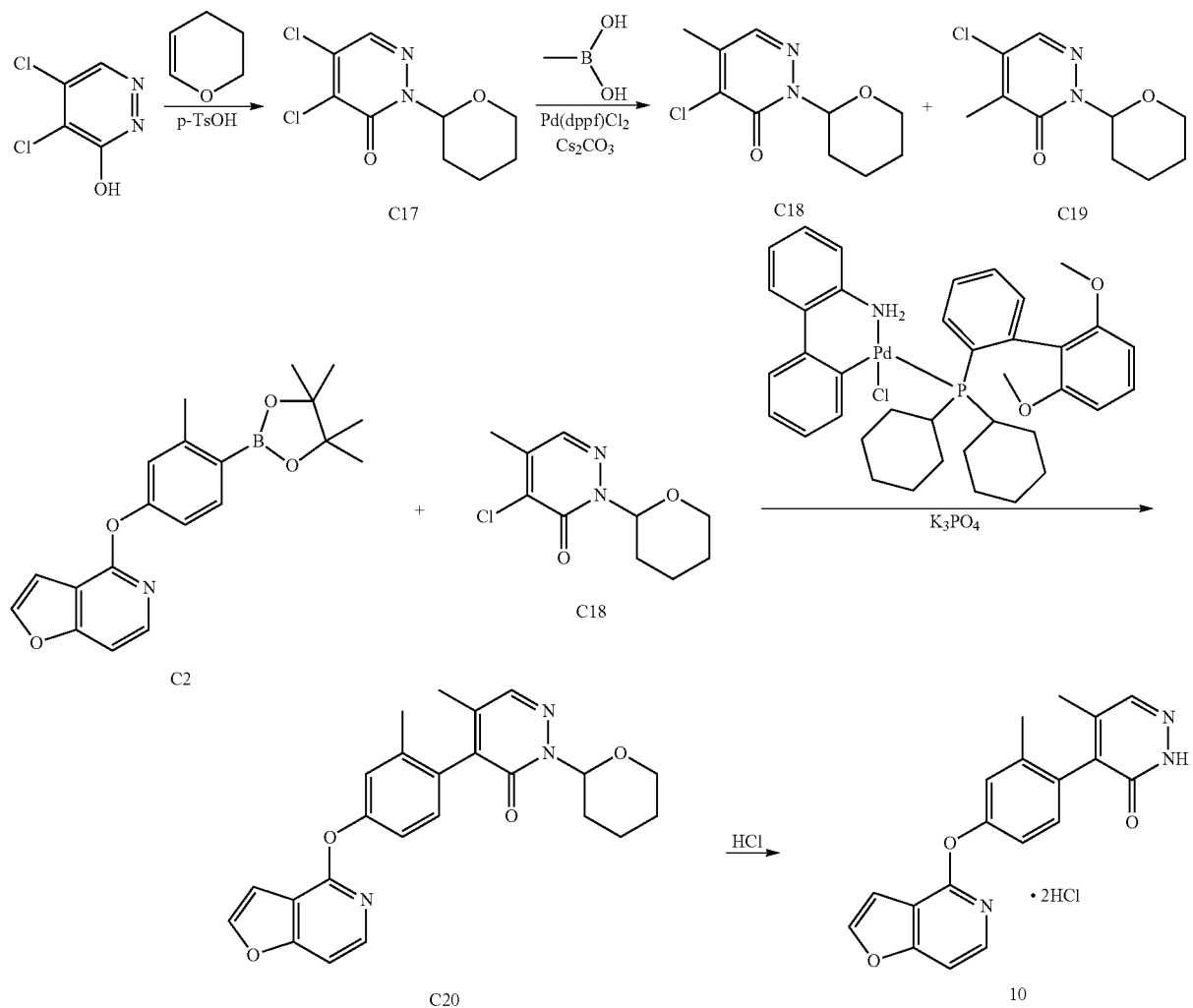

Step 1. Synthesis of 4,5-dichloro-2-(tetrahydro-2H-pyran-2-yl)pyridazin-3(2H)-one (C17)

A mixture of 4,5-dichloropyridazin-3-ol (42 g, 250 mmol), 3,4-dihydro-2H-pyran (168 g, 2.00 mol) and para-toluenesulfonic acid (8.8 g, 51 mmol) in tetrahydrofuran (2 L) was refluxed for 2 days. After cooling to room temperature, the mixture was concentrated under reduced pressure. The residue was purified by chromatography on silica gel dichloropalladium(II) (5 g, 7 mmol). The reaction mixture was stirred at 110° C. for 2 hours, then concentrated under reduced pressure. Purification by silica gel chromatography (Gradient: 3% to 5% ethyl acetate in petroleum ether) provided product C18 as a pale yellow solid (Yield: 9 g, 40 mmol, 25%) and product C19, also as a pale yellow solid (Yield: 9.3 g, 41 mmol, 26%). C18: LCMS m/z 250.8 (M+Na$^+$). $^1$H NMR (400 MHz, CDCl$_3$) δ 7.71 (s, 1H), 6.07 (dd, J=10.7, 2.1 Hz, 1H), 4.10-4.18 (m, 1H), 3.71-3.81 (m, 1H), 2.30 (s, 3H), 1.98-2.19 (m, 2H), 1.53-1.81 (m, 4H).
C19: LCMS m/z 250.7 (M+Na+). $^1$H NMR (400 MHz, CDCl$_3$) δ 7.77 (s, 1H), 6.02 (dd, J=10.7, 2.1 Hz, 1H), 4.10-4.17 (m, 1H), 3.71-3.79 (m, 1H), 2.27 (s, 3H), 1.99-2.22 (m, 2H), 1.51-1.79 (m, 4H).

Step 3. Synthesis of 4-[4-(furo-[3,2-c]pyridin-4-yloxy)-2-methylphenyl]-5-methyl-2-(tetrahydro-2H-pyran-2-yl)pyridazin-3(2H)-one (C20)

A mixture of 4-chloro-5-methyl-2-(tetrahydro-2H-pyran-2-yl)pyridazin-3(2H)-one (C18) (457 mg, 2.00 mmol), 4-[3-methyl-4-(4,4,5,5-tetramethyl-1,3,2-dioxaborolan-2-yl)phenoxy]furo[3,2-c]pyridine (C2) (702 mg, 2.00 mmol) and [2'-(azanidyl-κN)biphenyl-2-yl-κC$_2$](chloro)[dicyclohexyl (2',6'-dimethoxybiphenyl-2-yl)-λ$^5$-phosphanyl]palladium (29 mg, 0.040 mmol) was subjected to three rounds of vacuum evacuation followed by introduction of nitrogen. Degassed tetrahydrofuran (4 mL) was added, followed by degassed aqueous potassium phosphate solution (0.5 M, 8.0 mL, 4.0 mmol), and the reaction mixture was allowed to stir at room temperature for 23 hours. The reaction mixture was then partitioned between ethyl acetate (20 mL) and water (8 mL); the organic layer was dried over sodium sulfate, filtered, and concentrated in vacuo. Purification via silica gel chromatography (Gradient: 20% to 70% ethyl acetate in heptane) afforded the product as a white solid. By NMR, this was determined to consist of a diastereomeric mixture due to the tetrahydropyranyl group. Yield: 588 mg, 1.41 mmol, 70%. LCMS m/z 418.0 (M+H). $^1$H NMR (500 MHz, CDCl$_3$) δ 8.06 (d, J=5.9 Hz, 1H), 7.82 (d, J=2.8 Hz, 1H), 7.63 (d, J=2.3 Hz, 1H), 7.23-7.25 (m, 1H), 7.16-7.17 (m, 1H), 7.06-7.13 (m, 2H), 6.79-6.81 (m, 1H), 6.10 (dd, J=10.6, 2.2 Hz, 1H), 4.14-4.20 (m, 1H), 3.72-3.80 (m, 1H), 2.15-2.25 (m, 1H, assumed; partially obscured by methyl group), 2.14 and 2.15 (2 s, total 3H), 2.01-2.08 (m, 1H, assumed; partially obscured by methyl group), 2.03 and 2.04 (2 s, total 3H), 1.71-1.82 (m, 3H), 1.55-1.63 (m, 1H).

Step 4. Synthesis of 4-[4-(furo-[3,2-c]pyridin-4-yloxy)-2-methylphenyl]-5-methylpyridazin-3(2H)-one, bis-hydrochloride salt (10)

4-[4-(Furo[3,2-c]pyridin-4-yloxy)-2-methylphenyl]-5-methyl-2-(tetrahydro-2H-pyran-2-yl)pyridazin-3(2H)-one (C20) (580 mg, 1.39 mmol) was dissolved in methanol (3 mL), treated with a solution of hydrogen chloride in 1,4-dioxane (4 M, 5.0 mL, 20 mmol) and allowed to stir at room temperature for 3 hours. Removal of solvent under reduced pressure provided the product as a pale yellow solid, presumed to be the bis-hydrochloride salt. Yield: 550 mg, 1.35 mmol, 97%. LCMS m/z 334.0 (M+H). $^1$H NMR (400 MHz, DMSO-d$_6$) δ 13.01 (br s, 1H), 8.15 (d, J=2.3 Hz, 1H), 8.02 (d, J=5.8 Hz, 1H), 7.89 (s, 1H), 7.48 (dd, J=5.8, 1.1 Hz, 1H), 7.16-7.18 (m, 1H), 7.08-7.12 (m, 3H), 2.06 (br s, 3H), 1.95 (s, 3H).

Example 11

4-[4-(3-Chloro-5-methylpyridazin-4-yl)-3-methylphenoxy]furo[3,2-c]pyridine (11)

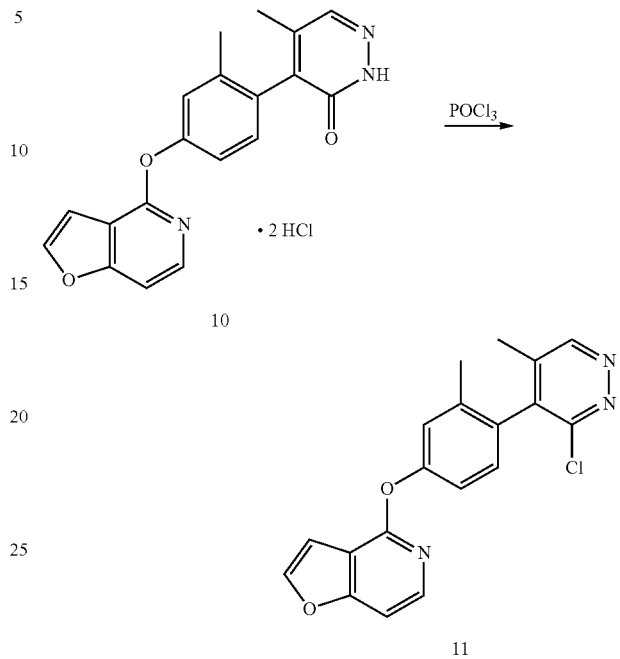

4-[4-(Furo[3,2-c]pyridin-4-yloxy)-2-methylphenyl]-5-methylpyridazin-3(2H)-one, bis-hydrochloride salt (10) (550 mg, 1.35 mmol) was suspended in phosphorus oxychloride (6.0 mL, 64 mmol), and the reaction mixture was heated at 90° C. for 2 hours. After removal of phosphorus oxychloride under reduced pressure, the residue was partitioned between dichloromethane (35 mL), water (10 mL), and saturated aqueous sodium bicarbonate solution (10 mL). The organic layer was dried over sodium sulfate, filtered, and concentrated in vacuo to afford the product as a foamy, pale amber solid. Yield: 465 mg, 1.32 mmol, 98%. LCMS m/z 352.0 (M+H). $^1$H NMR (400 MHz, CDCl$_3$) δ 9.07 (s, 1H), 8.11 (d, J=5.8 Hz, 1H), 7.69 (d, J=2.3 Hz, 1H), 7.31 (dd, J=5.9, 0.9 Hz, 1H), 7.25-7.28 (m, 1H, assumed; partially obscured by solvent peak), 7.21-7.24 (m, 1H), 7.09 (d, J=8.2 Hz, 1H), 6.84 (dd, J=2.2, 0.8 Hz, 1H), 2.19 (s, 3H), 2.08 (br s, 3H).

Example 12

4-[4-(3,5-Dimethylpyridazin-4-yl)-3-methylphenoxy]furo[3,2-c]pyridine (12)

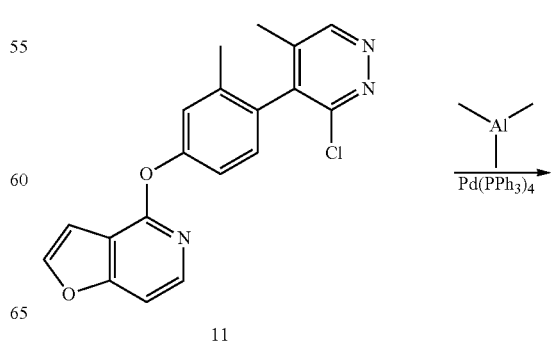

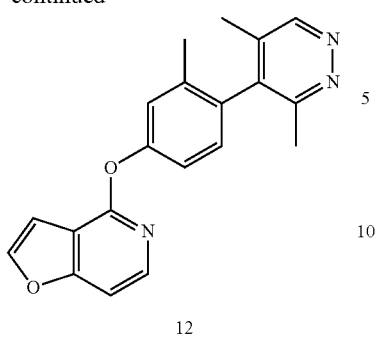

12

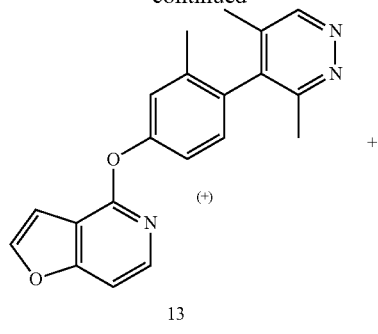

13

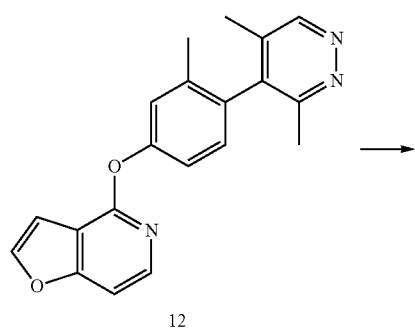

14

Nitrogen was bubbled into a mixture of tetrakis(triphenylphosphine)palladium(0) (31.0 mg, 0.027 mmol) and 4-[4-(3-chloro-5-methylpyridazin-4-yl)-3-methylphenoxy]furo[3,2-c]pyridine (11) (427 mg, 1.21 mmol) in 1,4-dioxane (12 mL) for 10 minutes. A solution of trimethylaluminum in toluene (2 M, 1.2 mL, 2.4 mmol) was added, and the reaction mixture was heated to 95° C. for 90 minutes, then cooled in an ice bath and treated drop-wise with methanol (12 mL) {Caution: gas evolution!}. The mixture was filtered through Celite and the filter cake was rinsed with additional methanol (35 mL); the filtrate was concentrated in vacuo and purified using silica gel chromatography (Eluent: 2.5% methanol in ethyl acetate) to provide the product as a solid. Yield: 320 mg, 0.966 mmol, 80%. LCMS m/z 332.1 (M+H). $^1$H NMR (500 MHz, CD$_3$OD) δ 9.05 (s, 1H), 7.99 (d, J=6.0 Hz, 1H), 7.90 (d, J=2.2 Hz, 1H), 7.39 (dd, J=5.9, 0.9 Hz, 1H), 7.26-7.27 (m, 1H), 7.19 (br dd, half of ABX pattern, J=8.3, 2.1 Hz, 1H), 7.15 (d, half of AB pattern, J=8.3 Hz, 1H), 6.94 (dd, J=2.2, 1.0 Hz, 1H), 2.42 (s, 3H), 2.16 (s, 3H), 2.03 (s, 3H).

Examples 13 and 14

(+)-4-[4-(3,5-Dimethylpyridazin-4-yl)-3-methylphenoxy]furo-[3,2-c]pyridine (13) and H-4-[4-(3,5-Dimethylpyridazin-4-yl)-3-methylphenoxy]furo-[3,2-c]pyridine (14)

Example 12 (4-[4-(3,5-dimethylpyridazin-4-yl)-3-methylphenoxy]furo[3,2-c]pyridine) (316 mg) was separated into its component atropenantiomers using supercritical fluid chromatography (Column: Chiralpak AS-H, 5 μm; Eluent: 7:3 carbon dioxide/ethanol). Both were obtained as solids. First-eluting atropenantiomer: 13 [designated as the (+) atropenantiomer according to its observed rotation data], yield: 137 mg, 43%. LCMS m/z 332.3 (M+H). $^1$H NMR (400 MHz, CD$_3$OD) δ 9.03 (s, 1H), 7.99 (d, J=5.8 Hz, 1H), 7.89 (d, J=2.2 Hz, 1H), 7.38 (br d, J=5.8 Hz, 1H), 7.24-7.27 (m, 1H), 7.19 (br dd, half of ABX pattern, J=8.3, 2.0 Hz, 1H), 7.14 (d, half of AB quartet, J=8.2 Hz, 1H), 6.91-6.94 (m, 1H), 2.41 (s, 3H), 2.14 (s, 3H), 2.02 (s, 3H). Second-eluting atropenantiomer: 14 [designated as the (−)-atropenantiomer according to its observed rotation data], yield: 132 mg, 42%. LCMS m/z 332.3 (M+H). $^1$H NMR (400 MHz, CD$_3$OD) δ 9.04 (s, 1H), 7.99 (d, J=6.0 Hz, 1H), 7.89 (d, J=2.2 Hz, 1H), 7.38 (dd, J=6.0, 1.0 Hz, 1H), 7.25-7.27 (m, 1H), 7.19 (br dd, half of ABX pattern, J=8.3, 2.2 Hz, 1H), 7.15 (d, half of AB quartet, J=8.2 Hz, 1H), 6.93 (dd, J=2.2, 1.0 Hz, 1H), 2.41 (s, 3H), 2.15 (s, 3H), 2.02 (s, 3H).

Example 15

4-[4-(1-tert-Butyl-4-methyl-1H-pyrazol-5-yl)-3-methylphenoxy]furo-[3,2-c]pyridine (15)

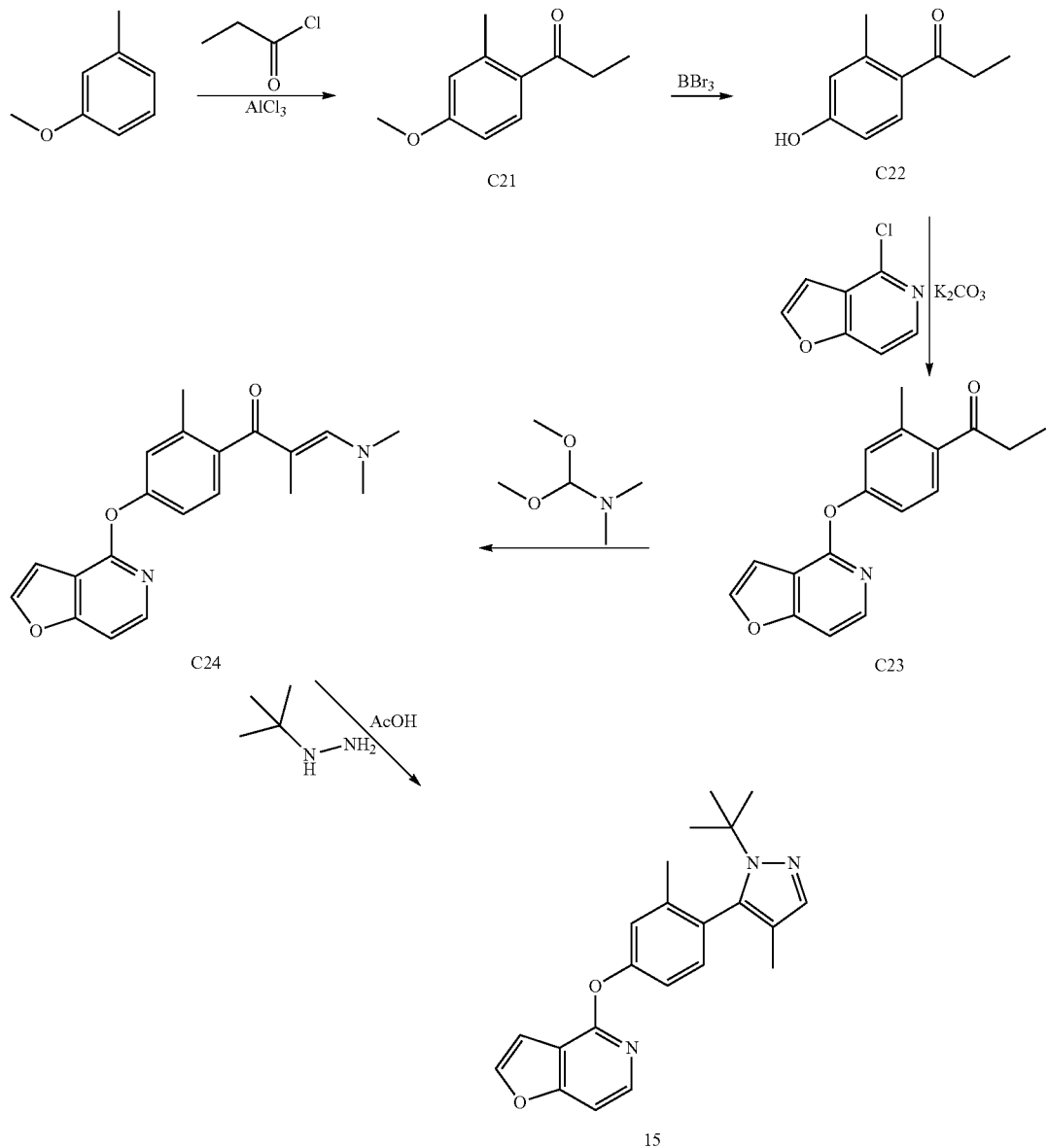

Step 1. Synthesis of 1-(4-methoxy-2-methylphenyl)propan-1-one (C21)

To a mixture of 1-methoxy-3-methylbenzene (12.2 g, 100 mmol) and propanoyl chloride (18.5 g, 200 mmol) in dichloromethane (200 mL) was added aluminum chloride (26.5 g, 199 mmol) in one portion, and the reaction mixture was stirred at room temperature for 4 hours. The reaction was quenched with aqueous hydrochloric acid (1 N, 100 mL), and the organic layer was dried over magnesium sulfate, filtered, and concentrated in vacuo. The residue was purified by silica gel chromatography to afford the product as a yellow solid. Yield: 3.87 g, 21.7 mmol, 22%.

Step 2. Synthesis of 1-(4-hydroxy-2-methylphenyl)propan-1-one (C22)

Boron tribromide (5.57 g, 22.2 mmol) was added to a solution of 1-(4-methoxy-2-methylphenyl)propan-1-one (C21) (3.87 g, 21.7 mmol) in dichloromethane (50 mL), and the reaction mixture was stirred at room temperature for 4 hours. Water (20 mL) was added, and the organic layer was separated, dried over magnesium sulfate, and concentrated under reduced pressure to provide the product as a yellow solid, which was used without further purification. Yield: 3.77 g, >100%.

Step 3. Synthesis of 1-[4-(furo-[3,2-c]pyridin-4-yloxy)-2-methylphenyl]propan-1-one (C23)

A mixture of 1-(4-hydroxy-2-methylphenyl)propan-1-one (C22) (1.64 g, <10.0 mmol), 4-chlorofuro[3,2-c]pyridine (1.53 g, 9.96 mmol), and potassium carbonate (2.76 g, 20.0 mmol) in N,N-dimethylformamide (50 mL) was heated to reflux for 8 hours. The reaction mixture was partitioned between water (50 mL) and ethyl acetate (150 mL); the organic layer was dried over magnesium sulfate and concentrated in vacuo to afford the product as a yellow oil, which was used without additional purification. Yield: 2.97 g, >100%.

Step 4. Synthesis of 3-(dimethylamino)-1-[4-(furo[3,2-c]pyridin-4-yloxy)-2-methylphenyl]-2-methylprop-2-en-1-one (C24)

1-[4-(Furo[3,2-c]pyridin-4-yloxy)-2-methylphenyl]propan-1-one (C23) (2.87 g, <10.7 mmol) in a mixture of N,N-dimethylformamide dimethyl acetal (10 mL) and N,N-dimethylformamide (10 mL) was heated to reflux for 30 minutes. After removal of solvent under reduced pressure, the residue was washed with ethyl acetate to provide the product as a yellow solid. Yield: 1.76 g, 5.23 mmol, >49%. LCMS m/z 337.1 (M+H). $^1$H NMR (400 MHz, CD$_3$OD) δ 7.94 (d, J=6.1 Hz, 1H), 7.87 (d, J=2.2 Hz, 1H), 7.35 (dd, J=5.9, 1.0 Hz, 1H), 7.14 (d, J=8.2 Hz, 1H), 7.04-7.07 (m, 2H), 7.00 (br dd, J=8.1, 2.4 Hz, 1H), 6.90 (dd, J=2.3, 1.0 Hz, 1H), 3.15 (s, 6H), 2.24 (s, 3H), 2.14 (s, 3H).

Step 5. Synthesis of 4-[4-(1-tert-butyl-4-methyl-1H-pyrazol-5-yl)-3-methylphenoxy]furo[3,2-c]pyridine (15)

A solution of 3-(dimethylamino)-1-[4-(furo[3,2-c]pyridin-4-yloxy)-2-methylphenyl]-2-methylprop-2-en-1-one (C24) in ethanol (0.125 M, 0.600 mL, 0.075 mmol) was combined with a solution of tert-butylhydrazine in 0.2 M aqueous hydrochloric acid (0.128 M, 0.700 mL, 0.090 mmol). Acetic acid (0.05 mL, 0.9 mmol) was added, and the reaction mixture was shaken at 100° C. for 3 hours. Solvents were removed in vacuo, and the residue was purified by HPLC (Column: Phenomenex Gemini C18, 5 µm; Mobile phase A: aqueous ammonium hydroxide, pH 10; Mobile phase B: acetonitrile; Gradient: 70% to 90% B) to afford the product. LCMS m/z 362 (M+H). Retention time: 3.056 min (Column: Welch XB-C18, 2.1×50 mm, 5 µm; Mobile phase A: 0.0375% trifluoroacetic acid in water; Mobile phase B: 0.01875% trifluoroacetic acid in acetonitrile; Gradient: 25% B for 0.50 minutes, 25% to 100% B over 3.0 minutes; Flow rate: 0.8 mL/minute).

Example 16

5-(Furo[3,2-c]pyridin-4-yloxy)-2-(imidazo[1,2-a]pyridin-5-yl)aniline (16)

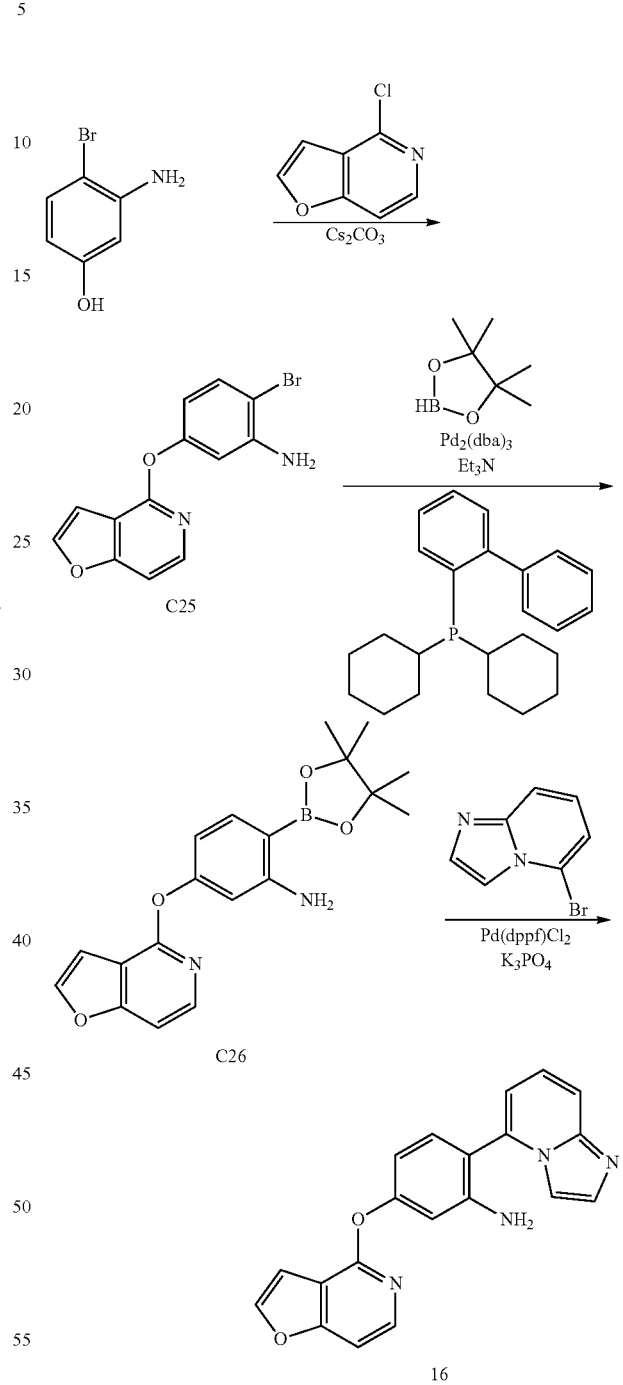

Step 1. Synthesis of 2-bromo-5-(furo[3,2-c]pyridin-4-yloxy)aniline (C25)

This reaction was carried out in two identical batches. A mixture of 3-amino-4-bromophenol (13 g, 69 mmol), cesium carbonate (45 g, 140 mmol) and 4-chlorofuro[3,2-c]pyridine (7.0 g, 46 mmol) in dimethyl sulfoxide (200 mL) was heated to 130° C. for 18 hours. The two batches were cooled to room temperature and combined, and the mixture was poured into ice water (800 mL) and extracted with ethyl acetate (5×1200 mL). The combined organic layers were washed with saturated aqueous sodium chloride solution (500 mL), dried over anhydrous sodium sulfate, filtered, and concentrated under reduced pressure. Purification using silica gel chromatography (Gradient: 17% to 25% ethyl acetate in petroleum ether) provided the product as a white solid. Yield: 25 g, 82 mmol, 89%.

Step 2. Synthesis of 5-(furo-[3,2-c]pyridin-4-yloxy)-2-(4,4,5,5-tetramethyl-1,3,2-dioxaborolan-2-yl)aniline (C26)

This reaction was carried out in two identical batches. To a solution of 2-bromo-5-(furo[3,2-c]pyridin-4-yloxy)aniline (C25) (10.9 g, 35.7 mmol), tris(dibenzylideneacetone)dipalladium(0) (3.3 g, 3.6 mmol), and biphenyl-2-yl(dicyclohexyl)phosphane (1.3 g, 3.7 mmol) in toluene (250 mL) was added triethylamine (10.9 g, 108 mmol) and 4,4,5,5-tetramethyl-1,3,2-dioxaborolane (13.8 g, 108 mmol), and the reaction mixture was heated to reflux for 18 hours. The two batches were cooled to room temperature and combined, then filtered and evaporated to dryness. The residue was dissolved in methanol, filtered and concentrated in vacuo. Purification via silica gel chromatography (Gradient: 9% to 25% ethyl acetate in petroleum ether) afforded the product as a yellow solid. Yield: 13.5 g, 38.3 mmol, 54%. $^1$H NMR (400 MHz, DMSO-$d_6$) δ 8.10 (d, J=2.0 Hz, 1H), 8.00 (d, J=5.9 Hz, 1H), 7.47 (dd, J=5.9, 0.8 Hz, 1H), 7.40 (d, J=8.2 Hz, 1H), 6.96 (dd, J=2.4, 0.8 Hz, 1H), 6.36 (d, J=2.0 Hz, 1H), 6.28 (dd, J=8.2, 2.4 Hz, 1H), 5.65 (br s, 2H), 1.29 (s, 12H).

Step 3. Synthesis of 5-(furo-[3,2-c]pyridin-4-yloxy)-2-(imidazol[1,2-a]pyridin-5-yl)aniline (16)

This reaction was carried out in two identical batches. A mixture of 5-(furo[3,2-c]pyridin-4-yloxy)-2-(4,4,5,5-tetramethyl-1,3,2-dioxaborolan-2-yl)aniline (C26) (4.5 g, 13 mmol), potassium phosphate trihydrate (9.6 g, 36 mmol), [1,1'-bis(diphenylphosphino)ferrocene]dichloropalladium (11) (1.1 g, 1.3 mmol) and 5-bromoimidazo[1,2-a]pyridine (3.8 g, 19 mmol) in 2-methyltetrahydrofuran (50 mL) and water (10 mL) was heated to 75° C. for 18 hours. The two batches were cooled to room temperature and combined. After filtration, the filter cake was washed with water, and the combined filtrates were extracted with ethyl acetate (4×100 mL). The combined organic layers were washed with saturated aqueous sodium chloride solution, dried over sodium sulfate, filtered, and concentrated in vacuo. The residue was combined with the filter cake and purified by silica gel chromatography (Gradient: 2% to 5% methanol in dichloromethane) to provide the product as a yellow solid. Yield: 4.2 g, 12 mmol, 46%. LCMS m/z 342.9 (M+H). $^1$H NMR (400 MHz, DMSO-$d_6$) δ 8.14 (d, J=2.2 Hz, 1H), 8.06 (d, J=5.9 Hz, 1H), 7.60 (br d, J=9.0 Hz, 1H), 7.58 (d, J=1.0 Hz, 1H), 7.50 (d, J=5.9, 0.8 Hz, 1H), 7.33 (dd, J=9.0, 6.8 Hz, 1H), 7.32 (br s, 1H), 7.19 (d, J=8.2 Hz, 1H), 7.07 (dd, J=2.2, 0.9 Hz, 1H), 6.89 (br dd, J=6.8, 0.7 Hz, 1H), 6.65 (d, J=2.4 Hz, 1H), 6.50 (dd, J=8.4, 2.4 Hz, 1H), 5.17 (br s, 2H).

Example 17

N-[4-(Imidazo[1,2-a]pyridin-5-yl)-3-methylphenyl] furo[3,2-c]pyridin-4-amine (17)

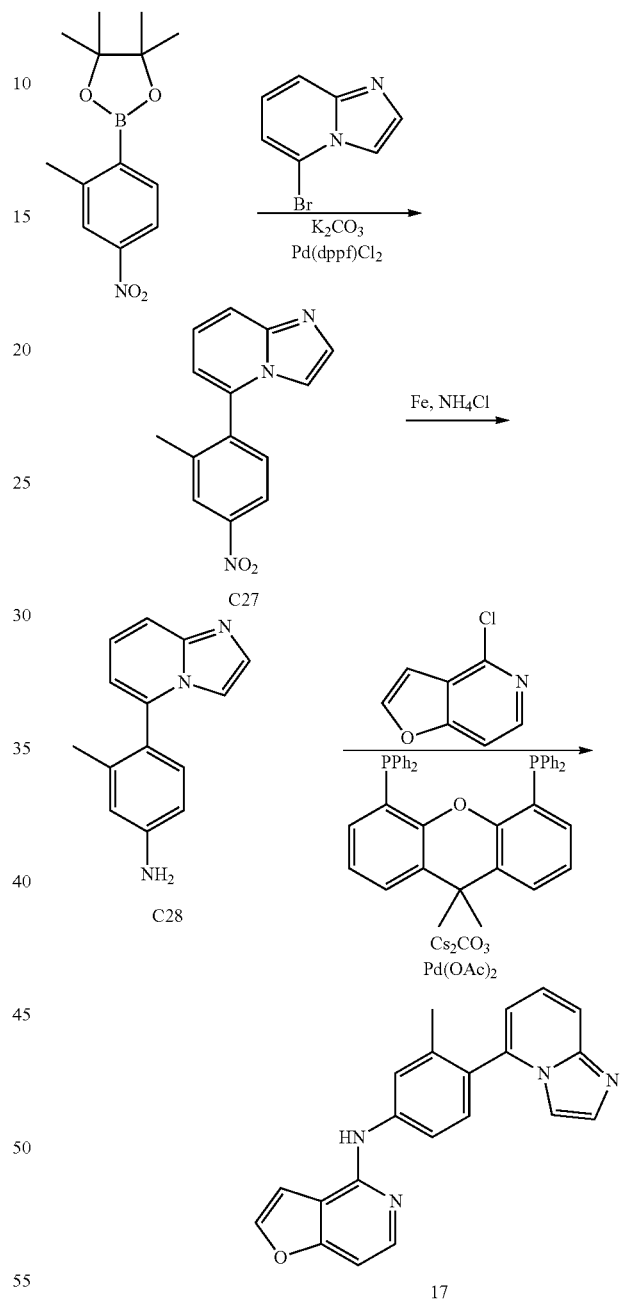

Step 1. Synthesis of 5-(2-methyl-4-nitrophenyl)imidazol[1,2-a]pyridine (C27)

A mixture of 4,4,5,5-tetramethyl-2-(2-methyl-4-nitrophenyl)-1,3,2-dioxaborolane (390 mg, 1.48 mmol), 5-bromoimidazo[1,2-a]pyridine (243 mg, 1.23 mmol), potassium carbonate (683 mg, 4.94 mmol) and [1,1'-bis(diphenylphosphino)ferrocene]dichloropalladium(II) (90 mg, 0.12 mmol)

in N,N-dimethylformamide (10 mL) was stirred at 120° C. for 1 hour. The reaction mixture was filtered and the filtrate was concentrated in vacuo. Purification via silica gel chromatography (Eluent: 2% methanol in dichloromethane) afforded the product as a yellow oil. Yield: 320 mg, 1.26 mmol, 100%. $^1$H NMR (400 MHz, CDCl$_3$) δ 8.27 (br s, 1H), 8.22 (br d, J=8.5 Hz, 1H), 7.73 (d, J=9.0 Hz, 1H), 7.66 (br s, 1H), 7.56 (d, J=8.0 Hz, 1H), 7.31 (dd, J=9.0, 7.0 Hz, 1H), 7.05 (s, 1H), 6.75 (d, J=6.5 Hz, 1H), 2.23 (s, 3H).

Step 2. Synthesis of 4-(imidazo[1,2-a]pyridin-5-yl)-3-methylaniline (C28)

A mixture of 5-(2-methyl-4-nitrophenyl)imidazo[1,2-a]pyridine (C27) (300 mg, 1.18 mmol), iron (199 mg, 3.56 mmol) and ammonium chloride (253 mg, 4.73 mmol) in ethanol (9 mL) and water (3 mL) was heated at reflux for 1 hour. The mixture was filtered and the filtrate was concentrated in vacuo; purification via silica gel chromatography (Eluent: 5% methanol in dichloromethane) provided the product as a solid. Yield: 224 mg, 1.00 mmol, 85%. $^1$H NMR (400 MHz, CDCl$_3$) δ 7.72 (br d, J=9 Hz, 1H), 7.61 (br s, 1H), 7.29-7.36 (m, 1H), 7.19 (br s, 1H), 7.12 (d, J=8.3 Hz, 1H), 6.74 (br d, J=6.5 Hz, 1H), 6.67-6.69 (m, 1H), 6.64 (dd, J=8, 2 Hz, 1H), 2.01 (s, 3H).

Step 3. Synthesis of N-[4-(imidazo[1,2-a]pyridin-5-yl)-3-methylphenyl]furo[3,2-c]pyridin-4-amine (17)

A mixture of 4-(imidazo[1,2-a]pyridin-5-yl)-3-methylaniline (C28) (185 mg, 0.828 mmol), 4-chlorofuro[3,2-c]pyridine (127 mg, 0.827 mmol), cesium carbonate (810 mg, 2.49 mmol), palladium(II) acetate (28 mg, 0.12 mmol) and 4,5-bis(diphenylphosphino)-9,9-dimethylxanthene (Xantphos, 72 mg, 0.12 mmol) in 1,4-dioxane (8 mL) was stirred at 120° C. for 2 hours. After the reaction mixture was filtered, the filtrate was diluted with ethyl acetate (100 mL), washed with saturated aqueous sodium chloride solution, and concentrated in vacuo. The residue was purified via preparative thin layer chromatography (Eluent: 5% methanol in dichloromethane) to afford the product as a yellow solid. Yield: 157 mg, 0.461 mmol, 56%. LCMS m/z 341.3 (M+H). $^1$H NMR (400 MHz, CDCl$_3$) δ 8.16 (d, J=6.0 Hz, 1H), 7.58-7.67 (m, 4H), 7.29 (d, J=8.0 Hz, 1H), 7.25-7.36 (br m, 1H, assumed; partially obscured by solvent peak), 7.21 (br s, 1H), 7.09 (br d, J=6 Hz, 1H), 6.92-7.03 (br m, 1H), 6.72-6.80 (br m, 2H), 2.11 (s, 3H).

Example 18

4-[4-(4-Chloro-6-methylpyrimidin-5-yl)-3-methylphenoxy]furo[3,2-c]pyridine (18)

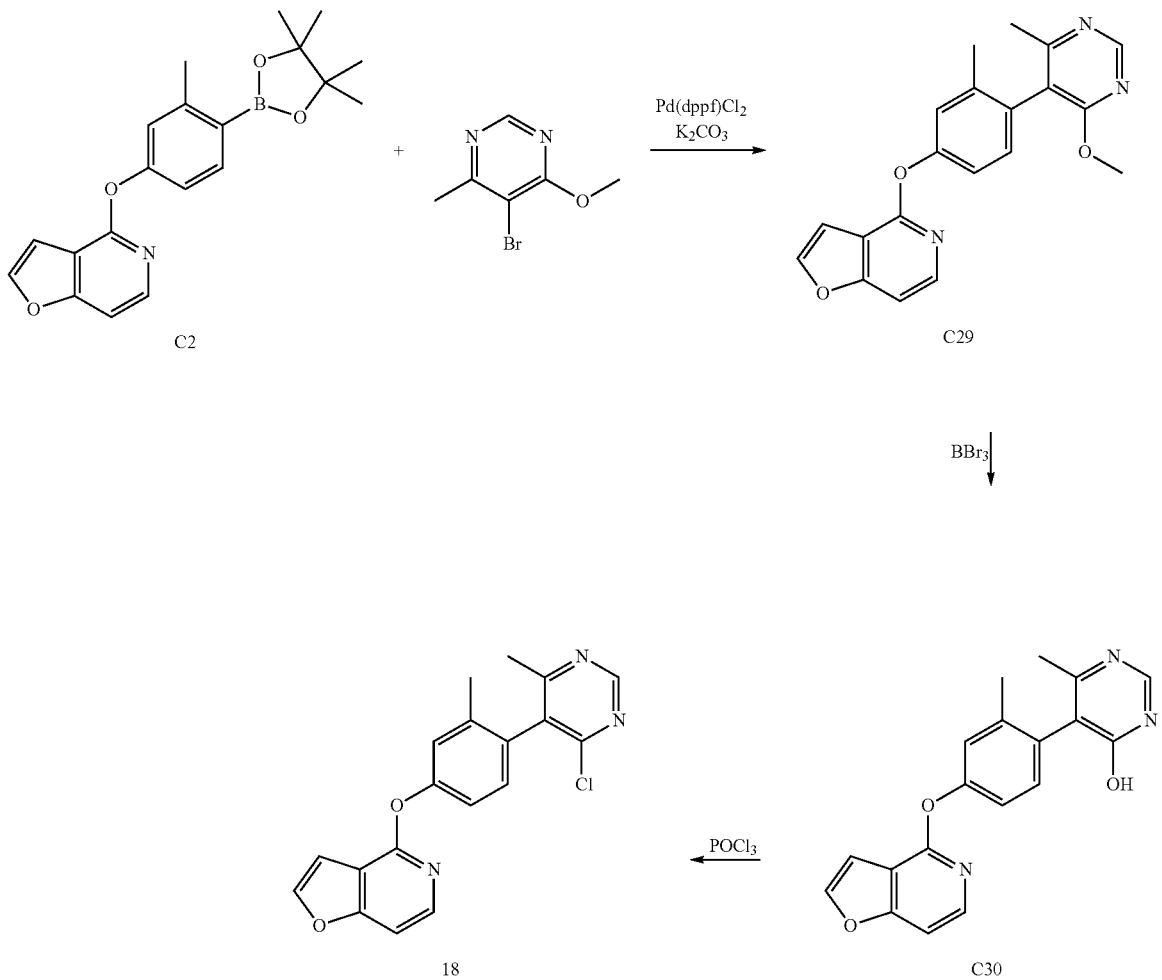

Step 1. Synthesis of 4-[4-(4-methoxy-6-methylpyrimidin-5-yl)-3-methylphenoxy]furo[3,2-c]pyridine (C29)

A mixture of 4-[3-methyl-4-(4,4,5,5-tetramethyl-1,3,2-dioxaborolan-2-yl)phenoxy]furo[3,2-c]pyridine (C2) (4.0 g, 11 mmol), 5-bromo-4-methoxy-6-methylpyrimidine (Z. Wang et al., *Synthesis* 2011, 1529-1531) (2.0 g, 10 mmol), [1,1'-bis(diphenylphosphino)ferrocene]dichloropalladium (II) (1.1 g, 1.4 mmol) and potassium carbonate (4.0 g, 29 mmol) in 1,4-dioxane (30 mL) containing 5 drops of water was heated at 120° C. for 2 hours. After filtration and concentration of the filtrate under reduced pressure, the residue was purified by silica gel chromatography (Eluent: 33% ethyl acetate in petroleum ether) to give the product as a yellow solid. Yield: 1.8 g, 5.2 mmol, 52%. $^1$H NMR (400 MHz, CDCl$_3$) δ 8.72 (s, 1H), 8.07 (d, J=6.0 Hz, 1H), 7.66 (d, J=2.3 Hz, 1H), 7.25 (dd, J=5.9, 0.9 Hz, 1H), 7.19-7.21 (m, 1H), 7.09-7.16 (m, 2H), 6.88 (dd, J=2.3, 0.8 Hz, 1H), 3.95 (s, 3H), 2.29 (s, 3H), 2.07 (s, 3H).

Step 2. Synthesis of 5-[4-(furo-[3,2-c]pyridin-4-yloxy)-2-methylphenyl]-6-methylpyrimidin-4-ol (C30)

Boron tribromide (20 g, 80 mmol) was slowly added to a solution of 4-[4-(4-methoxy-6-methylpyrimidin-5-yl)-3-methylphenoxy]furo[3,2-c]pyridine (C29) (1.8 g, 5.2 mmol) in dichloromethane (150 mL) at −60° C. The reaction mixture was allowed to warm to room temperature and stirred for 18 hours. Methanol (150 mL) was then added, and the pH was adjusted to 6 via addition of solid sodium bicarbonate. The mixture was filtered and the filtrate was concentrated in vacuo. This residue was mixed with acetone and filtered again; concentration of the filtrate afforded the product as a yellow solid. Yield: 1.5 g, 4.5 mmol, 87%.

Step 3. Synthesis of 4-[4-(4-chloro-6-methylpyrimidin-5-yl)-3-methylphenoxy]furo-[3,2-c]pyridine (18)

A mixture of 5-[4-(furo[3,2-c]pyridin-4-yloxy)-2-methylphenyl]-6-methylpyrimidin-4-ol (C30) (1.5 g, 4.5 mmol) and phosphorus oxychloride (100 g, 65 mmol) was heated at reflux for 2 hours. After concentration under reduced pressure, the residue was slowly treated with saturated aqueous sodium bicarbonate solution (200 mL). The resulting mixture was extracted with ethyl acetate (4×100 mL) and the combined organic layers were dried, filtered and concentrated in vacuo. Purification via silica gel chromatography (Eluent: 50% ethyl acetate in petroleum ether) provided the product as a yellow solid. Yield: 750 mg, 2.13 mmol, 47%. LCMS m/z 352.1 (M+H). $^1$H NMR (400 MHz, CD$_3$OD) δ 8.86 (s, 1H), 7.99 (br d, J=5.9 Hz, 1H), 7.88 (d, J=2.3 Hz, 1H), 7.38 (dd, J=5.9, 0.9 Hz, 1H), 7.22-7.25 (m, 1H), 7.20 (d, half of AB quartet, J=8.2 Hz, 1H), 7.16 (br dd, half of ABX pattern, J=8.3, 2.2 Hz, 1H), 6.88 (dd, J=2.3, 1.0 Hz, 1H), 2.35 (s, 3H), 2.08 (br s, 3H).

Example 19

5-[4-(Furo[3,2-c]pyridin-4-yloxy)-2-methylphenyl]-6-methylimidazo[1,2-a]pyrazin-8-ol (19)

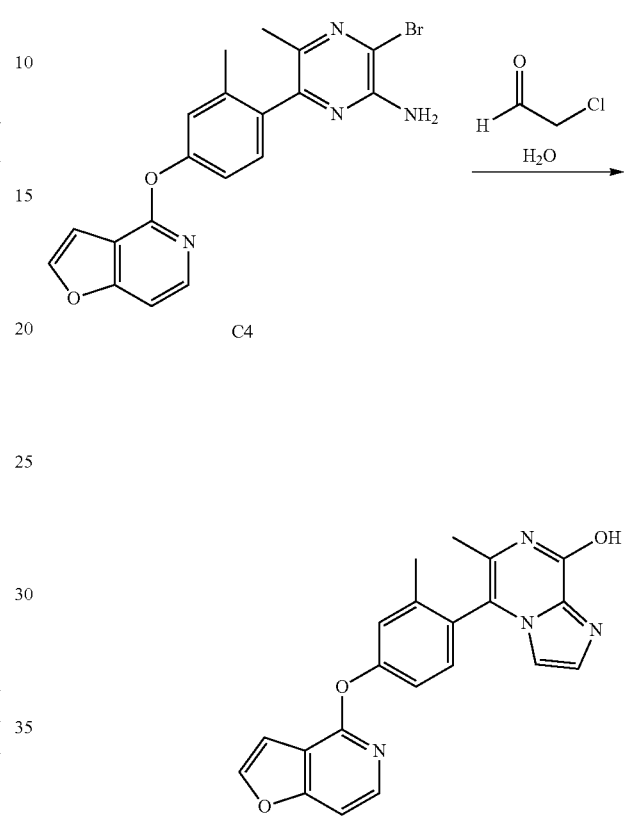

To a mixture of 3-bromo-6-[4-(furo[3,2-c]pyridin-4-yloxy)-2-methylphenyl]-5-methylpyrazin-2-amine (C4) (1.5 g, 3.6 mmol) in water (30 mL) was added chloroacetaldehyde (0.57 g, 7.3 mmol), and the reaction mixture was heated at reflux for 18 hours. After basification to pH 8 with solid sodium bicarbonate, the mixture was concentrated in vacuo. Purification via silica gel chromatography (Gradient: 2% to 5% methanol in dichloromethane) provided the product as a yellow solid. Yield: 255 mg, 0.685 mmol, 19%. LCMS m/z 372.8 (M+H). $^1$H NMR (400 MHz, CD$_3$OD) δ 7.98 (d, J=5.8 Hz, 1H), 7.93 (d, J=2.3 Hz, 1H), 7.46-7.48 (m, 1H), 7.43 (d, J=8.3 Hz, 1H), 7.40 (br d, J=5.8 Hz, 1H), 7.31 (d, J=2.3 Hz, 1H), 7.22 (dd, J=8.3, 2.5 Hz, 1H), 7.17-7.18 (m, 1H), 7.01-7.03 (m, 1H), 2.16 (s, 3H), 2.07 (s, 3H).

Example 20

[2-(4,6-Dimethylpyrimidin-5-yl)-5-(furo[3,2-c]pyridin-4-yloxy)phenyl]methanol (20)

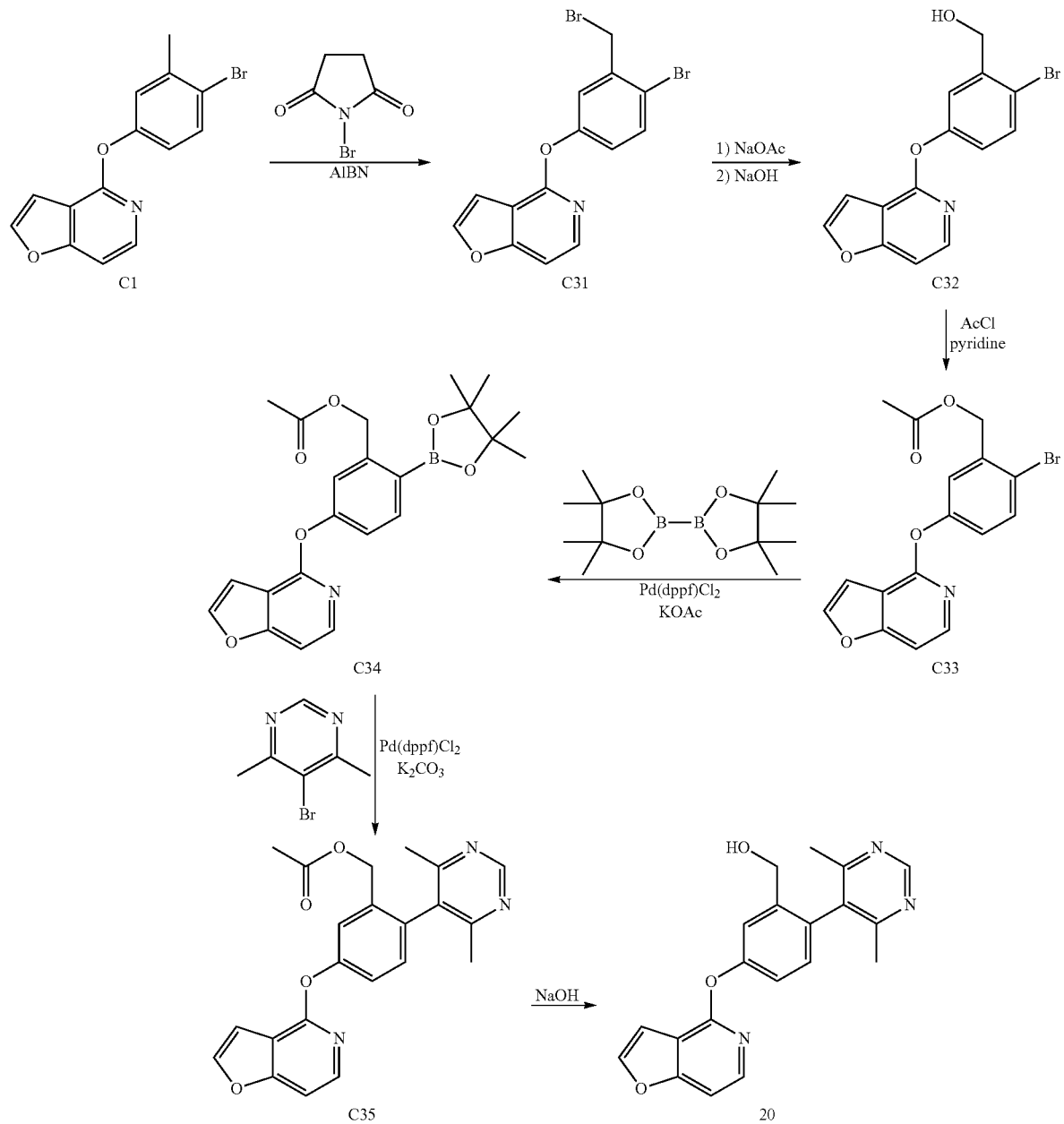

Step 1. Synthesis of 4-[4-bromo-3-(bromomethyl)phenoxy]furo[3,2-c]pyridine (C31)

To a solution of 4-(4-bromo-3-methylphenoxy)furo[3,2-c]pyridine (C1) (4.00 g, 13.2 mmol) in carbon tetrachloride (80 mL) was added N-bromosuccinimide (2.34 g, 13.2 mmol) and 2,2'-azobisisobutyronitrile (AIBN, 108 mg, 0.658 mmol) at room temperature. The reaction mixture was heated to reflux for 3 hours, cooled to room temperature, and treated with water (150 mL). The mixture was extracted with dichloromethane (3×50 mL), and the combined organic layers were dried over sodium sulfate and concentrated in vacuo to give the crude product. Yield: 5.04 g, 13.2 mmol, 100%. LCMS m/z 383.7 (M+H).

Step 2. Synthesis of [2-bromo-5-(furo[3,2-c]pyridin-4-yloxy)phenyl]methanol (C32)

To a solution of 4-[4-bromo-3-(bromomethyl)phenoxy]furo[3,2-c]pyridine (C31) (5.04 g, 13.2 mmol) in N,N-dimethylformamide (60 mL) was added sodium acetate (5.40 g, 65.8 mmol) at room temperature. The reaction mixture was heated to 80° C. for 3 hours, then cooled and partitioned between water (150 mL) and dichloromethane (200 mL). The aqueous layer was separated and extracted with dichloromethane (3×50 mL). The combined organic layers were dried over sodium sulfate and concentrated in vacuo; the resulting residue was dissolved in methanol (40 mL) and treated with aqueous sodium hydroxide solution (1 N, 13.1 mL, 13.1 mmol). After stirring for 1 hour at room temperature, the reaction mixture was partitioned between water (100 mL) and dichloromethane (100 mL). The aqueous layer was separated and extracted with dichloromethane (3×50 mL). The combined organic layers were dried over sodium sulfate and concentrated under reduced pressure to afford the crude product. Yield: 4.2 g, 13.1 mmol, 99%. LCMS m/z 321.7 (M+H).

Step 3. Synthesis of 2-bromo-5-(furo[3,2-c]pyridin-4-yloxy)benzyl acetate (C33)

[2-Bromo-5-(furo[3,2-c]pyridin-4-yloxy)phenyl]methanol (C32) (230 mg, 0.718 mmol), pyridine (170 mg, 2.15 mmol), and acetyl chloride (113 mg, 1.44 mmol) were combined in tetrahydrofuran (5 mL) at room temperature. The reaction mixture was subjected to microwave irradiation at 60° C. for 40 minutes, then poured into saturated aqueous sodium bicarbonate solution (30 mL). After extraction with dichloromethane (3×20 mL), the combined organic layers were dried over sodium sulfate, filtered, and concentrated in vacuo to afford the product. Yield: 260 mg, 0.718 mmol, 100%. $^1$H NMR (400 MHz, CDCl$_3$) δ 8.00 (d, J=5.8 Hz, 1H), 7.67 (d, J=2.0 Hz, 1H), 7.62 (d, J=8.5 Hz, 1H), 7.32 (d, J=2.5 Hz, 1H), 7.23 (d, J=6.0 Hz, 1H), 7.10 (dd, J=8.6, 2.6 Hz, 1H), 6.90-6.93 (m, 1H), 5.20 (s, 2H), 2.14 (s, 3H).

Step 4. Synthesis of 5-(furo-[3,2-c]pyridin-4-yloxy)-2-(4,4,5,5-tetramethyl-1,3,2-dioxaborolan-2-yl)benzyl acetate (C34)

To 2-bromo-5-(furo[3,2-c]pyridin-4-yloxy)benzyl acetate (C33) (260 mg, 0.718 mmol) in 1,4-dioxane (6 mL) were added 4,4,4',4',5,5,5',5'-octamethyl-2,2'-bi-1,3,2-dioxaborolane (237 mg, 0.933 mmol), potassium acetate (211 mg, 2.15 mmol) and [1,1'-bis(diphenylphosphino)ferrocene]dichloropalladium(II) (157 mg, 0.215 mmol) at room temperature. The mixture was heated to 80° C. and stirred for 3 hours, then cooled and filtered. The filtrate was concentrated in vacuo and purified by silica gel chromatography to provide the product. Yield: 164 mg, 0.401 mmol, 56%. $^1$H NMR (400 MHz, CD$_3$OD) δ 7.97 (d, J=6.0 Hz, 1H), 7.85-7.89 (m, 2H), 7.39 (d, J=6.0 Hz, 1H), 7.20-7.23 (m, 1H), 7.11-7.15 (m, 1H), 6.82-6.84 (m, 1H), 5.36 (s, 2H), 2.1 (s, 3H), 1.36 (s, 12H).

Step 5. Synthesis of 2-(4,6-dimethylpyrimidin-5-yl)-5-(furo-[3,2-c]pyridin-4-yloxy)benzyl acetate (C35)

To a solution of 5-(furo[3,2-c]pyridin-4-yloxy)-2-(4,4,5,5-tetramethyl-1,3,2-dioxaborolan-2-yl)benzyl acetate (C34) (82 mg, 0.20 mmol) in 1,4-dioxane (10 mL) were added 5-bromo-4,6-dimethylpyrimidine (41 mg, 0.22 mmol), potassium carbonate (83 mg, 0.6 mmol), [1,1'-bis(diphenylphosphino)ferrocene]dichloropalladium(II) (44 mg, 0.060 mmol) and water (5 drops) at room temperature. The reaction mixture was degassed with nitrogen for 5 minutes, then subjected to microwave irradiation at 120° C. for 50 minutes. After filtration of the reaction mixture, the filtrate was concentrated in vacuo; purification was carried out by preparative thin layer chromatography to give the product. Yield: 28 mg, 0.072 mmol, 36%. LCMS m/z 389.9 (M+H).

Step 6. Synthesis of [2-(4,6-dimethylpyrimidin-5-yl)-5-(furo[3,2-c]pyridin-4-yloxy)phenyl]methanol (20)

Aqueous sodium hydroxide solution (1 N, 0.36 mL, 0.36 mmol) was added to a solution of 2-(4,6-dimethylpyrimidin-5-yl)-5-(furo[3,2-c]pyridin-4-yloxy)benzyl acetate (C35) (28 mg, 0.072 mmol) in tetrahydrofuran (2 mL), and the reaction mixture was stirred at room temperature for 18 hours. Saturated aqueous sodium chloride solution was added, and the mixture was extracted with tetrahydrofuran (3×10 mL). The combined organic layers were concentrated in vacuo and purified by preparative thin layer chromatography on silica gel to give the product. Yield: 19 mg, 0.055 mmol, 76%. LCMS m/z 347.9 (M+H). $^1$H NMR (400 MHz, CDCl$_3$), characteristic peaks: δ 8.96 (s, 1H), 8.03 (d, J=5.5 Hz, 1H), 7.67 (br s, 1H), 7.53 (br s, 1H), 7.21-7.34 (m, 2H, assumed; partially obscured by solvent peak), 7.10 (d, J=8.0 Hz, 1H), 6.90 (br s, 1H), 4.33 (s, 2H), 2.26 (s, 6H).

Example 21

4-[4-(4,6-Dimethylpyrimidin-5-34)-3-(fluoromethyl)phenoxy]furo[3,2-c]pyridine (21)

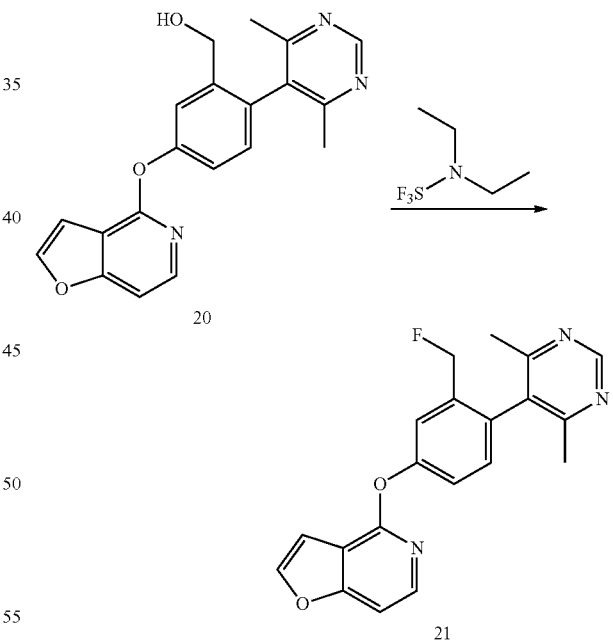

(Diethylamino)sulfur trifluoride (37 mg, 0.23 mmol) was added to a solution of [2-(4,6-dimethylpyrimidin-5-yl)-5-(furo[3,2-c]pyridin-4-yloxy)phenyl]methanol (20) (20 mg, 0.058 mmol) in dichloromethane (2 mL) at 0° C. The reaction mixture was stirred for 30 minutes at 40° C., then concentrated in vacuo. Purification by preparative thin layer chromatography on silica gel afforded the product. Yield: 10 mg, 0.029 mmol, 50%. LCMS m/z 350.0 (M+H). $^1$H NMR (400 MHz, CDCl$_3$) δ 9.01 (s, 1H), 8.07 (d, J=5.8 Hz, 1H), 7.69 (d, J=2.3 Hz, 1H), 7.49-7.52 (m, 1H), 7.39-7.43 (m, 1H), 7.29 (dd, J=5.9, 0.6 Hz, 1H), 7.18 (br d, J=8.0 Hz, 1H), 6.94 (dd, J=2.0, 0.7 Hz, 1H), 5.04 (d, $J_{HF}$=47.4 Hz, 2H), 2.28 (s, 6H).

Example 22

4-[4-(4,6-Dimethylpyrimidin-5-yl)-3-methylphenoxy]-3-methylfuro[3,2-c]pyridine (22)

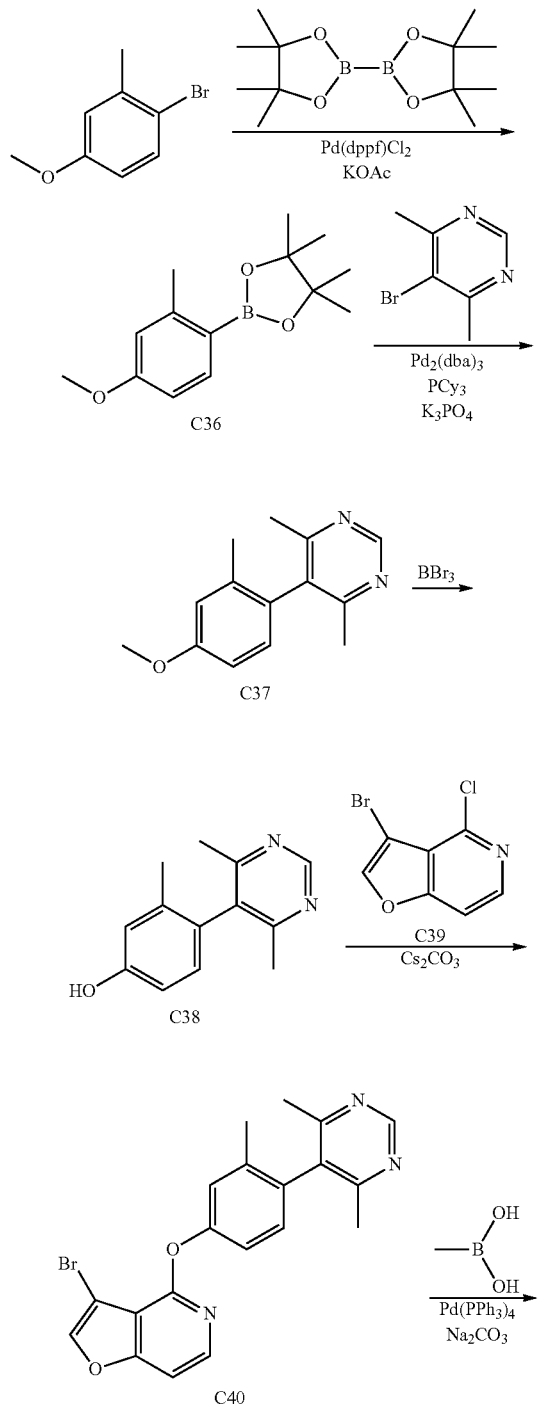

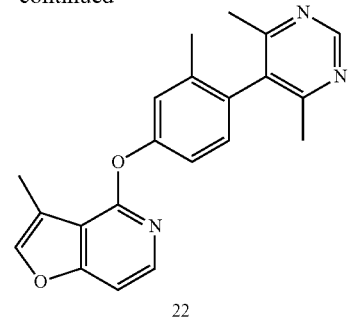

Step 1. Synthesis of 2-(4-methoxy-2-methylphenyl)-4,4,5,5-tetramethyl-1,3,2-dioxaborolane (C36)

Compound C36 was prepared from 1-bromo-4-methoxy-2-methylbenzene according to the general procedure for the synthesis of 4-[3-methyl-4-(4,4,5,5-tetramethyl-1,3,2-dioxaborolan-2-yl)phenoxy]furo[3,2-c]pyridine (C2) in Example 1. The product was obtained as a solid. Yield: 15 g, 60 mmol, 80%.

Step 2. Synthesis of 5-(4-methoxy-2-methylphenyl)-4,6-dimethylpyrimidine (C37)

The product was prepared from 2-(4-methoxy-2-methylphenyl)-4,4,5,5-tetramethyl-1,3,2-dioxaborolane (C36) and 5-bromo-4,6-dimethylpyrimidine according to the general procedure described in step 3 of Example 1. The product was obtained as a solid. Yield: 3.5 g, 15 mmol, 75%.

Step 3. Synthesis of 4-(4,6-dimethylpyrimidin-5-yl)-3-methylphenol (C38)

Boron tribromide (3.8 mL, 40 mmol) was added dropwise to a solution of 5-(4-methoxy-2-methylphenyl)-4,6-dimethylpyrimidine (C37) (3.0 g, 13 mmol) in dichloromethane (150 mL) at −70° C. The reaction mixture was stirred at room temperature for 16 hours, then adjusted to pH 8 with saturated aqueous sodium bicarbonate solution. The aqueous layer was extracted with dichloromethane (3×200 mL), and the combined organic layers were dried over sodium sulfate, filtered, and concentrated in vacuo. Silica gel chromatography (Gradient: 60% to 90% ethyl acetate in petroleum ether) afforded the product as a yellow solid. Yield: 1.2 g, 5.6 mmol, 43%. LCMS m/z 215.0 (M+H). $^1$H NMR (400 MHz, CDCl$_3$) δ 8.98 (s, 1H), 6.89 (d, J=8.0 Hz, 1H), 6.86 (d, J=2.3 Hz, 1H), 6.80 (dd, J=8.3, 2.5 Hz, 1H), 2.24 (s, 6H), 1.96 (s, 3H).

Step 4. Synthesis of 3-bromo-4-[4-(4,6-dimethylpyrimidin-5-yl)-3-methylphenoxy]furo[3,2-c]pyridine (C40)

3-Bromo-4-chlorofuro[3,2-c]pyridine (C39, prepared according to the method of Y. Miyazaki et al., *Bioorg. Med. Chem. Lett.* 2007, 17, 250-254; 430 mg, 1.85 mmol), dimethylpyrimidin-5-yl)-3-methylphenol (C38) (396 mg, 1.85 mmol) and cesium carbonate (1.21 g, 3.71 mmol) were combined in dimethyl sulfoxide (8.0 mL) and heated at 120° C. for 3 hours. The reaction mixture was filtered through Celite, the Celite pad was rinsed thoroughly with ethyl acetate, and the combined filtrates were washed twice with a 1:1 mixture of water and saturated aqueous sodium chloride solution, then washed twice with 1 N aqueous sodium hydroxide solution. The organic layer was dried over sodium sulfate, filtered, and concentrated in vacuo. Silica gel chromatographic purification (Gradient: 50% to 90% ethyl acetate in heptane) afforded the product as a white solid. Yield: 404 mg, 0.985 mmol, 53%. LCMS m/z 412.0 (M+H). $^1$H NMR (400 MHz, CDCl$_3$) δ 8.98 (s, 1H), 8.07 (d, J=5.9 Hz, 1H), 7.69 (s, 1H), 7.26-7.28 (m, 1H, assumed; partially obscured by solvent peak), 7.25 (d, J=5.9 Hz, 1H), 7.21-7.25 (m, 1H), 7.09 (br d, J=8.2 Hz, 1H), 2.28 (s, 6H), 2.05 (br s, 3H).

Step 5. Synthesis of 4-[4-(4,6-dimethylpyrimidin-5-yl)-3-methylphenoxy]-3-methylfuro[3,2-c]pyridine (22)

3-Bromo-4-[4-(4,6-dimethylpyrimidin-5-yl)-3-methylphenoxy]furo[3,2-c]pyridine (C40) (89.0 mg, 0.217 mmol), methylboronic acid (98%, 27 mg, 0.44 mmol) and tetrakis(triphenylphosphine)palladium(0) (15 mg, 0.013 mmol) were combined in a mixture of 1,4-dioxane (2.4 mL) and ethanol (0.78 mL), and the mixture was deoxygenated by bubbling nitrogen through it. Aqueous sodium carbonate solution (2 M, 0.34 mL, 0.68 mmol) was added, and the reaction mixture was subjected to microwave irradiation at 120° C. for 2 hours. As starting material was observed at this point by GCMS, additional methylboronic acid (2 equivalents) and tetrakis(triphenylphosphine)palladium(0) (0.06 equivalents) were added, the reaction mixture was again purged with nitrogen, and then subjected to microwave conditions for an additional 12 hours at 120° C. The mixture was filtered through a 0.45 μm filter, which was then rinsed with ethyl acetate; the combined filtrates were concentrated in vacuo and purified by HPLC (Column: Phenomenex Lux Cellulose-2, 5 μm; Mobile phase A: heptane; Mobile phase B: ethanol; Gradient: 5% to 100% B). The product was obtained as a yellow-orange solid. Yield: 10.1 mg, 0.0292 mmol, 13%. LCMS m/z 345.9 (M+H). $^1$H NMR (500 MHz, CDCl$_3$) δ 8.98 (s, 1H), 8.01 (d, J=5.9 Hz, 1H), 7.42-7.43 (m, 1H), 7.23 (br d, J=2.1 Hz, 1H), 7.18 (d, J=5.9 Hz, 1H), 7.17-7.20 (m, 1H), 7.08 (d, J=8.2 Hz, 1H), 2.44 (d, J=1.3 Hz, 3H), 2.28 (s, 6H), 2.04 (s, 3H).

Example 23

4-{[4-(4,6-Dimethylpyrimidin-5-yl)-1H-indol-7-yl]oxy}furo[3,2-c]pyridine (23)

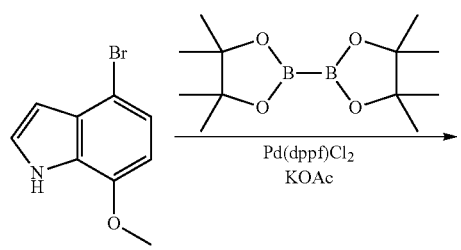

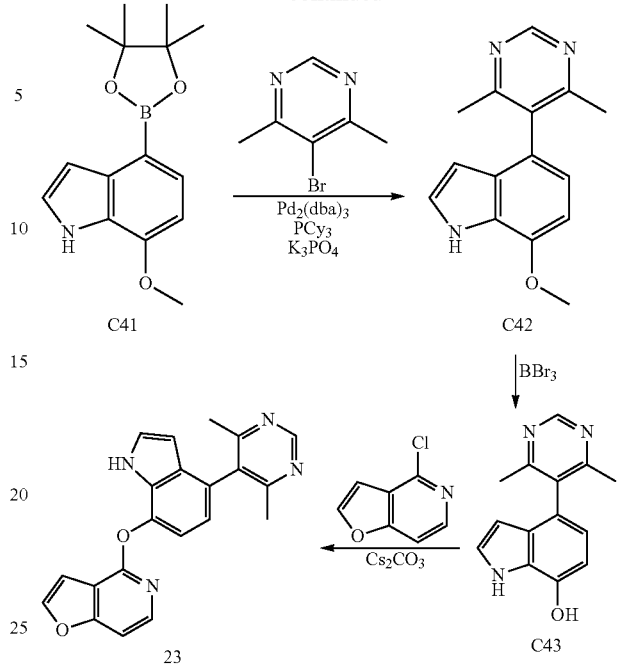

Step 1. Synthesis of 7-methoxy-4-(4,4,5,5-tetramethyl-1,3,2-dioxaborolan-2-yl)-1H-indole (C41)

Compound C41 was prepared from 4-bromo-7-methoxy-1H-indole according to the general procedure for the synthesis of 4-[3-methyl-4-(4,4,5,5-tetramethyl-1,3,2-dioxaborolan-2-yl)phenoxy]furo[3,2-c]pyridine (C2) in Example 1, except that the reaction solvent employed was 6% water in 1,4-dioxane. Purification in this case was carried out via silica gel chromatography (Gradient: 90% to 100% dichloromethane in heptane), to afford the product as a dark yellow solid. Yield: 371 mg, 1.36 mmol, 62%. GCMS m/z 273 (M$^+$). $^1$H NMR (400 MHz, CDCl$_3$) δ 7.70 (d, J=8.0 Hz, 1H), 7.55 (d, J=3.7 Hz, 1H), 7.10 (d, J=3.5 Hz, 1H), 6.81 (d, J=8.0 Hz, 1H), 3.97 (s, 3H), 1.37 (s, 12H).

Step 2. Synthesis of 4-(4,6-dimethylpyrimidin-5-yl)-7-methoxy-1H-indole (C42)

Compound C42 was prepared from 7-methoxy-4-(4,4,5,5-tetramethyl-1,3,2-dioxaborolan-2-yl)-1H-indole (C41) according to the general procedure for the synthesis of 4-[4-(4,6-dimethylpyrimidin-5-yl)-3-methylphenoxy]furo[3,2-c]pyridine (1) in Example 1, to provide the product as a yellow oil. Yield: 70 mg, 0.28 mmol, 24%. GCMS m/z 253 (M$^+$). $^1$H NMR (400 MHz, CDCl$_3$) δ 8.99 (s, 1H), 7.54 (d, J=3.7 Hz, 1H), 6.94 (AB quartet, J$_{AB}$=8.1 Hz, Δv$_{AB}$=24.6 Hz, 2H), 6.01 (d, J=3.7 Hz, 1H), 4.02 (s, 3H), 2.23 (s, 6H).

Step 3. Synthesis of 4-(4,6-dimethylpyrimidin-5-yl)-1H-indol-7-ol (C43)

Compound C43 was prepared from 4-(4,6-dimethylpyrimidin-5-yl)-7-methoxy-1H-indole (C42) according to the general procedure for the synthesis of 3-methyl-4-(2-methyl-1H-imidazo[4,5-c]pyridin-1-yl)phenol (C9) in Example 5. The crude product was triturated with ethyl acetate to afford a mustard-yellow solid containing some impurities. Yield: 53 mg, <0.22 mmol, <88%. LCMS m/z 240.1 (M+H). $^1$H NMR (400 MHz, CD$_3$OD), product peaks only: δ 9.29 (s, 1H), 7.29 (d, J=3.1 Hz, 1H), 6.75 (AB quartet, J$_{AB}$=7.8 Hz, Δv$_{AB}$=38.4 Hz, 2H), 6.04 (d, J=3.1 Hz, 1H), 2.49 (s, 6H).

Step 4. Synthesis of 4-{[4-(4,6-dimethylpyrimidin-5-yl)-1H-indol-7-yl]oxy}furo[3,2-c]pyridine (23)

4-(4,6-Dimethylpyrimidin-5-yl)-1H-indol-7-ol (C43) (50 mg, 0.21 mmol), 4-chlorofuro[3,2-c]pyridine (32 mg, 0.21 mmol) and cesium carbonate (136 mg, 0.417 mmol) were combined in dimethyl sulfoxide (1 mL), and the reaction mixture was heated to 120° C. for 19 hours. After cooling to room temperature, the mixture was filtered through Celite, the filter pad was rinsed with ethyl acetate, and the combined filtrates were washed twice with a 1:1 mixture of water and saturated aqueous sodium chloride solution, then washed twice with aqueous 1 N sodium hydroxide solution. The organic layer was dried over sodium sulfate, filtered, and concentrated in vacuo. Purification via silica gel chromatography (Gradient: 50% to 100% ethyl acetate in heptane) provided the product as an off-white solid. Yield: 3 mg, 0.008 mmol, 4%. LCMS m/z 357.2 (M+H). $^1$H NMR (500 MHz, CDCl$_3$) δ 9.01 (s, 1H), 8.67 (br s, 1H), 8.07 (d, J=5.9 Hz, 1H), 7.68 (d, J=2.2 Hz, 1H), 7.29 (br d, J=5.7 Hz, 1H), 7.22 (dd, J=2.9, 2.7 Hz, 1H), 7.17 (d, J=7.8 Hz, 1H), 6.92 (d, J=7.8 Hz, 1H), 6.86-6.87 (m, 1H), 6.12 (dd, J=2.9, 2.2 Hz, 1H), 2.31 (s, 6H).

Example 24

4-[4-(4-Ethoxy-6-methylpyrimidin-5-yl)-3-methylphenoxy]furo[3,2-c]pyridine (24)

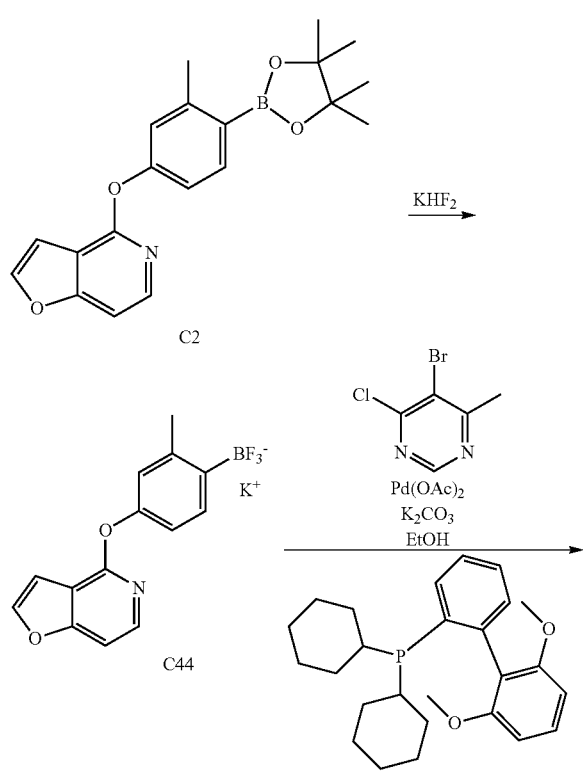

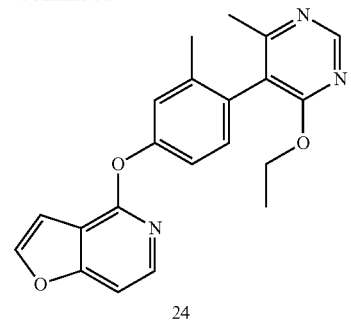

Step 1. Synthesis of potassium trifluoro[4-(furo[3,2-c]pyridin-4-yloxy)-2-methylphenyl]borate (C44)

A solution of potassium hydrogen difluoride (124 mg, 1.59 mmol) in water (0.50 mL) was added to a mixture of 4-[3-methyl-4-(4,4,5,5-tetramethyl-1,3,2-dioxaborolan-2-yl)phenoxy]furo[3,2-c]pyridine (C2) (186 mg, 0.530 mmol) in methanol (0.50 mL) and acetone (0.30 mL). After 1 hour, the volume of the reaction mixture was reduced in vacuo, and the resulting solid was isolated via filtration and rinsed with a small amount of methanol. The product was obtained as a white solid. Yield: 110 mg, 0.332 mmol, 63%. $^1$H NMR (400 MHz, DMSO-d$_6$) δ 8.13 (d, J=2.4 Hz, 1H), 7.97 (d, J=5.9 Hz, 1H), 7.68 (d, J=8.2 Hz, 1H), 7.47 (dd, J=5.9, 1.0 Hz, 1H), 7.04 (dd, J=2.2, 1.0 Hz, 1H), 7.03 (br d, J=2.4 Hz, 1H), 6.98 (br dd, J=8.0, 2.4 Hz, 1H), 2.47 (s, 3H).

Step 2. Synthesis of 4-[4-(4-ethoxy-6-methylpyrimidin-5-yl)-3-methylphenoxy]furo[3,2-c]pyridine (24)

5-Bromo-4-chloro-6-methylpyrimidine (65 mg, 0.31 mmol), potassium trifluoro[4-(furo[3,2-c]pyridin-4-yloxy)-2-methylphenyl]borate (C44) (110 mg, 0.332 mmol), potassium carbonate (130 mg, 0.941 mmol), palladium(II) acetate (0.40 mg, 0.0018 mmol) and dicyclohexyl(2',6'-dimethoxybiphenyl-2-yl)phosphane (1.20 mg, 0.0029 mmol) were dissolved in nitrogen-purged ethanol, and the reaction mixture was heated to 85° C. for 66 hours. After cooling to room temperature, the reaction mixture was diluted with methanol and ethyl acetate, filtered through Celite, and concentrated under reduced pressure. Purification via silica gel chromatography (Gradient: 0% to 70% ethyl acetate in heptane) afforded the product as a colorless oil. Yield: 24 mg, 0.066 mmol, 21%. LCMS m/z 362.4 (M+H). $^1$H NMR (400 MHz, CDCl$_3$) δ 8.67 (s, 1H), 8.06 (d, J=5.9 Hz, 1H), 7.63 (d, J=2.0 Hz, 1H), 7.23 (d, J=5.9 Hz, 1H), 7.16-7.19 (m, 1H), 7.13 (dd, half of ABX pattern, J=8.2, 2.0 Hz, 1H), 7.09 (d, half of AB pattern, J=8.2 Hz, 1H), 6.80-6.84 (m, 1H), 4.32-4.52 (m, 2H), 2.25 (s, 3H), 2.06 (s, 3H), 1.28 (t, J=7.0 Hz, 3H).

Example 25 and Example 26

(+)-5-[4-(Furo[3,2-c]pyridin-4-yloxy)-2-methylphenyl]-6-methylimidazo[1,2-a]pyrazine (25) and (−)-5-[4-(Furo[3,2-c]pyridin-4-yloxy)-2-methylphenyl]-6-methylimidazo[1,2-a]pyrazine (26)

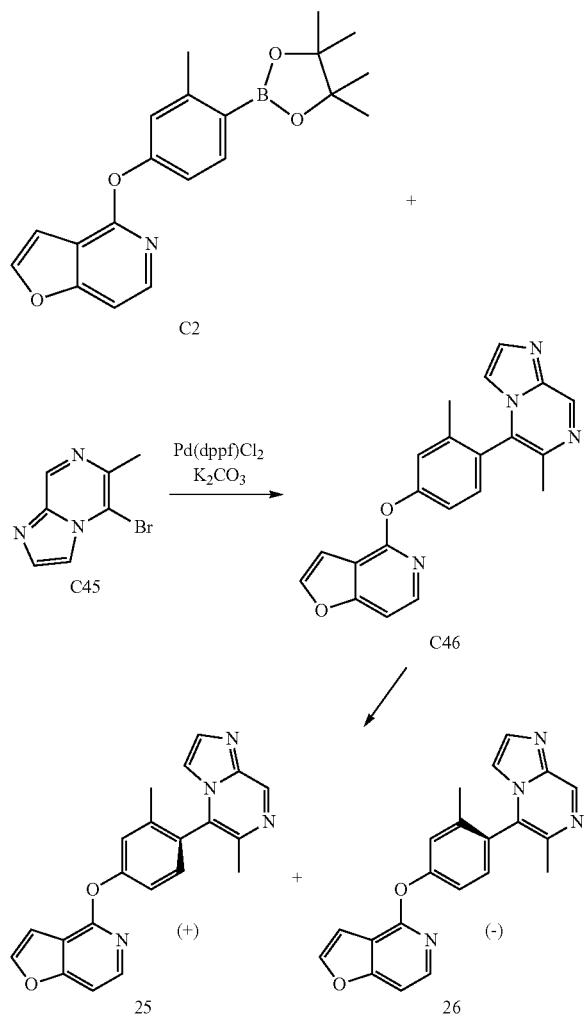

Step 1. Synthesis of 5-[4-(furo[3,2-c]pyridin-4-yloxy)-2-methylphenyl]-6-methylimidazo[1,2-a]pyrazine (C46)

To a solution of 4-[3-methyl-4-(4,4,5,5-tetramethyl-1,3,2-dioxaborolan-2-yl)phenoxy]furo[3,2-c]pyridine (C2) (13.5 g, 38.4 mmol) in 1,4-dioxane (200 mL) and water (10 mL) were added 5-bromo-6-methylimidazo[1,2-a]pyrazine (C45, see A. R. Harris et al., *Tetrahedron* 2011, 67, 9063-9066) (8.15 g, 38.4 mmol), potassium carbonate (15.9 g, 115 mmol) and [1,1′-bis(diphenylphosphino)ferrocene]dichloropalladium(II) (2.8 g, 3.8 mmol) at room temperature. The reaction mixture was degassed with nitrogen for 5 minutes, then stirred for 10 hours at reflux. The mixture was cooled to room temperature and filtered; the filtrate was concentrated in vacuo and purified via chromatography on silica gel (Gradient: 0% to 50% ethyl acetate in petroleum ether) to afford the product as a yellow solid. Yield: 12.4 g, 34.8 mmol, 91%. LCMS m/z 357.0 (M+H). $^1$H NMR (400 MHz, CD$_3$OD) δ 9.02 (s, 1H), 8.00 (d, J=6.0 Hz, 1H), 7.93 (d, J=2.0 Hz, 1H), 7.79-7.80 (m, 1H), 7.48-7.51 (m, 1H), 7.44 (d, J=8.5 Hz, 1H), 7.41 (dd, J=6.0, 1.0 Hz, 1H), 7.36 (br d, J=2.0 Hz, 1H), 7.28 (br dd, J=8, 2 Hz, 1H), 7.02-7.05 (m, 1H), 2.38 (s, 3H), 2.07 (s, 3H).

Step 2. Synthesis of (+)-5-[4-(furo[3,2-c]pyridin-4-yloxy)-2-methylphenyl]-6-methylimidazo[1,2-a]pyrazine (25) and (−)-5-[4-(furo[3,2-c]pyridin-4-yloxy)-2-methylphenyl]-6-methylimidazo[1,2-a]pyrazine (26)

5-[4-(Furo[3,2-c]pyridine-4-yloxy)-2-methylphenyl]-6-methylimidazo[1,2-a]pyrazine (C46) was separated into its atropenantiomers using supercritical fluid chromatography (Column: Chiralpak AD-H, 5 μm; Eluent: 3:1 carbon dioxide/methanol). Example 25 [designated the (+)-atropenantiomer according to its observed rotation data] was the first-eluting isomer, followed by Example 26. Example 26 [designated the (−)-atropenantiomer according to its observed rotation data] was examined by vibrational circular dichroism (VCD) spectroscopy [Chiral/R™ VCD spectrometer (BioTools, Inc.)], and on the basis of this work, the absolute configuration of Example 26 was assigned as (R).

Example 25

LCMS m/z 357.1 (M+H). $^1$H NMR (400 MHz, CDCl$_3$) δ 9.10 (s, 1H), 8.08 (d, J=5.8 Hz, 1H), 7.73 (d, J=1.0 Hz, 1H), 7.70 (d, J=2.2 Hz, 1H), 7.31-7.34 (m, 2H), 7.26-7.30 (m, 2H, assumed; partially obscured by solvent peak), 7.16-7.18 (m, 1H), 6.95 (dd, J=2.2, 1.0 Hz, 1H), 2.38 (s, 3H), 2.07 (br s, 3H).

Example 26

LCMS m/z 357.1 (M+H). $^1$H NMR (400 MHz, CDCl$_3$) δ 9.10 (s, 1H), 8.09 (d, J=5.8 Hz, 1H), 7.73 (d, J=1.0 Hz, 1H), 7.70 (d, J=2.3 Hz, 1H), 7.31-7.35 (m, 2H), 7.26-7.31 (m, 2H, assumed; partially obscured by solvent peak), 7.16-7.18 (m, 1H), 6.95 (dd, J=2.2, 0.9 Hz, 1H), 2.38 (s, 3H), 2.07 (br s, 3H).

Example 27

5-[2-Fluoro-4-(furo[3,2-c]pyridin-4-yloxy)phenyl]-4,6-dimethylpyridazin-3(2H)-one (27)

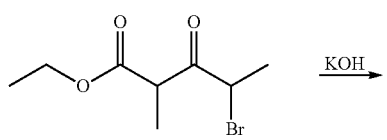 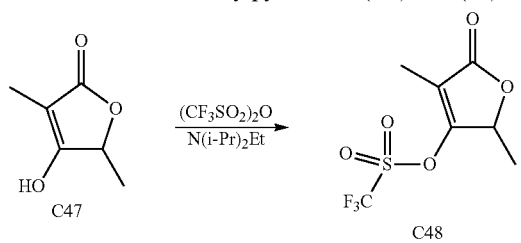

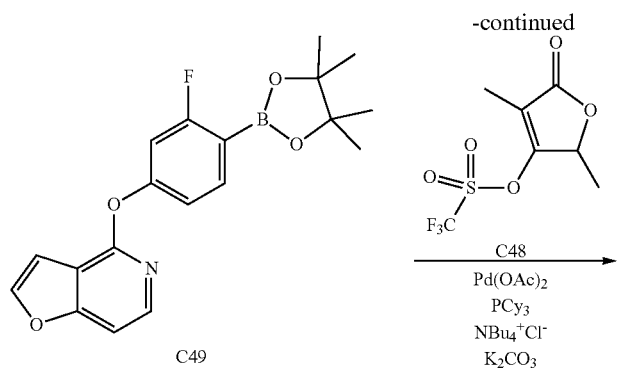
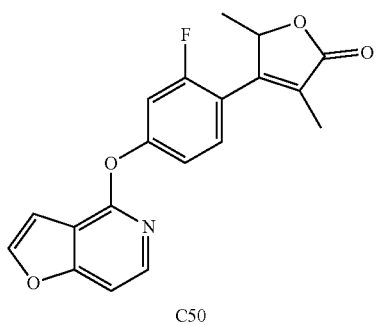
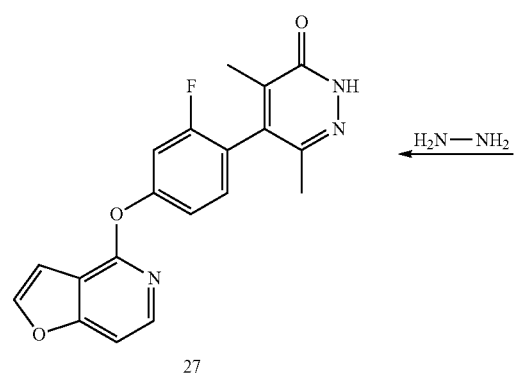
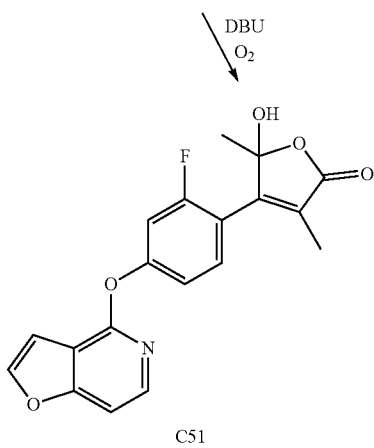

Step 1. Synthesis of 4-hydroxy-3,5-dimethylfuran-2(5H)-one (C47)

Methylation of ethyl 3-oxopentanoate (according to the method of D. Kalaitzakis et al., *Tetrahedron: Asymmetry* 2007, 18, 2418-2426) afforded ethyl 2-methyl-3-oxopentanoate; subsequent treatment with one equivalent of bromine in chloroform provided ethyl 4-bromo-2-methyl-3-oxopentanoate. This crude material (139 g, 586 mmol) was slowly added to a 0° C. solution of potassium hydroxide (98.7 g, 1.76 mol) in water (700 mL); the internal reaction temperature rose to 30° C. during the addition. The reaction mixture was subjected to vigorous stirring for 4 hours in an ice bath, at which point it was acidified via slow addition of concentrated hydrochloric acid. After extraction with ethyl acetate, the aqueous layer was saturated with solid sodium chloride and extracted three additional times with ethyl acetate. The combined organic layers were washed with saturated aqueous sodium chloride solution, dried over magnesium sulfate, filtered, and concentrated under reduced pressure to afford a mixture of oil and solid (81.3 g). This material was suspended in chloroform (200 mL); solids were filtered, then washed with chloroform (2×50 mL). The combined filtrates were concentrated in vacuo and treated with a 3:1 mixture of heptane and diethyl ether (300 mL). The mixture was vigorously swirled until some of the oil began to solidify, then concentrated under reduced pressure to afford an oily solid (60.2 g). After addition of a 3:1 mixture of heptane and diethyl ether (300 mL) and vigorous stirring for 10 minutes, filtration afforded the product as an off-white solid. Yield: 28.0 g, 219 mmol, 37%. $^1$H NMR (400 MHz, CDCl$_3$) δ 4.84 (br q, J=6.8 Hz, 1H), 1.74 (br s, 3H), 1.50 (d, J=6.8 Hz, 3H).

Step 2. Synthesis of 2,4-dimethyl-5-oxo-2,5-dihydrofuran-3-yl trifluoromethanesulfonate (C48)

Trifluoromethanesulfonic anhydride (23.7 mL, 140 mmol) was added portion-wise to a solution of 4-hydroxy-3,5-dimethylfuran-2(5H)-one (C47) (15.0 g, 117 mmol) and N,N-diisopropylethylamine (99%, 24.8 mL, 140 mmol) in dichloromethane (500 mL) at −20° C., at a rate that maintained the internal reaction temperature below −10° C. The reaction mixture was stirred at −20° C., then allowed to warm gradually to 0° C. over 5 hours. The reaction mixture was passed through a plug of silica gel, dried over magnesium sulfate, and concentrated in vacuo. The residue was suspended in diethyl ether and filtered; the filtrate was concentrated under reduced pressure. Purification using silica gel chromatography (Gradient: 0% to 17% ethyl acetate in heptane) afforded the product as a pale yellow oil. Yield: 21.06 g, 80.94 mmol, 69%. $^1$H NMR (400 MHz, CDCl$_3$) δ 5.09-5.16 (m, 1H), 1.94-1.96 (m, 3H), 1.56 (d, J=6.6 Hz, 3H).

Synthesis of 4-[3-fluoro-4-(4,4,5,5-tetramethyl-1,3,2-dioxaborolan-2-yl)phenoxy]furo-[3,2-c]pyridine (C49)

Compound C49 was synthesized using the method described for 4-[3-methyl-4-(4,4,5,5-tetramethyl-1,3,2-dioxaborolan-2-yl)phenoxy]furo[3,2-c]pyridine (C2) in Example 1, except that 4-bromo-3-fluorophenol was used in place of 4-bromo-3-methylphenol. The product was obtained as an off-white solid. Yield: 22.5 g, 63.3 mmol, 39% over 2 steps. LCMS m/z 356.1 (M+H). $^1$H NMR (400 MHz, CDCl$_3$) δ 8.04 (d, J=5.9 Hz, 1H), 7.80 (dd, J=8.2, 6.9

Hz, 1H), 7.65 (d, J=2.3 Hz, 1H), 7.25 (dd, J=5.8, 0.9 Hz, 1H), 7.02 (dd, J=8.3, 2.1 Hz, 1H), 6.94 (dd, J=10.2, 2.1 Hz, 1H), 6.85 (dd, J=2.3, 1.0 Hz, 1H), 1.37 (s, 12H).

Step 3. Synthesis of 4-[2-fluoro-4-(furo-[3,2-c]pyridine-4-yloxy)phenyl]-3,5-dimethylfuran-2(5H)-one (C50)

A solution of 4-[3-fluoro-4-(4,4,5,5-tetramethyl-1,3,2-dioxaborolan-2-yl)phenoxy]furo[3,2-c]pyridine (C49) (3.20 g, 9.01 mmol) and 2,4-dimethyl-5-oxo-2,5-dihydrofuran-3-yl trifluoromethanesulfonate (C48) (2.46 g, 9.45 mmol) in 1,4-dioxane (80 mL) was purged with nitrogen for 5 minutes. A mixture of tetrabutylammonium chloride (99%, 127 mg, 0.452 mmol), tricyclohexylphosphine (99%, 128 mg, 0.452 mmol) and palladium(II) acetate (101 mg, 0.450 mmol) was added, followed by an aqueous solution of potassium carbonate (3 M, 9.0 mL, 27.0 mmol), and the reaction mixture was heated at 50° C. for 18 hours. After cooling to room temperature, the reaction mixture was diluted with ethyl acetate, washed three times with water, washed once with saturated aqueous sodium chloride solution, and dried over magnesium sulfate. Filtration and removal of solvent under reduced pressure was followed by chromatographic purification on silica gel (Gradient: 15% to 50% ethyl acetate in heptane), affording the product as a tan oil that slowly solidified upon standing. Yield: 1.55 g, 4.57 mmol, 51%. LCMS m/z 340.3 (M+H). $^1$H NMR (400 MHz, CDCl$_3$) δ 8.06 (d, J=5.9 Hz, 1H), 7.70 (d, J=2.2 Hz, 1H), 7.33-7.38 (m, 1H), 7.31 (dd, J=5.9, 1.0 Hz, 1H), 7.13-7.20 (m, 2H), 6.94 (dd, J=2.2, 0.9 Hz, 1H), 5.43-5.51 (m, 1H), 1.99-2.01 (m, 3H), 1.38 (d, J=6.6 Hz, 3H).

Step 4. Synthesis of 4-[2-fluoro-4-(furo-[3,2-c]pyridine-4-yloxy)phenyl]-5-hydroxy-3,5-dimethylfuran-2(5H)-one (C51)

A solution of 4-[2-fluoro-4-(furo[3,2-c]pyridine-4-yloxy)phenyl]-3,5-dimethylfuran-2(5H)-one (C50) (5.0 g, 15 mmol) in tetrahydrofuran (200 mL) and N,N-dimethylformamide (100 mL) was treated with 1,8-diazabicyclo[5.4.0]undec-7-ene (6.61 mL, 44.2 mmol) and purged with oxygen for 10 minutes. A slight positive pressure of oxygen was introduced into the flask and the reaction mixture was heated at 50° C. with vigorous stirring for 5 hours. Upon heating, a slight additional pressure build-up was noted within the flask via examination of the rubber septum. LCMS analysis indicated approximately 6% of the starting material remaining; the flask was cooled to room temperature, recharged with oxygen, and heated at 50° C. for an additional 18 hours. The reaction was cooled to room temperature, diluted with ethyl acetate (300 mL) and washed sequentially with aqueous hydrochloric acid (0.25 M, 175 mL) and water (150 mL). The pH of the combined aqueous layers was adjusted from pH 3 to roughly pH 4-5, and the aqueous layer was extracted with ethyl acetate (300 mL). The combined organic layers were washed with saturated aqueous sodium chloride solution, dried over magnesium sulfate, filtered, and concentrated in vacuo. Purification via silica gel chromatography (Gradient: 0% to 40% ethyl acetate in heptane) afforded the product as a white foam. Yield: 4.20 g, 11.8 mmol, 79%. LCMS m/z 356.4 (M+H). $^1$H NMR (400 MHz, CDCl$_3$) δ 8.07 (d, J=5.8 Hz, 1H), 7.66-7.71 (m, 2H), 7.31 (br d, J=5.8 Hz, 1H), 7.11-7.17 (m, 2H), 6.93-6.94 (m, 1H), 3.95 (br s, 1H), 1.86-1.88 (m, 3H), 1.64 (s, 3H).

Step 5. Synthesis of 5-[2-fluoro-4-(furo-[3,2-c]pyridine-4-yloxy)phenyl]-4,6-dimethylpyridazin-3(2H)-one (27)

Anhydrous hydrazine (98.5%, 1.88 mL, 59.0 mmol) was added to a solution of 4-[2-fluoro-4-(furo[3,2-c]pyridine-4-yloxy)phenyl]-5-hydroxy-3,5-dimethylfuran-2(5H)-one (C51) (4.20 g, 11.8 mmol) in 1-butanol (75 mL), and the reaction mixture was heated at 110° C. for 2 hours. After cooling to room temperature and stirring at this temperature for 18 hours, the reaction mixture was stored in a refrigerator for 66 hours. The resulting suspension was filtered to afford a gray solid, which was dissolved in hot ethanol (150-175 mL) and filtered through a nylon syringe filter. The filtrate was concentrated in vacuo to provide the product as a white solid. Yield: 1.30 g, 3.70 mmol, 31%. LCMS m/z 352.2 (M+H). $^1$H NMR (400 MHz, DMSO-d$_6$) δ 12.89 (br s, 1H), 8.17 (d, J=2.2 Hz, 1H), 8.06 (d, J=5.8 Hz, 1H), 7.54 (br d, J=5.8 Hz, 1H), 7.38-7.46 (m, 2H), 7.25 (br dd, J=8.4, 2.2 Hz, 1H), 7.12-7.14 (m, 1H), 1.99 (s, 3H), 1.85 (s, 3H).

Example 28

5-[4-(Furo[3,2-c]pyridin-4-yloxy)phenyl]-4,6-dimethylpyridazin-3(2H)-one (28)

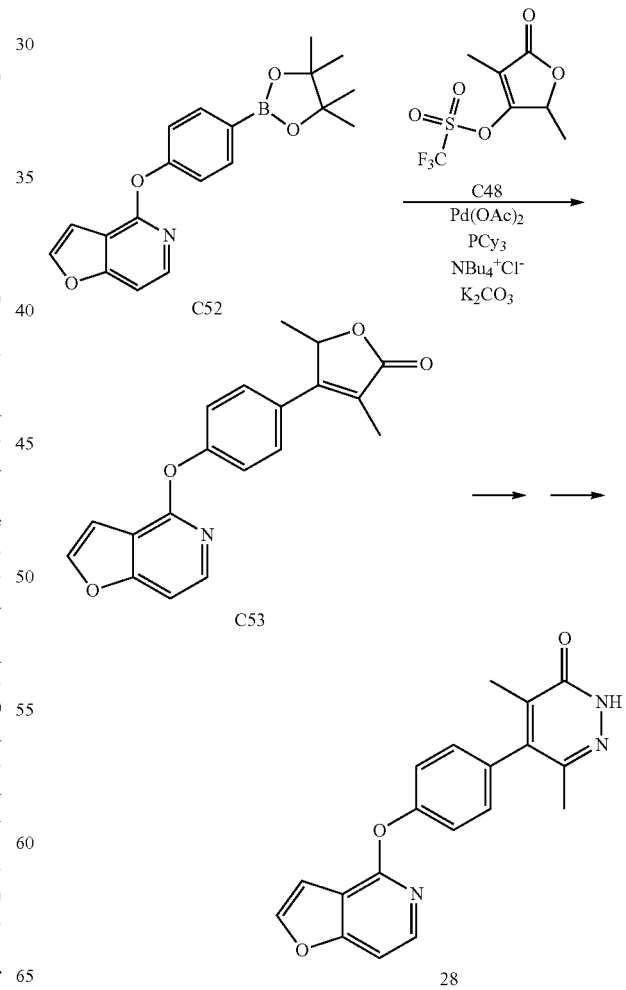

Step 1. Synthesis of 4-[4-(furo-[3,2-c]pyridin-4-yloxy)phenyl]-3,5-dimethylfuran-2(5H)-one (C53).

The product was prepared as an off-white solid, via reaction of 2,4-dimethyl-5-oxo-2,5-dihydrofuran-3-yl trifluoromethanesulfonate (C48) with 4-[4-(4,4,5,5-tetramethyl-1,3,2-dioxaborolan-2-yl)phenoxy]furo[3,2-c]pyridine (C52) [this may be prepared in a similar manner to 4-[3-methyl-4-(4,4,5,5-tetramethyl-1,3,2-dioxaborolan-2-yl)phenoxy]furo[3,2-c]pyridine (C2) in Example 1] as described for synthesis of 4-[2-fluoro-4-(furo[3,2-c]pyridine-4-yloxy)phenyl]-3,5-dimethylfuran-2(5H)-one (C50) in Example 27. Yield: 760 mg, 2.36 mmol, 80%. LCMS m/z 322.2 (M+H). $^1$H NMR (400 MHz, CDCl$_3$) δ 8.04 (d, J=5.9 Hz, 1H), 7.69 (d, J=2.2 Hz, 1H), 7.40 (br AB quartet, J$_{AB}$=8.8 Hz, Δν$_{AB}$=27.3 Hz, 4H), 7.26-7.29 (m, 1H, assumed; partially obscured by solvent peak), 6.93 (dd, J=2.2, 1.0 Hz, 1H), 5.43 (qq, J=6.7, 1.8 Hz, 1H), 2.09 (d, J=1.8 Hz, 3H), 1.43 (d, J=6.6 Hz, 3H).

Step 2. Synthesis of 5-[4-(furo[3,2-c]pyridine-4-yloxy)phenyl]-4,6-dimethylpyridazin-3(2H)-one (28)

4-[4-(Furo[3,2-c]pyridin-4-yloxy)phenyl]-3,5-dimethylfuran-2(5H)-one (C53) was converted to the product in a similar manner to that described for synthesis of 5-[2-fluoro-4-(furo[3,2-c]pyridine-4-yloxy)phenyl]-4,6-dimethyl-pyridazin-3(2H)-one (27) in Example 27. The crude product was subjected to silica gel chromatography (Eluent: 40% ethyl acetate in dichloromethane), then recrystallized from ethanol to afford the title product as a white solid. Yield: 270 mg, 0.810 mmol, 35% over 2 steps. LCMS m/z 334.0 (M+H). $^1$H NMR (400 MHz, DMSO-d$_6$) δ 12.79 (br s, 1H), 8.15 (d, J=2.4 Hz, 1H), 8.03 (d, J=5.9 Hz, 1H), 7.50 (dd, J=5.9, 1.0 Hz, 1H), 7.31-7.38 (m, 4H), 7.09 (dd, J=2.2, 1.0 Hz, 1H), 1.97 (s, 3H), 1.83 (s, 3H).

Example 29

4-[3,5-Dimethyl-4-(3-methylpyridin-4-yl)phenoxy]furo[3,2-c]pyridine (29)

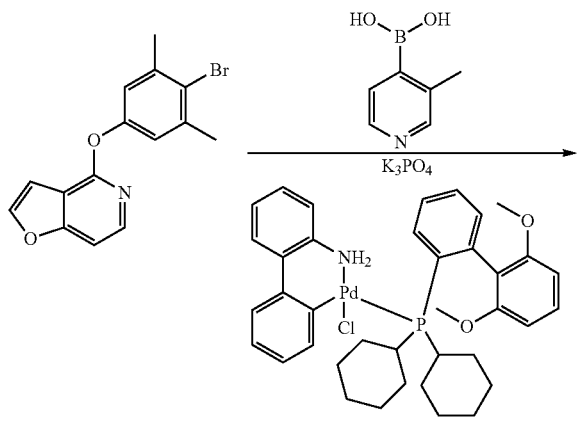

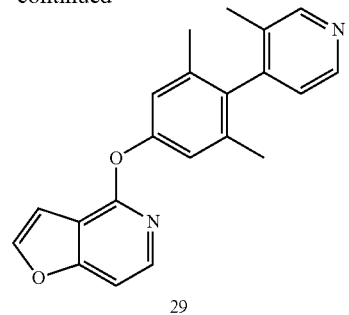

The product was prepared from 4-(4-bromo-3,5-dimethylphenoxy)furo[3,2-c]pyridine [synthesized via reaction of 4-bromo-3,5-dimethylphenol with 4-chlorofuro[3,2-c]pyridine] and (3-methylpyridin-4-yl)boronic acid, according to the general procedure for the synthesis of 5-(2-chloro-4-methoxyphenyl)-4,6-dimethylpyrimidine (C64) in Preparation P7. LCMS m/z 331.1 (M+H). $^1$H NMR (600 MHz, DMSO-d$_6$) δ 8.57 (br s, 1H), 8.49 (br d, J=4.8 Hz, 1H), 8.13 (d, J=2.2 Hz, 1H), 8.02 (d, J=5.9 Hz, 1H), 7.47 (dd, J=5.8, 1.0 Hz, 1H), 7.10 (br d, J=4.8 Hz, 1H), 7.05 (dd, J=2.2, 0.9 Hz, 1H), 7.02-7.04 (m, 2H), 1.97 (s, 3H), 1.89 (s, 6H).

Example 30

4-{[4-(Imidazo[1,2-a]pyridin-5-yl)naphthalen-1-yl]oxy}furo-[3,2-c]pyridine, trifluoroacetate salt (30)

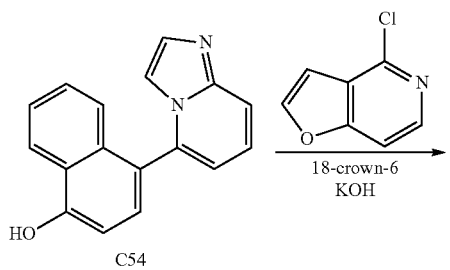

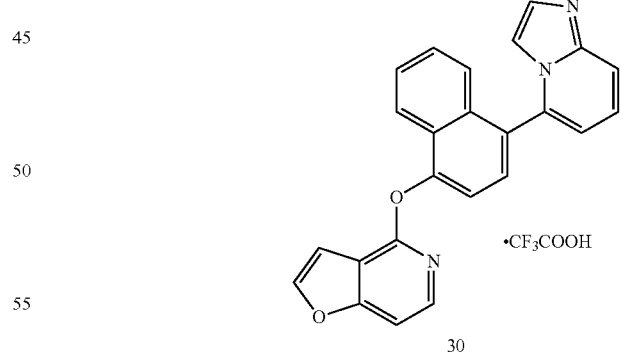

Potassium hydroxide (112 mg, 1.99 mmol) and 1,4,7,10, 13,16-hexaoxacyclooctadecane (18-crown-6; 13.3 mg, 0.050 mmol) were added to a solution of 4-(imidazo[1,2-a]pyridin-5-yl)naphthalen-1-ol (C54) [prepared via Suzuki reaction between (4-methoxynaphthalen-1-yl)boronic acid and 5-bromoimidazo[1,2-a]pyridine as described in Example 8, followed by boron tribromide-mediated methyl ether cleavage] (85 mg, 0.25 mmol) and 4-chlorofuro[3,2-c]pyridine (57.3 mg, 0.373 mmol) in xylene (3 mL), and the reaction mixture was heated to 140° C. for 24 hours. Solvent was removed in vacuo, and the crude material was combined with crude product from a similar reaction carried out on 30 mg of C54. After the reaction was partitioned between ethyl acetate (25 mL) and water (25 mL), the aqueous layer was extracted with ethyl acetate (3×30 mL), and the combined organic layers were dried over sodium sulfate. Purification was first effected via silica gel chromatography (Eluent: ethyl acetate), followed by HPLC (Column: XBridge C18, 5 μm, Mobile phase A: water with trifluoroacetic acid modifier; Mobile phase B: acetonitrile with trifluoroacetic acid modifier; Gradient: 30% to 50% B). The product was obtained as a colorless gum. Yield: 20 mg, 0.041 mmol, 12%. LCMS m/z 378.1 (M+H). $^1$H NMR (500 MHz, CD$_3$OD) δ 8.17 (dd, half of ABX pattern, J=9.0, 7.1 Hz, 1H), 8.15 (br d, J=8.0 Hz, 1H), 8.10 (br d, half of AB pattern, J=9 Hz, 1H), 7.99-8.01 (m, 2H), 7.89 (d, J=5.9 Hz, 1H), 7.83 (d, J=7.8 Hz, 1H), 7.70 (br d, J=2 Hz, 1H), 7.67 (dd, J=7.1, 1.0 Hz, 1H), 7.61 (ddd, J=8.3, 6.8, 1.2 Hz, 1H), 7.56 (ddd, J=8.3, 6.8, 1.2 Hz, 1H), 7.54 (d, J=7.6 Hz, 1H), 7.41-7.44 (m, 2H), 7.20 (dd, J=2.2, 1.0 Hz, 1H).

PREPARATIONS

Preparations P1-P15 describe preparations of some starting materials or intermediates used for preparation of certain compounds of the invention.

Preparation P1

5-(Furo[3,2-c]pyridin-4-yloxy)-2-(3-methylpyrazin-2-yl)phenol (P1)

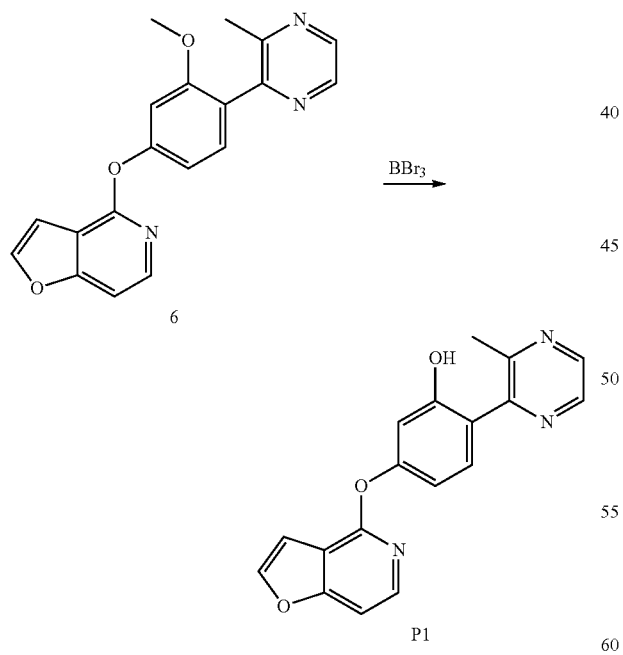

Boron tribromide (1.9 g, 7.6 mmol) was slowly added to a solution of 4-[3-methoxy-4-(3-methylpyrazin-2-yl)phenoxy]furo[3,2-c]pyridine (6) (2.3 g, 6.9 mmol) in dichloromethane (100 mL) at 0° C. The reaction mixture was stirred at 0° C. for 1 hour, then quenched with water, stirred and filtered. The filtrate was adjusted to neutral pH with saturated aqueous sodium bicarbonate solution and extracted with dichloromethane (3×50 mL). The combined organic layers were dried, filtered, and concentrated in vacuo. Silica gel chromatography (Gradient: 0% to 2% methanol in dichloromethane) afforded the product. Yield: 1.2 g, 3.8 mmol, 55%. LCMS m/z 320.1 (M+H). $^1$H NMR (400 MHz, CDCl$_3$) δ 11.83 (s, 1H), 8.48 (d, J=2.5 Hz, 1H), 8.36 (d, J=2.5 Hz, 1H), 8.08 (d, J=5.8 Hz, 1H), 7.68 (d, J=8.5 Hz, 1H), 7.66 (d, J=2.3 Hz, 1H), 7.25-7.28 (m, 1H, assumed; partially obscured by solvent peak), 6.95 (d, J=2.5 Hz, 1H), 6.90 (dd, J=2.3, 1.0 Hz, 1H), 6.86 (dd, J=8.8, 2.5 Hz, 1H), 2.87 (s, 3H).

Preparation P2

4-(6-Methylimidazo[1,2-a]pyridin-5-yl)phenol, hydrobromide salt (P2)

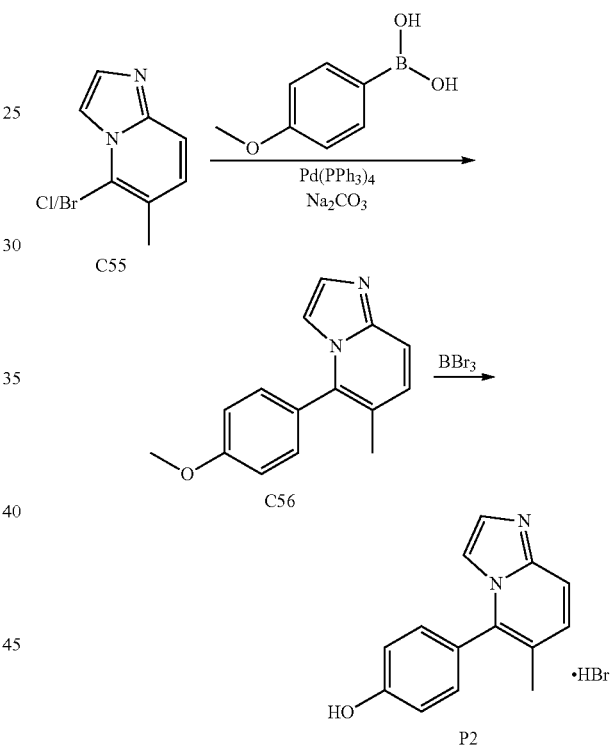

Step 1. Synthesis of 5-(4-methoxyphenyl)-6-methylimidazo[1,2-a]pyridine (C56)

The product was prepared from C55 (a 1:1 mixture of 5-bromo-6-methylimidazo[1,2-a]pyridine and 5-chloro-6-methylimidazo[1,2-a]pyridine, see A. R. Harris et al., Tetrahedron 2011, 67, 9063-9066) (210 mg, 1.00 mmol) and (4-methoxyphenyl)boronic acid (116 mg, 0.765 mmol) using the method of Example 6. Silica gel chromatography (Gradient: 0% to 40% [20% methanol in dichloromethane] in dichloromethane) afforded the product. Yield: 159 mg, 0.667 mmol, 87%. $^1$H NMR (500 MHz, CDCl$_3$) δ 7.55 (d, J=9.3 Hz, 1H), 7.50 (s, 1H), 7.30 (d, J=8.5 Hz, 2H), 7.14 (d, J=9.3 Hz, 1H), 7.12 (s, 1H), 7.07 (d, J=8.5 Hz, 2H), 3.89 (s, 3H), 2.13 (s, 3H).

Step 2. Synthesis of 4-(6-methylimidazo[1,2-a]pyridin-5-yl)phenol, hydrobromide salt (P2)

The product was prepared from 5-(4-methoxyphenyl)-6-methylimidazo[1,2-a]pyridine (C56) (159 mg, 0.667 mmol) as described for the synthesis of 6-(4-hydroxy-2-methylphenyl)-1,5-dimethylpyrazin-2(1H)-one (P8) in Preparation P8. In this case, after the second addition of methanol, the mixture was concentrated in vacuo, then azeotroped with heptane to provide the product as a brown solid. Yield: 193 mg, 0.63 mmol, 95%. LCMS m/z 225.0 (M+H). $^1$H NMR (400 MHz, CD$_3$OD) δ 7.97 (d, J=9.2 Hz, 1H), 7.91 (d, J=2.2 Hz, 1H), 7.83 (br d, J=9.4 Hz, 1H), 7.54 (dd, J=2.2, 0.7 Hz, 1H), 7.36 (br d, J=8.6 Hz, 2H), 7.08 (br d, J=8.8 Hz, 2H), 2.31 (s, 3H).

Preparation P3

7-Chloro-6-methyl[1,2,4]triazolo[1,5-a]pyrimidine (P3)

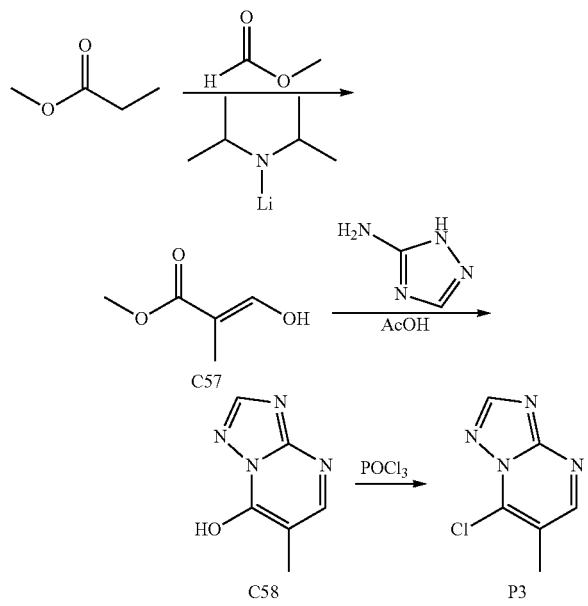

Step 1. Synthesis of methyl 3-hydroxy-2-methylprop-2-enoate (C57)

Methyl propanoate (44 g, 0.50 mol) was reacted with methyl formate (55.5 g, 0.75 mol) according to the method of F. Kido et al., *Tetrahedron* 1987, 43, 5467-5474. Purification by distillation (70-104° C.) gave compound C57 as a colorless liquid. Yield: 23 g, 0.20 mol, 40%. $^1$H NMR (400 MHz, CDCl$_3$), roughly 1:1 mixture of aldehyde and enol forms: δ 11.24 (d, J=11.5 Hz, 1H), 9.78 (s, 1H), 6.99 (d, J=10.5 Hz, 1H), 3.79 (s, 6H), 3.41 (q, J=7 Hz, 1H), 1.68 (s, 3H), 1.36 (d, J=7 Hz, 3H).

Step 2. Synthesis of 6-methyl[1,2,4]triazolo[1,5-a]pyrimidin-7-ol (C58)

A solution of methyl 3-hydroxy-2-methylprop-2-enoate (C57) (95 g, 0.82 mol) and 1H-1,2,4-triazol-5-amine (100 g, 1.19 mol) in a mixture of ethanol (300 mL) and acetic acid (150 mL) was heated to reflux for 12 hours. The reaction mixture was allowed to cool to ambient temperature and solids were filtered to afford the product as a white solid. Yield: 41 g, 27 mmol, 33%. $^1$H NMR (400 MHz, DMSO-d$_6$) δ 8.18 (s, 1H), 7.91 (s, 1H), 2.00 (s, 3H).

Step 3. Synthesis of 7-chloro-6-methyl[1,2,4]triazolo[1,5-a]pyrimidine (P3)

To a stirred suspension of 6-methyl[1,2,4]triazolo[1,5-a]pyrimidin-7-ol (C58) (105 g, 0.699 mol) in phosphorus oxychloride (500 mL) at room temperature was added drop-wise N,N-diisopropylethylamine (100 mL) and the reaction mixture was heated to reflux for 110 minutes. After the mixture cooled to ambient temperature, it was concentrated to near dryness in vacuo, poured into ice water, and adjusted to pH 9 by addition of potassium carbonate. The resulting solution was extracted three times with dichloromethane (800 mL) and the combined organic phases were washed with saturated aqueous sodium chloride solution, dried over sodium sulfate, and concentrated under reduced pressure. Silica gel chromatography (Gradient: 17% to 33% ethyl acetate in petroleum ether) provided the product as a white solid. Yield: 55 g, 330 mmol, 47%. LCMS m/z 169.2 (M+H). $^1$H NMR (400 MHz, CDCl$_3$) δ 8.70 (s, 1H), 8.52 (s, 1H), 2.54 (s, 3H).

Preparation P4

3-Bromo-2-methylimidazo[1,2-a]pyrazine (P4)

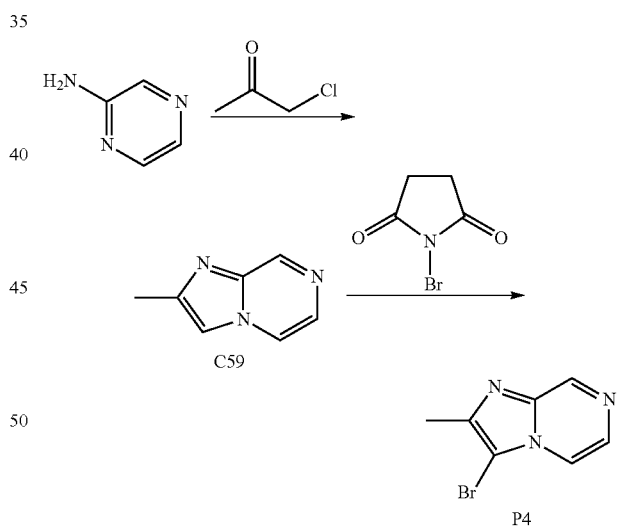

Step 1. Synthesis of 2-methylimidazo[1,2-a]pyrazine (C59)

Pyrazin-2-amine (1 g, 10 mmol) was dissolved in ethanol (15 mL) and 1-chloropropan-2-one (1.2 mL, 14 mmol) was added. The resulting solution was stirred at reflux for 2 hours, cooled to room temperature, and concentrated in vacuo. Saturated aqueous sodium bicarbonate solution (50 mL) was added, and the mixture was extracted three times with chloroform (20 mL); the combined organic layers were dried over sodium sulfate, filtered, and concentrated. Silica gel chromatography (Gradient: 0% to 50% methanol in ethyl acetate) gave C59 as an orange solid. Yield: 122 mg, 0.916 mmol, 9%. LCMS m/z 133.9 (M+H). $^1$H NMR (400 MHz, CDCl$_3$) δ 8.98 (br s, 1H), 7.99 (dd, J=4.6, 1.5 Hz, 1H), 7.83 (br d, J=4.5 Hz, 1H), 7.46 (br s, 1H), 2.53 (s, 3H).

Step 2. Synthesis of 3-bromo-2-methylimidazo[1,2-a]pyrazine (P4)

2-Methylimidazo[1,2-a]pyrazine (C59) (122 mg, 0.916 mmol) was dissolved in chloroform (2 mL) and treated with N-bromosuccinimide (189 mg, 1.1 mmol). The resulting mixture was stirred at ambient temperature for 1.5 hours and then concentrated in vacuo. Silica gel chromatography (Gradient: 33% to 100% ethyl acetate in heptane) afforded the product, still containing some succinimide. This material was dissolved in dichloromethane (25 mL) and washed with aqueous sodium hydroxide solution (0.5 M, 3×10 mL). The organic layer was dried over sodium sulfate, filtered, and concentrated in vacuo to afford the product as an off-white solid. Yield: 125 mg, 0.59 mmol, 64%. LCMS m/z 213.9 (M+H). $^1$H NMR (400 MHz, CDCl$_3$) δ 8.93 (s, 1H), 7.96 (br s, 2H), 2.51 (s, 3H).

Preparation P5

4-[4-(4,4,5,5-Tetramethyl-1,3,2-dioxaborolan-2-yl)-3-(trifluoromethyl)phenoxy]furo[3,2-c]pyridine (P5)

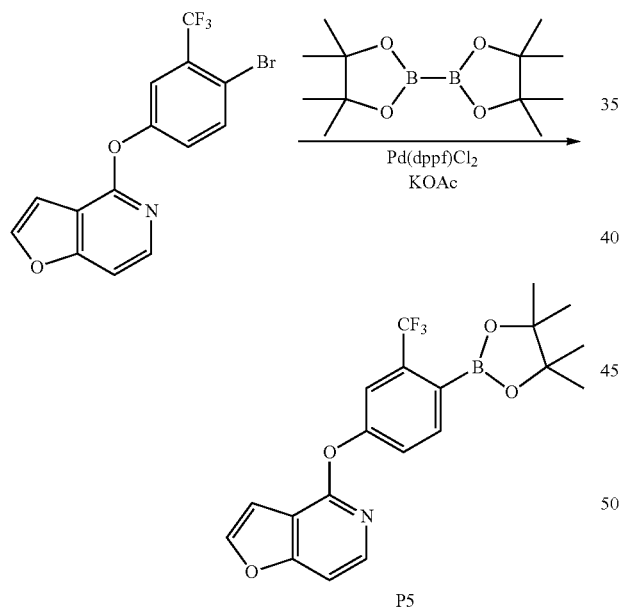

P5

4-[4-Bromo-3-(trifluoromethyl)phenoxy]furo[3,2-c]pyridine (3.58 g, 10.0 mmol) was reacted with 4,4,4',4',5,5,5',5'-octamethyl-2,2'-bi-1,3,2-dioxaborolane (99%, 3.33 g, 13.0 mmol), potassium acetate (95%, 4.13 g, 40.0 mmol) and [1,1'-bis(diphenylphosphino)ferrocene]dichloropalladium(II) (732 mg, 1.00 mmol) in analogous fashion to the synthesis of 4-[3-methyl-4-(4,4,5,5-tetramethyl-1,3,2-dioxaborolan-2-yl)phenoxy]furo[3,2-c]pyridine (C2) in Example 1. Silica gel chromatography (Gradient: 0% to 20% ethyl acetate in heptane) provided the product as a white solid. Yield: 2.035 g, 5.022 mmol, 50%. LCMS m/z 406.2 (M+H). $^1$H NMR (500 MHz, CDCl$_3$) δ 8.00 (d, J=5.9 Hz, 1H), 7.84 (br d, J=8.0 Hz, 1H), 7.66 (d, J=2.2 Hz, 1H), 7.55 (br d, J=2.2 Hz, 1H), 7.39 (br dd, J=8.2, 2.3 Hz, 1H), 7.25 (dd, J=5.9, 1.0 Hz, 1H), 6.87 (dd, J=2.2, 1.0 Hz, 1H), 1.38 (s, 12H).

Preparation P6

2,5-Dimethyl-4-(6-methylimidazo[1,2-a]pyrazin-5-yl)phenol (P6)

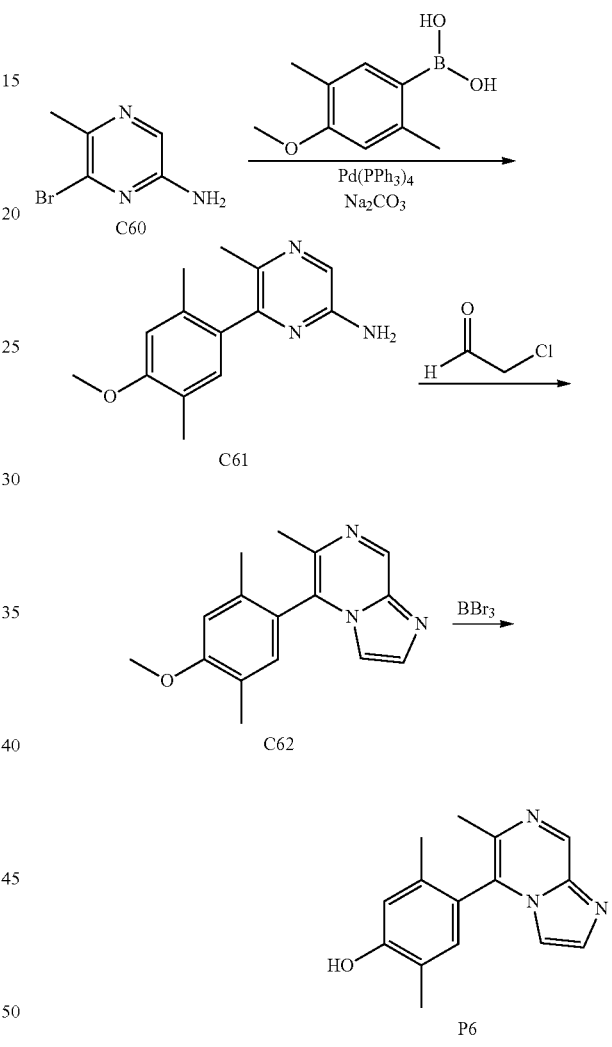

Step 1. Synthesis of 6-(4-methoxy-2,5-dimethylphenyl)-5-methylpyrazin-2-amine (C61)

6-Bromo-5-methylpyrazin-2-amine (C60, see A. R. Harris et al., *Tetrahedron* 2011, 67, 9063-9066; 111 mg, 0.590 mmol), (4-methoxy-2,5-dimethylphenyl)boronic acid (127 mg, 0.708 mmol) and tetrakis(triphenylphosphine)palladium(0) (95%, 40 mg, 0.033 mmol) were combined in a pressure tube and dissolved in 1,4-dioxane (2 mL) and water (0.6 mL). An aqueous solution of sodium carbonate (2.0 M, 0.885 mL, 1.77 mmol) was added, and the reaction was conducted in analogous fashion to the synthesis of 6-[4-(furo[3,2-c]pyridin-4-yloxy)-2-methylphenyl]-5-methylpyrazin-2-amine (C3) in Example 2. Silica gel chromatography (Gradient: 0% to 75% ethyl acetate in heptane) afforded the product. Yield: 116 mg, 0.477 mmol, 81%. LCMS m/z 244.1 (M+H). $^1$H NMR (400 MHz, CD$_3$CN) δ 7.83 (s, 1H), 6.90 (s, 1H), 6.82 (s, 1H), 4.93 (br s, 2H), 3.83 (s, 3H), 2.15 (br s, 3H), 2.11 (s, 3H), 2.05 (br s, 3H).

Step 2. Synthesis of 5-(4-methoxy-2,5-dimethylphenyl)-6-methylimidazo[1,2-a]pyrazine (C62)

Chloroacetaldehyde (55% solution in water, 0.28 mL, 2.38 mmol) was added to a mixture of 6-(4-methoxy-2,5-dimethylphenyl)-5-methylpyrazin-2-amine (C61) (116 mg, 0.477 mmol) in water (3.6 mL). The reaction mixture was heated to 115° C. for 2 hours in a microwave reactor and then cooled to room temperature, whereupon the solvent was removed in vacuo. Silica gel chromatography (Gradient: 0% to 10% methanol in dichloromethane) afforded the product. Yield: 115 mg, 0.43 mmol, 90%. LCMS m/z 268.1 (M+H). $^1$H NMR (400 MHz, CD$_3$CN) δ 9.45 (s, 1H), 7.99 (br s, 1H), 7.37 (br s, 1H), 7.08 (s, 1H), 7.04 (s, 1H), 3.91 (s, 3H), 2.41 (s, 3H), 2.20 (br s, 3H), 2.03 (br s, 3H).

Step 3. Synthesis of 2,5-dimethyl-4-(6-methylimidazo[1,2-a]pyrazin-5-yl)phenol (P6)

5-(4-Methoxy-2,5-dimethylphenyl)-6-methylimidazo[1,2-a]pyrazine (C62) (115 mg, 0.43 mmol) was dissolved in dichloromethane (5 mL) and the reaction mixture was cooled to −78° C. A solution of boron tribromide (1 M in dichloromethane, 2.58 mL, 2.58 mmol) was added slowly drop-wise, and the resulting mixture was stirred for 15 minutes; the cooling bath was then removed and the reaction mixture was stirred at room temperature for 18 hours. Methanol (5 mL) was added and the resulting mixture was heated to a gentle reflux for 30 minutes. The solvent was removed in vacuo and the resulting yellow residue was triturated three times with ethyl acetate (10 mL) to afford the product. Yield: 104 mg, 0.410 mmol, 95%. LCMS m/z 254.1 (M+H). $^1$H NMR (400 MHz, CD$_3$OD) δ 9.40 (s, 1H), 8.20 (d, J=2.0 Hz, 1H), 7.60-7.62 (m, 1H), 7.11 (s, 1H), 6.91 (s, 1H), 2.46 (s, 3H), 2.23 (br s, 3H), 1.98 (br s, 3H).

Preparation P7

3-Chloro-4-(4,6-dimethylpyrimidin-5-yl)phenol (P7)

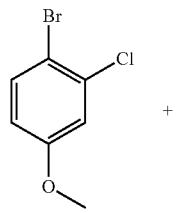

+

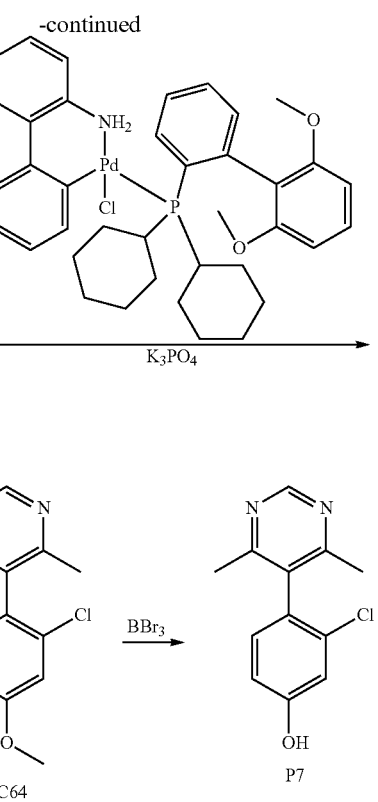

Step 1. Synthesis of 5-(2-chloro-4-methoxyphenyl)-4,6-dimethylpyrimidine (C64)

4,6-Dimethyl-5-(4,4,5,5-tetramethyl-1,3,2-dioxaborolan-2-yl)pyrimidine (C63, prepared from 5-bromo-4,6-dimethylpyrimidine using the method of Example 1, step 2) (750 mg, 3.2 mmol) and 1-bromo-2-chloro-4-methoxybenzene (1.46 g, 6.41 mmol) were dissolved in tetrahydrofuran (10 mL), and aqueous potassium phosphate solution (0.5 M, 12.8 mL) was added. Nitrogen was bubbled through the reaction mixture for 10 minutes. [2'-(Azanidyl-κN)biphenyl-2-yl-κC$_2$](chloro)[dicyclohexyl(2',6'-dimethoxybiphenyl-2-yl)-λ$^5$-phosphanyl]palladium (116 mg, 0.161 mmol) was added, and then nitrogen bubbling was continued for a few minutes. The reaction vessel was sealed and stirred at 70° C. for 18 hours. The reaction mixture was cooled to room temperature, diluted with ethyl acetate, washed with water and with saturated aqueous sodium chloride solution, dried over magnesium sulfate, filtered, and concentrated under reduced pressure. The crude material was purified by chromatography on silica gel (Eluent: 25% ethyl acetate in heptane) to afford the product as a light yellow oil, which solidified on standing. Yield: 320 mg, 1.29 mmol, 40%. $^1$H NMR (400 MHz, CDCl$_3$) δ 8.93 (s, 1H), 7.05 (d, J=2.5 Hz, 1H), 7.02 (d, J=8.6 Hz, 1H), 6.90 (dd, J=8.6, 2.5 Hz, 1H), 3.84 (s, 3H), 2.21 (s, 6H).

Step 2. Synthesis of 3-chloro-4-(4,6-dimethylpyrimidin-5-yl)phenol (P7)

5-(2-Chloro-4-methoxyphenyl)-4,6-dimethylpyrimidine (C64) (310 mg, 1.25 mmol) was converted to the product according to the general procedure for the synthesis of 5-[4-(furo[3,2-c]pyridin-4-yloxy)-2-methylphenyl]-6-methylpyrimidin-4-ol (C30) in Example 18. The product was obtained as an orange solid. Yield: 280 mg, 1.19 mmol, 95%. $^1$H NMR (400 MHz, CD$_3$OD) δ 8.82 (s, 1H), 7.05 (d, J=8.4 Hz, 1H), 6.98 (d, J=2.3 Hz, 1H), 6.85 (dd, J=8.4, 2.3 Hz, 1H), 2.20 (s, 6H).

Preparation P8

6-(4-Hydroxy-2-methylphenyl)-1,5-dimethyl-pyrazin-2(1H)-one (P8)

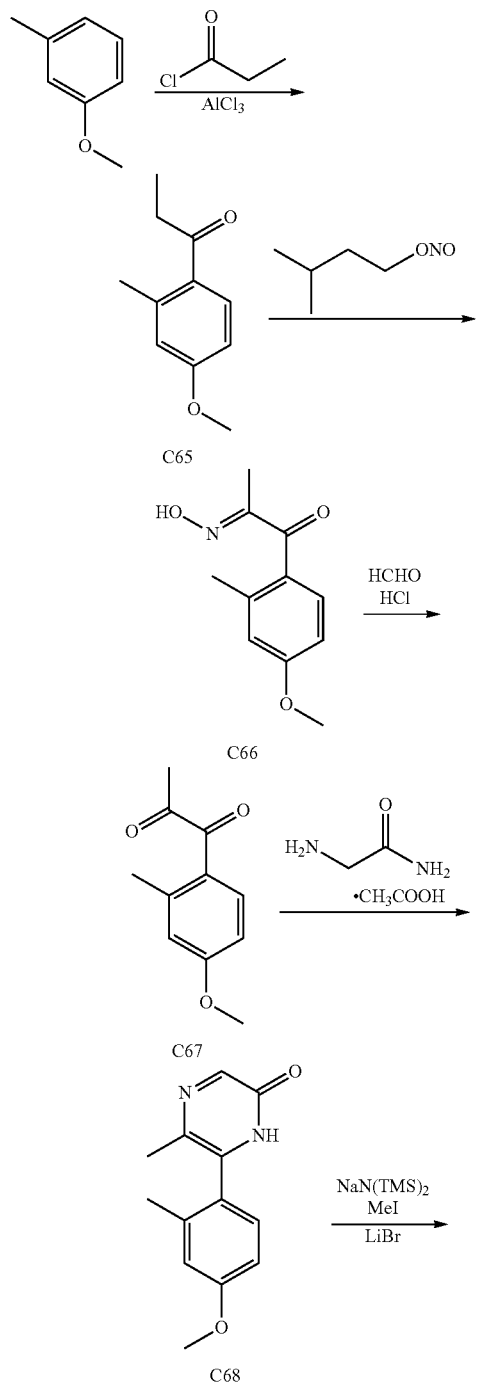

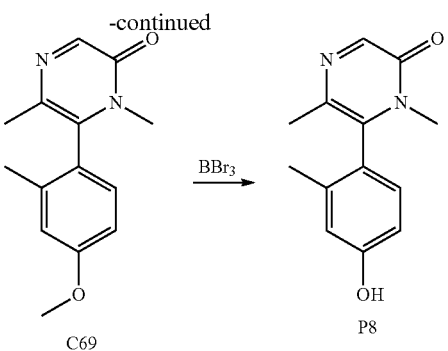

Step 1. Synthesis of 1-(4-methoxy-2-methylphenyl)propan-1-one (C65)

A mixture of 1-methoxy-3-methylbenzene (85.5 g, 0.700 mol) and aluminum chloride (138.6 g, 1.04 mol) in dichloromethane (2.5 L) was cooled in an ice bath; propanoyl chloride (97.1 g, 1.05 mol) was added drop-wise over a period of 30 minutes. The ice bath was removed, and the resulting mixture was stirred at room temperature for 20 minutes, then re-cooled in an ice bath. Water (150 mL) was added drop-wise followed by addition of more water (500 mL). The organic phase was separated and concentrated in vacuo. Silica gel chromatography (3% ethyl acetate in petroleum ether) gave the product as a colorless oil, which became a white solid upon standing at room temperature. By NMR, the product was contaminated with a small amount of another isomer. Yield: 100 g, 0.56 mol, 80%. $^1$H NMR (400 MHz, CDCl$_3$), product peaks: δ 7.73 (d, J=9.5 Hz, 1H), 6.73-6.78 (m, 2H), 3.84 (s, 3H), 2.91 (q, J=7.3 Hz, 2H), 2.55 (s, 3H), 1.19 (t, J=7.3 Hz, 3H).

Step 2. Synthesis of 2-(hydroxyimino)-1-(4-methoxy-2-methylphenyl)propan-1-one (C66)

To a mixture of 1-(4-methoxy-2-methylphenyl)propan-1-one (C65) (100 g, 0.56 mol) in tetrahydrofuran (2.5 L) was slowly added isoamyl nitrite (131 g, 1.12 mol) and hydrogen chloride (4 N in 1,4-dioxane, 200 mL). The mixture was stirred at room temperature for 24 hours, then concentrated in vacuo. Silica gel chromatography (Gradient: 3% to 10% ethyl acetate in petroleum ether) gave crude product (120 g), which was further purified by slurrying in a mixture of petroleum ether (1 L) and ethyl acetate (100 mL) at room temperature for 30 minutes. The mixture was filtered to yield the product as a solid. Yield: 75 g, 0.36 mol, 64%. $^1$H NMR (400 MHz, CDCl$_3$) δ 7.98-8.12 (br m, 1H), 7.46 (d, J=8.3 Hz, 1H), 6.72-6.79 (m, 2H), 3.84 (s, 3H), 2.40 (s, 3H), 2.16 (s, 3H).

Step 3. Synthesis of 1-(4-methoxy-2-methylphenyl)propane-1,2-dione (C67)

To a mixture of 2-(hydroxyimino)-1-(4-methoxy-2-methylphenyl)propan-1-one (C66) (37.5 g, 181 mmol) in water (720 mL) was slowly added formaldehyde solution (450 mL) and concentrated hydrochloric acid (270 mL). A second batch of the reaction was prepared in the same manner. Both mixtures were stirred at room temperature for 18 hours. The two batches were combined and extracted with ethyl acetate (3×2 L); the combined organic extracts were concentrated.

Silica gel chromatography (5% ethyl acetate in petroleum ether) gave the product as a yellow oil. Yield: 60 g, 310 mmol, 86%. $^1$H NMR (400 MHz, CDCl$_3$) δ 7.66 (d, J=8.5 Hz, 1H), 6.75-6.83 (m, 2H), 3.87 (s, 3H), 2.60 (s, 3H), 2.51 (s, 3H).

Step 4. Synthesis of 6-(4-methoxy-2-methylphenyl)-5-methylpyrazin-2(1H)-one (C68)

1-(4-Methoxy-2-methylphenyl)propane-1,2-dione (C67) (4.0 g, 21 mmol) and glycinamide acetate (2.79 g, 20.8 mmol) were dissolved in methanol (40 mL) and cooled to −10° C. Aqueous sodium hydroxide solution (12 N, 3.5 mL, 42 mmol) was added, and the resulting mixture was slowly warmed to room temperature. After stirring for 3 days, the reaction mixture was concentrated in vacuo. The residue was diluted with water, and 1 N aqueous hydrochloric acid was added until the pH was approximately 7. The aqueous phase was extracted several times with ethyl acetate, and the combined organic extracts were washed with saturated aqueous sodium chloride solution, dried over magnesium sulfate, filtered, and concentrated under reduced pressure. The resulting residue was slurried with 3:1 ethyl acetate/heptane, stirred for 5 minutes, and then filtered. The filtrate was concentrated under reduced pressure. Silica gel chromatography (Eluent: ethyl acetate) gave the product as a tan solid that contained 15% of an undesired regioisomer; this material was used without further purification. Yield: 2.0 g, 8.7 mmol, <41%. LCMS m/z 231.1 (M+H). $^1$H NMR (400 MHz, CDCl$_3$), product peaks: δ 8.09 (s, 1H), 7.14 (d, J=8.2 Hz, 1H), 6.82-6.87 (m, 2H), 3.86 (s, 3H), 2.20 (s, 3H), 2.11 (s, 3H).

Step 5. Synthesis of 6-(4-methoxy-2-methylphenyl)-1,5-dimethylpyrazin-2(1H)-one (C69)

6-(4-Methoxy-2-methylphenyl)-5-methylpyrazin-2(1H)-one (C68) (from the previous step, 1.9 g, <8.2 mmol) was dissolved in N,N-dimethylformamide (40 mL). Lithium bromide (0.86 g, 9.9 mmol) and sodium bis(trimethylsilyl)amide (95%, 1.91 g, 9.89 mmol) were added and the reaction mixture was stirred for 30 minutes. Methyl iodide (0.635 mL, 10.2 mmol) was added and the resulting solution was stirred at room temperature for 18 hours. The reaction mixture was diluted with water and brought to a pH of approximately 7 by slow portion-wise addition of 1 N aqueous hydrochloric acid. The aqueous layer was extracted with ethyl acetate and the combined ethyl acetate layers were washed several times with water, dried over magnesium sulfate, filtered, and concentrated. Silica gel chromatography (Gradient: 75% to 100% ethyl acetate in heptane) gave the product as a viscous orange oil. Yield: 1.67 g, 6.84 mmol, 33% over two steps. LCMS m/z 245.1 (M+H). $^1$H NMR (400 MHz, CDCl$_3$) δ 8.17 (s, 1H), 7.03 (br d, J=8 Hz, 1H), 6.85-6.90 (m, 2H), 3.86 (s, 3H), 3.18 (s, 3H), 2.08 (br s, 3H), 2.00 (s, 3H).

Step 6. Synthesis of 6-(4-hydroxy-2-methylphenyl)-1,5-dimethylpyrazin-2(1H)-one (P8)

To a cooled (−78° C.) solution of 6-(4-methoxy-2-methylphenyl)-1,5-dimethylpyrazin-2(1H)-one (C69) (1.8 g, 7.37 mmol) in dichloromethane was added a solution of boron tribromide in dichloromethane (1 M, 22 mL, 22 mmol). The cooling bath was removed after 30 minutes, and the reaction mixture was allowed to warm to room temperature and stir for 18 hours. The reaction was cooled to −78° C., and methanol (10 mL) was slowly added; the resulting mixture was slowly warmed to room temperature. The reaction mixture was concentrated in vacuo, methanol (20 mL) was added, and the mixture was again concentrated under reduced pressure. The residue was diluted with ethyl acetate (300 mL) and water (200 mL) and the resulting aqueous layer was brought to pH 7 via the portion-wise addition of saturated aqueous sodium carbonate solution. The mixture was extracted with ethyl acetate (3×200 mL). The combined organic extracts were washed with water and with saturated aqueous sodium chloride solution, dried over magnesium sulfate, filtered, and concentrated in vacuo to afford the product as a light tan solid. Yield: 1.4 g, 6.0 mmol, 81%. LCMS m/z 231.1 (M+H). $^1$H NMR (400 MHz, CDCl$_3$) δ 8.21 (s, 1H), 6.98 (d, J=8.2 Hz, 1H), 6.87-6.89 (m, 1H), 6.85 (br dd, J=8.2, 2.5 Hz, 1H), 3.22 (s, 3H), 2.06 (br s, 3H), 2.03 (s, 3H).

Preparation P9

3-Methyl-4-(3-methylimidazo[2,1-c][1,2,4]triazin-4-yl)phenol (P9)

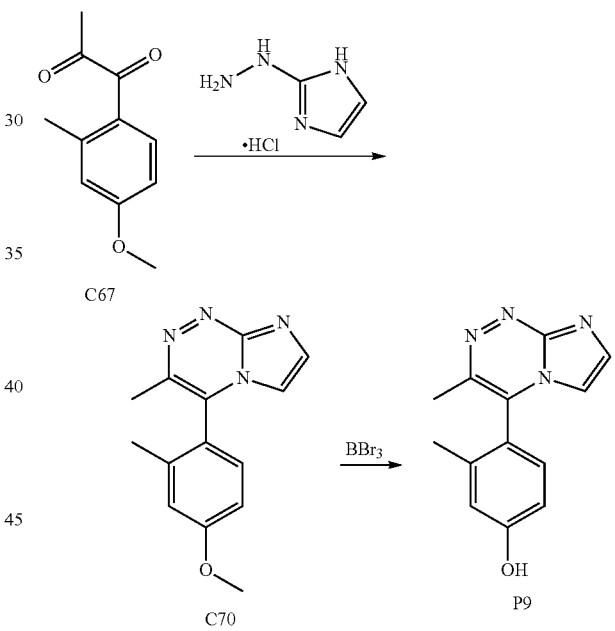

Step 1. Synthesis of 4-(4-methoxy-2-methylphenyl)-3-methylimidazo[2,1-c][1,2,4]triazine (C70)

A mixture of 1-(4-methoxy-2-methylphenyl)propane-1,2-dione (C67) (1.0 g, 5.2 mmol) and 2-hydrazinyl-1H-imidazole hydrochloride (1.05 g, 7.8 mmol) in N,N-dimethylformamide (8 mL) was heated to 100° C. in a microwave reactor for 20 minutes. After the progress of the reaction had been assessed by thin layer chromatography, the mixture was heated to 120° C. for 20 minutes. The solvent was removed in vacuo and the residue was taken up in ethyl acetate (30 mL) and water (10 mL). Saturated aqueous sodium bicarbonate solution was added to adjust the pH to roughly 8. The aqueous layer was extracted with additional ethyl acetate (30 mL) and the combined organic extracts were dried over magnesium sulfate, filtered, and concentrated in vacuo. Silica gel chromatography (Gradient: 50% to 100% ethyl acetate in heptane) afforded the product as a light yellow solid. Yield: 587 mg, 2.31 mmol, 44%. $^1$H NMR (400 MHz, CDCl$_3$) δ 8.06 (d, J=0.9 Hz, 1H), 7.21 (d, J=8.2 Hz, 1H), 7.15 (d, J=1.1 Hz, 1H), 6.95-7.00 (m, 2H), 3.91 (s, 3H), 2.63 (s, 3H), 2.03 (br s, 3H).

Step 2. Synthesis of 3-methyl-4-(3-methylimidazo[2,1-c][1,2,4]triazin-4-yl)phenol (P9)

4-(4-Methoxy-2-methylphenyl)-3-methylimidazo[2,1-c][1,2,4]triazine (C70) (587 mg, 2.31 mmol) in dichloromethane (5 mL) was reacted with boron tribromide (1 M in dichloromethane, 13.1 mL, 13.1 mmol) as described in Preparation P8. The product was obtained as a tan solid. Yield: 543 mg, 2.25 mmol, 97%. LCMS m/z 241.1 (M+H). $^1$H NMR (400 MHz, DMSO-d$_6$) δ 9.99 (s, 1H), 8.09 (d, J=1.0 Hz, 1H), 7.43 (d, J=1.2 Hz, 1H), 7.27 (d, J=8.4 Hz, 1H), 6.89 (br d, J=2.2 Hz, 1H), 6.83 (br dd, J=8.3, 2.4 Hz, 1H), 2.49 (s, 3H), 1.91 (br s, 3H).

Preparation P10

7-(4,6-Dimethylpyrimidin-5-yl)-2-methyl-2H-indazol-4-ol (P10)

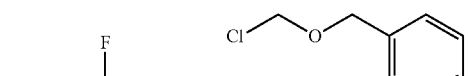

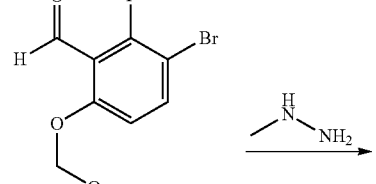

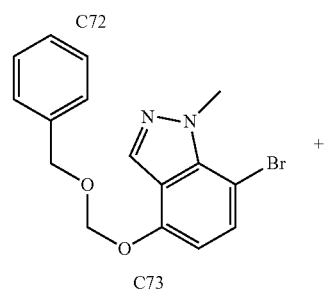

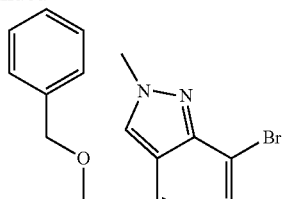

C74

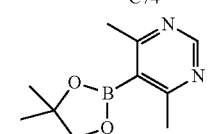

C63
K$_3$PO$_4$

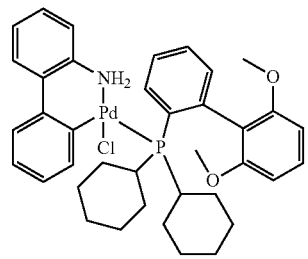

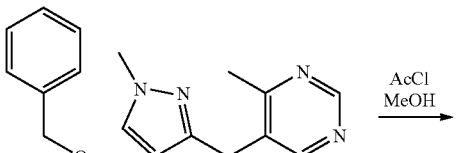

C75

AcCl
MeOH

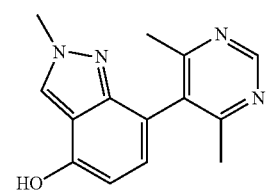

P10

Step 1. Synthesis of 4-[(benzyloxy)methoxy]-1-bromo-2-fluorobenzene (C71)

A solution of 4-bromo-3-fluorophenol (1.22 g, 6.39 mmol), benzyl chloromethyl ether (60%, 2.22 mL, 9.58 mmol) and diisopropylethylamine (2.23 mL, 12.8 mmol) in dichloromethane was heated at reflux for two hours. The reaction mixture was then concentrated in vacuo and purified by silica gel chromatography (Gradient: 15% to 40% ethyl acetate in heptane) to afford the product as a colorless oil. Yield: 2.35 g, >100%. $^1$H NMR (400 MHz, CD$_3$OD), characteristic peaks: δ 7.48 (dd, J=8.9, 8.1 Hz, 1H), 6.95 (dd, J=10.6, 2.7 Hz, 1H), 6.84 (ddd, J=8.9, 2.8, 1.1 Hz, 1H), 5.31 (s, 2H), 4.70 (s, 2H).

Step 2. Synthesis of 6-[(benzyloxy)methoxy]-3-bromo-2-fluorobenzaldehyde (C72)

A solution of 4-[(benzyloxy)methoxy]-1-bromo-2-fluorobenzene (C71) (from the previous step, 525 mg, <1.69 mmol) in tetrahydrofuran (20 mL) was cooled to −78° C. for 15 minutes. Lithium diisopropylamide (1.60 M, 1.58 mL, 2.53 mmol) was then added drop-wise over 15 minutes. After one hour at −78° C., N,N-dimethylformamide (0.197 mL, 2.53 mmol) in tetrahydrofuran (5 mL) was added. The reaction mixture was stirred at −78° C. for 30 minutes, quenched with 50% saturated aqueous sodium chloride solution (30 mL) and then allowed to reach room temperature. The reaction mixture was extracted with ethyl acetate (3×30 mL). The combined organic layers were dried over sodium sulfate, filtered, concentrated in vacuo and purified by silica gel chromatography (Gradient: 15% to 40% ethyl acetate in heptane) to afford the product as a light yellow oil. Yield: 397 mg, 1.17 mmol, 82% over two steps. $^1$H NMR (400 MHz, CDCl$_3$) δ 10.36 (d, J=1.4 Hz, 1H), 7.66 (dd, J=9.2, 7.6 Hz, 1H), 7.29-7.38 (m, 5H), 7.04 (dd, J=9.1, 1.5 Hz, 1H), 5.42 (s, 2H), 4.75 (s, 2H).

Step 3. Synthesis of 4-[(benzyloxy)methoxy]-7-bromo-1-methyl-1H-indazole (C73) and 4-[(benzyloxy)methoxy]-7-bromo-2-methyl-2H-indazole (C74)

A mixture of 6-[(benzyloxy)methoxy]-3-bromo-2-fluorobenzaldehyde (C72) (1.40 g, 4.13 mmol) and methylhydrazine (8.69 mL, 165 mmol) was dissolved in 1,4-dioxane (8 mL) in a pressure vessel and heated at 110° C. for 4 hours, then at 120° C. for 16 hours. The mixture was submitted to microwave irradiation at 150° C. for 90 minutes. The reaction mixture was concentrated in vacuo and purified by silica gel chromatography (Gradient: 15% to 40% ethyl acetate in heptane) to provide C73 as a colorless oil and C74 as a yellow oil. Yield: C73, 801 mg, 2.31 mmol, 56%; C74, 296 mg, 0.852 mmol, 21%. C73: $^1$H NMR (400 MHz, CDCl$_3$) δ 8.05 (s, 1H), 7.41 (d, J=8.2 Hz, 1H), 7.28-7.38 (m, 5H), 6.67 (d, J=8.2 Hz, 1H), 5.44 (s, 2H), 4.76 (s, 2H), 4.41 (s, 3H). C74: $^1$H NMR (400 MHz, CDCl$_3$) δ 8.06 (br s, 1H), 7.38 (d, J=7.9 Hz, 1H), 7.28-7.38 (m, 5H), 6.59 (d, J=8.0 Hz, 1H), 5.42 (s, 2H), 4.76 (s, 2H), 4.26 (br s, 3H).

Step 4. Synthesis of 4-[(benzyloxy)methoxy]-7-(4,6-dimethylpyrimidin-5-yl)-2-methyl-2H-indazole (C75)

A mixture of 4,6-dimethyl-5-(4,4,5,5-tetramethyl-1,3,2-dioxaborolan-2-yl)pyrimidine (C63) (152 mg, 0.649 mmol), 4-[(benzyloxy)methoxy]-7-bromo-2-methyl-2H-indazole (C74) (150 mg, 0.432 mmol), tetrahydrofuran (5 mL), and aqueous potassium phosphate solution (0.5 M, 2.59 mL, 1.30 mmol) was purged with nitrogen for two minutes before adding [2'-(azanidyl-κN)biphenyl-2-yl-κC$_2$](chloro)[dicyclohexyl(2',6'-dimethoxybiphenyl-2-yl)-λ$^5$-phosphanyl]palladium (31 mg, 0.043 mmol). The reaction mixture was heated at 70° C. for 40 hours, then filtered through a thin layer of Celite. The filtrate was concentrated in vacuo and purified by silica gel chromatography (Gradient: 5% to 10% methanol in dichloromethane) to give the product as a dark oil. Yield: 63 mg, 0.17 mmol, 39%. LCMS m/z 375.2 (M+H). $^1$H NMR (400 MHz, CDCl$_3$) δ 8.98 (s, 1H), 8.06 (s, 1H), 7.29-7.41 (m, 5H), 6.96 (d, J=7.6 Hz, 1H), 6.76 (d, J=7.6 Hz, 1H), 5.50 (s, 2H), 4.83 (s, 2H), 4.17 (s, 3H), 2.31 (s, 6H).

Step 5. Synthesis of 7-(4,6-dimethylpyrimidin-5-yl)-2-methyl-2H-indazol-4-ol (P10)

To a solution of acetyl chloride (98%, 0.122 mL, 1.68 mmol) in methanol (2 mL) was added a solution of 4-[(benzyloxy)methoxy]-7-(4,6-dimethylpyrimidin-5-yl)-2-methyl-2H-indazole (C75) (63 mg, 0.17 mmol) in methanol (2 mL). After 16 hours, the reaction mixture was concentrated in vacuo and purified by silica gel chromatography (Gradient: 5% to 10% methanol in dichloromethane) to afford the product as a glassy solid. Yield: 37 mg, 0.14 mmol, 82%. LCMS m/z 255.2 (M+H). $^1$H NMR (400 MHz, CD$_3$OD) δ 8.87 (s, 1H), 8.28 (s, 1H), 6.97 (d, J=7.6 Hz, 1H), 6.47 (d, J=7.6 Hz, 1H), 4.13 (s, 3H), 2.25 (s, 6H).

Preparation P11

7-(4,6-Dimethylpyrimidin-5-yl)-1-methyl-1H-indazol-4-ol (P11)

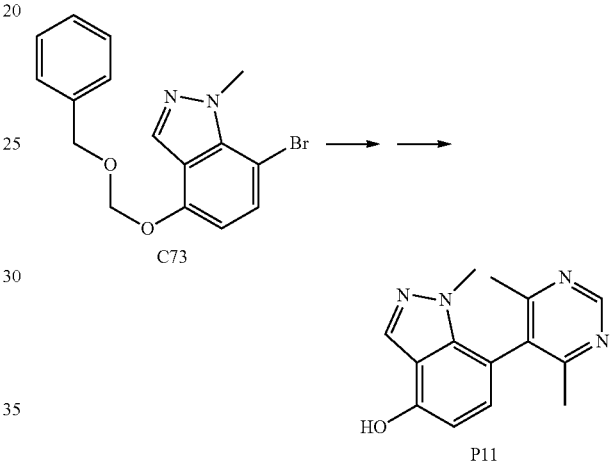

Compound P11 was prepared from 4-[(benzyloxy)methoxy]-7-bromo-1-methyl-1H-indazole (C73) according to steps 4 and 5 of the synthesis of 7-(4,6-dimethylpyrimidin-5-yl)-2-methyl-2H-indazol-4-ol (P10) in Preparation P10, to provide the product as an off-white solid. Yield: 36 mg, 0.14 mmol, 64%. LCMS m/z 255.2 (M+H). $^1$H NMR (400 MHz, DMSO-d$_6$) δ 10.40 (br s, 1H), 8.95 (s, 1H), 8.09 (s, 1H), 6.96 (d, J=7.6 Hz, 1H), 6.53 (d, J=7.8 Hz, 1H), 3.38 (s, 3H), 2.15 (s, 6H).

Preparation P12

5-(Furo[3,2-c]pyridin-4-yloxy)-2-(imidazo[1,2-a]pyridin-5-yl)benzoic acid (P12)

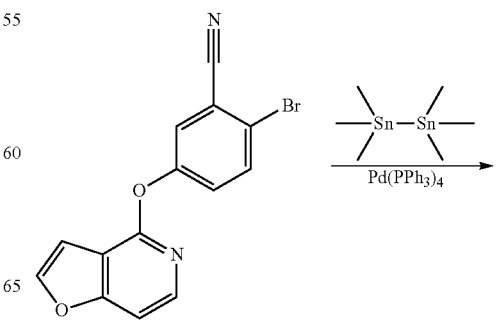

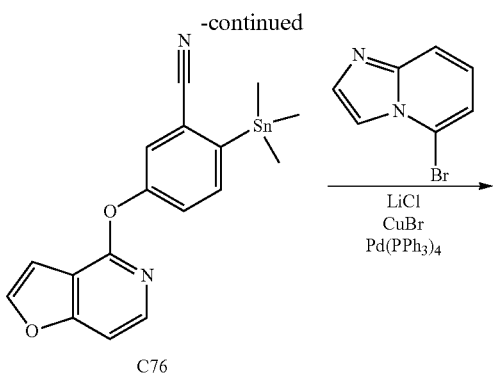

C76

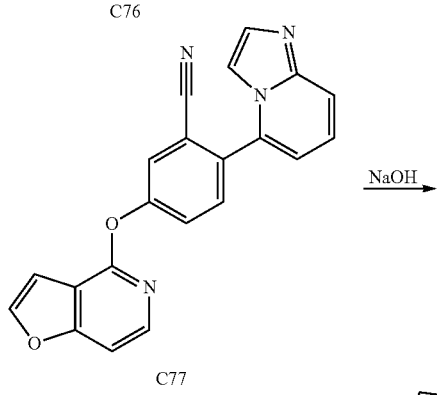

C77

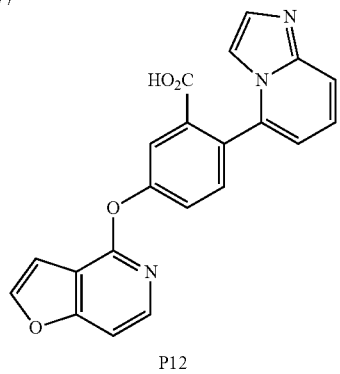

P12

Step 1. Synthesis of 5-(furo[3,2-c]pyridin-4-yloxy)-2-(trimethylstannanyl)benzonitrile (C76)

To a solution of 2-bromo-5-(furo[3,2-c]pyridin-4-yloxy)benzonitrile (prepared from 2-bromo-5-hydroxybenzonitrile and 4-iodofuro[3,2-c]pyridine by the method of Step 3 in Example 7; 4-iodofuro[3,2-c]pyridine was synthesized from 4-chlorofuro[3,2-c]pyridine with acetyl chloride and sodium iodide in acetonitrile) (7.0 g, 22 mmol) in 1,4-dioxane (70 mL) was added hexamethyldistannane (21.8 g, 66.6 mmol) and tetrakis(triphenylphosphine)palladium(0) (1.28 g, 1.11 mmol). The resulting mixture was heated at 120° C. for 18 hours. The reaction mixture was filtered and the filtrate was concentrated to give a crude residue, which was purified by silica gel chromatography (Eluent: 400:1 petroleum ether/ethyl acetate) to provide the product as a white solid. Yield: 6.0 g, 15 mmol, 67%. $^1$H NMR (400 MHz, CDCl$_3$) δ 8.01 (d, J=5.9 Hz, 1H), 7.68 (d, J=2.2 Hz, 1H), 7.62 (d, J=8.1 Hz, 1H), 7.55-7.58 (m, 1H), 7.42 (dd, J=8.0, 2.4 Hz, 1H), 7.26 (dd, J=5.8, 0.9 Hz, 1H), 6.93 (dd, J=2.2, 0.9 Hz, 1H), 0.47 (s, 9H).

Step 2. Synthesis of 5-(furo[3,2-c]pyridin-4-yloxy)-2-(imidazo[1,2-a]pyridin-5-yl)benzonitrile (C77)

To a solution of 5-(furo[3,2-c]pyridin-4-yloxy)-2-(trimethylstannyl)benzonitrile (C76) (8.3 g, 21 mmol) in tetrahydrofuran (160 mL) was added 5-bromoimidazo[1,2-a]pyridine (3.9 g, 20 mmol), lithium chloride (0.67 g, 15.8 mmol), copper(I) bromide (0.57 g, 4.0 mmol) and tetrakis(triphenylphosphine)palladium(0) (2.27 g, 2.0 mmol). The mixture was heated to reflux for 48 hours. The reaction mixture was filtered and the filtrate was concentrated to give crude product, which was purified by silica gel chromatography (Gradient: 7% to 20% ethyl acetate in petroleum ether) to give the product as a brown solid. Yield: 5 g, 13 mmol, 68%. LCMS m/z 353.0 (M+H). $^1$H NMR (400 MHz, CD$_3$OD, concentrated HCl), characteristic peaks: δ 8.23-8.26 (m, 1H), 8.12 (br d, half of AB quartet, J=8 Hz, 1H), 8.06 (br d, half of AB quartet, J=8 Hz, 1H), 7.93 (br d, J=6 Hz, 1H), 7.77-7.81 (m, 1H).

Step 3. Synthesis of 5-(furo[3,2-c]pyridin-4-yloxy)-2-(imidazo[1,2-a]pyridin-5-yl)benzoic acid (P12)

To an aqueous solution of sodium hydroxide (15% w/v, 25 mL) was added 5-(furo[3,2-c]pyridin-4-yloxy)-2-(imidazo[1,2-a]pyridine-5-yl)benzonitrile (C77) (4.35 g, 12.3 mmol) and ethanol (25 mL), and the reaction mixture was heated to reflux for 18 hours. The mixture was cooled to room temperature and extracted with dichloromethane. The aqueous layer was adjusted to pH 7 with 3 N aqueous hydrochloric acid; the resulting mixture was filtered, and the filter cake was washed with ethyl acetate and dichloromethane, then dried under vacuum to give the product as a yellow solid. Yield: 1.9 g, 5.1 mmol, 42%. LCMS m/z 371.9 (M+H). $^1$H NMR (400 MHz, DMSO-d$_6$), characteristic peaks: δ 8.17 (d, J=2.4 Hz, 1H), 8.04 (d, J=5.9 Hz, 1H), 7.52 (d, J=5.9 Hz, 1H), 6.72 (br d, J=6.7 Hz, 1H).

Preparation P13

4-{[7-(4,4,5,5-Tetramethyl-1,3,2-dioxaborolan-2-yl)-1,3-benzodioxol-4-yl]oxy}furo[3,2-c]pyridine (P13)

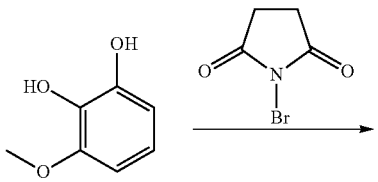

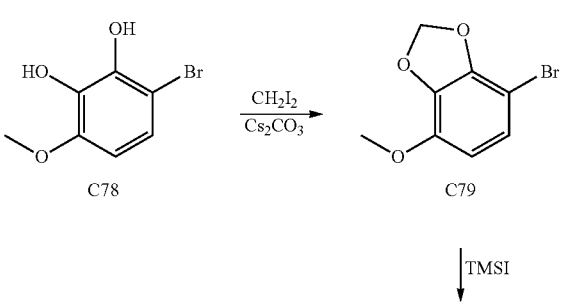

C78          C79

↓ TMSI

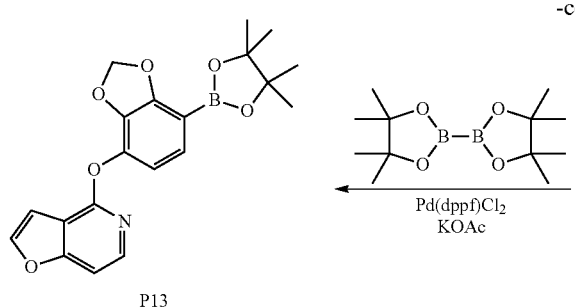
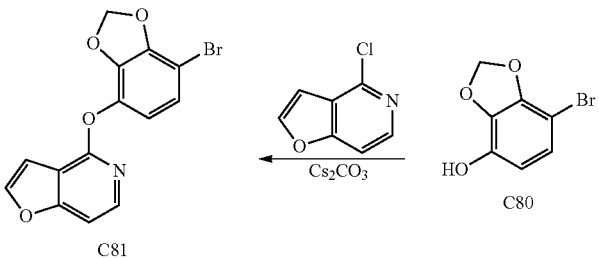

Step 1. Synthesis of 3-bromo-6-methoxybenzene-1,2-diol (C78)

To a mixture of 3-methoxybenzene-1,2-diol (578 mg, 4.12 mmol) in acetonitrile (10 mL) at 0° C. was slowly added N-bromosuccinimide (95%, 811 mg, 4.33 mmol) in acetonitrile (5 mL). After two hours at 0° C., aqueous sodium thiosulfate solution (1 M, 2 mL) was added. After ten minutes, the reaction mixture was concentrated in vacuo and purified by silica gel chromatography (Gradient: 20% to 40% ethyl acetate in heptane) to give the product as a white solid. Yield: 858 mg, 0.3.92 mmol, 95%. LCMS m/z 216.8 (M−H). $^1$H NMR (400 MHz, CDCl$_3$) δ 7.00 (d, J=9.0 Hz, 1H), 6.43 (d, J=9.0 Hz, 1H), 5.54 (s, 1H), 5.48 (s, 1H), 3.89 (s, 3H). Step 2. Synthesis of 4-bromo-7-methoxy-1,3-benzodioxole (C79).

To a solution of 3-bromo-6-methoxybenzene-1,2-diol (C78) (420 mg, 1.92 mmol) in N,N-dimethylformamide (5 mL) were added diiodomethane (0.170 mL, 2.11 mmol) and cesium carbonate (690 mg, 2.1 mmol). The reaction mixture was stirred at 100° C. for one hour, then cooled to room temperature and diluted with ethyl acetate (20 mL). The solid was removed by filtration and washed with ethyl acetate (30 mL). The filtrate was washed with 50% saturated aqueous sodium chloride solution (4×20 mL), dried over sodium sulfate, filtered, concentrated in vacuo, and purified by silica gel chromatography (Gradient: 20% to 40% ethyl acetate in heptane) to give the product as a white solid. Yield: 335 mg, 1.45 mmol, 76%. $^1$H NMR (400 MHz, CDCl$_3$) δ 6.92 (d, J=9.0 Hz, 1H), 6.46 (d, J=9.1 Hz, 1H), 6.05 (s, 2H), 3.90 (s, 3H). Step 3. Synthesis of 7-bromo-1,3-benzodioxol-4-ol (C80).

To a solution of 4-bromo-7-methoxy-1,3-benzodioxole (C79) (186 mg, 0.805 mmol) in acetonitrile (5 mL) was added trimethylsilyl iodide (0.343 mL, 2.42 mmol). The reaction mixture was heated at 85° C. for 18 hours and purified by silica gel chromatography (Gradient: 30% to 40% ethyl acetate in heptane) to give the product as an oil. Yield: 59 mg, 0.27 mmol, 34%. $^1$H NMR (400 MHz, CDCl$_3$) δ 6.86 (d, J=9.0 Hz, 1H), 6.44 (d, J=9.0 Hz, 1H), 6.05 (s, 2H).

Step 4. Synthesis of 4-[(7-bromo-1,3-benzodioxol-4-yl)oxy]furo-[3,2-c]pyridine (C81)

A mixture of 7-bromo-1,3-benzodioxol-4-ol (C80) (59 mg, 0.27 mmol), 4-chlorofuro[3,2-c]pyridine (62.7 mg, 0.408 mmol) and cesium carbonate (224 mg, 0.687 mmol) in dimethyl sulfoxide (2 mL) was heated at 140° C. for 4 hours. The reaction mixture was cooled to room temperature and combined with a similar reaction carried out on 16 mg of C80. Ethyl acetate was added and the solid was removed by filtration. The filtrate was washed with 50% saturated aqueous sodium chloride solution (3×15 mL), concentrated in vacuo and purified by silica gel chromatography (Gradient: 10% to 30% ethyl acetate in heptane) to afford the product as an oil. Yield: 61 mg, 0.182 mmol, 53%. LCMS m/z 335.9 (M+H).

Step 5. Synthesis of 4-{[7-(4,4,5,5-tetramethyl-1,3,2-dioxaborolan-2-yl)-1,3-benzodioxol-4-yl]oxy}furo[3,2-c]pyridine (P13)

A mixture of 4-[(7-bromo-1,3-benzodioxol-4-yl)oxy]furo[3,2-c]pyridine (C81) (61 mg, 0.18 mmol), 4,4,4',4',5,5,5',5'-octamethyl-2,2'-bi-1,3,2-dioxaborolane (99%, 70.3 mg, 0.274 mmol), 1,1'-bis(diphenylphosphino)ferrocene]dichloropalladium(II) (50%, 26.3 mg, 0.018 mmol) and potassium acetate (55 mg, 0.55 mmol) were combined in acetonitrile (3 mL). After bubbling nitrogen through the reaction mixture for five minutes, it was heated at 80° C. for 18 hours. The reaction mixture was then filtered through a thin layer of Celite, washing with ethyl acetate (20 mL). The filtrate was concentrated in vacuo and the residue was partitioned between water (15 mL) and ethyl acetate (20 mL). The aqueous layer was extracted with ethyl acetate (3×10 mL); the combined organic layers were dried over sodium sulfate, filtered, and concentrated in vacuo Purification by silica gel chromatography (Gradient: 15% to 50% ethyl acetate in heptane) provided the product as a light yellow gum. Yield: 25 mg, 0.066 mmol, 37%. $^1$H NMR (400 MHz, CDCl$_3$) δ 8.00 (d, J=5.8 Hz, 1H), 7.64 (d, J=2.2 Hz, 1H), 7.30 (d, J=8.4 Hz, 1H), 7.21 (dd, J=5.8, 1.0 Hz, 1H), 6.92 (dd, J=2.2, 0.9 Hz, 1H), 6.80 (d, J=8.5 Hz, 1H), 6.03 (s, 2H), 1.37 (s, 12H).

Preparation P14

8-(4,6-Dimethylpyrimidin-5-yl)isoquinolin-5-ol (P14)

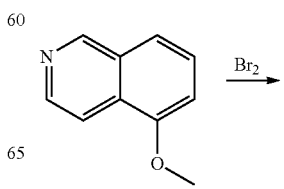

145

-continued

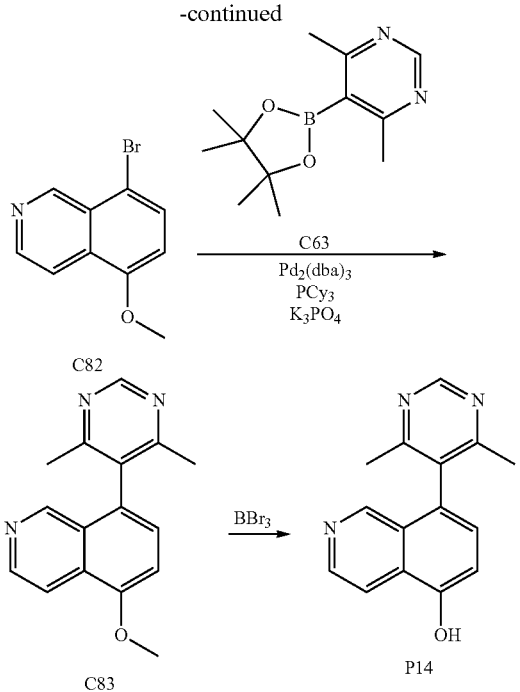

Step 1. Synthesis of 8-bromo-5-methoxyisoquinoline (C82)

To a solution of 5-methoxyisoquinoline (1.48 g, 9.30 mmol) in acetic acid (15 mL) was added a solution of bromine (2.1 g, 13 mmol) in acetic acid (5 mL). After three days at room temperature, the reaction mixture was cooled to 0° C., quenched with saturated aqueous sodium bicarbonate solution and extracted with dichloromethane (3×50 mL). The combined organic layers were dried over sodium sulfate, filtered, concentrated in vacuo and purified by silica gel chromatography (Gradient: 5% to 33% ethyl acetate in petroleum ether) to give the product as a solid. Yield: 1.72 g, 7.22 mmol, 78%. $^1$H NMR (400 MHz, DMSO-$d_6$) δ 9.40 (s, 1H), 8.64 (d, J=6.0 Hz, 1H), 7.99 (d, J=5.5 Hz, 1H), 7.90 (d, J=8.5 Hz, 1H), 7.18 (d, J=8.5 Hz, 1H), 4.00 (s, 3H).

Step 2. Synthesis of 8-(4,6-dimethylpyrimidin-5-yl)-5-methoxyisoquinoline (C83)

To a solution of 8-bromo-5-methoxyisoquinoline (C82) (1.72 g, 7.22 mmol) in 1,4-dioxane (75 mL) and water (5 mL) were added 4,6-dimethyl-5-(4,4,5,5-tetramethyl-1,3,2-dioxaborolan-2-yl)pyrimidine (C63) (2.20 g, 9.40 mmol), tris(dibenzylideneacetone)dipalladium(0) (659 mg, 0.72 mmol), tricyclohexylphosphine (403 mg, 1.44 mmol) and potassium phosphate (3.07 g, 14.46 mmol). The reaction mixture was degassed with nitrogen for five minutes, then stirred for 6 hours at 120° C. More 4,6-dimethyl-5-(4,4,5,5-tetramethyl-1,3,2-dioxaborolan-2-yl)pyrimidine (C63) (1.1 g, 4.7 mmol) was added. The reaction mixture was stirred for 7 hours at 120° C. and then filtered. The filtrate was concentrated in vacuo and purified by silica gel chromatography (Gradient: 0.5% to 2.5% methanol in dichloromethane) to provide the product as a solid. Yield: 1.0 g, 3.8 mmol, 53%. $^1$H NMR (400 MHz, DMSO-$d_6$) δ 9.00 (s, 1H), 8.56-8.60 (m, 2H), 8.07 (dd, J=5.8, 0.8 Hz, 1H), 7.51 (d, J=7.8 Hz, 1H), 7.36 (d, J=8.0 Hz, 1H), 4.07 (s, 3H), 2.08 (s, 6H).

146

Step 3. Synthesis of 8-(4,6-dimethylpyrimidin-5-yl)isoquinolin-5-ol (P14)

To a solution of 8-(4,6-dimethylpyrimidin-5-yl)-5-methoxyisoquinoline (C83) (1.0 g, 3.8 mmol) in dichloromethane (60 mL) was slowly added boron tribromide (4.7 g, 19 mmol) at −78° C. The mixture was allowed to warm to room temperature and stirred overnight before being quenched at −20° C. with methanol. The reaction mixture was washed with saturated aqueous sodium bicarbonate solution; the aqueous layer was extracted with dichloromethane (5×50 mL) and ethyl acetate (5×50 mL). The combined organic layers were dried over sodium sulfate, filtered, concentrated in vacuo and purified by silica gel chromatography (Gradient: 0.5% to 5% methanol in dichloromethane) to give the product as a solid. Yield: 300 mg, 1.19 mmol, 31%. $^1$H NMR (400 MHz, DMSO-$d_6$) δ 10.88 (br s, 1H), 8.98 (s, 1H), 8.49-8.55 (m, 2H), 8.04 (br d, J=6 Hz, 1H), 7.36 (d, J=7.8 Hz, 1H), 7.21 (d, J=7.8 Hz, 1H), 2.07 (s, 6H).

Preparation P15

4-(3,5-Dimethylpyridazin-4-yl)-3-methoxyphenol (P15)

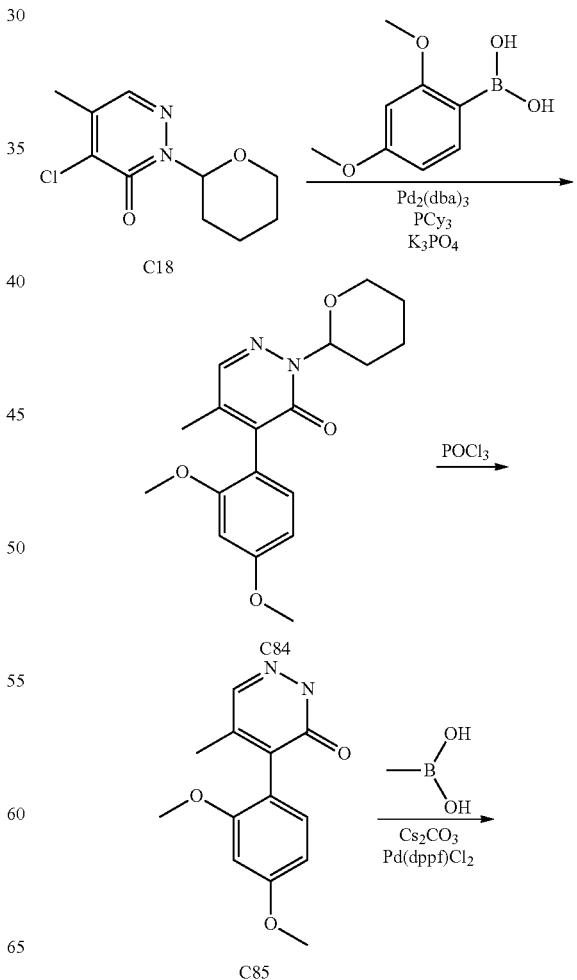

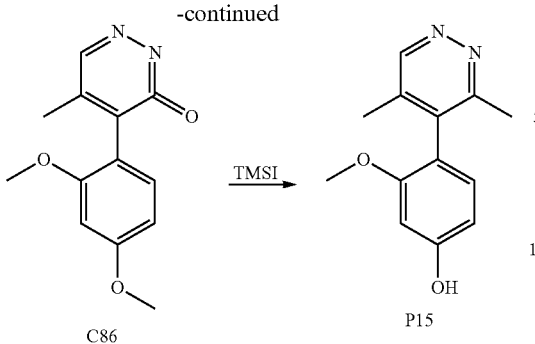

Step 1. Synthesis of 4-(2,4-dimethoxyphenyl)-5-methyl-2-(tetrahydro-2H-pyran-2-yl)pyridazin-3(2H)-one (C84)

A mixture of 4-chloro-5-methyl-2-(tetrahydro-2H-pyran-2-yl)pyridazin-3(2H)-one (C18) (30 g, 130 mmol), (2,4-dimethoxyphenyl)boronic acid (26 g, 140 mmol), tris(dibenzylideneacetone)dipalladium(0) (9.69 g, 10.6 mmol), tricyclohexylphosphine (7.5 g, 27 mmol) and potassium phosphate monohydrate (69 g, 300 mmol) in 1,4-dioxane (250 mL) was heated at reflux for 3 hours and then cooled to room temperature, filtered, and concentrated in vacuo. Silica gel chromatography (Gradient: 9% to 17% ethyl acetate in petroleum ether) afforded the product as a yellow solid. Yield: 40 g, 120 mmol, 92%. $^1$H NMR (400 MHz, CDCl$_3$), mixture of diastereomers, characteristic peaks: δ 7.76 and 7.77 (2 s, total 1H), [7.10 (d, J=8.3 Hz) and 7.07 (d, J=8.3 Hz), total 1H], 6.51-6.59 (m, 2H), 6.06-6.12 (m, 1H), 4.11-4.20 (m, 1H), 3.85 (s, 3H), 3.74 and 3.76 (2 s, total 3H), 1.99 and 2.00 (2 s, total 3H).

Step 2. Synthesis of 3-chloro-4-(2,4-dimethoxyphenyl)-5-methylpyridazine (C85)

4-(2,4-Dimethoxyphenyl)-5-methyl-2-(tetrahydro-2H-pyran-2-yl)pyridazin-3(2H)-one (C84) (30 g, 91 mmol) was dissolved in phosphorus oxychloride (158 mL) and the mixture was heated at reflux for 5 hours, cooled to room temperature, and poured into ice water. Careful addition of potassium carbonate to neutralize the reaction was followed by extraction with ethyl acetate (3×500 mL). The combined organic extracts were concentrated in vacuo. Silica gel chromatography (Gradient: 17% to 50% ethyl acetate in petroleum ether) gave the product as an orange solid. Yield: 20 g, 76 mmol, 83%. LCMS m/z 264.7 (M+H). $^1$H NMR (400 MHz, CD$_3$OD) δ 8.90 (s, 1H), 6.88 (d, J=8.3 Hz, 1H), 6.60 (d, J=2.3 Hz, 1H), 6.53 (dd, J=8.2, 2.1 Hz, 1H), 3.73 (s, 3H), 2.36 (s, 3H), 2.10 (s, 3H).

Step 3. Synthesis of 4-(2,4-dimethoxyphenyl)-3,5-dimethylpyridazine (C86)

A mixture of 3-chloro-4-(2,4-dimethoxyphenyl)-5-methylpyridazine (C85) (18 g, 68 mmol), methylboronic acid (17 g, 280 mmol), [1,1'-bis(diphenylphosphino)ferrocene]dichloropalladium(II) (5.2 g, 70 mmol), and cesium carbonate (46 g, 140 mmol) in 1,4-dioxane (300 mL) was heated at reflux for 2.5 hours and then cooled to room temperature, filtered, and concentrated in vacuo. Silica gel chromatography (Gradient: 17% to 50% ethyl acetate in petroleum ether) gave the product as an orange solid. Yield: 14 g, 57 mmol, 84%). LCMS m/z 245.0 (M+H).

Step 4. Synthesis of 4-(3,5-dimethylpyridazin-4-yl)-3-methoxyphenol (P15)

Trimethylsilyl iodide (58 g, 290 mmol) was added to a stirred solution of 4-(2,4-dimethoxyphenyl)-3,5-dimethylpyridazine (C86) (12 g, 49 mmol) in acetonitrile (100 mL), and the mixture was heated at reflux for 18 hours. The reaction mixture was cooled to 0° C., slowly diluted with methanol, and concentrated in vacuo. The residue was partitioned between ethyl acetate and saturated aqueous sodium thiosulfate solution. The aqueous layer was extracted with ethyl acetate (4×150 mL) and the combined organic extracts were dried over sodium sulfate, filtered, and concentrated in vacuo. Silica gel chromatography (Gradient: 50% to 100% ethyl acetate in petroleum ether) provided the product as a yellow solid. Yield: 3.0 g, 13 mmol, 26%. LCMS m/z 230.7 (M+H). $^1$H NMR (400 MHz, CD$_3$OD) δ 8.90 (s, 1H), 6.88 (d, J=8.0 Hz, 1H), 6.60 (d, J=2.0 Hz, 1H), 6.53 (dd, J=8.3, 2.3 Hz, 1H), 3.73 (s, 3H), 2.36 (s, 3H), 2.10 (s, 3H).

METHODS

Methods M1-M7 describe specific methods for preparations of certain compounds of the invention.

Method M1

Palladium-Catalyzed Reaction of Phenols with 4-chlorofuro-[3,2-c]pyridines

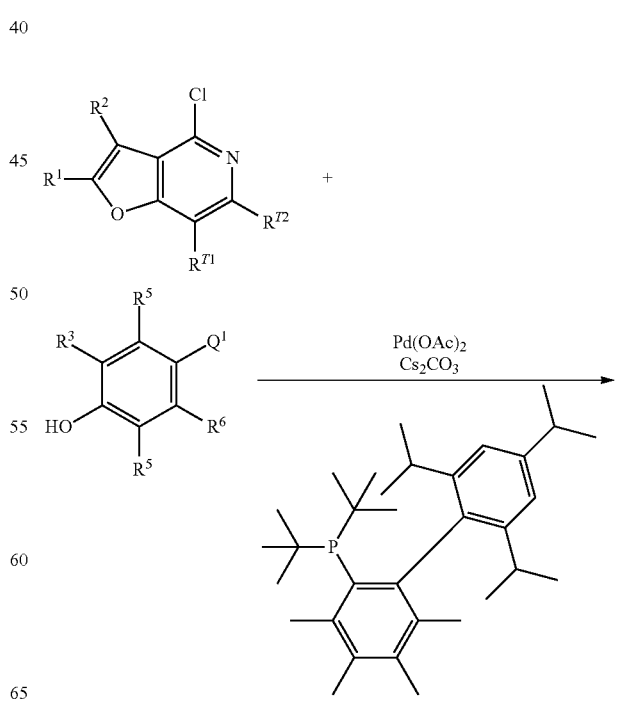

-continued

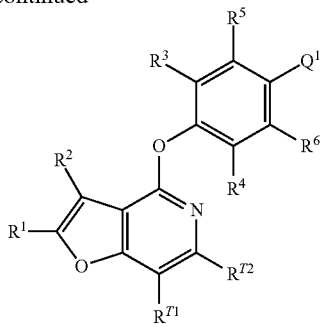

Solutions of the appropriate phenol and 4-chlorofuro[3,2-c]pyridine were prepared at 0.2 M using degassed 1,4-dioxane. A 2-dram vial was charged with the phenol solution (0.5 mL, 0.1 mmol) and the 4-chlorofuro[3,2-c]pyridine solution (0.5 mL, 0.1 mmol). Cesium carbonate (100 mg, 0.3 mmol), palladium(II) acetate (2.5 mg, 0.01 mmol) and di-tert-butyl[3,4,5,6-tetramethyl-2',4',6'-tri(propan-2-yl)biphenyl-2-yl]phosphane (10 mg, 0.02 mmol) were added. The vial was subjected to three rounds of vacuum evacuation followed by nitrogen fill and the resulting mixture was shaken and heated at 100° C. for 12 hours. The reaction mixture was cooled to room temperature, partitioned between water (1.5 mL) and ethyl acetate (2.5 mL), vortexed, and allowed to settle. The organic layer was passed through a solid phase extraction cartridge filled with sodium sulfate (1.0 g); this extraction procedure was repeated twice, and the combined filtrates were concentrated in vacuo. The products were generally purified by HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: increasing percentage of B, starting with 10% or 20% B).

Method M2

Alkylation of Phenols

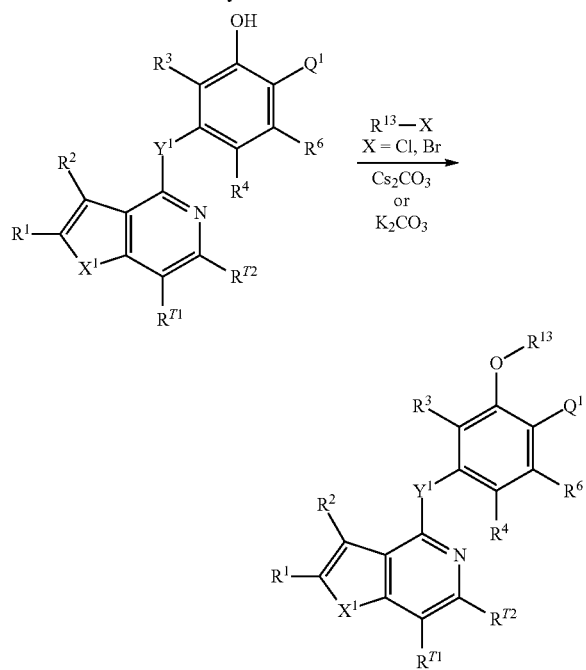

A solution of the appropriate phenol (0.050 mmol, 1.0 eq) in anhydrous N,N-dimethylformamide dimethyl acetal or N,N-dimethylformamide (0.2 mL) was treated with either cesium carbonate or potassium carbonate (0.10 mmol, 2.0 eq), sodium iodide (0.008 mmol, 0.2 eq), and the appropriate bromide or chloride reagent (0.075 mmol, 1.5 eq). The reaction vial was capped and shaken at 80° C. for 16 hours. The reaction mixture was concentrated and the crude residue was purified by reversed phase HPLC (Gradient: increasing concentration of either acetonitrile in water containing 0.225% formic acid, or acetonitrile in aqueous pH 10 ammonium hydroxide solution) to provide the final compound.

Method M3

Amide Formation Employing O-(7-azabenzotriazol-1-yl)-N,N,N',N'-tetramethyluronium hexafluorophosphate

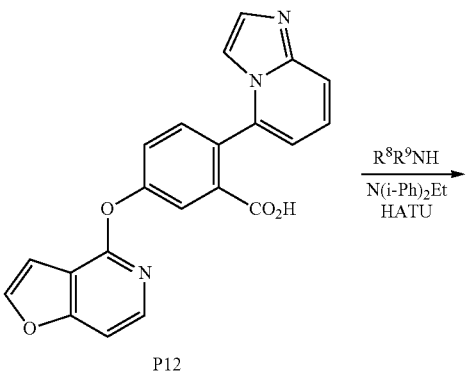

P12

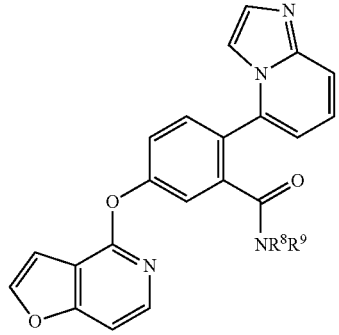

A solution of 5-(furo[3,2-c]pyridin-4-yloxy)-2-(imidazo[1,2-a]pyridine-5-yl)benzoic acid (P12) (0.060 mmol, 1.0 eq) in anhydrous N,N-dimethylformamide (0.2 mL) was treated with the appropriate commercially available amine (0.090 mmol, 1.5 eq), O-(7-azabenzotriazol-1-yl)-N,N,N',N'-tetramethyluronium hexafluorophosphate (HATU, 0.060 mmol, 1.0 eq), and diisopropylethylamine (0.240 mmol, 4.0 eq). The reaction vial was capped and shaken at 30° C. for 16 hours. The reaction mixture was concentrated and the crude residue was purified by reversed phase HPLC (Gradient: increasing concentration of either acetonitrile in water containing 0.225% formic acid, or acetonitrile in aqueous pH 10 ammonium hydroxide solution) to provide the final compound.

Method M4

Mitsunobu Reaction of Phenols

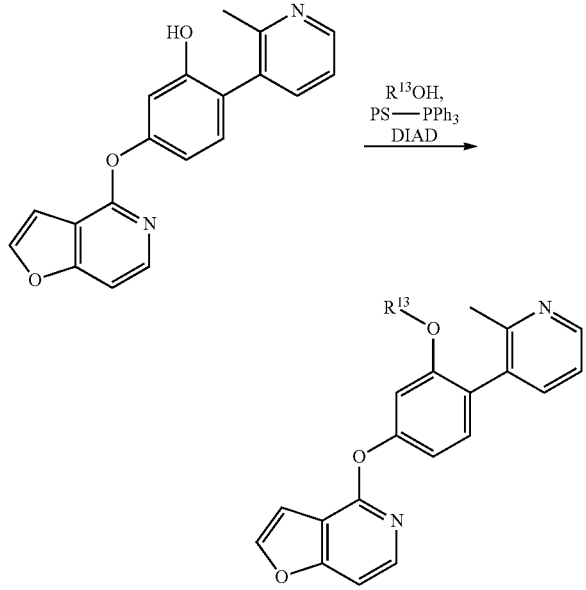

A solution of 5-(furo[3,2-c]pyridin-4-yloxy)-2-(2-methyl-pyridin-3-yl)phenol (prepared via methyl ether cleavage of Example 181) (0.075 mmol, 1.0 eq) in tetrahydrofuran/dichloromethane (v/v=1:1, 1.0 mL) was added to a vial containing the appropriate commercially available primary alcohol (0.120 mmol, 1.6 eq) and polymer-supported triphenylphosphine (0.225 mmol, 3.0 eq). Diisopropyl azodicarboxylate (DIAD; 0.150 mmol, 2.0 eq) was added to the reaction vial, which was then capped and shaken at 30° C. for 16 hours. The reaction mixture was concentrated and the crude residue was purified by reversed phase HPLC (Gradient: increasing concentration of either acetonitrile in water containing 0.225% formic acid, or acetonitrile in aqueous pH 10 ammonium hydroxide solution) to provide the final compound.

Method M5

Reductive Amination of Aldehydes

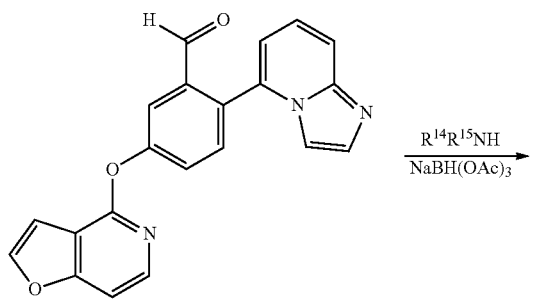

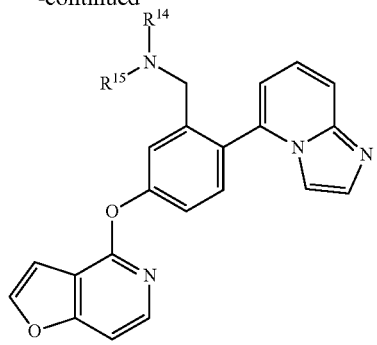

A solution of 5-(furo[3,2-c]pyridin-4-yloxy)-2-(imidazo[1,2-a]pyridine-5-yl)benzaldehyde [prepared from 4-bromo-3-(1,3-dioxan-2-yl)phenol (see F. Kaiser et al., *J. Org. Chem.* 2002, 67, 9248-9256) using the procedures of Example 1, followed by deprotection with aqueous hydrochloric acid in tetrahydrofuran] (0.094 mmol, 1.25 eq) in dichloromethane (1.0 mL) was added to a vial containing the appropriate commercially available amine (0.075 mmol, 1.0 eq). Sodium bicarbonate (18 mg, 0.225 mmol, 3.0 eq) was added, and the reaction vial was capped and shaken at 30° C. for 16 hours. Sodium triacetoxyborohydride (47 mg, 0.225 mmol, 3.0 eq) was added, and the reaction mixture was shaken at 30° C. for an additional 5 hours. The reaction mixture was concentrated and the crude residue was purified by reversed phase HPLC (Gradient: increasing concentration of acetonitrile in water containing 0.1% trifluoroacetic acid) to provide the final compound.

Method M6

Amine Displacement of Heteroaryl Chlorides

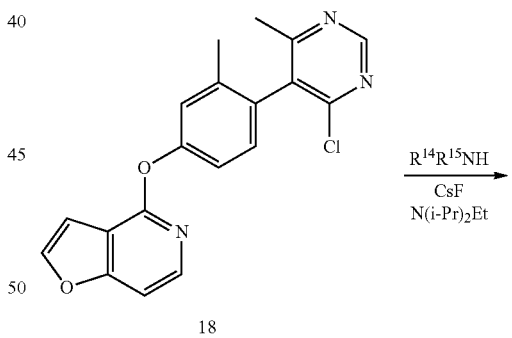

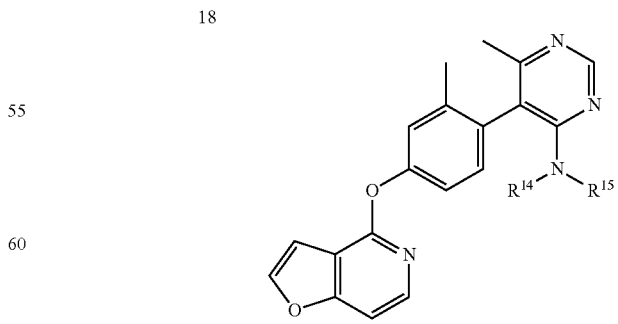

A solution of 4-[4-(4-chloro-6-methylpyrimidin-5-yl)-3-methylphenoxy]furo[3,2-c]pyridine (Example 18) (0.50 mmol, 1.0 eq) in anhydrous dimethyl sulfoxide (0.5 mL) was added to a vial containing the appropriate commercially available amine (0.110 mmol, 2.2 eq). Diisopropylethylamine (0.170 mmol, 3.4 eq) and cesium fluoride (15 mg, 0.100 mmol, 2.0 eq) were added, and the reaction vial was capped and shaken at 120° C. for 16 hours. The reaction mixture was concentrated and the crude residue was purified by reversed phase HPLC (Gradient: increasing concentration of acetonitrile in water containing either 0.225% formic acid or 0.1% trifluoroacetic acid) to provide the final compounds.

Method M7

Microbial Oxidation Employing *Pseudomonas putida*

Step 1. Biocatalyst Production

A frozen seed vial containing *Pseudomonas putida* (ATCC 17453) was removed from a −80° C. freezer, thawed and used to inoculate IOWA medium (1 L; IOWA medium consists of glucose [20 g], sodium chloride[5 g], potassium hydrogenphosphate[5 g], soy flour [5 g] and yeast extract [5 g]; the mixture was adjusted to pH 7.0 before sterilization in an autoclave) in a 3-liter baffled shake flask (Corning, #431253). The cultures were grown for 2-4 days while shaking at 30° C. and 160 rpm on an orbital shaker with a 2 inch throw. The cells were harvested by centrifugation; the cell pellet was frozen at −80° C.

Step 2. Oxidation Reaction

Cells of *Pseudomonas putida* (ATCC 17453) were suspended in aqueous potassium phosphate buffer (25 mM, pH 7.0) at a concentration of 45 g cells per 150 mL buffer. This suspension was added to a 1 liter baffled shake flask (Nalge, 4116-1000) and a solution of substrate (30 mg) in dimethyl sulfoxide (3 mL) was added to the suspension. The flask was incubated at 30 to 40° C. and 300 rpm for 24-96 hours on an orbital shaker with a 1 inch throw.

Step 3. Reaction Work-Up

The reaction was extracted with ethyl acetate, and the combined organic layers were concentrated in vacuo. The product was isolated using chromatographic techniques.

TABLE 1

Examples 31-208

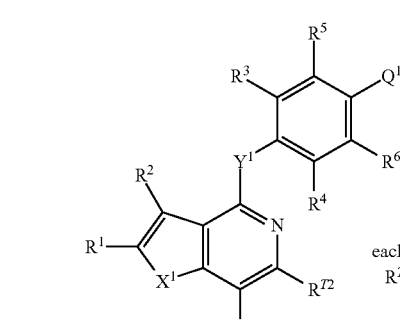

each of $R^1$, $R^2$, $R^{T1}$, and $R^{T2}$ is H; and $X^1$ = O

| Example No. | 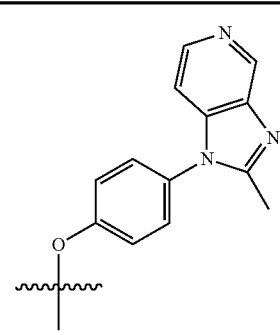 | Method of Preparation; Non-commercial Starting Materials | $^1$H NMR (400 MHz, CDCl$_3$), δ (ppm); Mass spectrum, observed ion m/z (M + H) or HPLC retention time (minutes); Mass spectrum m/z (M + H) (unless otherwise indicated) |
|---|---|---|---|
| 31 | | Ex 5 | 9.07 (br s, 1H), 8.40 (d, J = Hz, 1H), 8.07 (d, J = 5.8 Hz, 1H), 7.71 (d, J = 2.2 Hz, 1H), 7.45 (br AB quartet, J$_{AB}$ = 8.9 Hz, Δv$_{AB}$ = 28.6 Hz, 4H), 7.30 (dd, J = 5.8, 0.8 Hz, 1H), 7.17 (dd, J = 5.6, 0.8 Hz, 1H), 6.98 (dd, J = 2.2, 0.8 Hz, 1H), 2.60 (s, 3H); 343.1 |

TABLE 1-continued
| | | | |
|---|---|---|---|
| 32 | 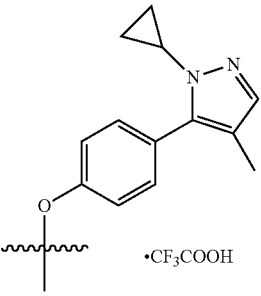 [SMILES: *Oc1ccc(-c2c(C)cnn2C2CC2)cc1 ; "·CF3COOH"] ·CF₃COOH | Ex 15 | 3.012 min¹; 332 |
| 33 | 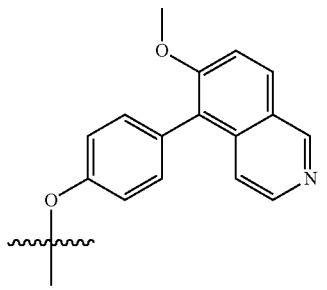 [SMILES: *Oc1ccc(-c2c(OC)ccc3cnccc23)cc1] | Ex 1⁶⁵ | 2.501 min²; 369 |
| 34 | 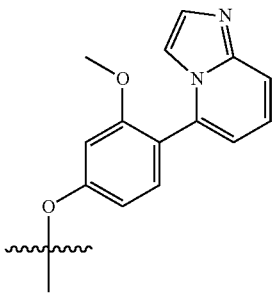 [SMILES: *Oc1ccc(-c2cccc3nccn23)c(OC)c1] | Ex 16; C10 | 8.08 (d, J = 5.8 Hz, 1H), 7.69 (d, J = 2.2 Hz, 1H), 7.65 (br d, J = 9.0 Hz, 1H), 7.60 (d, J = 1.4 Hz, 1H), 7.40-7.43 (m, 1H), 7.30-7.31 (m, 1H), 7.28 (dd, J = 5.8, 1.0 Hz, 1H, assumed; partially obscured by solvent peak), 7.26 (dd, J = 9.0, 6.8 Hz, 1H, assumed; partially obscured by solvent peak), 6.94-6.98 (m, 3H), 6.77 (dd, J = 6.8, 1.0 Hz, 1H), 3.75 (s, 3H); 358.0 |
| 35 | 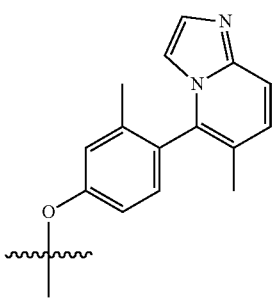 [SMILES: *Oc1ccc(-c2c(C)ccc3nccn23)c(C)c1] | Ex 6; C2, C55 | Selected peaks: 8.08 (d, J = 5.8 Hz, 1H), 7.68 (d, J = 2.2 Hz, 1H), 7.17 (d, J = 9.3 Hz, 1H), 6.93 (dd, J = 2.2, 1.0 Hz, 1H), 2.12 (s, 3H), 2.02 (s, 3H); 356.3 |
| 36 | 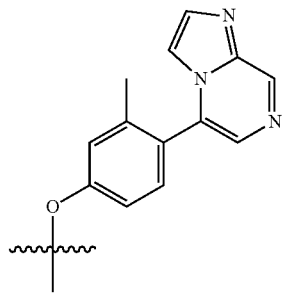 [SMILES: *Oc1ccc(-c2cncc3nccn23)c(C)c1] | Ex 6; C2 | ¹H NMR (500 MHz, DMSO-d₆) δ 9.15 (s, 1H), 8.18 (d, J = 2.2 Hz, 1H), 8.05 (d, J = 5.9 Hz, 1H), 7.92 (s, 1H), 7.87 (d, J = 1.1 Hz, 1H), 7.57-7.58 (m, 1H), 7.55 (d, J = 8.3 Hz, 1H), 7.53 (dd, J = 5.7, 1.0 Hz, 1H), 7.37 (br d, J = 2.2 Hz, 1H), 7.27 (br dd, J = 8.3, 2.4 Hz, 1H), 7.14 (dd, J = 2.2, 1.0 Hz, 1H), 2.10 (s, 3H); 343.0 |

TABLE 1-continued

| # | Structure | Method | Data |
|---|---|---|---|
| 37 | (2-methoxy-4-oxy-phenyl with 8-methyl-imidazo[1,2-a]pyridine) | Ex 6; C10, C55 | A. 8.01 (d, J = 5.8 Hz, 1H); 7.70 (d, J = 2.3 Hz, 1H), 7.57 (br d, J = 9.2 Hz, 1H), 7.52 (d, J = 1.2 Hz, 1H), 7.28-7.31 (m, 2H), 7.16 (d, J = 9.2 Hz, 1H), 7.11-7.13 (m, 1H), 7.02 (d, half of AB pattern, J = 2.2 Hz, 1H), 6.99 (dd, half of ABX pattern, J = 8.2, 2.2 Hz, 1H), 6.94 (dd, J = 2.2, 1.0 Hz, 1H), 3.73 (s, 3H), 2.17 (s, 3H); 372.2 |
| 38 | (2-methylamino-4-oxy-phenyl with imidazo[1,2-a]pyridine) | Ex 16[3] | $^1$H NMR (400 MHz, DMSO-d$_6$) δ 8.14 (d, J = 2.0 Hz, 1H), 8.05 (d, J = 5.9 Hz, 1H), 7.61 (br d, J = 9.0 Hz, 1H), 7.56 (br s, 1H), 7.49 (br d, J = 5.9 Hz, 1H), 7.33 (dd, J = 9.0, 7.0 Hz, 1H), 7.24 (br s, 1H), 7.19 (d, J = 8.2 Hz, 1H), 7.05-7.09 (m, 1H), 6.88 (d, J = 6.6 Hz, 1H), 6.53-6.56 (m, 1H), 6.51 (dd, J = 8.2, 2.0 Hz, 1H), 5.14-5.20 (m, 1H), 2.59 (d, J = 5.1 Hz, 3H); 357.0 |
| 39 | (2-chloro-4-oxy-phenyl with 2-methyl-imidazo[4,5-c]pyridine) | Ex 5[4] | 9.06 (d, J = 0.8 Hz, 1H), 8.39 (d, J = 5.6 Hz, 1H), 8.07 (d, J = 5.8 Hz, 1H), 7.71 (d, J = 2.2 Hz, 1H), 7.61 (dd, J = 2.2, 0.8 Hz, 1H), 7.39-7.44 (m, 2H), 7.32 (dd, J = 5.8, 1.0 Hz, 1H), 7.02 (dd, J = 5.5, 1.0 Hz, 1H), 6.97 (dd, J = 2.2, 1.0 Hz, 1H), 2.51 (s, 3H); 377.0 |
| 40 | (thiazol-4-ylmethoxy-phenyl with imidazo[1,2-a]pyridine) •CF$_3$COOH | Method M2 | 2.353 min[5]; 441 |
| 41 | (2-oxobutoxy-phenyl with imidazo[1,2-a]pyridine) •CF$_3$COOH | Method M2 | 2.388 min[5]; 414 |

TABLE 1-continued
| 42 | 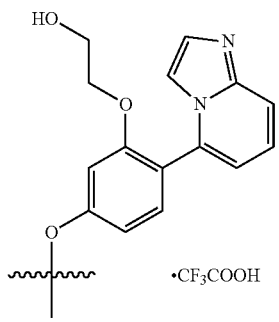 •CF₃COOH | Method M2 | 2.437 min[6]; 388 |
| --- | --- | --- | --- |
| 43 | 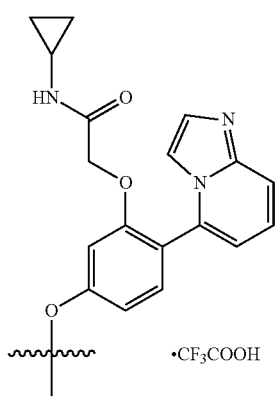 •CF₃COOH | Method M2 | 2.457 min[6]; 441 |
| 44 | 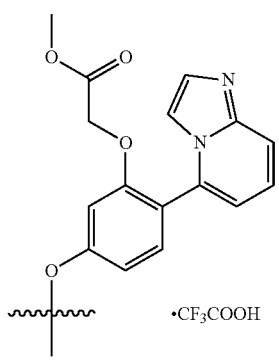 •CF₃COOH | Method M2 | 2.574 min[6]; 416 |
| 45 | 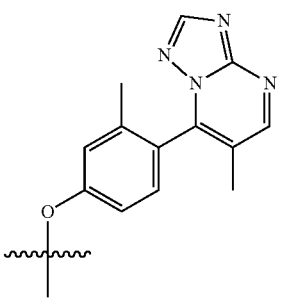 [SMILES: *Oc1ccc(-c2c(C)cnc3ncnn23)c(C)c1] | Ex 20; C2, P3 | $^1$H NMR (500 MHz, CDCl₃) δ 8.83 (s, 1H), 8.43 (s, 1H), 8.08 (d, J = 5.7 Hz, 1H), 7.69 (d, J = 2.2 Hz, 1H), 7.28-7.33 (m, 4H), 6.93 (dd, J = 2.2, 1.0 Hz, 1H), 2.32 (s, 3H), 2.08 (br s, 3H); 358.0 |

TABLE 1-continued
| | | | |
|---|---|---|---|
| 46 | 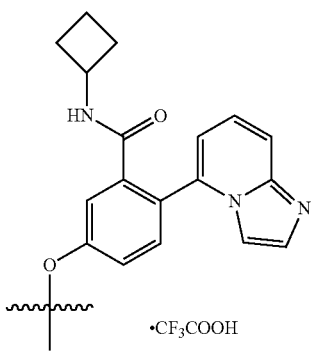 [SMILES: *Oc1ccc(-c2cccc3nccn23)c(C(=O)NC2CCC2)c1 ; "·CF3COOH"] •CF$_3$COOH | Method M3 | 2.329 min[5]; 425 |
| 47 | 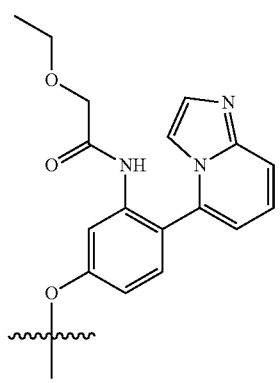 [SMILES: *Oc1ccc(-c2cccc3nccn23)c(NC(=O)COCC)c1] | Ex 16[76] | 2.574 min[6]; 429 |
| 48 | 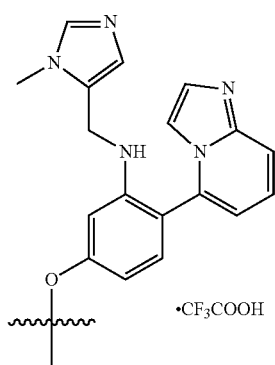 •CF$_3$COOH | Ex 16[7] | 2.25 min[6]; 437 |
| 49 | 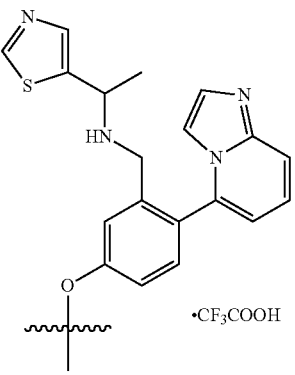 •CF$_3$COOH | Method M5 | 2.097 min[6]; 468 |

TABLE 1-continued

| | Structure | Method | Data |
|---|---|---|---|
| 50 | (pyridin-2-ylmethyl)(methyl)amino-benzyl / imidazo[1,2-a]pyrazine derivative •CF₃COOH | Method M5 | 1.907 min⁵; 462 |
| 51 | methoxy-methyl-cyanopyridine-phenyl derivative •CF₃COOH | Ex 6; C10⁸ | 3.17 min⁹; 358.1 |
| 52 | 2-methylpyridine-methylphenyl derivative | Ex 6; C2 | 2.31 min⁹; 317.1 |
| 53 | methylpyrazin-amine-methylphenyl derivative •CF₃COOH | Ex 6; C2, C60 | 2.40 min⁹; 333.2 |
| 54 | CF₃-phenyl-imidazo[1,2-a]pyridine derivative | Ex 20; P5 | characteristics peaks: 8.07 (d, J = 6.0 Hz, 1H), 7.80 (d, J = 2.0 Hz, 1H), 7.73 (d, J = 2.5 Hz, 1H), 7.65 (br dd, J = 8, 2 Hz, 1H), 7.54 (br d, J = 8.5 Hz, 1H), 7.33 (d, J = 6.0 Hz, 1H), 7.14-7.17 (m, 1H), 6.99-7.01 (m, 1H); 396.0 |
| 55 | N,N-dimethylamino-methylphenyl-imidazo[1,2-a]pyridine derivative | Ex 17¹⁰ | characteristics peaks: 8.20 (d, J = 5.8 Hz, 1H), 7.72-7.78 (m, 1H), 7.39 (d, J = 2.3 Hz, 1H), 7.38-7.46 (m, 1H), 7.31 (d, J = 8.3 Hz, 1H), 7.19-7.23 (m, 2H), 7.16 (dd, J = 8.2, 2.1 Hz, 1H), 7.06 (br d, J = 5.8 Hz, 1H), 6.88 (br d, J = 6.5 Hz, 1H), 5.73-5.76 (m, 1H), 3.68 (s, 3H), 2.07 (s, 3H); 355.5 |

TABLE 1-continued
| 56 | 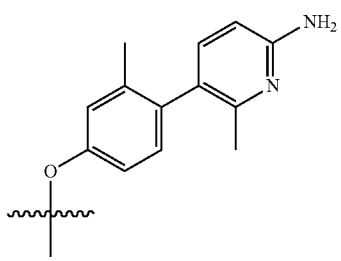 [SMILES: *Oc1ccc(-c2ccc(N)nc2C)c(C)c1] | Ex 6; C2 | 2.40 min[9]; 332.3 |
| 57 | 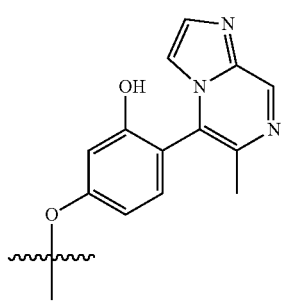 [SMILES: *Oc1ccc(-c2c(C)ncc3nccn23)c(O)c1] | Ex 6[11]; C10, C45 | $^1$H NMR (400 MHz, CD$_3$OD) δ 8.95 (s, 1H), 8.02 (d, J = 5.8 Hz, 1H), 7.92 (d, J = 2.3 Hz, 1H), 7.61 (d, J = 1.2 Hz, 1H), 7.59-7.61 (m, 1H), 7.38-7.43 (m, 2H), 6.99-7.00 (m, 1H), 6.87-6.91 (m, 2H), 2.44 (s, 3H); 359.1 |
| 58 | 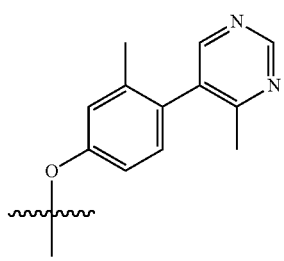 [SMILES: *Oc1ccc(-c2cncnc2C)c(C)c1] | Ex 1 | $^1$H NMR (500 MHz, CDCl$_3$) δ 9.12 (s, 1H), 8.50 (s, 1H), 8.07 (d, J = 5.9 Hz, 1H), 7.68 (d, J = 2.2 Hz, 1H), 7.25 (dd, J = 5.8, 0.9 Hz, 1H), 7.21-7.22 (m, 1H), 7.17 (AB quartet, J$_{AB}$ = 8 Hz, Δν$_{AB}$ = 4 Hz, 2H), 6.94 (dd, J = 2.2, 1.0 Hz, 1H), 2.39 (s, 3H), 2.12 (br s, 3H); 318.1 |
| 59 | 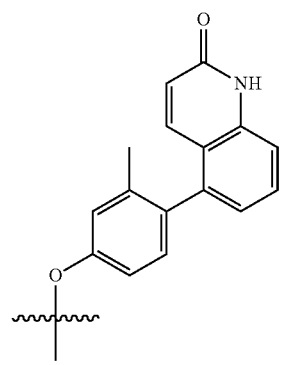 [SMILES: *Oc1ccc(-c2cccc3[nH]c(=O)ccc23)c(C)c1] | Ex 1 | 3.06 min[9]; 369.0 |
| 60 | 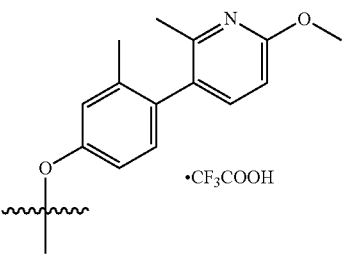 | Ex 6; C2 | 3.77 min[12]; 347.2 |

TABLE 1-continued
| | | | |
|---|---|---|---|
| 61 | 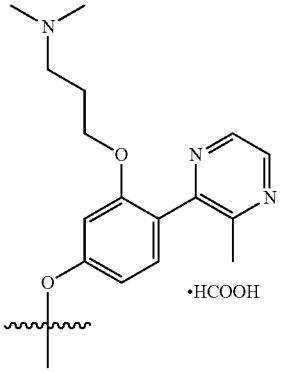 [SMILES: *Oc1ccc(-c2nccnc2C)c(OCCCN(C)C)c1 ; "·HCOOH"] •HCOOH | Method M2 | 2.497 min[6]; 405 |
| 62 | 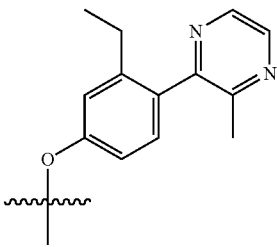 [SMILES: *Oc1ccc(-c2nccnc2C)c(CC)c1] | Ex 1[13] | 8.47-8.50 (m, 2H), 8.05 (d, J = 6 Hz, 1H), 7.64 (d, J = 2 Hz, 1H), 7.12-7.26 (m, 4H, assumed; partially obscured by solvent peak), 6.83-6.85 (m, 1H), 2.46 (s, 3H), 2.45 (q, J = 7 Hz, 2H), 1.06 (t, J = 7 Hz, 3H); 332.3 |
| 63 | 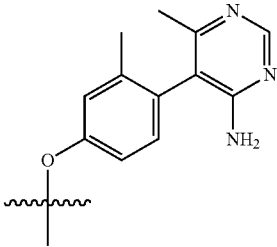 [SMILES: *Oc1ccc(-c2c(C)ncnc2N)c(C)c1] | Ex 1 | 2.07 min[9]; 333.1 |
| 64 | 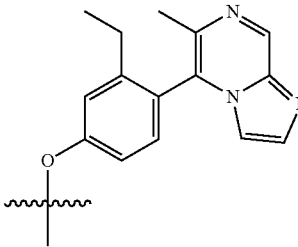 | Ex 1[13]; C45 | $^1$H NMR (400 MHz, CD$_3$OD) δ 9.36 (s, 1H), 8.16 (d, J = 1.4 Hz, 1H), 8.00 (d, J = 5.9 Hz, 1H), 7.95 (d, J = 2.3 Hz, 1H), 7.82-7.85 (m, 1H), 7.45-7.49 (m, 2H), 7.43 (dd, J = 5.9, 0.9 Hz, 1H), 7.34 (dd, J = 8.3, 2.4 Hz, 1H), 7.06 (dd, J = 2.3, 0.9 Hz, 1H), 2.50 (s, 3H), 2.30-2.47 (m, 2H), 1.08 (t, J = 7.5 Hz, 3H); 371.1 |
| 65 | 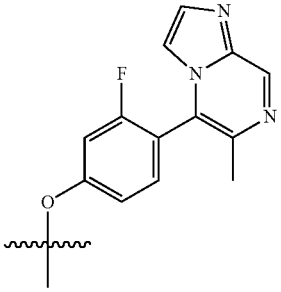 [SMILES: *Oc1ccc(-c2c(C)ncc3nccn23)c(F)c1] | Ex 1; C45, C49 | $^1$H NMR (400 MHz, CD$_3$OD) δ 9.02 (s, 1H), 8.04 (d, J = 5.8 Hz, 1H), 7.95 (d, J = 2.3 Hz, 1H), 7.81 (d, J = 1.2 Hz, 1H), 7.64-7.69 (m, 2H), 7.45 (dd, J = 5.9, 0.9 Hz, 1H), 7.38 (dd, J = 10.5, 2.3 Hz, 1H), 7.33 (br dd, J = 8.3, 2.3 Hz, 1H), 7.07 (dd, J = 2.3, 1.0 Hz, 1H), 2.44 (s, 3H); 361.3 |

TABLE 1-continued
| 66 | 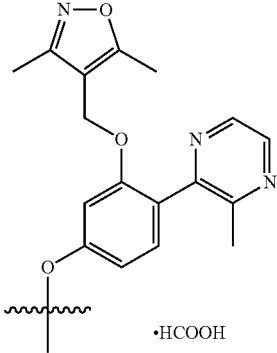 [SMILES: *Oc1ccc(-c2nccnc2C)c(OCc2c(C)noc2C)c1 ; "·HCOOH"] •HCOOH | Method M2 | 3.091 min[6]; 429 |
| --- | --- | --- | --- |
| 67 | 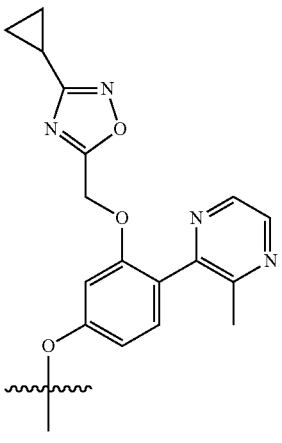 [SMILES: *Oc1ccc(-c2nccnc2C)c(OCc2nc(C3CC3)no2)c1] | P1[14] | 8.46-8.49 (m, 2H), 8.05 (d, J = 5.9 Hz, 1H), 7.67 (d, J = 2.1 Hz, 1H), 7.41 (d, J = 8.3 Hz, 1H), 7.26-7.29 (m, 1H, assumed; partially obscured by solvent peak), 7.04 (dd, J = 8.3, 2.0 Hz, 1H), 6.96 (d, J = 2.1 Hz, 1H), 6.88 (dd, J = 2.2, 0.9 Hz, 1H), 5.17 (s, 2H), 2.54 (s, 3H), 2.04-2.12 (m, 1H), 1.01-1.08 (m, 2H), 0.94-0.99 (m, 2H); 441.9 |
| 68 | 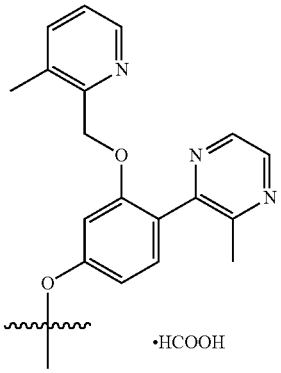 [SMILES: *Oc1ccc(-c2nccnc2C)c(OCc2ncccc2C)c1 ; "·HCOOH"] •HCOOH | Method M2 | 2.623 min[6]; 425 |
| 69 | 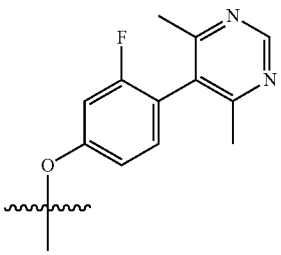 [SMILES: *Oc1ccc(-c2c(C)ncnc2C)c(F)c1] | Ex 23[15] | 8.99 (s, 1H), 8.08 (d, J = 5.8 Hz, 1H), 7.70 (d, J = 2.2 Hz, 1H), 7.31 (dd, J = 5.8, 0.9 Hz, 1H), 7.17-7.22 (m, 3H), 6.94 (dd, J = 2.2, 1.0 Hz, 1H), 2.37 (s, 6H); 336.2 |

TABLE 1-continued

| | | | |
|---|---|---|---|
| 70 | (structure) | Ex 1; C49 | $^1$H NMR (400 MHz, CD$_3$OD) δ 9.21 (s, 1H), 8.05 (d, J = 5.9 Hz, 1H), 7.92 (d, J = 2.3 Hz, 1H), 7.57 (dd, J = 8.4, 8.4 Hz, 1H), 7.44 (dd, J = 5.9, 1.0 Hz, 1H), 7.32 (dd, J = 10.7, 2.3 Hz, 1H), 7.27 (ddd, J = 8.4, 2.3, 0.5 Hz, 1H), 7.00 (dd, J = 2.2, 0.9 Hz, 1H), 2.54 (s, 3H); 347.1 |
| 71 | (structure) | Ex 1; C10 | $^1$H NMR (400 MHz, CD$_3$OD) δ 8.84 (s, 1H), 8.00 (d, J = 5.8 Hz, 1H), 7.91 (d, J = 2.0 Hz, 1H), 7.40 (br d, J = 6.0 Hz, 1H), 7.19 (d, J = 8.3 Hz, 1H), 7.06 (d, J = 2.3 Hz, 1H), 6.94-6.96 (m, 1H), 6.91 (dd, J = 8.3, 2.3 Hz, 1H), 3.77 (s, 3H), 2.31 (s, 6H); 347.9 |
| 72 | (structure) | Ex 71[11] | $^1$H NMR (400 MHz, CD$_3$OD) δ 8.84 (s, 1H), 8.01 (d, J = 6.0 Hz, 1H), 7.89 (d, J = 2.3 Hz, 1H), 7.38-7.41 (m, 1H), 7.11-7.14 (m, 1H), 6.88-6.90 (m, 1H), 6.78-6.82 (m, 2H), 2.35 (s, 6H); 333.9 |
| 73 | (structure) ·HCOOH | Method M4 | 1.997 min[5]; 404 |
| 74 | (structure) ·HCOOH | Method M4 | 1.997 min[5]; 404 |

TABLE 1-continued

| # | Structure | Method | Data |
|---|---|---|---|
| 75 | (4,6-dimethyl-2-aminopyrimidin-5-yl)(2-methylphenyl) ether | Ex 1 | 2.32 min[9]; 347.2 |
| 76 | (4-methoxy-6-methylpyrimidin-5-yl)(2-fluorophenyl) ether | Ex 20[16]; C49 | 8.72 (s, 1H), 8.08 (d, J = 5.8 Hz, 1H), 7.69 (d, J = 2.0 Hz, 1H), 7.23-7.31 (m, 2H, assumed; partially obscured by solvent peak), 7.11-7.16 (m, 2H), 6.91-6.94 (m, 1H), 3.96 (s, 3H), 2.37 (br s, 3H); 351.9 |
| 77 | (4,6-dimethylpyrimidin-5-yl)phenyl ether | Ex 5 | $^1$H NMR (400 MHz, CD$_3$OD) δ 8.86 (s, 1H), 7.99 (d, J = 6.0 Hz, 1H), 7.90 (d, J = 2.2 Hz, 1H), 7.38 (dd, J = 5.9, 1.0 Hz, 1H), 7.32-7.37 (m, 4H), 6.94 (dd, J = 2.2, 1.0 Hz, 1H), 2.35 (s, 6H); 318.1 |
| 78 | (2-methylpyridin-3-yl)phenyl with oxadiazole-ethyl linker | Method M4 | 2.691 min[6]; 429 |
| 79 | (4,6-dimethyl-2-hydroxypyrimidin-5-yl)phenyl ether | Ex 1; C52 | $^1$H NMR (500 MHz, CDCl$_3$) δ 8.05 (d, J = 5.6 Hz, 1H), 7.68 (d, J = 2.2 Hz, 1H), 7.34 (br d, J = 8.5 Hz, 2H), 7.25-7.28 (m, 1H, assumed; partially obscured by solvent peak), 7.22 (br d, J = 8.5 Hz, 2H), 6.92 (dd, J = 2.2, 0.7 Hz, 1H), 2.26 (s, 6H); 334.1 |
| 80 | imidazo-pyrazine with CF$_3$ and methylphenyl | Ex 6; C2[17] | 9.17 (s, 1H), 8.09 (d, J = 5.8 Hz, 1H), 7.71 (d, J = 2.3 Hz, 1H), 7.46 (s, 1H), 7.35-7.38 (m, 1H), 7.29-7.33 (m, 3H), 6.97 (dd, J = 2.1, 0.9 Hz, 1H), 2.41 (s, 3H), 2.09 (s, 3H); 425.0 |

TABLE 1-continued

| | | | |
|---|---|---|---|
| 81 | (structure) | Ex 18[18] | 8.61 (s, 1H), 8.05 (d, J = 6.0 Hz, 1H), 7.69 (d, J = 2.3 Hz, 1H), 7.24-7.28 (m, 2H, assumed; partially obscured by solvent peak), 7.18-7.22 (m, 1H), 7.14 (d, half of AB quartet, J = 8.3 Hz, 1H), 6.95 (dd, J = 2.3, 1.0 Hz, 1H), 4.64 (br s, 1H), 2.98 (d, J = 5.0 Hz, 3H), 2.13 (s, 3H), 2.09 (s, 3H); 347.0 |
| 82 | (structure) (+) | Ex 20; C2[19,20] | 9.19 (s, 1H), 8.06 (d, J = 5.9 Hz, 1H), 7.65 (br d, J = 2.2 Hz, 1H), 7.21-7.28 (m, 3H), 7.16 (d, J = 8.2 Hz, 1H), 6.82-6.84 (m, 1H), 2.45 (s, 3H), 2.12 (s, 3H); 343.4 |
| 83 | (structure) (−) | Ex 20; C2[19,20] | 9.19 (s, 1H), 8.06 (d, J = 5.9 Hz, 1H), 7.65 (d, J = 2.2 Hz, 1H), 7.21-7.28 (m, 3H), 7.16 (d, J = 8.2 Hz, 1H), 6.82-6.84 (m, 1H), 2.45 (s, 3H), 2.11 (s, 3H); 343.4 |
| 84 | (structure) | Ex 1[21] | 8.08 (d, J = 6.0 Hz, 1H), 7.64 (d, J = 2.3 Hz, 1H), 7.25-7.28 (m, 1H, assumed; partially obscured by solvent peak), 7.22-7.24 (m, 1H), 7.17-7.20 (m, 1H), 7.15 (d, half of AB quartet, J = 8.3 Hz, 1H), 6.79-6.81 (m, 1H), 5.29 (br s, 2H), 2.25 (s, 3H), 2.15 (s, 3H); 358.0 |
| 85 | (structure) | Ex 20; C2, P4 | 9.06 (d, J = 1.5 Hz, 1H), 8.08 (d, J = 5.9 Hz, 1H), 7.84 (d, J = 4.5 Hz, 1H), 7.70 (d, J = 2.2 Hz, 1H), 7.65 (dd, J = 4.6, 1.5 Hz, 1H), 7.34 (d, J = 8.2 Hz, 1H), 7.30-7.32 (m, 1H), 7.28 (dd, J = 5.9, 1.0 Hz, 1H), 7.24 (br dd, J = 8.3, 2.4 Hz, 1H), 6.96 (dd, J = 2.2, 1.0 Hz, 1H), 2.46 (s, 3H), 2.10 (br s, 3H); 357.2 |
| 86 | (structure) | Ex 16; C2 | $^1$H NMR (400 MHz, CD$_3$OD) δ 7.94 (d, J = 6.0 Hz, 1H), 7.91 (d, J = 2.7 Hz, 1H), 7.84 (d, J = 2.2 Hz, 1H), 7.33 (br d, J = 6.0 Hz, 1H), 7.10-7.13 (m, 2H), 7.04 (dd, J = 8.3, 2.3 Hz, 1H), 6.90 (d, J = 2.7 Hz, 1H), 6.84-6.86 (m, 1H), 2.15 (s, 3H), 2.07 (s, 3H); 332.2 |

TABLE 1-continued

| | | | |
|---|---|---|---|
| 87 | [structure] | Ex 18[18] | $^1$H NMR (400 MHz, CD$_3$OD) δ 8.40 (s, 1H), 7.99 (d, J = 5.8 Hz, 1H), 7.89 (d, J = 2.3 Hz, 1H), 7.39 (dd, J = 5.9, 0.9 Hz, 1H), 7.24 (d, J = 8.3 Hz, 1H), 7.18 (br d, J = 2.3 Hz, 1H), 7.11 (br dd, J = 8.3, 2.5 Hz, 1H), 6.89 (dd, J = 2.1, 0.9 Hz, 1H), 2.86 (s, 6H), 2.10 (2 s, total 6H); 361.1 |
| 88 | [structure] | Ex 20; C2[22] | 8.47 (dd, J = 4.9, 1.8 Hz, 1H), 8.07 (d, J = 5.9 Hz, 1H), 7.66 (d, J = 2.2 Hz, 1H), 7.43 (dd, J = 7.6, 1.8 Hz, 1H), 7.23-7.27 (m, 2H, assumed; partially obscured by solvent peak), 7.18 (br d, J = 2.2 Hz, 1H), 7.14 (br dd, J = 8.2, 2.5 Hz, 1H), 7.09 (dd, J = 7.6, 4.7 Hz, 1H), 6.92 (dd, J = 2.2, 0.9 Hz, 1H), 2.18 (s, 3H), 1.78-1.86 (m, 1H), 1.08-1.16 (m, 2H), 0.78-0.93 (m, 2H); 343 |
| 89 | [structure] ·CF$_3$COOH | Ex 6; C2 | 4.07 min[9]; 330.2 |
| 90 | [structure] | Ex 1[77] | 2.455 min[5]; 352 |
| 91 | [structure] | Ex 6; P5, C60 | $^1$H NMR (400 MHz, CD$_3$CN) δ 7.99 (d, J = 5.8 Hz, 1H), 7.93 (s, 1H), 7.85 (d, J = 2.3 Hz, 1H), 7.68-7.69 (m, 1H), 7.54 (ddq, J = 8.4, 2.4, 0.6 Hz, 1H), 7.41-7.45 (m, 1H), 7.36 (dd, J = 5.8, 1.0 Hz, 1H), 7.02 (dd, J = 2.2, 1.1 Hz, 1H), 5.02 (br s, 2H), 2.14 (s, 3H); 386.9 |
| 92 | [structure] | Ex 1; C49 | 2.25 min[5]; 321 |

TABLE 1-continued

| | | | |
|---|---|---|---|
| 93 | [structure] | Ex 1; C49 | 2.751 min[6]; 337 |
| 94 | [structure] ·HCOOH | Ex 1; C10 | 2.423 min[5]; 399 |
| 95 | [structure] ·HCOOH | Method M6 | 2.463 min[5]; 373 |
| 96 | [structure] ·CF$_3$COOH | Method M6 | 2.286 min[5]; 425 |
| 97 | [structure] ·HCOOH | Method M6 | 2.464 min[5]; 391 |

TABLE 1-continued

| | | | |
|---|---|---|---|
| 98 | (structure: 3-fluoropyrrolidinyl pyrimidine with methyl, aryl-O-linker; •CF₃COOH) | Method M6 | 2.522 min⁵; 405 |
| 99 | (structure: dimethylpyrimidine-aryl-O-linker with methyls) | Ex 1 | 8.98 (s, 1H), 8.01 (d, J = 5.8 Hz, 1H), 7.66 (d, J = 2.3 Hz, 1H), 7.23 (br d, J = 5.8 Hz, 1H), 7.12 (d, J = 8.3 Hz, 1H), 6.94 (d, J = 8.3 Hz, 1H), 6.87-6.89 (m, 1H), 2.27 (s, 6H), 2.23 (s, 3H), 2.00 (s, 3H); 346.0 |
| 100 | (structure: imidazo-pyrazine with CF₃-aryl-O-linker) | Ex 2; Ex 91 | ¹H NMR (400 MHz, CD₃CN) δ 9.00 (s, 1H), 8.05 (d, J = 5.8 Hz, 1H), 7.91 (br d, J = 2.5 Hz, 1H), 7.88 (br d, J = 2 Hz, 1H), 7.75 (ddq, J = 8.4, 2.3, 0.6 Hz, 1H), 7.67 (d, J = 1.0 Hz, 1H), 7.60 (br d, J = 8.4 Hz, 1H), 7.42 (dd, J = 5.8, 1.1 Hz, 1H), 7.15-7.16 (m, 1H), 7.05 (dd, J = 2.2, 1.0 Hz, 1H), 2.25 (s, 3H); 410.9 |
| 101 | (structure: imidazo-pyrazine with dimethyl-aryl-O-linker) | Ex 5; P6 | 2.51 min⁹; 371.2 |
| 102 | (structure: N-methyl imidazole-aryl-O-linker with methyls) | Ex 6; C2³³ | ¹H NMR (400 MHz, CD₃OD) δ 8.92 (s, 1H), 7.98 (d, J = 5.8 Hz, 1H), 7.92 (d, J = 2.3 Hz, 1H), 7.37-7.43 (m, 2H), 7.30 (br d, J = 2.3 Hz, 1H), 7.21 (dd, J = 8.5, 2.3 Hz, 1H), 6.99 (dd, J = 2.2, 0.9 Hz, 1H), 3.65 (s, 3H), 3.01 (s, 3H), 2.19 (br s, 3H); 319.9 |
| 103 | (structure: dimethylpyrimidine-aryl-O-linker with dimethyls) | Ex 5²⁴ | ¹H NMR (500 MHz, CDCl₃) δ 9.01 (s, 1H), 8.07 (d, J = 5.9 Hz, 1H), 7.66 (d, J = 2.2 Hz, 1H), 7.25 (dd, J = 5.9, 0.8 Hz, 1H), 7.05-7.08 (m, 2H), 6.87 (dd, J = 2.2, 0.9 Hz, 1H), 2.24 (s, 6H), 1.95 (br s, 6H); 346.2 |

TABLE 1-continued

| # | Structure | Ref | Data |
|---|---|---|---|
| 104 | 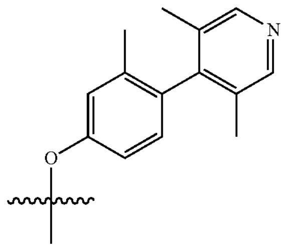 [SMILES: *Oc1ccc(-c2c(C)cncc2C)c(C)c1] | Ex 6; C2 | 1.90 min[9]; 331.1 |
| 105 | 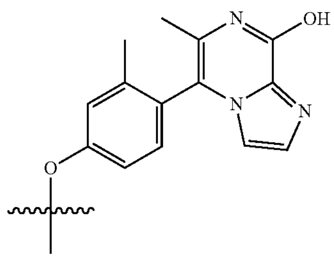 [SMILES: *Oc1ccc(-c2c(C)nc(O)c3nccn23)c(C)c1] | Ex 19[25] | 11.15 (br s, 1H), 8.08 (d, J = 5.8 Hz, 1H), 7.70 (d, J = 2.3 Hz, 1H), 7.51-7.53 (m, 1H), 7.35 (d, J = 8.5 Hz, 1H), 7.22-7.31 (m, 3H, assumed; partially obscured by solvent peak), 6.93-6.97 (m, 2H), 2.20 (s, 3H), 2.15 (s, 3H); 372.8 |
| 106 | 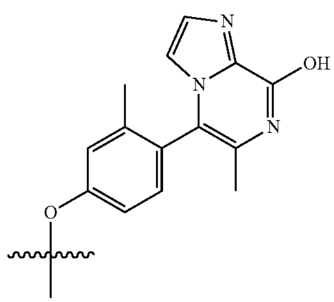 [SMILES: *Oc1ccc(-c2c(C)nc(O)c3nccn23)c(C)c1] | Ex 19[26] | 11.28 (br s, 1H), 8.08 (d, J = 5.8 Hz, 1H), 7.70 (d, J = 2.0 Hz, 1H), 7.50-7.53 (m, 1H), 7.34 (d, J = 8.0 Hz, 1H), 7.22-7.31 (m, 3H, assumed; partially obscured by solvent peak), 6.92-6.97 (m, 2H), 2.20 (s, 3H), 2.15 (s, 3H); 372.8 |
| 107 | 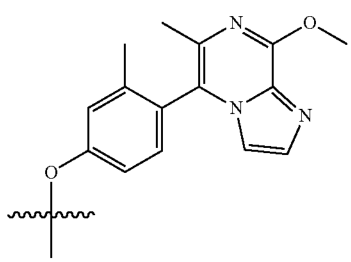 [SMILES: *Oc1ccc(-c2c(C)nc(OC)c3nccn23)c(C)c1] | C4[27] | 8.08 (d, J = 5.5 Hz, 1H), 7.69 (d, J = 2.0 Hz, 1H), 7.61 (br s, 1H), 7.23-7.33 (m, 4H, assumed; partially obscured by solvent peak), 7.08 (br s, 1H), 6.93-6.96 (m, 1H), 4.21 (s, 3H), 2.25 (s, 3H), 2.08 (s, 3H); 387.1 |
| 108 | 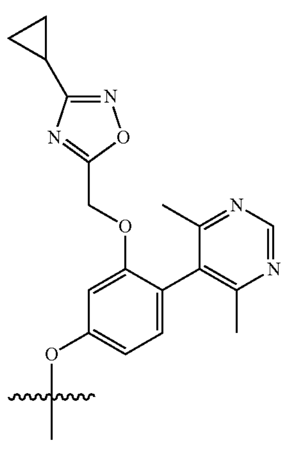 [SMILES: *Oc1ccc(-c2c(C)ncnc2C)c(OCc2nc(C3CC3)no2)c1] | Ex 72[14] | 8.96 (s, 1H), 8.06 (d, J = 5.8 Hz, 1H), 7.68 (d, J = 2.1 Hz, 1H), 7.28 (dd, J = 5.8, 0.8 Hz, 1H), 7.14 (d, J = 8.3 Hz, 1H), 7.02 (dd, J = 8.3, 2.1 Hz, 1H), 6.94 (d, J = 2.1 Hz, 1H), 6.88 (dd, J = 2.1, 0.8 Hz, 1H), 5.17 (s, 2H), 2.33 (s, 6H), 2.03-2.11 (m, 1H), 1.01-1.08 (m, 2H), 0.92-0.98 (m, 2H); 455.9 |

TABLE 1-continued

| | | | |
|---|---|---|---|
| 109 | (structure) | C4[28] | $^1$H NMR (400 MHz, CD$_3$OD) δ 8.26 (s, 1H), 8.11 (d, J = 6.0 Hz, 1H), 8.01-8.03 (m, 1H), 7.86-7.90 (m, 1H), 7.52-7.60 (m, 2H), 7.48-7.51 (m, 1H), 7.37-7.43 (m, 1H), 6.92-6.96 (m, 1H), 3.06 (s, 3H), 2.48 (s, 3H), 2.15 (s, 3H); 370.9 |
| 110 | (structure) | Ex 1[29] | $^1$H NMR (400 MHz, CD$_3$OD) δ 8.63 (s, 1H), 8.00 (d, J = 5.9 Hz, 1H), 7.93 (d, J = 2.3 Hz, 1H), 7.67-7.69 (m, 1H), 7.41-7.44 (m, 2H), 7.36-7.38 (m, 1H), 7.27-7.31 (m, 2H), 7.03 (dd, J = 2.1, 0.9 Hz, 1H), 2.23 (s, 3H), 2.08 (br s, 3H); 357.1 |
| 111 | (structure) | Ex 1[29] | $^1$H NMR (400 MHz, CD$_3$OD) δ 8.64 (s, 1H), 8.00 (d, J = 6.0 Hz, 1H), 7.94 (d, J = 2.5 Hz, 1H), 7.68-7.70 (m, 1H), 7.40-7.45 (m, 2H), 7.36-7.39 (m, 1H), 7.27-7.32 (m, 2H), 7.03-7.05 (m, 1H), 2.23 (s, 3H), 2.08 (br s, 3H); 357.1 |
| 112 | (structure) | C4[30] | $^1$H NMR (400 MHz, CD$_3$OD) δ 7.99 (d, J = 5.9 Hz, 1H), 7.93 (d, J = 2.3 Hz, 1H), 7.58-7.60 (m, 1H), 7.39-7.43 (m, 2H), 7.30-7.33 (m, 2H), 7.21-7.25 (m, 1H), 7.02 (dd, J = 2.3, 0.9 Hz, 1H), 2.17 (s, 3H), 2.11 (br s, 3H); 371.9 |
| 113 | (structure) | Ex 16; C10 | $^1$H NMR (400 MHz, CD$_3$OD) δ 7.97 (d, J = 6.0 Hz, 1H), 7.86-7.88 (m, 2H), 7.36 (dd, J = 6.0, 1.0 Hz, 1H), 7.15 (d, J = 8.2 Hz, 1H), 6.96 (br d, J = 2.7 Hz, 1H), 6.95 (br d, J = 2.2 Hz, 1H), 6.88 (dd, J = 2.2, 1.0 Hz, 1H), 6.82 (dd, J = 8.2, 2.2 Hz, 1H), 3.74 (s, 3H), 2.20 (s, 3H); 348.1 |

TABLE 1-continued

| | Structure | Prep/Ref | ¹H NMR; MS |
|---|---|---|---|
| 114 | (2,6-difluoro-4-oxyphenyl)-4,6-dimethylpyrimidine | Prep P7; C63[31] | ¹H NMR (400 MHz, CD₃CN) δ 8.95 (s, 1H), 8.06 (d, J = 5.8 Hz, 1H), 7.86 (d, J = 2.2 Hz, 1H), 7.42 (dd, J = 5.8, 1.0 Hz, 1H), 7.10-7.15 (m, 2H), 7.00 (dd, J = 2.2, 1.0 Hz, 1H), 2.33 (s, 6H); 354.0 |
| 115 | 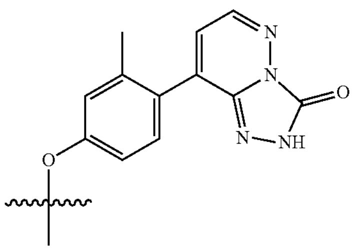 [SMILES: *Oc1ccc(-c2ccnn3c(=O)[nH]nc23)c(C)c1] | Ex 11[32] | ¹H NMR (600 MHz, DMSO-d₆) δ 8.27 (s, 1H), 8.15 (d, J = 2.2 Hz, 1H), 8.03 (d, J = 6.1 Hz, 1H), 7.49 (dd, J = 5.9, 1.1 Hz, 1H), 7.28 (d, J = 8.4 Hz, 1H), 7.25 (br d, J = 2.6 Hz, 1H), 7.17 (br dd, J = 8.4, 2.2 Hz, 1H), 7.10 (dd, J = 2.2, 0.9 Hz 1H), 2.09 (s, 3H), 2.03 (s, 3H); 374.0 |
| 116 | 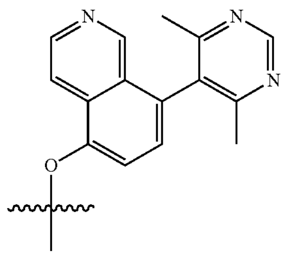 [SMILES: *Oc1ccc(-c2c(C)ncnc2C)c2cnccc12] | Method M1; P14 | ¹H NMR (400 MHz, CD₃OD) δ 9.04 (s, 1H), 8.74 (s, 1H), 8.54 (d, J = 5.5 Hz, 1H), 7.97-8.00 (m, 2H), 7.92 (d, J = 6.0 Hz, 1H), 7.76 (d, J = 8.0 Hz, 1H), 7.63 (d, J = 8.0 Hz, 1H), 7.41-7.45 (m, 1H), 7.17 (dd, J = 2.0, 1.0 Hz, 1H), 2.26 (s, 6H); 369.0 |
| 117 | 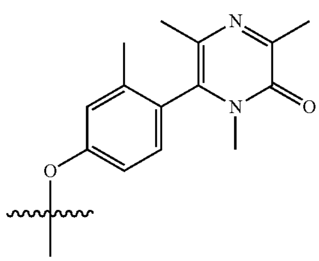 [SMILES: *Oc1ccc(-c2c(C)nc(C)c(=O)n2C)c(C)c1] | Ex 5; P8[33] | ¹H NMR (600 MHz, DMSO-d₆) δ 8.15 (d, J = 2.2 Hz, 1H), 8.04 (d, J = 5.8 Hz, 1H), 7.51 (dd, J = 5.8, 1.0 Hz, 1H), 7.32 (d, J = 8.4 Hz, 1H), 7.30 (br d, J = 2 Hz, 1H), 7.22 (br dd, J = 8, 2 Hz, 1H), 7.09 (dd, J = 2.2, 1.0 Hz, 1H), 3.08 (s, 3H), 2.35 (s, 3H), 2.08 (s, 3H), 1.90 (s, 3H); 362.2 |
| 118 | 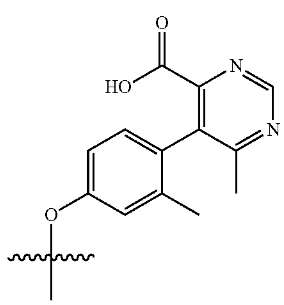 [SMILES: *Oc1ccc(-c2c(C)ncnc2C(=O)O)c(C)c1] | Ex 82[34] | ¹H NMR (400 MHz, CD₃OD) δ 9.10 (s, 1H), 8.01 (d, J = 5.8 Hz, 1H), 7.85 (d, J = 2.0 Hz, 1H), 7.39 (d, J = 6.0 Hz, 1H), 7.08-7.20 (m, 3H), 6.75-6.78 (m, 1H), 2.38 (s, 3H), 2.08 (s, 3H); 362.1 |
| 119 | 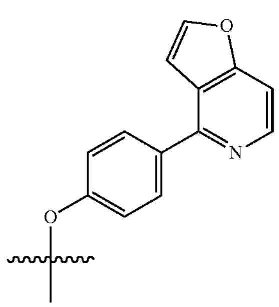 [SMILES: *Oc1ccc(-c2nccc3occc23)cc1] | Ex 6; C52 | 8.60 (d, J = 5.7 Hz, 1H), 8.03-8.08 (m, 3H), 7.72 (d, J = 2.2 Hz, 1H), 7.66 (d, J = 2.2 Hz, 1H), 7.44 (dd, J = 5.8, 1.1 Hz, 1H), 7.38-7.42 (m, 2H), 7.25 (dd, J = 5.8, 1.0 Hz, 1H), 7.14 (dd, J = 2.3, 1.0 Hz, 1H), 6.90 (dd, J = 2.2, 1.0 Hz, 1H); 3.29.1 |

TABLE 1-continued

| | | | |
|---|---|---|---|
| 120 | 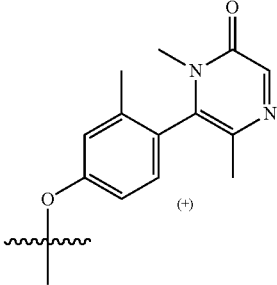 [SMILES: *Oc1ccc(-c2c(C)ncc(=O)n2C)c(C)c1] (+) | Ex 5; P8[35] | ¹H NMR (400 MHz, CD₃OD) δ 8.10 (s, 1H), 7.99 (d, J = 5.8 Hz, 1H), 7.91 (d, J = 2.2 Hz, 1H), 7.40 (dd, J = 5.8, 1.0 Hz, 1H), 7.31 (d, J = 8.4 Hz, 1H), 7.29 (br d, J = 2.3 Hz, 1H), 7.22 (br dd, J = 8.3, 2.2 Hz, 1H), 6.97 (dd, J = 2.2, 0.9 Hz, 1H), 3.28 (s, 3H), 2.15 (br s, 3H), 2.06 (s, 3H); 348.1 |
| 121 | 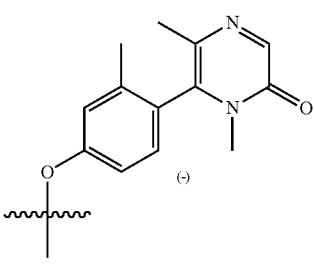 [SMILES: *Oc1ccc(-c2c(C)ncc(=O)n2C)c(C)c1] (-) | Ex 5; P8[35] | ¹H NMR (400 MHz, CD₃OD) δ 8.10 (s, 1H), 7.99 (d, J = 5.8 Hz, 1H), 7.91 (d, J = 2.2 Hz, 1H), 7.40 (dd, J = 5.8, 1.0 Hz, 1H), 7.31 (d, J = 8.4 Hz, 1H), 7.28-7.30 (m, 1H), 7.22 (br dd, J = 8, 2 Hz, 1H), 6.97 (dd, J = 2.2, 1.0 Hz, 1H), 3.28 (s, 3H), 2.15 (br s, 3H), 2.06 (s, 3H); 348.1 |
| 122 | 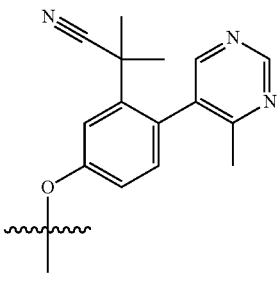 [SMILES: *Oc1ccc(-c2cncnc2C)c(C(C)(C)C#N)c1] | Footnote 36 | 9.17 (s, 1H), 8.59 (s, 1H), 8.06 (d, J = 5.8 Hz, 1H), 7.70 (d, J = 2.3 Hz, 1H), 7.47 (d, J = 2.5 Hz, 1H), 7.32 (dd, J = 8.3, 2.5 Hz, 1H), 7.29 (br d, J = 5.8 Hz, 1H), 7.14 (d, J = 8.3 Hz, 1H), 6.94-6.97 (m, 1H), 2.42 (s, 3H), 1.74 (s, 3H), 1.66 (s, 3H); 371.1 |
| 123 | 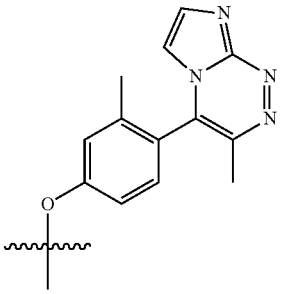 [SMILES: *Oc1ccc(-c2c(C)nnc3nccn23)c(C)c1] | Ex 5; P9 | ¹H NMR (600 MHz, DMSO-d₆) δ 8.18 (d, J = 2.2 Hz, 1H), 8.14 (d, J = 0.9 Hz, 1H), 8.08 (d, J = 5.7 Hz, 1H), 7.56 (d, J = 8.4 Hz, 1H), 7.55 (dd, J = 5.7, 0.9 Hz, 1H), 7.49 (d, J = 1.3 Hz, 1H), 7.42 (br d, J = 2.2 Hz, 1H), 7.33 (dd, J = 8.4, 2.6 Hz, 1H), 7.13 (dd, J = 2.2, 0.9 Hz, 1H), 2.55 (s, 3H), 2.02 (s, 3H); 358.2 |
| 124 | 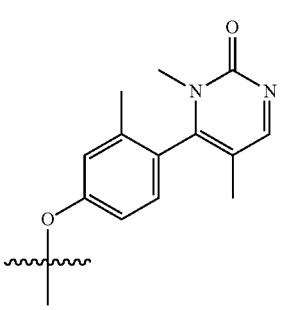 [SMILES: *Oc1ccc(-c2c(C)cnc(=O)n2C)c(C)c1] | C24[37] | ¹H NMR (400 MHz, CD₃OD) δ 8.58 (s, 1H), 7.99 (d, J = 5.8 Hz, 1H), 7.91 (d J = 2.3 Hz, 1H), 7.40 (dd, J = 5.9, 0.9 Hz, 1H), 7.23-7.32 (m, 3H), 6.98 (dd, J = 2.3, 1.0 Hz, 1H), 3.33 (s, 3H), 2.16 (s, 3H), 1.88 (s, 3H); 348.1 |

TABLE 1-continued

| | | | |
|---|---|---|---|
| 125 | [structure] | Ex 1[38]; C19 | $^1$H NMR (400 MHz, CD$_3$OD) δ 7.97 (d, J = 6.0 Hz, 1H), 7.89 (d, J = 2.3 Hz, 1H), 7.75 (s, 1H), 7.38 (dd, J = 5.8, 0.8 Hz, 1H), 7.23 (d, J = 8.3 Hz, 1H), 7.21 (br d, J = 2.3 Hz, 1H), 7.14 (dd, J = 8.3, 2.5 Hz, 1H), 6.93 (dd, J = 2.1, 0.9 Hz, 1H), 2.18 (br s, 3H), 2.01 (s, 3H); 333.9 |
| 126 | [structure] | Ex 16; C2 | $^1$H NMR (600 MHz, DMSO-d$_6$) δ 8.15 (d, J = 2.2 Hz, 1H), 8.02 (d, J = 5.7 Hz, 1H), 7.50 (dd, J = 5.7, 0.7 Hz, 1H), 7.47 (dd, J = 9.1, 6.7 Hz, 1H), 7.33 (d, J = 8.4 Hz, 1H), 7.25 (br d, J = 2.2 Hz, 1H), 7.17 (br dd, J = 8.1, 2.4 Hz, 1H), 7.11 (dd, J = 2.2, 0.9 Hz, 1H), 6.45 (dd, J = 9.1, 1.2 Hz, 1H), 6.13 (dd, J = 6.8, 1.3 Hz, 1H), 3.13 (s, 3H), 2.12 (s, 3H); 333.2 |
| 127 | [structure] | Method M1; P7 | 1.06 min[39]; 352.0 |
| 128 | [structure] | Method M1, Prep P7 | 1.03 min[39]; 354.1 |
| 129 | [structure] | Method M1, Prep P7[40] | 1.03 min[39]; 350.1 |
| 130 | [structure] | Method M1, Prep P7 | 0.97 min[39]; 336.1 |

TABLE 1-continued

| | | | |
|---|---|---|---|
| 131 | (structure: 3-fluoro-2-methyl-4-oxyphenyl attached to 4,6-dimethylpyrimidin-5-yl) | Method M1, Prep P7 | 1.02 min[39]; 350.1 |
| 132 | (structure: 2-methyl-4-oxyphenyl attached to 4,6-dimethylpyrimidin-5-yl) ·HCOOH | Ex 17[41] | 1.85 min[5]; 331 |
| 133 | (structure: 2-methyl-4-oxyphenyl attached to 7-hydroxy-6-methylimidazo[1,2-a]pyrimidin-5-yl) | Method M7[42]; Ex 146 | $^1$H NMR (400 MHz, CD$_3$OD) δ 7.98 (d, J = 5.9 Hz, 1H), 7.92 (d, J = 2.2 Hz, 1H), 7.41 (br d, J = 8.4 Hz, 1H), 7.40 (dd, J = 5.9, 1.0 Hz, 1H), 7.32 (br d, J = 2.4 Hz, 1H), 7.25 (br dd, J = 8.3, 2.4 Hz, 1H), 7.11 (br d, J = 2 Hz, 1H), 7.02 (dd, J = 2.2, 1.0 Hz, 1H), 6.80 (br d, J = 2 Hz, 1H), 2.17 (br s, 3H), 1.91 (s, 3H); 373.2 |
| 134 | (structure: 2-methyl-4-oxyphenyl attached to 4,6-dimethylpyridazin-3(2H)-one) (+) | Ex 27[43]; C2 | $^1$H NMR (400 MHz, DMSO-d$_6$) δ 12.82 (br s, 1H), 8.15 (d, J = 2.3 Hz, 1H), 8.04 (d, J = 5.8 Hz, 1H), 7.50 (br d, J = 5.8 Hz, 1H), 7.24-7.27 (m, 1H), 7.18 (br dd, half of ABX pattern, J = 8.4, 2.2 Hz, 1H), 7.15 (br d, half of AB quartet, J = 8.2 Hz, 1H), 7.05-7.07 (m, 1H), 2.03 (s, 3H), 1.88 (s, 3H), 1.75 (s, 3H); 348.0 |
| 135 | (structure: 2-methyl-4-oxyphenyl attached to 5-methoxy-3-methylpyridazin-4-yl) | Ex 12; C2[44] | 8.99 (s, 1H), 8.06 (d, J = 5.9 Hz, 1H), 7.66 (d, J = 2.3 Hz, 1H), 7.26 (dd, J = 5.9, 1.0 Hz, 1H), 7.21 (br d, J = 2 Hz, 1H), 7.17 (br dd, J = 8, 2 Hz, 1H), 7.07 (d, J = 8.2 Hz, 1H), 6.89 (dd, J = 2.2, 1.0 Hz, 1H), 3.93 (s, 3H), 2.46 (s, 3H), 2.04 (br s, 3H); 348.2 |

TABLE 1-continued

| | | | |
|---|---|---|---|
| 136 | (structure) | Ex 5; C68[45] | $^1$H NMR (600 MHz, DMSO-d$_6$) δ 8.15 (d, J = 2.2 Hz, 1H), 8.02 (d, J = 5.7 Hz, 1H), 7.99 (s, 1H), 7.49 (dd, J = 6, 1 Hz, 1H), 7.32 (d, J = 8.4 Hz, 1H), 7.22 (br d, J = 2 Hz, 1H), 7.15 (br dd, J = 8.4, 2.2 Hz, 1H), 7.07 (dd, J = 2.2, 0.9 Hz, 1H), 2.13 (s, 3H), 2.07 (br s, 3H); 334.1 |
| 137 | (structure) | Ex 1[46,38] | $^1$H NMR (400 MHz, CD$_3$OD) δ 8.01 (d, J = 2.3 Hz, 1H), 7.99 (d, J = 6.0 Hz, 1H), 7.94 (d, J = 2.3 Hz, 1H), 7.77 (d, J = 2.3 Hz, 1H), 7.50 (d, J = 8.3 Hz, 1H), 7.43 (dd, J = 5.9, 0.9 Hz, 1H), 7.24-7.35 (m, 4H), 7.02 (dd, J = 2.1, 0.9 Hz, 1H), 2.14 (s, 3H); 357.8 |
| 138 | (structure) (structure) | Ex 12[47] | $^1$H NMR (600 MHz, DMSO-d$_6$), roughly 1:1 mixture of regioisomeric N-oxides; δ 8.35 and 8.51 (2 s, total 1H), 8.14-8.16 (m, 1H), 8.04 (br s, J = 5.7 Hz, 1H), 7.49-7.52 (m, 1H), 7.26-7.30 (m, 1H), 7.18-7.23 (m, 2H), [7.07 (dd, J = 2.2, 0.9 Hz) and 7.08 (dd, J = 2.2, 0.9 Hz), total 1H], 2.08 and 2.10 (2 s, total 3H), 2.00 and 2.02 (2 s, total 3H), 1.94 (s, 3H); 348.2 |
| 139 | (structure) | Ex 5[48] | $^1$H NMR (600 MHz, DMSO-d$_6$) δ 8.97 (s, 1H), 8.21 (d, J = 2.2 Hz, 1H), 8.03 (d, J = 5.7 Hz, 1H), 7.68 (dd, J = 9.6, 6.7 Hz, 1H), 7.62 (dd, J = 10.3, 6.8 Hz, 1H), 7.55 (dd, J = 5.8, 0.5 Hz, 1H), 7.22 (dd, J = 2.1, 0.8 Hz, 1H), 2.29 (s, 6H); 354.1 |
| 140 | (structure) | Ex 12; C49 | $^1$H NMR (400 MHz, DMSO-d$_6$) δ 9.12 (s, 1H), 8.18 (d, J = 2.3 Hz, 1H), 8.07 (d, J = 5.9 Hz, 1H), 7.55 (dd, J = 5.9, 1.0 Hz, 1H), 7.46 (dd, J = 8.4, 8.4 Hz, 1H), 7.44 (dd, J = 10.8, 2.2 Hz, 1H), 7.27 (br dd, J = 8.3, 2.3 Hz, 1H), 7.14 (dd, J = 2.2, 1.0 Hz, 1H), 2.41 (s, 3H), 2.12 (s, 3H); 336.2 |

TABLE 1-continued

| | | | |
|---|---|---|---|
| 141 | (structure) | Ex 5[49] | $^1$H NMR (600 MHz, DMSO-d$_6$) δ 8.98 (s, 1H), 8.21 (d, J = 2.2 Hz, 1H), 8.03 (d, J = 5.7 Hz, 1H), 7.56 (dd, J = 5.9, 0.9 Hz, 1H), 7.43-7.47 (m, 1H), 7.32-7.36 (m, 1H), 7.23 (dd, J = 2.2, 0.9 Hz, 1H), 2.29 (s, 6H); 354.1 |
| 142 | (structure) (−) | Ex 12; C10[50] | 8.95 (s, 1H), 8.08 (d, J = 5.9 Hz, 1H), 7.68 (d, J = 2.2 Hz, 1H), 7.28 (dd, J = 5.9, 1.0 Hz, 1H), 7.03-7.06 (m, 1H), 6.93-6.96 (m, 2H), 6.91 (dd, J = 2.2, 1.0 Hz, 1H), 3.74 (s, 3H), 2.47 (s, 3H), 2.12 (s, 3H); 348.2 |
| 143 | (structure) (+) | Ex 12; C10[50] | 8.96 (s, 1H), 8.08 (d, J = 5.9 Hz, 1H), 7.68 (d, J = 2.2 Hz, 1H), 7.28 (dd, J = 5.9, 1.0 Hz, 1H), 7.03-7.07 (m, 1H), 6.93-6.97 (m, 2H), 6.91 (dd, J = 2.3, 1.0 Hz, 1H), 3.75 (s, 3H), 2.47 (s, 3H), 2.12 (s, 3H); 348.2 |
| 144 | (structure) | Method M1; P10 | $^1$H NMR (600 MHz, DMSO-d$_6$) δ 8.93 (s, 1H), 8.19 (s, 1H), 8.18 (d, J = 2.2 Hz, 1H), 8.02 (d, J = 5.9 Hz, 1H), 7.53 (dd, J = 5.8, 1.0 Hz, 1H), 7.19 (d, J = 7.5 Hz, 1H), 7.13 (dd, J = 2.2, 1.1 Hz, 1H), 7.00 (d, J = 7.5 Hz, 1H), 4.06 (s, 3H), 2.20 (s, 6H); 372.0 |
| 145 | (structure) | Ex 12[51] | $^1$H NMR (600 MHz, DMSO-d$_6$) δ 9.16 (d, J = 5.0 Hz, 1H), 8.15 (d, J = 2.2 Hz, 1H), 8.02 (d, J = 5.7 Hz, 1H), 7.52 (d, J = 5.0 Hz, 1H), 7.49 (dd, J = 5.8, 1.0 Hz, 1H), 7.23-7.26 (m, 2H), 7.17 (br dd, J = 8.2, 2.3 Hz, 1H), 7.10 (dd, J = 2.2, 0.9 Hz, 1H), 2.43 (s, 3H), 2.04 (s, 3H); 318.1 |
| 146 | (structure) | Ex 20; C2[52,53,54] | Characteristics peaks: 8.57 (s, 1H), 8.08 (d, J = 5.5 Hz, 1H), 7.17 (d, J = 2.0 Hz, 1H), 7.05 (br s, 1H), 6.94-6.98 (m, 1H), 2.19 (s, 3H), 2.07 (s, 3H); 357.1 |

TABLE 1-continued

| | Structure | Method/Ex | Data |
|---|---|---|---|
| 147 | (structure) | Ex 20; C2[52,53,54] | Characteristics peaks: 8.56 (s, 1H), 8.08 (d, J = 6.0 Hz, 1H), 7.72-7.75 (m, 1H), 7.70 (d, J = 2.0 Hz, 1H), 7.02-7.05 (m, 1H), 6.95-6.97 (m, 1H), 2.19 (s, 3H), 2.07 (s, 3H); 357.0 |
| 148 | (structure) ·CF₃COOH | Method M1; P11 | $^1$H NMR (600 MHz, DMSO-d$_6$) δ 9.01 (s, 1H), 8.18 (d, J = 1.8 Hz, 1H), 8.03 (d, J = 5.7 Hz, 1H), 7.86 (s, 1H), 7.55 (br d, J = 6.2 Hz, 1H), 7.25 (d, J = 7.9 Hz, 1H), 7.15-7.17 (m, 1H), 7.10 (d, J = 7.5 Hz, 1H), 3.46 (s, 3H), 2.21 (s, 6H); 372.1 |
| 149 | (structure) | Ex 152[55] | $^1$H NMR (400 MHz, CD$_3$OD) δ 7.98 (d, J = 6.0 Hz, 1H), 7.88 (d, J = 2.0 Hz, 1H), 7.38 (d, J = 6.0 Hz, 1H), 7.20-7.23 (m, 1H), 7.11-7.17 (m, 2H), 6.89-6.92 (m, 1H), 4.03 (s, 3H), 2.19 (s, 6H), 2.05 (s, 3H); 361.9 |
| 150 | (structure) | Ex 12; C52 | 8.99 (s, 1H), 8.06 (d, J = 5.8 Hz, 1H), 7.68 (d, J = 2.2 Hz, 1H), 7.37-7.41 (m, 2H), 7.26-7.29 (m, 1H, assumed; partially obscured by solvent peak), 7.19-7.23 (m, 2H), 6.93 (dd, J = 2.3, 1.0 Hz, 1H), 2.53 (s, 3H), 2.17 (s, 3H); 318.0 |
| 151 | (structure) ·CF₃COOH | Ex 11[56] | 2.80 min[12]; 361.2 |
| 152 | (structure) | Ex 1[57] | 8.06 (d, J = 6.0 Hz, 1H), 7.67 (d, J = 2.3 Hz, 1H), 7.25-7.28 (m, 1H, assumed; partially obscured by solvent peak), 7.22 (br d, J = 2.3 Hz, 1H), 7.16 (br dd, half of ABX pattern, J = 8, 2 Hz, 1H), 7.10 (d, half of AB quartet, J = 8.0, 1H), 6.90 (dd, J = 2, 1 Hz, 1H), 2.18 (s, 6H), 2.12 (br s, 3H); 347.9 |

TABLE 1-continued

| | | | |
|---|---|---|---|
| 153 | (structure) | Ex 37[11] | ¹H NMR (400 MHz, CD₃OD) δ 8.39 (d, J = 6.6 Hz, 1H), 8.20 (d, J = 2.3 Hz, 1H), 8.03-8.06 (m, 2H), 7.97 (br d, half of AB quartet, J = 9.2 Hz, 1H), 7.92 (dd, J = 6.7, 0.9 Hz, 1H), 7.75 (dd, J = 2.2, 0.7 Hz, 1H), 7.63 (d, J = 8.4 Hz, 1H), 7.26 (d, J = 2.3 Hz, 1H), 7.22 (dd, J = 8.4, 2.3 Hz, 1H), 6.65 (dd, J = 2.3, 1.0 Hz, 1H), 2.39 (s, 3H); LCMS m/z 356.1 (M – H). |
| 154 | (structure) | Ex 22[58]; Ex 11 | ¹H NMR (600 MHz, DMSO-d₆) δ 9.23 (s, 1H), 9.00 (s, 1H), 8.15 (d, J = 2.2 Hz, 1H), 8.02 (d, J = 5.7 Hz, 1H), 7.49 (dd, J = 5.7, 0.9 Hz, 1H), 7.26 (br d, J = 2.2 Hz, 1H), 7.25 (d, J = 8.4 Hz, 1H), 7.18 (br dd, J = 8.4, 2.6 Hz, 1H), 7.10 (dd, J = 2.2, 0.9 Hz, 1H), 2.15 (s, 3H), 2.05 (s, 3H); 318.0 |
| 155 | (structure) | Ex 8; C63[59] | ¹H NMR (600 MHz, DMSO-d₆) δ 8.93 (s, 1H), 8.34 (d, J = 5.7 Hz, 1H), 8.10 (d, J = 2.2 Hz, 1H), 7.61-7.62 (m, 1H), 7.58 (dd, J = 5.7, 0.9 Hz, 1H), 7.49 (br dd, J = 7.9, 1.8 Hz, 1H), 7.21 (d, J = 7.9 Hz, 1H), 6.59 (dd, J = 2.2, 0.9 Hz, 1H), 2.15 (s, 6H), 1.96 (s, 3H); 348.0 |
| 156 | (structure) | Ex 6; P13 | ¹H NMR (600 MHz, DMSO-d₆) δ 8.92 (s, 1H), 8.17 (d, J = 2.2 Hz, 1H), 8.03 (d, J = 5.7 Hz, 1H), 7.50 (dd, J = 5.7, 0.9 Hz, 1H), 7.14 (dd, J = 2.2, 1.1 Hz, 1H), 6.92 (AB quartet, $J_{AB}$ = 8.6 Hz, $\Delta\nu_{AB}$ = 58.5 Hz, 2H), 6.04 (s, 2H), 2.32 (s, 6H); 362.0 |
| 157 | (structure) | Ex 11[60] | ¹H NMR (600 MHz, DMSO-d₆) δ 8.88 (s, 1H), 8.14 (d, J = 2.2 Hz, 1H), 8.03 (d, J = 5.7 Hz, 1H), 7.49 (dd, J = 5.7, 0.9 Hz, 1H), 7.21-7.23 (m, 1H), 7.12-7.17 (m, 2H), 7.05 (dd, J = 2.2, 0.9 Hz, 1H), 4.53 (dq, J = 10.8, 7.0 Hz, 1H), 4.43 (dq, J = 10.8, 7.0 Hz, 1H), 2.03 (s, 3H), 1.99 (s, 3H), 1.26 (t, J = 7.0 Hz, 3H); 362.0 |
| 158 | (structure) | Ex 10; C63[61] | ¹H NMR (500 MHz, CDCl₃), δ 9.04 (s, 1H), 8.89 (dd, J = 4.2, 1.7 Hz, 1H), 8.51 (dd, J = 8.5, 1.8 Hz, 1H), 8.03 (d, J = 5.7 Hz, 1H), 7.74 (d, J = 2.2 Hz, 1H), 7.54 (AB quartet, $J_{AB}$ = 7.8 Hz, $\Delta\nu_{AB}$ = 28.4 Hz, 2H), 7.45 (dd, J = 8.4, 4.2 Hz, 1H), 7.30-7.32 (m, 1H), 7.00-7.01 (m, 1H), 2.24 (s, 6H); 368.9 |

TABLE 1-continued

| | | | |
|---|---|---|---|
| 159 | (structure) | Ex 134[62] | 8.06 (d, J = 5.8 Hz, 1H), 7.66 (d, J = 2 Hz, 1H), 7.25-7.28 (m, 1H, assumed; partially obscured by solvent peak), 7.20-7.22 (m, 1H), 7.17 (dd, J = 8.2, 2.3 Hz, 1H), 7.02 (d, J = 8.2 Hz, 1H), 6.86-6.89 (m, 1H), 3.83 (s, 3H), 2.08 (s, 3H), 2.00 (s, 3H), 1.96 (s, 3H); 362.1 |
| 160 | (structure) | Ex 27[77] | 8.08 (d, J = 5.9 Hz, 1H), 7.70 (d, J = 2.2 Hz, 1H), 7.49 (d, J = 2.4 Hz, 1H), 7.29-7.35 (m, 2H), 7.17 (d, J = 8.4 Hz, 1H), 6.93 (dd, J = 2.4, 1.0 Hz, 1H), 2.07 (s, 3H), 2.00 (s, 3H); 368.0 |
| 161 | (structure) | Ex 6; C52, C55 | 8.09 (d, J = 5.8 Hz, 1H), 7.70 (d, J = 2.2 Hz, 1H), 7.57 (br d, J = 9.2 Hz, 1H), 7.54 (d, J = 1.2 Hz, 1H), 7.43-7.49 (m, 4H), 7.29 (dd, J = 5.8, 1.0 Hz, 1H), 7.23-7.24 (m, 1H), 7.17 (d, J = 9.2 Hz, 1H), 6.96 (dd, J = 2.2, 1.0 Hz, 1H), 2.21 (s, 3H); 342.1 |
| 162 | (structure) | Ex 5, Prep P6[63] | 2.53 min[9]; 371.1 |
| 163 | (structure) ·HCOOH | Method M6 | 2.511 min[5]; 405 |

TABLE 1-continued
| | | | |
|---|---|---|---|
| 164 | 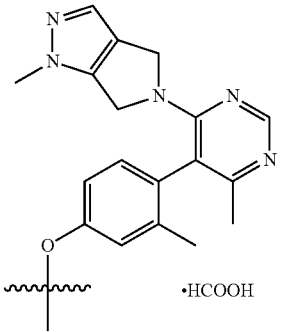 [SMILES: *Oc1ccc(-c2c(C)ncnc2N2Cc3cnn(C)c3C2)c(C)c1 ; "·HCOOH"] ·HCOOH | Method M6 | 2.382 min[5]; 439 |
| 165 | 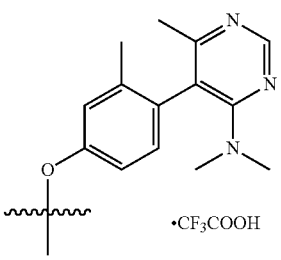 [SMILES: *Oc1ccc(-c2c(C)ncnc2N(C)C)c(C)c1 ; "·CF3COOH"] ·CF₃COOH | Method M6 | 2.413 min[5]; 361 |
| 166 | 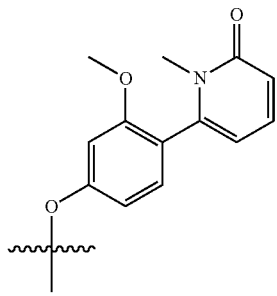 [SMILES: *Oc1ccc(-c2cccc(=O)n2C)c(OC)c1] | Ex 16; C10[64] | $^1$H NMR (600 MHz, DMSO-d$_6$) δ 8.16 (d, J = 2.2 Hz, 1H), 8.03 (d, J = 5.7 Hz, 1H), 7.51 (d, J = 5.7 Hz, 1H), 7.43 (dd, J = 9.0, 6.8 Hz, 1H), 7.31 (d, J = 7.9 Hz, 1H), 7.11 (br d, J = 1.8 Hz, 1H), 7.08 (d, J = 2.2 Hz, 1H), 6.91 (dd, J = 8.3, 2.2 Hz, 1H), 6.42 (dd, J = 9.2, 0.9 Hz, 1H), 6.13 (dd, J = 6.6, 1.3 Hz, 1H), 3.78 (s, 3H), 3.18 (s, 3H); 349.2 |
| 167 | 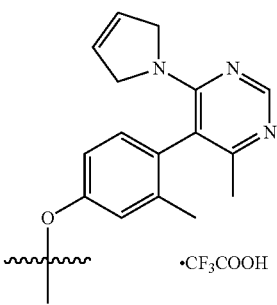 ·CF₃COOH | Method M6 | 2.552 min[5]; 385 |
| 168 | 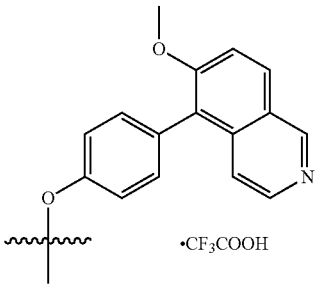 ·CF₃COOH | Ex 8[65]; C52 | $^1$H NMR (500 MHz, CD$_3$OD) δ 9.16 (s, 1H), 8.26 (d, J = 6.3 Hz, 1H), 8.21 (d, J = 9.0 Hz, 1H), 8.00 (d, J = 6.1 Hz, 1H), 7.90 (d, J = 2.2 Hz, 1H), 7.70 (d, J = 9.0 Hz, 1H), 7.52 (d, J = 6.3 Hz, 1H), 7.37-7.42 (m, 3H), 7.31-7.36 (m, 2H), 6.93-6.98 (m, 1H), 3.96 (s, 3H); 369.0 |

TABLE 1-continued

| | | | |
|---|---|---|---|
| 169 | [structure] | Ex 12; C10 | $^1$H NMR (400 MHz, CD$_3$OD) δ 8.94 (s, 1H), 7.97 (d, J = 6.0 Hz, 1H), 7.87 (d, J = 2.3 Hz, 1H), 7.37 (dd, J = 6.0, 1.1 Hz, 1H), 7.14 (d, J = 8.4 Hz, 1H), 7.04 (d, J = 2.1 Hz, 1H), 6.88-6.93 (m, 2H), 3.73 (s, 3H), 2.40 (s, 3H), 2.14 (s, 3H); 348.0 |
| 170 | [structure] | Ex 6[77] | 2.554 min[5]; 363 |
| 171 | [structure] | Ex 12; C2[66] | 8.99 (s, 1H), 8.07 (d, J = 5.9 Hz, 1H), 7.67 (d, J = 2.2 Hz, 1H), 7.15-7.27 (m, 3H), 7.07 (d, J = 8.2 Hz, 1H), 6.89 (dd, J = 2.2, 1.0 Hz, 1H), 3.94 (s, 3H), 2.48 (s, 3H), 2.04 (s, 3H); 348.2 |
| 172 | [structure] | Ex 6; C45, C52 | 2.00 min[67]; 343.1 |
| 173 | [structure] | Ex 6; C45, C10 | $^1$H NMR (500 MHz, CDCl$_3$) δ 9.33 (br s, 1H), 8.10 (d, J = 5.9 Hz, 1H), 7.82 (br s, 1H), 7.72 (d, J = 2.2 Hz, 1H), 7.37 (d, J = 8.0 Hz, 1H), 7.35-7.37 (m, 1H), 7.33 (dd, J = 5.7, 0.9 Hz, 1H), 7.04-7.08 (m, 2H), 6.98 (dd, J = 2.1, 0.8 Hz, 1H), 3.76 (s, 3H), 2.51 (s, 3H); 373.0 |

TABLE 1-continued
| | | | |
|---|---|---|---|
| 174 | 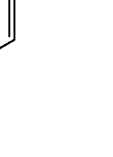 | Ex 16; C2 | 8.03 (d, J = 5.9 Hz, 1H), 7.65 (d, J = 2.3 Hz, 1H), 7.63 (br d, J = 9.2 Hz, 1H), 7.59 (d, J = 1.4 Hz, 1H), 7.35 (d, J = 8.2 Hz, 1H), 7.16-7.27 (m, 5 H), 6.92 (dd, J = 2.1, 1.0 Hz, 1H), 6.70 (dd, J = 6.8, 1.0 Hz, 1H), 2.08 (s, 3H); 342.1 |
| 175 | 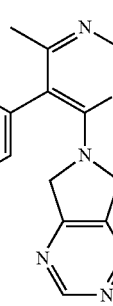 | Method M6 | 2.525 min$^6$; 437 |
| 176 | 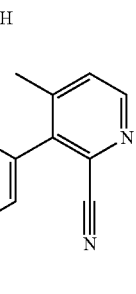 | Ex 6; C2$^{68}$ | 3.26 min$^9$; 342.1 |
| 177 | 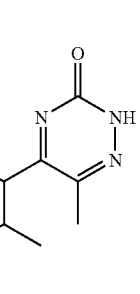 | Ex 5; C67$^{69}$ | 8.07 (d, J = 5.9 Hz, 1H), 7.67 (d, J = 2.4 Hz, 1H), 7.27-7.31 (m, 2H), 7.17-7.22 (m, 2H), 6.85 (dd, J = 2.2, 1.0 Hz, 1H), 2.31 (s, 3H), 2.25 (s, 3H); 335.3 |
| 178 | 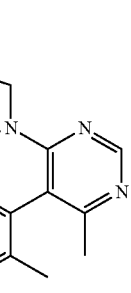 | Method M6 | 2.586 min$^5$; 387 |

TABLE 1-continued
| 179 | 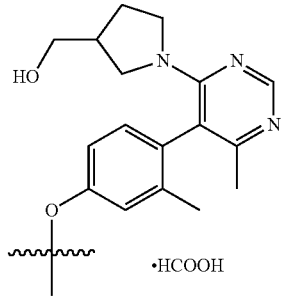 [SMILES: *Oc1ccc(-c2c(C)ncnc2N2CCC(CO)C2)c(C)c1 ; "·HCOOH"] •HCOOH | Method M6 | 2.521 min[6]; 417 |
|---|---|---|---|
| 180 | 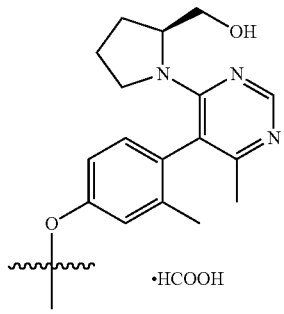 [SMILES: *Oc1ccc(-c2c(C)ncnc2N2CCC[C@H]2CO)c(C)c1 ; "·HCOOH"] •HCOOH | Method M6 | 2.388 min[5]; 417 |
| 181 | 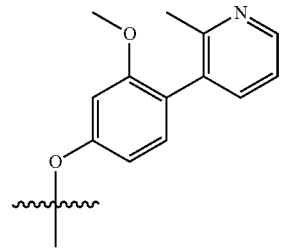 [SMILES: *Oc1ccc(-c2cccnc2C)c(OC)c1] | Ex 6; C10 | $^1$H NMR (400 MHz, CD$_3$OD) δ 8.71 (dd, J = 5.8, 1.3 Hz, 1H), 8.45 (dd, J = 7.8, 1.3 Hz, 1H), 7.95-8.02 (m, 2H), 7.92 (d, J = 2.5 Hz, 1H), 7.42 (dd, J =6.0, 1.0 Hz, 1H), 7.36 (d, J = 8.5 Hz, 1H), 7.11 (d, J = 2.0 Hz, 1H), 6.95-6.99 (m, 2H), 3.81 (s, 3H), 2.67 (s, 3H); 333.2 |
| 182 | 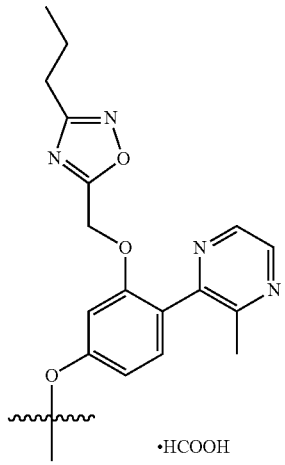 [SMILES: *Oc1ccc(-c2nccnc2C)c(OCc2nc(CCC)no2)c1 ; "·HCOOH"] •HCOOH | Method M2 | 3.271 min[6]; 444 |

US 9,617,275 B2
TABLE 1-continued
| 183 | 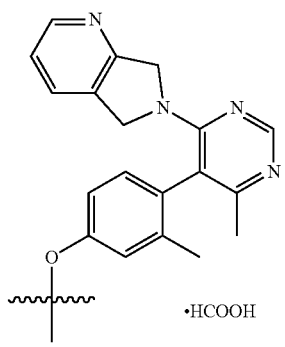 [SMILES: *Oc1ccc(-c2c(C)ncnc2N2Cc3cccnc3C2)c(C)c1 ; "·HCOOH"] •HCOOH | Method M6 | 2.422 min⁵; 436 |
| 184 | 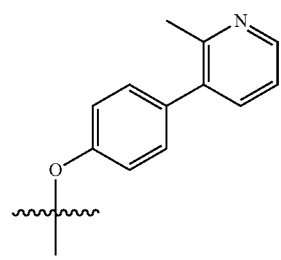 [SMILES: *Oc1ccc(-c2cccnc2C)cc1] | Ex 1; C52 | 2.174 min⁵; 303 |
| 185 | 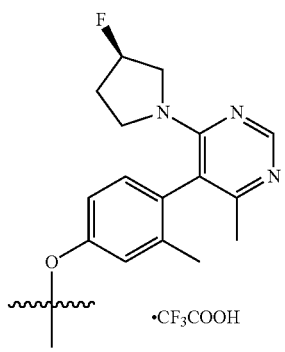 [SMILES: *Oc1ccc(-c2c(C)ncnc2N2CC[C@@H](F)C2)c(C)c1 ; "·CF3COOH"] •CF₃COOH | Method M6 | 2.519 min⁵; 405 |
| 186 | 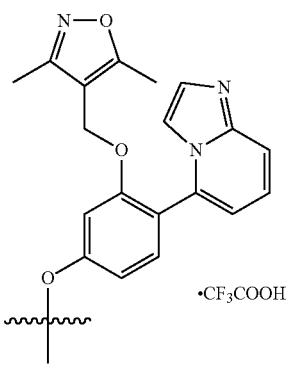 •CF₃COOH | Method M2 | 2.448 min⁵; 453 |

TABLE 1-continued
| | | | |
|---|---|---|---|
| 187 | 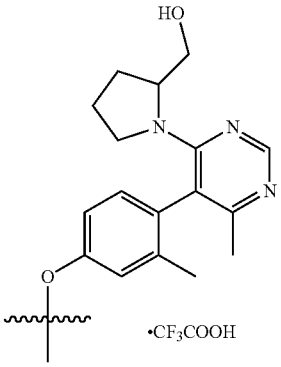 [SMILES: *Oc1ccc(-c2c(C)ncnc2N2CCCC2CO)c(C)c1 ; "·CF3COOH"] •CF$_3$COOH | Method M6 | 2.393 min[5]; 417 |
| 188 | 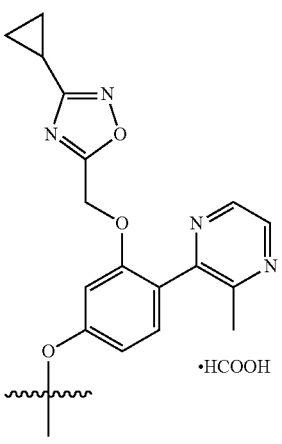 [SMILES: *Oc1ccc(-c2nccnc2C)c(OCc2nc(C3CC3)no2)c1 ; "·HCOOH"] •HCOOH | Method M2 | 3.175 min[6]; 442 |
| 189 | 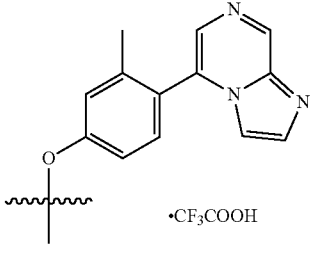 [SMILES: *Oc1ccc(-c2cncc3nccn23)c(C)c1 ; "·CF3COOH"] •CF$_3$COOH | Ex 6; C2 | 2.45 min[9]; 343.2 |
| 190 | 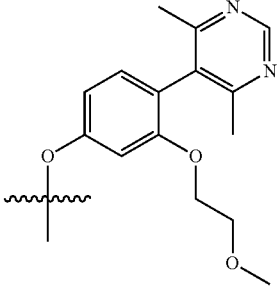 [SMILES: *Oc1ccc(-c2c(C)ncnc2C)c(OCCOC)c1] | Ex 72[70] | 9.12 (s, 1H), 8.07 (d, J = 6.0 Hz, 1H), 7.70 (d, J = 2.0 Hz, 1H), 7.31 (d, J = 5.5 Hz, 1H), 7.11 (br d, J = 8.5 Hz, 1H), 6.99-7.04 (m, 2H), 6.93 (br s, 1H), 4.07-4.13 (m, 2H), 3.52-3.58 (m, 2H), 3.27 (s, 3H), 2.60 (s, 6H); 392.0 |
| 191 | 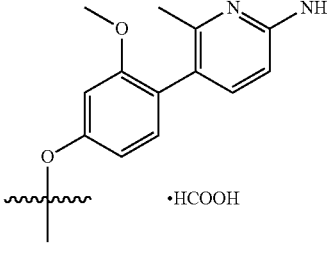 •HCOOH | Ex 1; C10 | 2.569 min[6]; 348 |

TABLE 1-continued
| 192 | 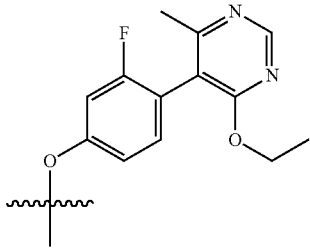 [SMILES: *Oc1ccc(-c2c(C)ncnc2OCC)c(F)c1] | Ex 20; C49[71] | 8.68 (s, 1H), 8.08 (d, J = 6.0 Hz, 1H), 7.68 (d, J = 2.5 Hz, 1H), 7.24-7.31 (m, 2H), 7.10-7.16 (m, 2H), 6.91 (br d, J = 2 Hz, 1H), 4.37-4.50 (m, 2H), 2.36 (s, 3H), 1.31 (t, J = 7.0 Hz, 3H); 366.1 |
| --- | --- | --- | --- |
| 193 | 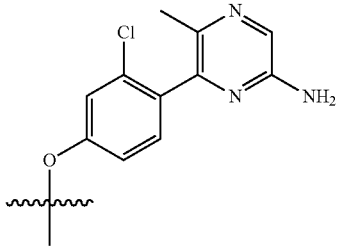 [SMILES: *Oc1ccc(-c2nc(N)cnc2C)c(Cl)c1] | Ex 1[77] | 2.634 min[5]; 353 |
| 194 | 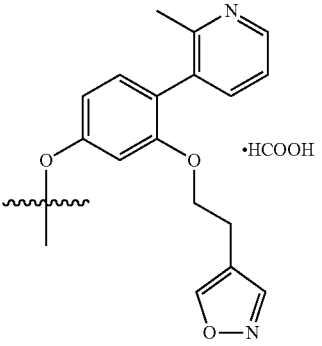 [SMILES: *Oc1ccc(-c2cccnc2C)c(OCCc2cnoc2)c1 ; "·HCOOH"] | Method M4 | 2.646 min[6] |
| 195 | 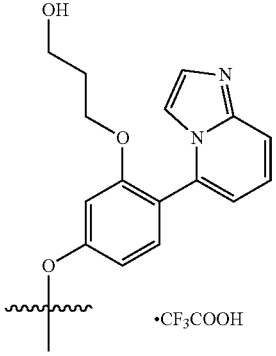 [SMILES: *Oc1ccc(-c2cccc3nccn23)c(OCCCO)c1 ; "·CF3COOH"] | Method M2 | 2.685 min[72]; 402 |
| 196 | 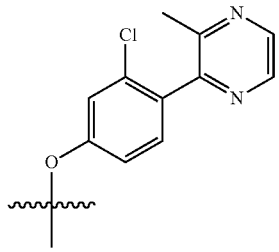 [SMILES: *Oc1ccc(-c2nccnc2C)c(Cl)c1] | Ex 1[77] | 2.911 min[5]; 338 |

TABLE 1-continued
| | | | |
|---|---|---|---|
| 197 | 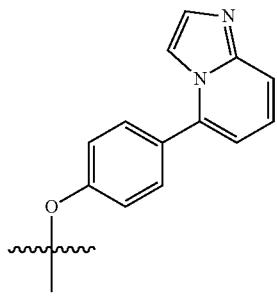 [SMILES: *Oc1ccc(-c2cccc3nccn23)cc1] | Ex 8; C52 | 8.07 (d, J = 5.8 Hz, 1H), 7.74-7.76 (m, 1H), 7.69-7.73 (m, 3H), 7.63-7.67 (m, 2H), 7.42 (br d, J = 8.6 Hz, 2H), 7.26-7.31 (m, 2H, assumed; partially obscured by solvent peak), 6.97 (dd, J = 2.2, 1.0 Hz, 1H), 6.79 (dd, J = 6.9, 1.1 Hz, 1H); 328.0 |
| 198 | 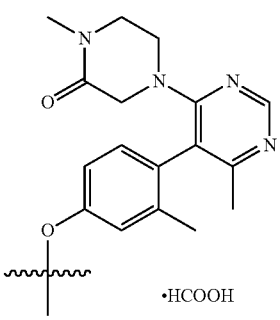 [SMILES: *Oc1ccc(-c2c(C)ncnc2N2CCN(C)C(=O)C2)c(C)c1 ; "·HCOOH"] | Method M6 | 2.452 min$^6$; 430 |
| 199 | 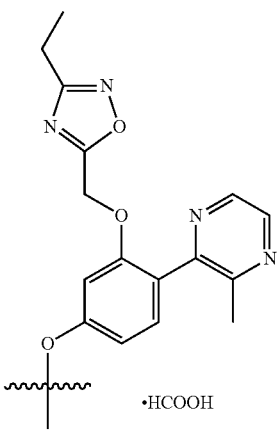 [SMILES: *Oc1ccc(-c2nccnc2C)c(OCc2nc(CC)no2)c1 ; "·HCOOH"] | Method M2 | 3.121 min$^6$; 430 |
| 200 | 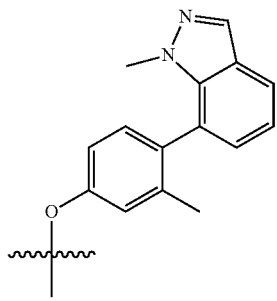 [SMILES: *Oc1ccc(-c2cccc3cnn(C)c23)c(C)c1] | Ex 6; C1 | $^1$H NMR (500 MHz, CDCl$_3$) δ 8.08 (d, J = 5.9 Hz, 1H), 8.04 (s, 1H), 7.74 (dd, J = 6.6, 2.7 Hz, 1H), 7.67 (d, J = 2.2 Hz, 1H), 7.34 (d, J = 8.3 Hz, 1H), 7.25 (d, J = 5.9 Hz, 1H), 7.18-7.22 (m, 3H), 7.10-7.18 (m, 1H), 6.88-6.96 (m, 1H), 3.60 (s, 3H), 2.08 (s, 3H); 356.1 |

TABLE 1-continued
| | | | |
|---|---|---|---|
| 201 | 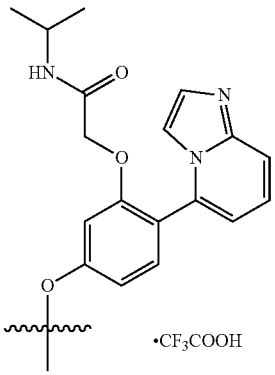 [SMILES: *Oc1ccc(-c2cccc3nccn23)c(OCC(=O)NC(C)C)c1 ; "·CF3COOH"] •CF₃COOH | Method M2 | 2.523 min⁶; 443 |
| 202 | 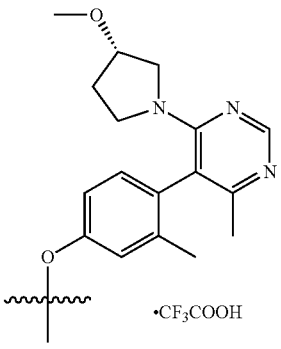 [SMILES: *Oc1ccc(-c2c(C)ncnc2N2CC[C@H](OC)C2)c(C)c1 ; "·CF3COOH"] •CF₃COOH | Method M6 | 2.721 min⁷²; 417 |
| 203 | 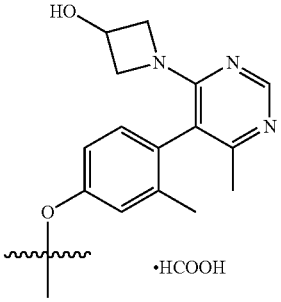 [SMILES: *Oc1ccc(-c2c(C)ncnc2N2CC(O)C2)c(C)c1 ; "·HCOOH"] •HCOOH | Method M6 | 2.427 min⁶; 389 |
| 204 | 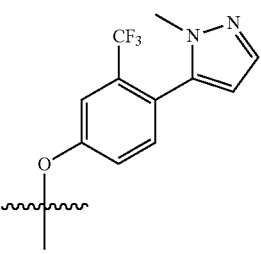 [SMILES: *Oc1ccc(-c2ccnn2C)c(C(F)(F)F)c1] | Ex 20⁷³ | 8.05 (d, J = 6.0 Hz, 1H), 7.71 (d, J = 2.0 Hz, 1H), 7.70 (d, J = 2.5 Hz, 1H), 7.51-7.57 (m, 2H), 7.42 (d, J = 8.5 Hz, 1H), 7.31 (br d, J = 5.8 Hz, 1H), 6.97-6.99 (m, 1H), 6.31-6.33 (m, 1H), 3.70 (s, 3H); 360.3 |
| 205 | 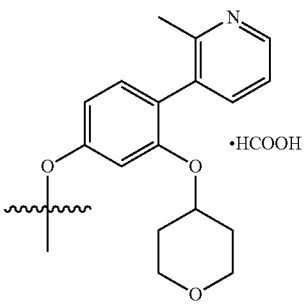 [SMILES: *Oc1ccc(-c2cccnc2C)c(OC2CCOCC2)c1 ; "·HCOOH"] •HCOOH | Method M4 | 2.616 min⁶; 403 |

TABLE 1-continued

| # | Structure | Ex | Data |
|---|---|---|---|
| 206 | (structure) | Ex 24[74] | 8.71 (s, 1H), 8.07 (d, J = 5.9 Hz, 1H), 7.66 (d, J = 2.2 Hz, 1H), 7.25 (dd, J = 5.9, 0.8 Hz, 1H), 7.19 (br d, J = 2.2 Hz, 1H), 7.14 (dd, half of ABX pattern, J = 8.2, 2.4 Hz, 1H), 7.10 (d, half of AB pattern, J = 8.2 Hz, 1H), 6.88 (dd, J = 2.2, 0.8 Hz, 1H), 3.93 (s, 3H), 2.27 (s, 3H), 2.06 (br s, 3H); 348.4 |
| 207 | (structure) | Ex 2[75]; C4 | 8.09 (d, J = 5.8 Hz, 1H), 7.91 (br s, 1H), 7.72 (d, J = 2.0 Hz, 1H), 7.30-7.38 (m, 5H), 6.97 (br d, J = 2 Hz, 1H), 2.43 (s, 3H), 2.07 (s, 3H); 381.9 |
| 208 | (structure) | Ex 18, step 1; C52 | $^1$H NMR (400 MHz, CD$_3$OD) δ 9.26 (s, 1H), 8.01 (d, J = 5.9 Hz, 1H), 7.87-7.93 (m, 3H), 7.81 (dd, J = 8.6, 1.0 Hz, 1H), 7.67-7.72 (m, 1H), 7.51 (dd, J = 7.8, 2.0 Hz, 1H), 7.40-7.46 (m, 3H), 6.98 (dd, J = 2.2, 0.9 Hz, 1H), 4.12 (s, 3H); 370.1 |

1. HPLC conditions. Column: Welch XB-C18, 2.1×50 mm, 5 μm; Mobile phase A: 0.05% ammonium hydroxide in water (v/v); Mobile phase B: acetonitrile.
2. HPLC Conditions. Column: Welch XB-C18, 2.1×50 mm, 5 μm; Mobile phase A: 0.05% trifluoroacetic acid in water (v/v); Mobile phase B: acetonitrile.
3. Example 16 was N-formylated to provide N-[5-(furo[3,2-c]pyridin-4-yloxy)-2-(imidazo[1,2-a]pyridin-5-yl)phenyl]formamide by heating in methyl formate in the presence of sodium hydride and [1,1'-bis(diphenylphosphino)ferrocene]dichloropalladium(II). Reduction with borane-dimethylsulfide complex provided Example 38.
4. In this case, 4-amino-3-chlorophenol was used as starting material, and the phenol was carried through construction of the imidazo[4,5-c]pyridine without protection.
5. HPLC conditions. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.
6. HPLC conditions. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes, then 5% to 100% B over 3.4 minutes; Flow rate: 0.8 mL/minute.
7. This example was prepared via reductive amination of Example 16 with 1-methyl-1H-imidazole-5-carbaldehyde.
8. Coupling partner 3-bromo-4-methylpyridine-2-carbonitrile may be prepared from 3-bromo-4-methylpyridine by generation of the pyridine N-oxide through reaction with hydrogen peroxide, followed by cyanation according to the method of T. Sakamoto et al., *Chem. Pharm. Bull.* 1985, 33, 565-571.
9. HPLC conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B over 4.0 minutes, linear; Flow rate: 2 mL/minute.
10. Example 17 was N-methylated using sodium hydride and methyl iodide.
11. The final step in the synthesis was cleavage of the methyl ether using boron tribromide.
12. HPLC conditions. Column: Waters XBridge C18, 4.6×50 mm, 5 μm; Mobile phase A: 0.03% ammonium hydroxide in water (v/v); Mobile phase B: 0.03% ammonium hydroxide in acetonitrile (v/v); 5.0% to 95% B over 4.0 minutes, linear; Flow rate: 2 mL/minute.
13. In this case, the Suzuki coupling was carried out using tetrakis(triphenylphosphine)palladium(0) and potassium carbonate or sodium carbonate.
14. The starting material was alkylated using 5-(chloromethyl)-3-cyclopropyl-1,2,4-oxadiazole and cesium carbonate.
15. 1-Bromo-2-fluoro-4-methoxybenzene was used as starting material.
16. 5-Bromo-4-methoxy-6-methylpyrimidine was prepared by reaction of 5-bromo-4-chloro-6-methylpyrimidine with sodium methoxide.
17. The requisite 5-bromo-6-methyl-2-(trifluoromethyl)imidazo[1,2-a]pyrazine was prepared via reaction of C60 with 3-bromo-1,1,1-trifluoropropan-2-one.
18. Example 18 was treated with the appropriate amine.
19. The requisite 5-bromo-6-methylpyrimidine-4-carbonitrile was prepared via reaction of 5-bromo-4-chloro-6-methylpyrimidine with tetra-n-butylammonium cyanide.

20. The product was separated into its component atropenantiomers using supercritical fluid chromatography (Column: Chiralpak AD-H, 5 μm; Eluent: 3:1 carbon dioxide/propanol). The first-eluting compound was Example 83 and the second-eluting atropenantiomer was Example 82.

21. The requisite 2-amino-5-bromo-6-methylpyrimidine-4-carbonitrile may be prepared via reaction of 5-bromo-4-chloro-6-methylpyrimidin-2-amine with tetraethylammonium cyanide and 1,4-diazabicyclo[2.2.2]octane in a mixture of acetonitrile and N,N-dimethylformamide.

22. The required 3-bromo-2-cyclopropylpyridine was prepared via reaction of 2,3-dibromopyridine with cyclopropylboronic acid at 100° C. in the presence of palladium(II) acetate, tricyclohexylphosphine and potassium phosphate.

23. The requisite 5-bromo-1,4-dimethyl-1H-imidazole may be prepared via methylation of 5-bromo-4-methyl-1H-imidazole using sodium hydride and methyl iodide.

24. Suzuki reaction of (4-methoxy-2,6-dimethylphenyl)boronic acid with 5-bromo-4,6-dimethylpyrimidine, mediated by tris(dibenzylideneacetone)dipalladium(0) and dicyclohexyl(2',6'-dimethoxybiphenyl-2-yl)phosphane, followed by cleavage of the methyl ether, afforded the requisite phenol.

25. Obtained from supercritical fluid chromatographic separation of Example 19 [Column: Chiralcel AS, 20 μm; Mobile phase 7:3 carbon dioxide/(methanol containing 0.2% diethylamine)]. This Example was the second-eluting atropenantiomer from the column.

26. This was the first-eluting atropenantiomer from the separation described in footnote 25.

27. Compound C4 was heated with aqueous chloroacetaldehyde at reflux for 2 hours, affording 8-bromo-5-[4-(furo[3,2-c]pyridin-4-yloxy)-2-methylphenyl]-6-methylimidazo[1,2-a]pyrazine. Reaction of this intermediate with sodium methoxide in methanol provided Example 107.

28. The 8-bromo intermediate from footnote 27 was subjected to reaction with trimethylboroxin in the presence of [1,1'-bis(diphenylphosphino)ferrocene]dichloropalladium(II) and potassium carbonate to provide Example 109.

29. Reaction of chloroacetaldehyde with 2-amino-5-methylpyrimidin-4-ol afforded a mixture of 6-methylimidazo[1,2-a]pyrimidin-5-ol and 6-methylimidazo[1,2-a]pyrimidin-7-ol, which was subjected to reaction with phosphorus oxychloride, providing a mixture of 5-chloro-6-methylimidazo[1,2-a]pyrimidine and 7-chloro-6-methylimidazo[1,2-a]pyrimidine. Reaction of this mixture with C2 yielded a separable mixture of Examples 110 and 111. The structures of these two compounds were subsequently assigned using NOE studies carried out on the separated intermediates 6-methylimidazo[1,2-a]pyrimidin-5-ol and 6-methylimidazo[1,2-a]pyrimidin-7-ol.

30. The 8-bromo intermediate from footnote 27 was subjected to reaction with tert-butyl carbamate in the presence of palladium(II) acetate, 1,1'-binaphthalene-2,2'-diylbis(diphenylphosphane) and cesium carbonate, at 120° C. for 2 hours, to afford Example 112.

31. The requisite 4-(4-bromo-3,5-difluorophenoxy)furo[3,2-c]pyridine was prepared from 4-chlorofuro[3,2-c]pyridine and 4-bromo-3,5-difluorophenol, using the general method of Example 17, step 3.

32. Example 11 was reacted with hydrazine. The resulting 4-[4-(3-hydrazinyl-5-methylpyridazin-4-yl)-3-methylphenoxy]furo[3,2-c]pyridine was cyclized with 1,1'-carbonyldiimidazole to provide the product.

33. Example 117 was isolated as a side product during the synthesis of Examples 120 and 121, derived from an overmethylated contaminant in P8.

34. The racemic version of Example 82 was hydrolyzed with aqueous sodium hydroxide in ethanol to provide the product.

35. The racemic product was separated via supercritical fluid chromatography (Column: Chiralcel OJ-H, 5 μm; Eluent: 3:1 carbon dioxide/methanol). Example 121 eluted first, followed by Example 120.

36. (2-Chloro-5-methoxyphenyl)acetonitrile (see C. Pierre and O. Baudoin, *Org. Lett.* 2011, 13, 1816-1819) may be dimethylated using sodium hydride and methyl iodide to provide 2-(2-chloro-5-methoxyphenyl)-2-methylpropanenitrile. Suzuki reaction with 4-methyl-5-(4,4,5,5-tetramethyl-1,3,2-dioxaborolan-2-yl)pyrimidine was followed by cleavage of the methyl ether with the sodium salt of ethanethiol, which afforded the requisite 2-[5-hydroxy-2-(4-methylpyrimidin-5-yl)phenyl]-2-methylpropanenitrile. Reaction with 4-chlorofuro[3,2-c]pyridine was mediated by tris(dibenzylideneacetone)dipalladium(0), tricyclohexylphosphine and cesium carbonate.

37. Compound C24 was reacted with 1-methylurea and p-toluenesulfonic acid to provide the product.

38. The protecting group was removed in the final step, with a solution of hydrogen chloride in methanol.

39. HPLC conditions: Column: Acquity HSS T3, 2.1×50 mm, 1.8 μm; Mobile phase A: 0.05% trifluoroacetic acid in water (v/v); Mobile phase B: 0.05% trifluoroacetic acid in acetonitrile (v/v); Gradient: 5.0% to 98% B over 1.6 minutes; Flow rate: 1.3 mL/minute.

40. Reaction of 1-fluoro-2-methoxy-4-methylbenzene with N-bromosuccinimide provided the requisite 1-bromo-5-fluoro-4-methoxy-2-methylbenzene.

41. In this case, reduction of the nitro group to the aniline was achieved by hydrogenation with Pd/C in a 1:1 mixture of ethanol and methanol. The final coupling reaction employed tris(dibenzylideneacetone)dipalladium(0) as the palladium source.

42. The crude metabolite mixture was first purified by silica gel chromatography (Eluent: 10% 2-propanol in toluene), then subjected to HPLC separation (Column: Kromasil C18, 10 μm; Eluent: 3:2 methanol/water). Product fractions were concentrated in vacuo, and the aqueous residue was extracted with ethyl acetate (2×50 mL). The combined organic layers were concentrated under reduced pressure to provide the product.

43. The racemic product was separated into atropenantiomers via HPLC (Column: Phenomenex Lux Cellulose-3, 5 μm; Gradient: 5% to 95% ethanol in heptane). The first-eluting atropenantiomer is the compound of this Example.

44. Compound C2 was coupled with 4-chloro-5-methoxy-2-(tetrahydro-2H-pyran-2-yl)pyridazin-3(2H)-one, which may be prepared according to B. Dyck et al., *J. Med. Chem.* 2006, 49, 3753-3756, in the presence of [1,1'-bis(diphenylphosphino)ferrocene]dichloropalladium(II) and cesium carbonate. The resulting 4-[4-(furo[3,2-c]pyridin-4-yloxy)-2-methylphenyl]-5-methoxy-2-(tetrahydro-2H-pyran-2-yl)pyridazin-3(2H)-one was converted to the product using the methods of Examples 10, 11 and 12. The racemic product was separated into its component atropenantiomers using supercritical fluid chromatography (Column: Chiralpak AS-H, 5 μm; Eluent: 3:1 carbon dioxide/methanol). Example 135 was the first-eluting atropenantiomer.

45. Cleavage of the methyl ether of C68 with boron tribromide gave the requisite 6-(4-hydroxy-2-methylphenyl)-5-methylpyrazin-2-ol.

46. Reaction of 2-amino-6-bromopyridin-3-ol with chloroacetaldehyde, followed by protection with benzyl chloromethyl ether, afforded the requisite 8-[(benzyloxy)methoxy]-5-bromoimidazo[1,2-a]pyridine.

47. Example 12 was reacted with hydrogen peroxide and maleic anhydride to provide a roughly 1:1 mixture of 4-[4-(3,5-dimethyl-2-oxidopyridazin-4-yl)-3-methylphenoxy]furo[3,2-c]pyridine and 4-[4-(3,5-dimethyl-1-oxidopyridazin-4-yl)-3-methylphenoxy]furo[3,2-c]pyridine.

48. 4-(4,6-Dimethylpyrimidin-5-yl)-2,5-difluorophenol was prepared from (2,5-difluoro-4-methoxyphenyl)boronic acid and 5-bromo-4,6-dimethylpyrimidine using the general method of Example 6, followed by cleavage of the methyl ether.

49. 5-Bromo-4,6-dimethylpyrimidine was reacted with (2,3-difluoro-4-methoxyphenyl)boronic acid according to the general procedure for the synthesis of 1 in Example 1. The resulting 5-(2,3-difluoro-4-methoxyphenyl)-4,6-dimethylpyrimidine was deprotected with boron tribromide to yield the requisite 4-(4,6-dimethylpyrimidin-5-yl)-2,3-difluorophenol.

50. The racemic product was separated via supercritical fluid chromatography (Column: Chiralpak AS-H, 5 μm; Eluent: 4:1 carbon dioxide/methanol). Example 143 eluted first, followed by Example 142.

51. Starting material 4-bromo-2-(tetrahydro-2H-pyran-2-yl) pyridazin-3(2H)-one was prepared according to C. Aciro et al., *PCT Int. Appl.* (2010) WO 2010131147 A1 20101118.

52. 2-Amino-5-methylpyrimidin-4-ol was reacted with chloroacetaldehyde to afford 6-methylimidazo[1,2-a]pyrimidin-5-ol; this was chlorinated with phosphorus oxychloride to provide the requisite 5-chloro-6-methylimidazo[1,2-a]pyrimidine.

53. Chiral separation was carried out using supercritical fluid chromatography (Column: Chiralpak AD-H, 5 μm; Eluent: 65:35 carbon dioxide/ethanol).

54. On Chiralpak AD-H analysis [5 μm, supercritical fluid chromatography; Gradient: 5% to 40% (ethanol containing 0.05% diethylamine) in carbon dioxide], Example 147 eluted first, followed by Example 146.

55. Reaction of Example 152 with phosphorus oxychloride, followed by displacement with sodium methoxide in methanol, provided this Example.

56. Example 11 was reacted with dimethylamine and sodium carbonate to provide the product.

57. 5-Bromo-4,6-dimethylpyrimidin-2-ol was protected as its triisopropylsilyl ether, and used in the Suzuki reaction.

58. In this case, potassium phosphate was used, and the catalyst for the reaction with methylboronic acid was bis (tri-tert-butylphosphine)palladium(0). Example 154 resulted from dechlorination of Example 11.

59. The catalyst employed for the Suzuki reaction was the same as that used during the synthesis of Example 10, step 3.

60. The product was synthesized via reaction of Example 11 with sodium ethoxide in ethanol.

61. The Suzuki reaction was carried out using the conditions of Example 10. Coupling partner 8-chloro-5-(furo[3,2-c] pyridin-4-yloxy)quinoline was synthesized in the following manner: Skraup reaction of 2-chloro-5-methoxyaniline with propane-1,2,3-triol afforded 8-chloro-5-methoxyquinoline, which was demethylated with aqueous hydrobromic acid. The resulting 8-chloroquinolin-5-ol was then reacted with 4-chlorofuro[3,2-c]pyridine using cesium carbonate in dimethyl sulfoxide.

62. Example 134 was reacted with lithium bromide, sodium bis(trimethylsilyl)amide and methyl iodide to afford the product.

63. In this case, the first step was carried out using [2'-(azanidyl-κN)biphenyl-2-yl-κC$_2$](chloro){dicyclohexyl[2', 4',6'-tri(propan-2-yl)biphenyl-2-yl]-λ$^5$-phosphanyl}palladium as catalyst.

64. 6-Bromo-1-methylpyridin-2(1H)-one was used as the coupling partner.

65. The requisite 5-bromo-6-methoxyisoquinoline may be prepared according to P. Chen et al., *Bioorg. Med. Chem. Lett.* 2003, 13, 1345-1348.

66. In this case, C17 was reacted with sodium methoxide, to provide 4-chloro-5-methoxy-2-(tetrahydro-2H-pyran-2-yl) pyridazin-3(2H)-one, prior to the Suzuki reaction.

67. HPLC conditions. Column: Waters Sunfire C18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B over 4.0 minutes; Flow rate: 2 mL/minute.

68. The requisite 3-bromo-4-methylpyridine-2-carbonitrile may be prepared from the N-oxide of 3-bromo-4-methylpyridine via the method of B. Elman, *Tetrahedron* 1985, 41, 4941-4948.

69. Cyclization of C67 with hydrazinecarboxamide, followed by boron tribromide-mediated cleavage of the methyl ether, afforded 5-(4-hydroxy-2-methylphenyl)-6-methyl-1, 2,4-triazin-3(2H)-one.

70. Example 72 was reacted with 2-bromoethyl methyl ether and cesium carbonate.

71. The requisite 5-bromo-4-ethoxy-6-methylpyrimidine was prepared from 5-bromo-4-chloro-6-methylpyrimidine via treatment with sodium ethoxide in ethanol.

72. HPLC conditions. Column: XBridge C18, 2.1×50 mm, 5 μm; Mobile phase A: 0.05% ammonium hydroxide in water; Mobile phase B: acetonitrile; Gradient: 5% to 100% B over 3.4 minutes; Flow rate: 0.8 mL/minute.

73. 4-[4-Bromo-3-(trifluoromethyl)phenoxy]furo[3,2-c] pyridine was reacted with (1-methyl-1H-pyrazol-5-yl)boronic acid.

74. In this case, the final reaction was carried out in methanol.

75. Compound C4 was converted to 8-bromo-5-[4-(furo[3, 2-c]pyridin-4-yloxy)-2-methylphenyl]6-methylimidazo[1, 2-a]pyrazine via reaction with chloroacetaldehyde. Subsequent reaction with potassium cyanide and 1,4,7,10,13,16-hexaoxacyclooctadecane (18-crown-6) afforded the product.

76. Example 16 was converted to the product by reaction with ethoxyacetic acid and 2-chloro-1,3-dimethylimidazolinium chloride (DMC) in the presence of N,N-diisopropylethylamine.

77. Intermediate 4-[3-chloro-4-(4,4,5,5-tetramethyl-1,3,2-dioxaborolan-2-yl)phenoxy]furo[3,2-c]pyridine was synthesized by using the method of Example 1, but employing 4-bromo-3-chlorophenol in place of 4-bromo-3-methylphenol.

TABLE 2

Examples 209-214

| Example | Structure | Method of Preparation; Non-commercial Starting Materials | $^1$H NMR (400 MHz, CDCl$_3$), δ (ppm); Mass spectrum, observed ion m/z (M + H) or HPLC retention time (minutes); Mass spectrum m/z (M + H) (unless otherwise indicated) |
|---|---|---|---|
| 209 | 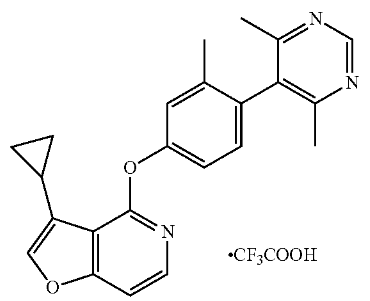 [SMILES: Cc1cc(Oc2nccc3occ(C4CC4)c23)ccc1-c1c(C)ncnc1C ; "·CF3COOH"] | C40[1] | 3.39 min[2]; 372.0 |
| 210 | 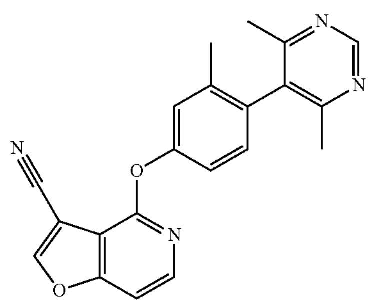 [SMILES: Cc1cc(Oc2nccc3occ(C#N)c23)ccc1-c1c(C)ncnc1C] | Ex 5[3]; C39, C38 | 2.75 min[2]; 357.1 |
| 211 | 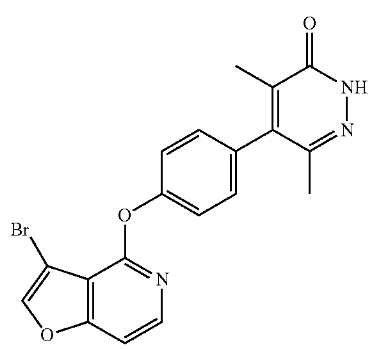 [SMILES: Cc1n[nH]c(=O)c(C)c1-c1ccc(Oc2nccc3occ(Br)c23)cc1] | Ex 5[4]; C39[5] | 2.97 min[2]; 412.0, 414.0 |
| 212 | 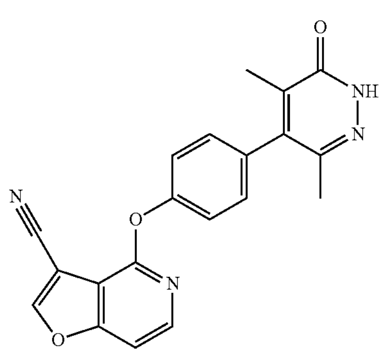 [SMILES: Cc1n[nH]c(=O)c(C)c1-c1ccc(Oc2nccc3occ(C#N)c23)cc1] | Ex 211[6] | 8.22 (s, 1H), 8.17 (d, J = 5.9 Hz, 1H), 7.47 (d, J = 8.6 Hz, 2H), 7.33 (d, J = 5.9 Hz, 1H), 7.19-7.25 (m, 2H), 2.10 (s, 3H), 2.04 (s, 3H); 359.0 |

TABLE 2-continued

Examples 209-214

| Example | Structure | Method of Preparation; Non-commercial Starting Materials | $^1$H NMR (400 MHz, CDCl$_3$), δ (ppm); Mass spectrum, observed ion m/z (M + H) or HPLC retention time (minutes); Mass spectrum m/z (M + H) (unless otherwise indicated) |
|---|---|---|---|
| 213 | 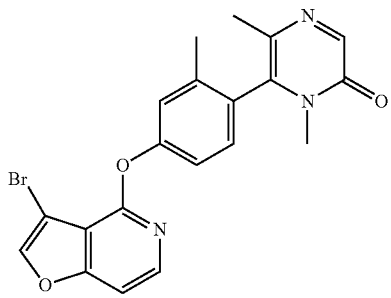 [SMILES: Cc1cc(Oc2nccc3occ(Br)c23)ccc1-c1c(C)ncc(=O)n1C] | Ex 5; C39[7] | 8.21 (s, 1H), 8.07 (d, J = 6.0 Hz, 1H), 7.70 (s, 1H), 7.26-7.32 (m, 3H, assumed; partially obscured by solvent peak), 7.19 (d, J = 8.2 Hz, 1H), 3.26 (s, 3H), 2.15 (s, 3H), 2.08 (s, 3H); 426.0, 428.0 |
| 214 | 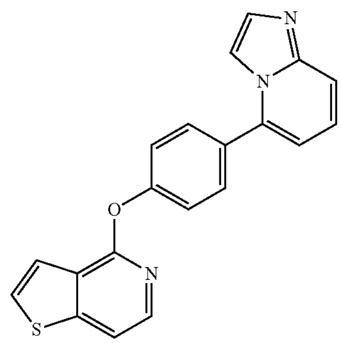 [SMILES: c1cc(-c2ccc(Oc3nccc4sccc34)cc2)n2ccnc2c1] | Ex 5[8] | 2.15 min[9]; 344.1 |
| 215 | 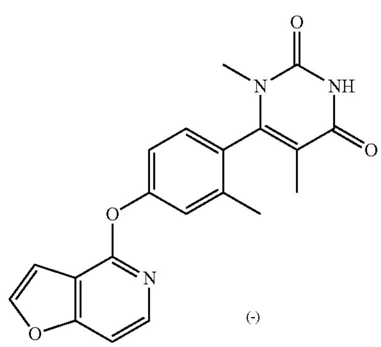 [SMILES: Cc1cc(Oc2nccc3occc23)ccc1-c1c(C)c(=O)[nH]c(=O)n1C] | Method M7[10]; Ex 124[11] | 14.04 min[12]; 8.31 (br s, 1H), 8.06 (d, J = 5.8 Hz, 1H), 7.69 (d, J = 2.2 Hz, 1H), 7.29 (dd, J = 5.8, 1.0 Hz, 1H), 7.22-7.26 (m, 2H), 7.15 (br d, J = 8.2 Hz, 1H), 6.91 (dd, J = 2.3, 1.0 Hz, 1H), 3.07 (s, 3H), 2.21 (br s, 3H), 1.69 (s, 3H) |

1. Compound C40 was subjected to a Suzuki reaction with cyclopropylboronic acid using the conditions described in footnote 22, Table 1.
2. HPLC conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B over 4.0 minutes, linear; Flow rate: 2 mL/minute.
3. Replacement of bromide by a cyano group was carried out as the final step, using copper(I) cyanide in N,N-dimethylformamide.
4. The protecting group was removed in the final step, with a solution of hydrogen chloride in methanol.
5. The required 5-(4-hydroxyphenyl)-4,6-dimethyl-2-(tetrahydro-2H-pyran-2-yl)pyridazin-3(2H)-one was prepared in the following manner: (4-{[tert-butyl(dimethyl)silyl]oxy}phenyl)boronic acid and 2,4-dimethyl-5-oxo-2,5-dihydrofuran-3-yl trifluoromethanesulfonate (C48) were reacted according to Example 27 to provide 4-(4-{[tert-butyl(dimethyl)silyl]oxy}phenyl)-3,5-dimethylfuran-2(5H)-one. The silyl protecting group was removed with tetrabutylammonium fluoride, and replaced with a benzyl protecting group, yielding 4-[4-(benzyloxy)phenyl]-3,5-dimethylfuran-2(5H)-one. This was subjected to reaction with oxygen, followed by hydrazine, as described in Example 27, to afford 5-[4-(benzyloxy)phenyl]-4,6-dimethylpyridazin-3(2H)-one. Nitrogen protection with 3,4-dihydro-2H-pyran as in Example 10, followed by hydrogenolysis of the benzyl group, provided the requisite phenol.
6. Prior to the acidic removal of the tetrahydropyran protecting group in Example 211, the bromine was replaced by a cyano group using copper(I) cyanide in N,N-dimethylformamide. Removal of the protecting group afforded Example 212.
7. The requisite 6-(4-hydroxy-2-methylphenyl)-1,5-dimethylpyrazin-2(1H)-one was prepared in the following manner:

Suzuki reaction between (4-methoxy-2-methylphenyl)boronic acid and 2-bromo-3-methylpyrazine afforded 2-(4-methoxy-2-methylphenyl)-3-methylpyrazine. After formation of the N-oxide and rearrangement with acetic anhydride (see A. Ohta et al., *J. Het. Chem.* 1985, 19, 465-473), the resulting 6-(4-methoxy-2-methylphenyl)-5-methylpyrazin-2-ol was N-methylated, and then deprotected with boron tribromide.

8. 4-(Imidazo[1,2-a]pyridin-5-yl)phenol was prepared from (4-hydroxyphenyl)boronic acid and 5-bromoimidazo[1,2-a]pyridine, using the method of Example 6.

9. HPLC conditions. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); 15.0% to 95% B, linear, over 4.0 minutes; Flow rate: 2 mL/minute.

10. In this case, the incubation was carried out for 2.25 hours rather than 24-96 hours.

11. Example 124 was separated into its component atropenantiomers via supercritical fluid chromatography (Column: Chiralpak AD-H, 5 μm; Eluent: 7:3 carbon dioxide/propanol). The second-eluting enantiomer [(−)-6-[4-(furo[3,2-c]pyridin-4-yloxy)-2-methylphenyl]-1,5-dimethylpyrimidin-2(1H)-one] was used in the biotransformation. The crude biotransformation product was purified via silica gel chromatography (Eluant: 70% ethyl acetate in heptane).

12. Supercritical fluid chromatography conditions. Column: Phenomenex Cellulose-4, 4.6×250 mm, 5 μm; Eluent: 55:45 carbon dioxide/methanol; Flow rate 2.5 mL/minute.

Example 216

6-[4-(Furo[3,2-c]pyridin-4-yloxy)phenyl]-1,5-dimethylpyrimidine-2,4(1H,3H)-dione, trifluoroacetate salt (216)

Step 1. Synthesis of 6-amino-1,5-dimethylpyrimidine-2,4(1H,3H)-dione, hydrochloride salt (C87)

1-Methylurea (98%, 8.26 g, 109 mmol) and ethyl 2-cyanopropanoate (95%, 13.2 mL, 99.6 mmol) were dissolved in methanol (75 mL) and treated with sodium methoxide (25 weight percent solution in methanol, 27 mL, 120 mmol). The resulting mixture was heated at reflux for 18 hours. After cooling to room temperature, the reaction mixture was concentrated under reduced pressure to remove the bulk of the methanol. The solvent was subsequently exchanged by repeated addition of acetonitrile (3×50 mL) followed by concentration in vacuo. The resulting solid was dissolved in acetonitrile (100 mL) and water (100 mL), and 6 M aqueous hydrochloric acid was added until the pH reached approximately 2. During this acidification, a white precipitate formed. After the mixture had stirred for an hour, the solid was collected via filtration and washed with tert-butyl methyl ether, providing the product as a white solid. Yield: 15.2 g, 79.3 mmol, 80%. LCMS m/z 156.3 [M+H]. $^1$H NMR (400 MHz, DMSO-d$_6$) δ 10.37 (br s, 1H), 6.39 (br s, 2H), 3.22 (s, 3H), 1.67 (s, 3H).

Step 2. Synthesis of 6-bromo-1,5-dimethylpyrimidine-2,4(1H,3H)-dione (C88)

A 1:1 mixture of acetonitrile and water (60 mL) was added to a mixture of 6-amino-1,5-dimethylpyrimidine-2,4(1H,3H)-dione, hydrochloride salt (C87) (5.00 g, 26.1 mmol), sodium nitrite (98%, 2.76 g, 39.2 mmol) and copper (II) bromide (99%, 11.8 g, 52.3 mmol) {Caution: bubbling and slight exotherm observed}, and the reaction mixture was allowed to stir at room temperature for 18 hours. Upon dilution with aqueous sulfuric acid (1 N, 100 mL) and ethyl

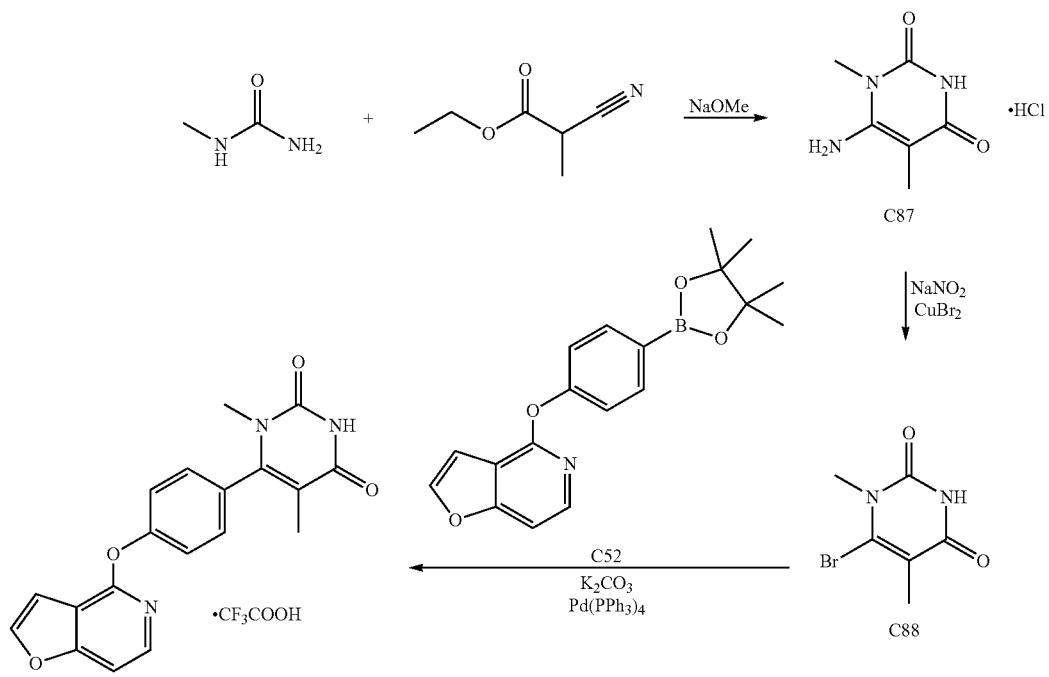

acetate (100 mL), a precipitate formed; this was isolated via filtration and washed with water and with ethyl acetate to afford the product as a solid (3.65 g). The filtrate was concentrated in vacuo to approximately 25% of its original volume, during which more precipitate was observed. Filtration and washing of this solid with water and ethyl acetate afforded additional product (0.60 g). Total yield: 4.25 g, 19.4 mmol, 74%. LCMS m/z 219.0, 221.0 [M+H]. $^1$H NMR (400 MHz, DMSO-d$_6$) δ 11.58 (br s, 1H), 3.45 (s, 3H), 1.93 (s, 3H).

Step 3. Synthesis of 6-[4-(furo-[3,2-c]pyridin-4-yloxy)phenyl]-1,5-dimethylpyrimidine-2,4(1H,3H)-dione, trifluoroacetate salt (216)

6-Bromo-1,5-dimethylpyrimidine-2,4(1H,3H)-dione (C88) (78.0 mg, 0.356 mmol), 4-[4-(4,4,5,5-tetramethyl-1,3,2-dioxaborolan-2-yl)phenoxy]furo[3,2-c]pyridine (C52) (60.0 mg, 0.178 mmol), potassium carbonate (99%, 74.5 mg, 0.534 mmol) and tetrakis(triphenylphosphine)palladium(0) (99%, 10.5 mg, 0.0090 mmol) were combined in ethanol (5 mL) and heated to 80° C. for 18 hours. The reaction mixture was diluted with water, made slightly acidic by addition of 1.0 M aqueous hydrochloric acid, and extracted several times with ethyl acetate. The combined organic layers were washed with saturated aqueous sodium chloride solution, dried over magnesium sulfate, filtered, and concentrated in vacuo. Purification via silica gel chromatography (Gradient: 75% to 100% ethyl acetate in heptane) followed by reversed-phase HPLC (Column: Waters Sunfire C18, 5 μm; Mobile phase A:

0.05% trifluoroacetic acid in water (v/v); Mobile phase B: 0.05% trifluoroacetic acid in acetonitrile (v/v); Gradient: 20% to 100% B) afforded the product as a solid. Yield: 20 mg, 0.057 mmol, 32%. LCMS m/z 350.0 [M+H]. $^1$H NMR (600 MHz, DMSO-d$_6$) δ 8.14 (d, J=2.2 Hz, 1H), 8.04 (d, J=5.9 Hz, 1H), 7.51 (br d, J=5.9 Hz, 1H), 7.42 (br AB quartet, $J_{AB}$=8.8 Hz, $\Delta v_{AB}$=16.7 Hz, 4H), 7.08 (dd, J=2.2, 0.9 Hz, 1H), 2.94 (s, 3H), 1.55 (s, 3H).

Example AA

Human D1 Receptor Binding Assay and Data

The affinity of the compounds described herein was determined by competition binding assays similar to those described in Ryman-Rasmussen et al., "Differential activation of adenylate cyclase and receptor internalization by novel dopamine D1 receptor agonists", *Molecular Pharmacology* 68(4):1039-1048 (2005). This radioligand binding assay used [$^3$H]-SCH23390, a radio D1 ligand, to evaluate the ability of a test compound to compete with the radioligand when binding to a D1 receptor.

D1 binding assays were performed using over-expressing LTK human cell lines. To determine basic assay parameters, ligand concentrations were determined from saturation binding studies where the Kd for [$^3$H]-SCH23390 was found to be 1.3 nM. From tissue concentration curve studies, the optimal amount of tissue was determined to be 1.75 mg/mL per 96 well plate using 0.5 nM of [$^3$H]-SCH23390. These ligand and tissue concentrations were used in time course studies to determine linearity and equilibrium conditions for binding. Binding was at equilibrium with the specified amount of tissue in 30 minutes at 37° C. From these parameters, K$_i$ values were determined by homogenizing the specified amount of tissue for each species in 50 mM Tris (pH 7.4 at 4° C.) containing 2.0 mM MgCl$_2$ using a Polytron and spun in a centrifuge at 40,000×g for 10 minutes. The pellet was resuspended in assay buffer (50 mM Tris (pH 7.4@ RT) containing 4 mM MgSO$_4$ and 0.5 mM EDTA). Incubations were initiated by the addition of 200 μL of tissue to 96-well plates containing test drugs (2.5 μL) and 0.5 nM [$^3$H]-SCH23390 (50 μL) in a final volume of 250 μL. Non-specific binding was determined by radioligand binding in the presence of a saturating concentration of (+)-Butaclamol (10 μM), a D1 antagonist. After a 30 minute incubation period at 37° C., assay samples were rapidly filtered through Unifilter-96 GF/B PEI-coated filter plates and rinsed with 50 mM Tris buffer (pH 7.4 at 4° C.). Membrane bound [$^3$H]-SCH23390 levels were determined by liquid scintillation counting of the filterplates in Ecolume. The IC$_{50}$ value (concentration at which 50% inhibition of specific binding occurs) was calculated by linear regression of the concentration-response data in Microsoft Excel. K$_i$ values were calculated according to the Cheng-Prusoff equation.

$$K_i = \frac{IC_{50}}{1+([L]/K_d)}$$

where [L]=concentration of free radioligand and K$_d$=dissociation constant of radioligand for D1 receptor (1.3 nM for [$^3$H]-SCH23390).

Example BB

D1 cAMP HTRF Assay and Data

The D1 cAMP (Cyclic Adenosine Monophosphate) HTRF (Homogeneous Time-Resolved Fluorescence) Assay used and described herein is a competitive immunoassay between native cAMP produced by cells and cAMP labeled with XL-665. This assay was used to determine the ability of a test compound to agonize (including partially agonize) D1. A Mab anti-cAMP labeled Cryptate visualizes the tracer. The maximum signal is achieved if the samples do not contain free cAMP due to the proximity of donor (Eucryptate) and acceptor (XL665) entities. The signal, therefore, is inversely proportional to the concentration of cAMP in the sample. A time resolved and ratiometric measurement (em 665 nm/em 620 nm) minimizes the interference with medium. cAMP HTRF assays are commercially available, for example, from Cisbio Bioassays, IBA group.

Materials and Methods

Materials:

The cAMP Dynamic kit was obtained from Cisbio International (Cisbio 62AM4PEJ). Multidrop Combi (Thermo Scientific) was used for assay additions. Envision (PerkinElmer) reader was used to read HTRF.

Cell Culture:

A HEK293T/hD1#1 stable cell line was constructed internally (Pfizer Ann Arbor). The cells were grown as adherent cells in NuncT$_{500}$ flasks in high glucose DMEM (Invitrogen 11995-065), 10% fetal bovine serum dialyzed (Invitrogen 26400-044), 1×MEM NEAA (Invitrogen 1140, 25 mM HEPES (Invitrogen 15630), 1×Pen/Strep (Invitrogen 15070-063) and 500 μg/mL Genenticin (Invitrogen 10131-035) at 37° C. and 5% CO$_2$. At 72 or 96 hours post growth, cells were rinsed with DPBS and 0.25% Trypsin-EDTA was added to dislodge the cells. Media was then added and cells were centrifuged and media removed. The cell pellets were re-suspended in Cell Culture Freezing Medium (Invitrogen 12648-056) at a density of 4e7 cells/mL. One mL aliquots of the cells were made in Cryo-vials and frozen at −80° C. for future use in the D1 HTRF assay.

D1 cAMP HTRF assay procedure: Frozen cells were quickly thawed, re-suspended in 50 mL warm media and allowed to sit for 5 min prior to centrifugation (1000 rpm) at room temperature. Media was removed and cell pellet was re-suspended in PBS/0.5 μM IBMX generating 2e5 cells/mL. Using a Multidrop Combi, 5 μL cells/well was added to the assay plate (Greiner 784085) which already contained 5 μL of a test compound. Compound controls [5 μM dopamine (final) and 0.5% DMSO (final)] were also included on every plate for data analysis. Cells and compounds were incubated at room temperature for 30 min. Working solutions of cAMP-D2 and anti-cAMP-cryptate were prepared according to Cisbio instructions. Using Multidrop, 5 μL cAMP-D2 working solution was added to the assay plate containing the test compound and cells. Using Multidrop, 5 μL anti-cAMP-cryptate working solutions was added to assay plate containing test compound, cells and cAMP-D2. Assay plate was incubated for 1 hour at room temperature. Assay plate was read on Envision plate reader using Cisbio recommended settings. A cAMP standard curve was generated using cAMP stock solution provided in the Cisbio kit.

Data Analysis:

Data analysis was done using computer software. Percent effects were calculated from the compound controls. Ratio $EC_{50}$ was determined using the raw ratio data from the Envision reader. The cAMP standard curve was used in an analysis program to determine cAMP concentrations from raw ratio data. cAMP $EC_{50}$ was determined using the calculated cAMP data.

TABLE 3

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (μM); Geometric mean of 2-6 determinations | Human D1 cAMP HTRF, $EC_{50}$ (μM); Geometric mean of 2-4 determinations |
|---|---|---|---|---|
| 1 | 4-[4-(4,6-Dimethylpyrimidin-5-yl)-3-methylphenoxy]furo[3,2-c]pyridine | 27.3[a] | 0.135[b] | 0.129[a] |
| 2 | 5-[4-(Furo[3,2-c]pyridin-4-yloxy)-2-methylphenyl]-6-methyl-[8-2H]-imidazo[1,2-a]pyrazine | 5.88 | 0.153 | N.D.[c] |
| 3 | (+)-5-[4-(Furo[3,2-c]pyridin-4-yloxy)-2-methylphenyl]-6-methyl-[8-²H]-imidazo[1,2-a]pyrazine | 2.56 | 0.0436 | 0.0629 |
| 4 | (−)-5-[4-(Furo[3,2-c]pyridin-4-yloxy)-2-methylphenyl]-6-methyl-[8-²H]-imidazo[1,2-a]pyrazine | 19.7 | 0.235 | 0.346[d] |
| 5 | 1-[4-(Furo[3,2-c]pyridin-4-yloxy)-2-methylphenyl]-2-methyl-1H-imidazo[4,5-c]pyridine | 68.3[a] | 0.423[b] | 0.899[a] |
| 6 | 4-[3-Methoxy-4-(3-methylpyrazin-2-yl)phenoxy]furo[3,2-c]pyridine | 169 | 0.804 | 0.897 |
| 7 | 4-[4-(1-Methyl-1H-pyrazol-5-yl)phenoxy]thieno[3,2-c]pyridine | 788 | N.D. | N.D. |
| 8 | 4-{[4-(1-Methyl-1H-pyrazol-5-yl)phenyl]sulfanyl}furo[3,2-c]pyridine, trifluoroacetate salt | 283 | N.D. | 0.854 |
| 9 | 2-(4,6-Dimethylpyrimidin-5-yl)-5-(furo[3,2-c]pyridin-4-yloxy)benzonitrile | 116[a] | 0.396[b] | 0.696[d] |
| 10 | 4-[4-(Furo[3,2-c]pyridin-4-yloxy)-2-methylphenyl]-5-methylpyridazin-3(2H)-one, bis-hydrochloride salt | 2280[d] | >30.0 | N.D. |
| 11 | 4-[4-(3-Chloro-5-methylpyridazin-4-yl)-3-methylphenoxy]furo[3,2-c]pyridine | 11.8 | 0.186 | N.D. |
| 12 | 4-[4-(3,5-Dimethylpyridazin-4-yl)-3-methylphenoxy]furo[3,2-c]pyridine | 14.3 | 0.166 | 0.395[d] |
| 13 | (+)-4-[4-(3,5-Dimethylpyridazin-4-yl)-3-methylphenoxy]furo[3,2-c]pyridine | 10.7 | 0.0807[b] | N.D. |
| 14 | (−)-4-[4-(3,5-Dimethylpyridazin-4-yl)-3-methylphenoxy]furo[3,2-c]pyridine | 212 | 1.04 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (μM); Geometric mean of 2-6 determinations | Human D1 cAMP HTRF, $EC_{50}$ (μM); Geometric mean of 2-4 determinations |
|---|---|---|---|---|
| 15 | 4-[4-(1-tert-Butyl-4-methyl-1H-pyrazol-5-yl)-3-methylphenoxy]furo[3,2-c]pyridine | 121 | N.D. | $0.895^d$ |
| 16 | 5-(Furo[3,2-c]pyridin-4-yloxy)-2-(imidazo[1,2-a]pyridin-5-yl)aniline | 146 | N.D. | $0.415^d$ |
| 17 | N-[4-(Imidazo[1,2-a]pyridin-5-yl)-3-methylphenyl]furo[3,2-c]pyridin-4-amine | 111 | N.D. | 0.957 |
| 18 | 4-[4-(4-Chloro-6-methylpyrimidin-5-yl)-3-methylphenoxy]furo[3,2-c]pyridine | $15.6^d$ | 0.118 | $0.511^d$ |
| 19 | 5-[4-(Furo[3,2-c]pyridin-4-yloxy)-2-methylphenyl]-6-methylimidazo[1,2-a]pyrazin-8-ol | 24.7 | 0.246 | 0.426 |
| 20 | [2-(4,6-Dimethylpyrimidin-5-yl)-5-(furo[3,2-c]pyridin-4-yloxy)phenyl]methanol | 138 | 0.622 | N.D. |
| 21 | 4-[4-(4,6-Dimethylpyrimidin-5-yl)-3-(fluoromethyl)phenoxy]furo[3,2-c]pyridine | 36.2 | 0.0858 | N.D. |
| 22 | 4-[4-(4,6-Dimethylpyrimidin-5-yl)-3-methylphenoxy]-3-methylfuro[3,2-c]pyridine | 162 | 0.774 | $1.34^d$ |
| 23 | 4-{[4-(4,6-Dimethylpyrimidin-5-yl)-1H-indol-7-yl]oxy}furo[3,2-c]pyridine | 30.6 | 0.848 | N.D. |
| 24 | 4-[4-(4-Ethoxy-6-methylpyrimidin-5-yl)-3-methylphenoxy]furo[3,2-c]pyridine | 33.0 | $2.06^b$ | $2.59^a$ |
| 25 | (+)-5-[4-(Furo[3,2-c]pyridin-4-yloxy)-2-methylphenyl]-6-methylimidazo[1,2-a]pyrazine | $5.76^a$ | $0.037^b$ | $0.0457^a$ |
| 26 | (−)-5-[4-(Furo[3,2-c]pyridin-4-yloxy)-2-methylphenyl]-6-methylimidazo[1,2-a]pyrazine | $21.6^a$ | 0.170 | 0.128 |
| 27 | 5-[2-Fluoro-4-(furo[3,2-c]pyridin-4-yloxy)phenyl]-4,6-dimethylpyridazin-3(2H)-one | 4.67 | 0.0239 | N.D. |
| 28 | 5-[4-(Furo[3,2-c]pyridin-4-yloxy)phenyl]-4,6-dimethylpyridazin-3(2H)-one | 19.3 | $0.110^b$ | N.D. |
| 29 | 4-[3,5-Dimethyl-4-(3-methylpyridin-4-yl)phenoxy]furo[3,2-c]pyridine | $329^d$ | 2.82 | N.D. |
| 30 | 4-{[4-(Imidazo[1,2-a]pyridin-5-yl)naphthalen-1-yl]oxy}furo[3,2-c]pyridine, trifluoroacetate salt | 220 | N.D. | 2.48 |
| 31 | 1-[4-(furo[3,2-c]pyridin-4-yloxy)phenyl]-2-methyl-1H-imidazo[4,5-c]pyridine | $316^a$ | $1.03^b$ | $1.19^a$ |
| 32 | 4-[4-(1-cyclopropyl-4-methyl-1H-pyrazol-5-yl)phenoxy]furo[3,2-c]pyridine, trifluoroacetate salt | 281 | N.D. | 2.24 |
| 33 | 5-[4-(furo[3,2-c]pyridin-4-yloxy)phenyl]-6-methoxyisoquinoline | 111 | N.D. | 2.27 |
| 34 | 4-[4-(imidazo[1,2-a]pyridin-5-yl)-3-methoxyphenoxy]furo[3,2-c]pyridine | 20.0 | N.D. | 0.182 |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 35 | 4-[3-methyl-4-(6-methylimidazo[1,2-a]pyridin-5-yl)phenoxy]furo[3,2-c]pyridine | 6.86 | N.D. | 0.0636 |
| 36 | 5-[4-(furo[3,2-c]pyridin-4-yloxy)-2-methylphenyl]imidazo[1,2-a]pyrazine | 120 | 0.378 | 0.412 |
| 37 | 4-[3-methoxy-4-(6-methylimidazo[1,2-a]pyridin-5-yl)phenoxy]furo[3,2-c]pyridine | $3.54^a$ | N.D. | 0.0469 |
| 38 | 5-(furo[3,2-c]pyridin-4-yloxy)-2-(imidazo[1,2-a]pyridin-5-yl)-N-methylaniline | 36.0 | N.D. | $0.200^d$ |
| 39 | 1-[2-chloro-4-(furo[3,2-c]pyridin-4-yloxy)phenyl]-2-methyl-1H-imidazo[4,5-c]pyridine | 91.0 | N.D. | $0.415^d$ |
| 40 | 4-[4-(imidazo[1,2-a]pyridin-5-yl)-3-(1,3-thiazol-4-ylmethoxy)phenoxy]furo[3,2-c]pyridine, trifluoroacetate salt | 107 | N.D. | $1.27^d$ |
| 41 | 1-[5-(furo[3,2-c]pyridin-4-yloxy)-2-(imidazo[1,2-a]pyridin-5-yl)phenoxy]butan-2-one, trifluoroacetate salt | 72.1 | N.D. | $0.517^d$ |
| 42 | 2-[5-(furo[3,2-c]pyridin-4-yloxy)-2-(imidazo[1,2-a]pyridin-5-yl)phenoxy]ethanol, trifluoroacetate salt | 118 | N.D. | $0.406^d$ |
| 43 | N-cyclopropyl-2-[5-(furo[3,2-c]pyridin-4-yloxy)-2-(imidazo[1,2-a]pyridin-5-yl)phenoxy]acetamide, trifluoroacetate salt | 211 | N.D. | $0.605^d$ |
| 44 | methyl [5-(furo[3,2-c]pyridin-4-yloxy)-2-(imidazo[1,2-a]pyridin-5-yl)phenoxy]acetate, trifluoroacetate salt | 129 | N.D. | $0.651^d$ |
| 45 | 7-[4-(furo[3,2-c]pyridin-4-yloxy)-2-methylphenyl]-6-methyl[1,2,4]triazolo[1,5-a]pyrimidine | 182 | N.D. | 1.14 |
| 46 | N-cyclobutyl-5-(furo[3,2-c]pyridin-4-yloxy)-2-(imidazo[1,2-a]pyridin-5-yl)benzamide, trifluoroacetate salt | 316 | N.D. | $2.12^d$ |
| 47 | 2-ethoxy-N-[5-(furo[3,2-c]pyridin-4-yloxy)-2-(imidazo[1,2-a]pyridin-5-yl)phenyl]acetamide | 302 | N.D. | $0.935^d$ |
| 48 | 5-(furo[3,2-c]pyridin-4-yloxy)-2-(imidazo[1,2-a]pyridin-5-yl)-N-[(1-methyl-1H-imidazol-5-yl)methyl]aniline, trifluoroacetate salt | 68.8 | N.D. | $2.07^d$ |
| 49 | N-[5-(furo[3,2-c]pyridin-4-yloxy)-2-(imidazo[1,2-a]pyridin-5-yl)benzyl]-1-(1,3-thiazol-5-yl)ethanamine, trifluoroacetate salt | 121 | N.D. | $3.68^d$ |
| 50 | 1-[5-(furo[3,2-c]pyridin-4-yloxy)-2-(imidazo[1,2-a]pyridin-5-yl)phenyl]-N-methyl-N-(pyridin-2-ylmethyl)methanamine, trifluoroacetate salt | 55.1 | N.D. | $1.13^d$ |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 51 | 3-[4-(furo[3,2-c]pyridin-4-yloxy)-2-methoxyphenyl]-4-methylpyridine-2-carbonitrile, trifluoroacetate salt | 61.7 | 0.799 | $1.22^a$ |
| 52 | 4-[3-methyl-4-(2-methylpyridin-3-yl)phenoxy]furo[3,2-c]pyridine | $53.0^a$ | N.D. | 0.463 |
| 53 | 6-[4-(furo[3,2-c]pyridin-4-yloxy)-2-methylphenyl]-5-methylpyrazin-2-amine, trifluoroacetate salt | 173 | N.D. | 0.953 |
| 54 | 4-[4-(imidazo[1,2-a]pyridin-5-yl)-3-(trifluoromethyl)phenoxy]furo[3,2-c]pyridine | $10.2^a$ | N.D. | 0.243 |
| 55 | N-[4-(imidazo[1,2-a]pyridin-5-yl)-3-methylphenyl]-N-methylfuro[3,2-c]pyridin-4-amine | 244 | N.D. | >29.9 |
| 56 | 5-[4-(furo[3,2-c]pyridin-4-yloxy)-2-methylphenyl]-6-methylpyridin-2-amine | $98.7^a$ | 0.633 | 0.435 |
| 57 | 5-(furo[3,2-c]pyridin-4-yloxy)-2-(6-methylimidazo[1,2-a]pyrazin-5-yl)phenol | 17.4 | N.D. | $0.116^d$ |
| 58 | 4-[3-methyl-4-(4-methylpyrimidin-5-yl)phenoxy]furo[3,2-c]pyridine | 160 | 0.900 | 1.11 |
| 59 | 5-[4-(furo[3,2-c]pyridin-4-yloxy)-2-methylphenyl]quinolin-2(1H)-one | 103 | 1.01 | 1.15 |
| 60 | 4-[4-(6-methoxy-2-methylpyridin-3-yl)-3-methylphenoxy]furo[3,2-c]pyridine, trifluoroacetate salt | 178 | 2.91 | $1.04^a$ |
| 61 | 3-[5-(furo[3,2-c]pyridin-4-yloxy)-2-(3-methylpyrazin-2-yl)phenoxy]-N,N-dimethylpropan-1-amine, formate salt | 228 | 1.11 | 0.811 |
| 62 | 4-[3-ethyl-4-(3-methylpyrazin-2-yl)phenoxy]furo[3,2-c]pyridine | 130 | 0.975 | $0.0966^d$ |
| 63 | 5-[4-(furo[3,2-c]pyridin-4-yloxy)-2-methylphenyl]-6-methylpyrimidin-4-amine | 210 | 1.35 | $0.843^a$ |
| 64 | 5-[2-ethyl-4-(furo[3,2-c]pyridin-4-yloxy)phenyl]-6-methylimidazo[1,2-a]pyrazine | 12.1 | 0.134 | N.D. |
| 65 | 5-[2-fluoro-4-(furo[3,2-c]pyridin-4-yloxy)phenyl]-6-methylimidazo[1,2-a]pyrazine | 61.1 | 0.193 | $0.300^a$ |
| 66 | 4-{3-[(3,5-dimethyl-1,2-oxazol-4-yl)methoxy]-4-(3-methylpyrazin-2-yl)phenoxy}furo[3,2-c]pyridine, formate salt | $85.4^d$ | N.D. | $0.737^d$ |
| 67 | 4-{3-[(3-cyclopropyl-1,2,4-oxadiazol-5-yl)methoxy]-4-(3-methylpyrazin-2-yl)phenoxy}furo[3,2-c]pyridine | N.D. | 0.809 | N.D. |
| 68 | 4-{4-(3-methylpyrazin-2-yl)-3-[(3-methylpyridin-2-yl)methoxy]phenoxy}furo[3,2-c]pyridine, formate salt | 154 | N.D. | $1.48^d$ |
| 69 | 4-[4-(4,6-dimethylpyrimidin-5-yl)-3-fluorophenoxy]furo[3,2-c]pyridine | 77.7 | 0.201 | $0.203^d$ |
| 70 | 5-[2-fluoro-4-(furo[3,2-c]pyridin-4-yloxy)phenyl]-6-methylpyrimidine-4-carbonitrile | 124 | 0.424 | 1.02 |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 71 | 4-[4-(4,6-dimethylpyrimidin-5-yl)-3-methoxyphenoxy]furo[3,2-c]pyridine | 50.5 | 0.298 | 0.965 |
| 72 | 2-(4,6-dimethylpyrimidin-5-yl)-5-(furo[3,2-c]pyridin-4-yloxy)phenol | 91.4 | N.D. | 0.989 |
| 73 | 3-[5-(furo[3,2-c]pyridin-4-yloxy)-2-(2-methylpyridin-3-yl)phenoxy]-N,N-dimethylpropan-1-amine, formate salt | 37.7 | 0.748 | 0.966 |
| 74 | 1-[5-(furo[3,2-c]pyridin-4-yloxy)-2-(2-methylpyridin-3-yl)phenoxy]-N,N-dimethylpropan-2-amine, formate salt | N.D. | 0.832 | N.D. |
| 75 | 5-[4-(furo[3,2-c]pyridin-4-yloxy)-2-methylphenyl]-4,6-dimethylpyrimidin-2-amine | 21.6 | N.D. | 0.364 |
| 76 | 4-[3-fluoro-4-(4-methoxy-6-methylpyrimidin-5-yl)phenoxy]furo[3,2-c]pyridine | 139 | 0.903 | 2.17 |
| 77 | 4-[4-(4,6-dimethylpyrimidin-5-yl)phenoxy]furo[3,2-c]pyridine | 45.6 | 0.200 | 0.674 |
| 78 | 4-{3-[(3-ethyl-1,2,4-oxadiazol-5-yl)methoxy]-4-(2-methylpyridin-3-yl)phenoxy}furo[3,2-c]pyridine | 48.3 | 0.885 | 1.23[d] |
| 79 | 5-[4-(furo[3,2-c]pyridin-4-yloxy)phenyl]-4,6-dimethylpyrimidin-2-ol | 140 | 2.55 | 1.68 |
| 80 | 5-[4-(furo[3,2-c]pyridin-4-yloxy)-2-methylphenyl]-6-methyl-2-(trifluoromethyl)imidazo[1,2-a]pyrazine | 6.13 | 1.20 | 0.987[d] |
| 81 | 5-[4-(furo[3,2-c]pyridin-4-yloxy)-2-methylphenyl]-N,6-dimethylpyrimidin-4-amine | 270[d] | 1.77 | N.D. |
| 82 | (+)-5-[4-(furo[3,2-c]pyridin-4-yloxy)-2-methylphenyl]-6-methylpyrimidine-4-carbonitrile | 21.3 | 0.113 | 0.781[d] |
| 83 | (−)-5-[4-(furo[3,2-c]pyridin-4-yloxy)-2-methylphenyl]-6-methylpyrimidine-4-carbonitrile | 82.1 | 0.854 | 0.944[d] |
| 84 | 2-amino-5-[4-(furo[3,2-c]pyridin-4-yloxy)-2-methylphenyl]-6-methylpyrimidine-4-carbonitrile | 116 | 0.360 | N.D. |
| 85 | 3-[4-(furo[3,2-c]pyridin-4-yloxy)-2-methylphenyl]-2-methylimidazo[1,2-a]pyrazine | 75.3[d] | 1.12 | 4.88[d] |
| 86 | 5-[4-(furo[3,2-c]pyridin-4-yloxy)-2-methylphenyl]-6-methylpyridin-3-amine | 113 | 0.833 | 4.87 |
| 87 | 5-[4-(furo[3,2-c]pyridin-4-yloxy)-2-methylphenyl]-N,N,6-trimethylpyrimidin-4-amine | 22.5 | 0.600 | 0.482[d] |
| 88 | 4-[4-(2-cyclopropylpyridin-3-yl)-3-methylphenoxy]furo[3,2-c]pyridine | 117 | 0.710 | 1.52[d] |
| 89 | 4-[(2,2',6'-trimethylbiphenyl-4-yl)oxy]furo[3,2-c]pyridine, trifluoroacetate salt | 123 | 1.86 | N.D. |
| 90 | 5-[2-chloro-4-(furo[3,2-c]pyridin-4-yloxy)phenyl]-6-methylpyridin-2-amine | 25.4 | 0.448 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 91 | 6-[4-(furo[3,2-c]pyridin-4-yloxy)-2-(trifluoromethyl)phenyl]-5-methylpyrazin-2-amine | 61.2 | 0.580 | N.D. |
| 92 | 4-[3-fluoro-4-(2-methylpyridin-3-yl)phenoxy]furo[3,2-c]pyridine | 25.2 | 0.746 | N.D. |
| 93 | 6-[2-fluoro-4-(furo[3,2-c]pyridin-4-yloxy)phenyl]-5-methylpyrazin-2-amine | $88.0^d$ | 0.761 | N.D. |
| 94 | 5-[4-(furo[3,2-c]pyridin-4-yloxy)-2-methoxyphenyl]-6-methoxyisoquinoline, formate salt | 7.08 | 0.837 | N.D. |
| 95 | 4-{4-[4-(azetidin-1-yl)-6-methylpyrimidin-5-yl]-3-methylphenoxy}furo[3,2-c]pyridine, formate salt | 27.3 | 0.444 | N.D. |
| 96 | 4-{4-[4-(4,6-dihydropyrrolo[3,4-c]pyrazol-5(1H)-yl)-6-methylpyrimidin-5-yl]-3-methylphenoxy}furo[3,2-c]pyridine, trifluoroacetate salt | 24.5 | 0.306 | N.D. |
| 97 | 4-{4-[4-(3-fluoroazetidin-1-yl)-6-methylpyrimidin-5-yl]-3-methylphenoxy}furo[3,2-c]pyridine, formate salt | 7.52 | 0.205 | N.D. |
| 98 | 4-{4-[4-(3-fluoropyrrolidin-1-yl)-6-methylpyrimidin-5-yl]-3-methylphenoxy}furo[3,2-c]pyridine, trifluoroacetate salt | 28.6 | 0.956 | N.D. |
| 99 | 4-[4-(4,6-dimethylpyrimidin-5-yl)-2,3-dimethylphenoxy]furo[3,2-c]pyridine | $1370^d$ | $3.04^b$ | $>9.95^d$ |
| 100 | 5-[4-(furo[3,2-c]pyridin-4-yloxy)-2-(trifluoromethyl)phenyl]-6-methylimidazo[1,2-a]pyrazine | 11.0 | 0.112 | $0.580^d$ |
| 101 | 5-[4-(furo[3,2-c]pyridin-4-yloxy)-2,5-dimethylphenyl]-6-methylimidazo[1,2-a]pyrazine | $431^d$ | 3.45 | N.D. |
| 102 | 4-[4-(1,4-dimethyl-1H-imidazol-5-yl)-3-methylphenoxy]furo[3,2-c]pyridine | 84.6 | 0.714 | N.D. |
| 103 | 4-[4-(4,6-dimethylpyrimidin-5-yl)-3,5-dimethylphenoxy]furo[3,2-c]pyridine | 23.9 | 0.392 | $0.870^d$ |
| 104 | 4-[4-(3,5-dimethylpyridin-4-yl)-3-methylphenoxy]furo[3,2-c]pyridine | 24.1 | 0.502 | N.D. |
| 105 | 5-[4-(furo[3,2-c]pyridin-4-yloxy)-2-methylphenyl]-6-methylimidazo[1,2-a]pyrazin-8-ol | 24.8 | 0.297 | N.D. |
| 106 | 5-[4-(furo[3,2-c]pyridin-4-yloxy)-2-methylphenyl]-6-methylimidazo[1,2-a]pyrazin-8-ol | 106 | 1.31 | N.D. |
| 107 | 5-[4-(furo[3,2-c]pyridin-4-yloxy)-2-methylphenyl]-8-methoxy-6-methylimidazo[1,2-a]pyrazine | 26.2 | 0.669 | N.D. |
| 108 | 4-{3-[(3-cyclopropyl-1,2,4-oxadiazol-5-yl)methoxy]-4-(4,6-dimethylpyrimidin-5-yl)phenoxy}furo[3,2-c]pyridine | $55.5^d$ | 0.673 | N.D. |
| 109 | 5-[4-(furo[3,2-c]pyridin-4-yloxy)-2-methylphenyl]-6,8-dimethylimidazo[1,2-a]pyrazine | 57.5 | 0.429 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 110 | 5-[4-(furo[3,2-c]pyridin-4-yloxy)-2-methylphenyl]-6-methylimidazo[1,2-a]pyrimidine | 2.89 | 0.0338 | N.D. |
| 111 | 7-[4-(furo[3,2-c]pyridin-4-yloxy)-2-methylphenyl]-6-methylimidazo[1,2-a]pyrimidine | 41.2 | 0.335 | N.D. |
| 112 | 5-[4-(furo[3,2-c]pyridin-4-yloxy)-2-methylphenyl]-6-methylimidazo[1,2-a]pyrazin-8-amine | 13.8 | 0.156 | N.D. |
| 113 | 5-[4-(furo[3,2-c]pyridin-4-yloxy)-2-methoxyphenyl]-6-methylpyridin-3-amine | 133 | 1.02 | N.D. |
| 114 | 4-[4-(4,6-dimethylpyrimidin-5-yl)-3,5-difluorophenoxy]furo[3,2-c]pyridine | 21.2 | 0.103 | N.D. |
| 115 | 8-[4-(furo[3,2-c]pyridin-4-yloxy)-2-methylphenyl]-7-methyl[1,2,4]triazolo[4,3-b]pyridazin-3(2H)-one | 194 | 0.777 | N.D. |
| 116 | 8-(4,6-dimethylpyrimidin-5-yl)-5-(furo[3,2-c]pyridin-4-yloxy)isoquinoline | 481 | 3.44 | N.D. |
| 117 | 6-[4-(furo[3,2-c]pyridin-4-yloxy)-2-methylphenyl]-1,3,5-trimethylpyrazin-2(1H)-one | 23.1 | 0.452 | N.D. |
| 118 | 5-[4-(furo[3,2-c]pyridin-4-yloxy)-2-methylphenyl]-6-methylpyrimidine-4-carboxylic acid | >986 | >30.0 | N.D. |
| 119 | 4-[4-(furo[3,2-c]pyridin-4-yloxy)phenyl]furo[3,2-c]pyridine | $2240^d$ | N.D. | >11.2 |
| 120 | (+)-6-[4-(furo[3,2-c]pyridin-4-yloxy)-2-methylphenyl]-1,5-dimethylpyrazin-2(1H)-one | 30.9 | $0.124^b$ | N.D. |
| 121 | (−)-6-[4-(furo[3,2-c]pyridin-4-yloxy)-2-methylphenyl]-1,5-dimethylpyrazin-2(1H)-one | $9.42^a$ | $0.0504^b$ | N.D. |
| 122 | 2-[5-(furo[3,2-c]pyridin-4-yloxy)-2-(4-methylpyrimidin-5-yl)phenyl]-2-methylpropanenitrile | 211 | 4.59 | N.D. |
| 123 | 4-[4-(furo[3,2-c]pyridin-4-yloxy)-2-methylphenyl]-3-methylimidazo[2,1-c][1,2,4]triazine | N.D. | 0.878 | N.D. |
| 124 | 6-[4-(furo[3,2-c]pyridin-4-yloxy)-2-methylphenyl]-1,5-dimethylpyrimidin-2(1H)-one | 29.4 | $0.188^b$ | N.D. |
| 125 | 5-[4-(furo[3,2-c]pyridin-4-yloxy)-2-methylphenyl]-4-methylpyridazin-3(2H)-one | 23.0 | $0.0917^b$ | N.D. |
| 126 | 6-[4-(furo[3,2-c]pyridin-4-yloxy)-2-methylphenyl]-1-methylpyridin-2(1H)-one | 39.9 | 0.546 | N.D. |
| 127 | 4-[3-chloro-4-(4,6-dimethylpyrimidin-5-yl)phenoxy]furo[3,2-c]pyridine | 14.0 | 0.127 | N.D. |
| 128 | 4-[4-(4,6-dimethylpyrimidin-5-yl)-2,6-difluorophenoxy]furo[3,2-c]pyridine | $379^d$ | 5.48 | N.D. |
| 129 | 4-[4-(4,6-dimethylpyrimidin-5-yl)-2-fluoro-5-methylphenoxy]furo[3,2-c]pyridine | 32.3 | 0.268 | N.D. |
| 130 | 4-[4-(4,6-dimethylpyrimidin-5-yl)-2-fluorophenoxy]furo[3,2-c]pyridine | $73.0^d$ | 1.05 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (μM); Geometric mean of 2-6 determinations | Human D1 cAMP HTRF, $EC_{50}$ (μM); Geometric mean of 2-4 determinations |
|---|---|---|---|---|
| 131 | 4-[4-(4,6-dimethylpyrimidin-5-yl)-2-fluoro-3-methylphenoxy]furo[3,2-c]pyridine | 135[d] | 1.55 | N.D. |
| 132 | N-[4-(4,6-dimethylpyrimidin-5-yl)-3-methylphenyl]furo[3,2-c]pyridin-4-amine, formate salt | 39.9[d] | 2.26 | N.D. |
| 133 | 5-[4-(furo[3,2-c]pyridin-4-yloxy)-2-methylphenyl]-6-methylimidazo[1,2-a]pyrimidin-7-ol | 31.5 | 0.172 | N.D. |
| 134 | (+)-5-[4-(furo[3,2-c]pyridin-4-yloxy)-2-methylphenyl]-4,6-dimethylpyridazin-3(2H)-one | 1.82[a] | 0.0106[b] | N.D. |
| 135 | 4-[4-(5-methoxy-3-methylpyridazin-4-yl)-3-methylphenoxy]furo[3,2-c]pyridine | 38.7 | 0.276 | N.D. |
| 136 | 6-[4-(furo[3,2-c]pyridin-4-yloxy)-2-methylphenyl]-5-methylpyrazin-2-ol | 225 | 2.41 | N.D. |
| 137 | 5-[4-(furo[3,2-c]pyridin-4-yloxy)-2-methylphenyl]imidazo[1,2-a]pyridin-8-ol | 42.0 | 0.209[b] | N.D. |
| 138 | 4-[4-(3,5-dimethyl-2-oxidopyridazin-4-yl)-3-methylphenoxy]furo[3,2-c]pyridine and 4-[4-(3,5-dimethyl-1-oxidopyridazin-4-yl)-3-methylphenoxy]furo[3,2-c]pyridine | 17.1 | 0.262 | N.D. |
| 139 | 4-[4-(4,6-dimethylpyrimidin-5-yl)-2,5-difluorophenoxy]furo[3,2-c]pyridine | 119 | 0.287 | N.D. |
| 140 | 4-[4-(3,5-dimethylpyridazin-4-yl)-3-fluorophenoxy]furo[3,2-c]pyridine | 48.0[d] | 0.292 | N.D. |
| 141 | 4-[4-(4,6-dimethylpyrimidin-5-yl)-2,3-difluorophenoxy]furo[3,2-c]pyridine | 69.9 | 0.298[b] | N.D. |
| 142 | (−)-4-[4-(3,5-dimethylpyridazin-4-yl)-3-methoxyphenoxy]furo[3,2-c]pyridine | 10.8 | 0.0772 | N.D. |
| 143 | (+)-4-[4-(3,5-dimethylpyridazin-4-yl)-3-methoxyphenoxy]furo[3,2-c]pyridine | 64.9 | 0.273 | N.D. |
| 144 | 4-{[7-(4,6-dimethylpyrimidin-5-yl)-2-methyl-2H-indazol-4-yl]oxy}furo[3,2-c]pyridine | 246[d] | 3.49 | N.D. |
| 145 | 4-[3-methyl-4-(3-methylpyridazin-4-yl)phenoxy]furo[3,2-c]pyridine | 110[d] | 1.44 | N.D. |
| 146 | 5-[4-(furo[3,2-c]pyridin-4-yloxy)-2-methylphenyl]-6-methylimidazo[1,2-a]pyrimidine | 49.7 | 0.324[b] | N.D. |
| 147 | 5-[4-(furo[3,2-c]pyridin-4-yloxy)-2-methylphenyl]-6-methylimidazo[1,2-a]pyrimidine | 3.60 | 0.068[b] | N.D. |
| 148 | 4-{[7-(4,6-dimethylpyrimidin-5-yl)-1-methyl-1H-indazol-4-yl]oxy}furo[3,2-c]pyridine, trifluoroacetate salt | 111 | 0.777 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (μM); Geometric mean of 2-6 determinations | Human D1 cAMP HTRF, $EC_{50}$ (μM); Geometric mean of 2-4 determinations |
|---|---|---|---|---|
| 149 | 4-[4-(2-methoxy-4,6-dimethylpyrimidin-5-yl)-3-methylphenoxy]furo[3,2-c]pyridine | 31.4 | 0.464[b] | N.D. |
| 150 | 4-[4-(3,5-dimethylpyridazin-4-yl)phenoxy]furo[3,2-c]pyridine | 67.0 | 0.443 | N.D. |
| 151 | 4-[4-(furo[3,2-c]pyridin-4-yloxy)-2-methylphenyl]-N,N,5-trimethylpyridazin-3-amine, trifluoroacetate salt | 101 | 1.12 | N.D. |
| 152 | 5-[4-(furo[3,2-c]pyridin-4-yloxy)-2-methylphenyl]-4,6-dimethylpyrimidin-2-ol | 79.5 | 0.565 | N.D. |
| 153 | 5-(furo[3,2-c]pyridin-4-yloxy)-2-(6-methylimidazo[1,2-a]pyridin-5-yl)phenol | 5.99 | 0.0518 | N.D. |
| 154 | 4-[3-methyl-4-(5-methylpyridazin-4-yl)phenoxy]furo[3,2-c]pyridine | 402[d] | 2.16 | N.D. |
| 155 | 4-{[4-(4,6-dimethylpyrimidin-5-yl)-3-methylphenyl]sulfanyl}furo[3,2-c]pyridine | 138[d] | 1.01 | N.D. |
| 156 | 4-{[7-(4,6-dimethylpyrimidin-5-yl)-1,3-benzodioxol-4-yl]oxy}furo[3,2-c]pyridine | 1820[d] | >15.1 | N.D. |
| 157 | 4-[4-(3-ethoxy-5-methylpyridazin-4-yl)-3-methylphenoxy]furo[3,2-c]pyridine | 354[d] | 3.52 | N.D. |
| 158 | 8-(4,6-dimethylpyrimidin-5-yl)-5-(furo[3,2-c]pyridin-4-yloxy)quinoline | 280[d] | 2.69 | N.D. |
| 159 | 5-[4-(furo[3,2-c]pyridin-4-yloxy)-2-methylphenyl]-2,4,6-trimethylpyridazin-3(2H)-one | 11.6 | 0.212 | N.D. |
| 160 | 5-[2-chloro-4-(furo[3,2-c]pyridin-4-yloxy)phenyl]-4,6-dimethylpyridazin-3(2H)-one | 5.24 | 0.013 | N.D. |
| 161 | 4-[4-(6-methylimidazo[1,2-a]pyridin-5-yl)phenoxy]furo[3,2-c]pyridine | 8.49 | 0.0947 | 0.173 |
| 162 | 5-[4-(furo[3,2-c]pyridin-4-yloxy)-2,6-dimethylphenyl]-6-methylimidazo[1,2-a]pyrazine | 10.6 | 0.251 | 0.446[d] |
| 163 | 4-(4-{4-[(3S)-3-fluoropyrrolidin-1-yl]-6-methylpyrimidin-5-yl}-3-methylphenoxy)furo[3,2-c]pyridine, formate salt | 12.8 | 0.389 | N.D. |
| 164 | 4-{3-methyl-4-[4-methyl-6-(1-methyl-4,6-dihydropyrrolo[3,4-c]pyrazol-5(1H)-yl)pyrimidin-5-yl]phenoxy}furo[3,2-c]pyridine, formate salt | 15.2 | 0.625 | N.D. |
| 165 | 5-[4-(furo[3,2-c]pyridin-4-yloxy)-2-methylphenyl]-N,N,6-trimethylpyrimidin-4-amine, trifluoroacetate salt | 15.6 | 0.182 | N.D. |
| 166 | 6-[4-(furo[3,2-c]pyridin-4-yloxy)-2-methoxyphenyl]-1-methylpyridin-2(1H)-one | 22.9 | 0.310 | N.D. |
| 167 | 4-{4-[4-(2,5-dihydro-1H-pyrrol-1-yl)-6-methylpyrimidin-5-yl]-3-methylphenoxy}furo[3,2-c]pyridine, trifluoroacetate salt | 24.4 | 0.354 | N.D. |
| 168 | 5-[4-(furo[3,2-c]pyridin-4-yloxy)phenyl]-6-methoxyisoquinoline, trifluoroacetate salt | 28.6 | N.D. | 0.458[d] |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (μM); Geometric mean of 2-6 determinations | Human D1 cAMP HTRF, $EC_{50}$ (μM); Geometric mean of 2-4 determinations |
|---|---|---|---|---|
| 169 | 4-[4-(3,5-dimethylpyridazin-4-yl)-3-methoxyphenoxy]furo[3,2-c]pyridine | 29.2 | $0.150^b$ | N.D. |
| 170 | 5-[2-chloro-4-(furo[3,2-c]pyridin-4-yloxy)phenyl]imidazo[1,2-a]pyrazine | 30.0 | 0.657 | N.D. |
| 171 | 4-[4-(5-methoxy-3-methylpyridazin-4-yl)-3-methylphenoxy]furo[3,2-c]pyridine | 31.1 | 0.487 | N.D. |
| 172 | 5-[4-(furo[3,2-c]pyridin-4-yloxy)phenyl]-6-methylimidazo[1,2-a]pyrazine | 32.7 | N.D. | $0.408^d$ |
| 173 | 5-[4-(furo[3,2-c]pyridin-4-yloxy)-2-methoxyphenyl]-6-methylimidazo[1,2-a]pyrazine | 36.8 | N.D. | 0.564 |
| 174 | 4-[4-(imidazo[1,2-a]pyridin-5-yl)-3-methylphenoxy]furo[3,2-c]pyridine | 37.9 | N.D. | $0.200^d$ |
| 175 | 6-{5-[4-(furo[3,2-c]pyridin-4-yloxy)-2-methylphenyl]-6-methylpyrimidin-4-yl}-6,7-dihydro-5H-pyrrolo[3,4-d]pyrimidine, formate salt | 41.4 | 0.475 | N.D. |
| 176 | 3-[4-(furo[3,2-c]pyridin-4-yloxy)-2-methylphenyl]-4-methylpyridine-2-carbonitrile | 44.2 | N.D. | 0.780 |
| 177 | 5-[4-(furo[3,2-c]pyridin-4-yloxy)-2-methylphenyl]-6-methyl-1,2,4-triazin-3(2H)-one | $46.4^d$ | 2.55 | N.D. |
| 178 | 4-{3-methyl-4-[4-methyl-6-(pyrrolidin-1-yl)pyrimidin-5-yl]phenoxy}furo[3,2-c]pyridine, trifluoroacetate salt | 46.4 | 1.16 | N.D. |
| 179 | (1-{5-[4-(furo[3,2-c]pyridin-4-yloxy)-2-methylphenyl]-6-methylpyrimidin-4-yl}pyrrolidin-3-yl)methanol, formate salt | 47.2 | 0.921 | N.D. |
| 180 | [(2S)-1-{5-[4-(furo[3,2-c]pyridin-4-yloxy)-2-methylphenyl]-6-methylpyrimidin-4-yl}pyrrolidin-2-yl]methanol, formate salt | 52.9 | 0.812 | N.D. |
| 181 | 4-[3-methoxy-4-(2-methylpyridin-3-yl)phenoxy]furo[3,2-c]pyridine | 53.1 | 0.803 | N.D. |
| 182 | 4-{4-(3-methylpyrazin-2-yl)-3-[(3-propyl-1,2,4-oxadiazol-5-yl)methoxy]phenoxy}furo[3,2-c]pyridine, formate salt | 58.0 | N.D. | $0.641^d$ |
| 183 | 4-{4-[4-(5,7-dihydro-6H-pyrrolo[3,4-b]pyridin-6-yl)-6-methylpyrimidin-5-yl]-3-methylphenoxy}furo[3,2-c]pyridine, formate salt | 62.4 | 1.40 | N.D. |
| 184 | 4-[4-(2-methylpyridin-3-yl)phenoxy]furo[3,2-c]pyridine | 63.3 | 0.881 | N.D. |
| 185 | 4-(4-{4-[(3R)-3-fluoropyrrolidin-1-yl]-6-methylpyrimidin-5-yl}-3-methylphenoxy)furo[3,2-c]pyridine, trifluoroacetate salt | 64.2 | 1.16 | N.D. |
| 186 | 4-{3-[(3,5-dimethyl-1,2-oxazol-4-yl)methoxy]-4-(imidazo[1,2-a]pyridin-5-yl)phenoxy}furo[3,2-c]pyridine, trifluoroacetate salt | 64.6 | N.D. | $1.02^d$ |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 187 | (1-{5-[4-(furo[3,2-c]pyridin-4-yloxy)-2-methylphenyl]-6-methylpyrimidin-4-yl}pyrrolidin-2-yl)methanol, trifluoroacetate salt | 65.7 | 0.984 | N.D. |
| 188 | 4-{3-[(3-cyclopropyl-1,2,4-oxadiazol-5-yl)methoxy]-4-(3-methylpyrazin-2-yl)phenoxy}furo[3,2-c]pyridine, formate salt | 72.5 | 0.464 | $0.447^d$ |
| 189 | 5-[4-(furo[3,2-c]pyridin-4-yloxy)-2-methylphenyl]imidazo[1,2-a]pyrazine, trifluoroacetate salt | 77.6 | N.D. | 0.308 |
| 190 | 4-[4-(4,6-dimethylpyrimidin-5-yl)-3-(2-methoxyethoxy)phenoxy]furo[3,2-c]pyridine | $79.3^d$ | 2.65 | N.D. |
| 191 | 5-[4-(furo[3,2-c]pyridin-4-yloxy)-2-methoxyphenyl]-6-methylpyridin-2-amine, formate salt | 85.8 | 1.12 | N.D. |
| 192 | 4-[4-(4-ethoxy-6-methylpyrimidin-5-yl)-3-fluorophenoxy]furo[3,2-c]pyridine | 86.4 | 0.737 | 1.50 |
| 193 | 6-[2-chloro-4-(furo[3,2-c]pyridin-4-yloxy)phenyl]-5-methylpyrazin-2-amine | 87.5 | 0.944 | N.D. |
| 194 | 4-{4-(2-methylpyridin-3-yl)-3-[2-(1,2-oxazol-4-yl)ethoxy]phenoxy}furo[3,2-c]pyridine, formate salt | 88.5 | 1.68 | 1.33 |
| 195 | 3-[5-(furo[3,2-c]pyridin-4-yloxy)-2-(imidazo[1,2-a]pyridin-5-yl)phenoxy]propan-1-ol, trifluoroacetate salt | $90.4^d$ | N.D. | $0.565^d$ |
| 196 | 4-[3-chloro-4-(3-methylpyrazin-2-yl)phenoxy]furo[3,2-c]pyridine | $91.7^d$ | 1.40 | N.D. |
| 197 | 4-[4-(imidazo[1,2-a]pyridin-5-yl)phenoxy]furo[3,2-c]pyridine | $97.0^a$ | 0.801 | 1.09 |
| 198 | 4-{5-[4-(furo[3,2-c]pyridin-4-yloxy)-2-methylphenyl]-6-methylpyrimidin-4-yl}-1-methylpiperazin-2-one, formate salt | $97.0^d$ | 1.14 | N.D. |
| 199 | 4-{3-[(3-ethyl-1,2,4-oxadiazol-5-yl)methoxy]-4-(3-methylpyrazin-2-yl)phenoxy}furo[3,2-c]pyridine, formate salt | 104 | N.D. | $0.782^d$ |
| 200 | 4-[3-methyl-4-(1-methyl-1H-indazol-7-yl)phenoxy]furo[3,2-c]pyridine | 111 | N.D. | $1.24^d$ |
| 201 | 2-[5-(furo[3,2-c]pyridin-4-yloxy)-2-(imidazo[1,2-a]pyridin-5-yl)phenoxy]-N-(propan-2-yl)acetamide, trifluoroacetate salt | 113 | N.D. | $0.889^d$ |
| 202 | 4-(4-{4-[(3S)-3-methoxypyrrolidin-1-yl]-6-methylpyrimidin-5-yl}-3-methylphenoxy)furo[3,2-c]pyridine, trifluoroacetate salt | $114^d$ | 1.29 | N.D. |
| 203 | 1-{5-[4-(furo[3,2-c]pyridin-4-yloxy)-2-methylphenyl]-6-methylpyrimidin-4-yl}azetidin-3-ol, formate salt | 118 | 0.799 | N.D. |

TABLE 3-continued

Biological Data for Examples 1-216

| Example Number | Compound Name | Human D1 Receptor Binding, $K_i$ (nM); Geometric mean of 2-4 determinations | Human D1 cAMP HTRF, $EC_{50}$ (µM); Geometric mean of 2-6 determinations | Human D1 cAMP HTRF, $EC_{50}$ (µM); Geometric mean of 2-4 determinations |
|---|---|---|---|---|
| 204 | 4-[4-(1-methyl-1H-pyrazol-5-yl)-3-(trifluoromethyl)phenoxy]furo[3,2-c]pyridine | 130[a] | 1.17 | 0.627 |
| 205 | 4-[4-(2-methylpyridin-3-yl)-3-(tetrahydro-2H-pyran-4-yloxy)phenoxy]furo[3,2-c]pyridine, formate salt | 148[d] | 4.63 | 3.57 |
| 206 | 4-[4-(4-methoxy-6-methylpyrimidin-5-yl)-3-methylphenoxy]furo[3,2-c]pyridine | 160[d] | 0.768[b] | 1.25 |
| 207 | 5-[4-(furo[3,2-c]pyridin-4-yloxy)-2-methylphenyl]-6-methylimidazo[1,2-a]pyrazine-8-carbonitrile | 161[d] | 0.796 | N.D. |
| 208 | 4-[4-(furo[3,2-c]pyridin-4-yloxy)phenyl]-8-methoxyquinazoline | 170 | N.D. | 1.55 |
| 209 | 3-cyclopropyl-4-[4-(4,6-dimethylpyrimidin-5-yl)-3-methylphenoxy]furo[3,2-c]pyridine, trifluoroacetate salt | 131 | 5.62 | N.D. |
| 210 | 4-[4-(4,6-dimethylpyrimidin-5-yl)-3-methylphenoxy]furo[3,2-c]pyridine-3-carbonitrile | 18.8 | 0.655 | N.D. |
| 211 | 5-{4-[(3-bromofuro[3,2-c]pyridin-4-yl)oxy]phenyl}-4,6-dimethylpyridazin-3(2H)-one | 6.86 | 0.098 | N.D. |
| 212 | 4-[4-(3,5-dimethyl-6-oxo-1,6-dihydropyridazin-4-yl)phenoxy]furo[3,2-c]pyridine-3-carbonitrile | 18.7 | 0.119 | N.D. |
| 213 | 6-{4-[(3-bromofuro[3,2-c]pyridin-4-yl)oxy]-2-methylphenyl}-1,5-dimethylpyrazin-2(1H)-one | 64.5 | 0.694 | N.D. |
| 214 | 4-[4-(imidazo[1,2-a]pyridin-5-yl)phenoxy]thieno[3,2-c]pyridine | 67.6 | N.D. | 0.457 |
| 215 | (−)-6-[4-(furo[3,2-c]pyridin-4-yloxy)-2-methylphenyl]-1,5-dimethylpyrimidine-2,4(1H,3H)-dione | 1.06[a] | 0.00139 | N.D. |
| 216 | 6-[4-(furo[3,2-c]pyridin-4-yloxy)phenyl]-1,5-dimethylpyrimidine-2,4(1H,3H)-dione, trifluoroacetate salt | 4.2 | 0.00938 | N.D. |

[a]Value represents the geometric mean of ≥5 determinations.
[b]Value represents the geometric mean of 7-15 determinations.
[c]Not determined.
[d]Value represents a single determination Example CC D1R Mutant Studies Fourteen different potential binding site residue mutations of the D1R were made to more precisely determine where the D1 agonists of the present invention were binding. Generally, there is very good agreement between the fold-shift values of the D1 agonists of the present invention when compared to those of known catechol derivative full (or super) D1 agonists and partial agonists; however 4 of those 14 residues (Ser188, Ser198, Ser202, and Asp103) showed statistically significant deviations and representative results are shown herein.

Human Dopamine D1 receptor agonist activity was measured using Cisbio Dynamic 3'-5'-cyclic adenosine monophosphate (cAMP) detection kit (Cisbio International 62AM4PEJ). cAMP was measured using a homogeneous time-resolved fluorescence (HTRF) competitive immunoassay between native cAMP and cAMP labeled with the dye d2.

A monoclonal anti-cAMP antibody labeled cryptate bound the labeled cAMP. Europiumcryptate donor was added, and the transfer of energy to the d2 acceptor was measured. The maximum signal was achieved if the samples did not contain free cAMP, due to the proximity of Eu-cryptate donor and d2 acceptor entities. The signal, therefore, was inversely proportional to the concentration of native cAMP in the sample. A time resolved and ratiometric measurement (em 665 nm/em 620 nm) was obtained, which was then converted to cAMP concentrations using a standard curve. All cAMP experiments were performed in the presence of 500 nM IBMX to inhibit phosphodiesterase (PDE) activity.

The cAMP standard curve was generated using cAMP provided in the Cisbio cAMP detection kit. Preparation of the standard curve is as follows. (1) Prepared 2848 nM cAMP stock solution in Dµlbecco's Phosphate Buffered Saline (PBS, from Sigma, Cat#D8537), this stock solution was aliquoted (40 µl/vial) and frozen at −20° C. 2) On the day of assay, 40 µl PBS was added to two column of a 96-well compound plate (Costar, Cat#3357). 2) On the day of assay, 40 µl 2848 nM cAMP stock solution was transferred to first well and mixed with 40 µl PBS (see the figure below), and then a 16 pt, 2 fold dilution was made by transfer 40 µl from higher conc. to lower conc. (3) Manually transfer 10 µl/well (in triplicate) of cAMP solution to assay plate.

Stable HEK293T cells expressing hD1R (wild type or a mutant thereof) were grown in high glucose DMEM (Invitrogen 11995-065), 10% fetal bovine serum dialyzed (Invitrogen 26400-044), 1×MEM NEAA (Invitrogen 1140), 25 mM HEPES (Invitrogen 15630), 1× Penicillin/Streptomycin (Invitrogen 15070-063) and 500 µg/mL Genticin (Invitrogen 10131-035) at 37 C and 5% CO2. At 72 to 96 hours post seeding, cells were rinsed with phosphate buffered saline and 0.25% Trypsin-EDTA was added to dislodge the cells. Media was then added and cells were centrifuged and media removed. The cell pellets were re-suspended in Cell Culture Freezing Medium (Invitrogen 12648-056) at a density of 40 million cells/mL. One mL aliquots of the cells were made in Cryo-vials and frozen at −80° C. for use in the hD1 (or a mutant thereof) HTRF cAMP assay.

Frozen cells were quickly thawed, re-suspended in warm media and allowed to sit for 5 min prior to centrifugation (1000 rpm) at room temperature. Media was removed and the cell pellet was re-suspended in PBS containing 500 nM IBMX. Using a Multidrop Combi (Thermo Scientific), 5 µL cells/well at a cell density of approximately 1000 cells/well were added to the assay plate (Greiner 784085) which contained 5 µL of test compound. The exact cell density could vary depending on the cAMP concentration relative to the standard curve. Each plate contained positive controls of 5 uM dopamine (final concentration) and negative controls of 0.5% DMSO (final concentration). Cells and compounds were incubated at room temperature for 30 min. Working solutions of cAMP-d2 and anti-cAMPcryptate were prepared according to Cisbio instructions. Using the Multidrop Combi, 5 µL cAMP-d2 working solution was added to the assay plate containing the test compound and cells. Using the Multidrop Combi, 5 µL anti-cAMP-cryptate working solutions was added to assay plate containing test compound, cells and cAMP-d2. Assay plates were incubated for 1 hour at room temperature, then read using an Envision plate reader (Perkin Elmer) using Cisbio recommended settings. A cAMP standard curve was generated using cAMP stock solution provided in the Cisbio kit, which was then used to convert the raw ratio data to cAMP concentrations. $EC_{50}$ values were determined using a logistic 4 parameter fit model. The percent efficacy for each curve was determined by the maximum asymptote of that fitted curve, and expressed as a percent of the maximum response produced by the positive controls (5 µM dopamine) on each plate.

Wild type 3xHA-h D1 expression construct (in pcDNA3.1+) was obtained from Missouri S&T cDNA Resource Center. Several mutations were created using mutagenesis methods (e.g., Stratagene Quick Change Mutagenesis Kit). All mutations were confirmed via sequencing. Wild type and mutant(s) expressing HEK293 cells were generated (for cAMP assays) via transient transfection (48 hrs.) in Freestyle HEK 293F cells (Invitrogen). The number of cells/paste used per data point was based on relative expression levels as determined via western blot analysis.

D1R WT refers to wild type. Several mutants were designed based upon a computational homology model of D1 and mutant numbering is consistent with what has been previously published in the literature. See e.g., N J Pollock, et. al, "Serine mutations in transmembrane V of the dopamine D1 receptor affect ligand interactions and receptor activation." J. Biol. Chem. 1992, 267 [25], 17780-17786. Mutants are designated by the number corresponding to their position in the primary sequence and the three-letter amino acid code. For example, D103A mutant refers to the amino acid aspartate (D) at the $103^{rd}$ position in the primary sequence mutated to the amino acid alanine (A); S188I mutant refers to the amino acid Serine (S) at the $188^{th}$ position in the primary sequence mutated to the amino acid isoleucine (I); and S198A mutant refers to the amino acid Serine (S) at the $198^{th}$ position in the primary sequence mutated to the amino acid alanine (A).

Relative 3xHA-hD1 mutant expression levels were normalized to wild type hD1 levels by western blot analysis. Soluble RIPA lysates of transiently transfected HEK293F cells were prepared by lysing cells at 4° C. for 30 minutes in RIPA Buffer (Sigma) with protease and phosphatase inhibitors (Pierce). Equivalent amounts of total soluble RIPA lysates (determined by BCA total protein assay, Pierce) were run on SDS-PAGE, transferred to nitrocellulose and probed with anti-HA as well as anti-GAPDH antibodies (Sigma). Total mutant hD1 HA immunoreactivity was quantitated verses GAPDH immunoreactivity (HA/GAPDH) and finally normalized to wild type 3xHA-hD1 (HA/GAPDH) using LiCor/Odyssey software. Based on this relative HA/GAPDH ratios as compared to wild type, the relative amount of cell paste or cell number/well was adjusted for each mutants' expression levels.

A first run of cAMP assays was conducted. From the first run, it was determined that the results were at the upper end of linear range (for agonists) of the standard curve (the range is provided by Cisbo), indicating this first run is at a higher density of cells/well. Typically, a higher density of cells/well run (within the linear range) is suitable for mutants that are either lower expressers or have low activity; but not as suitable for the higher activity/expressing mutants. Table 4 shows $EC_{50}$ data in the first run of cAMP assays. A second run of cAMP assays was conducted. According to a comparison with the standard curve, this run of assays was at a lower density of cells/well because the results were at the lower end of linear range (for agonists) of the standard curve. Typically, assays at a lower density of cells/well (within the liner range) are more suitable for the higher activity/expressing mutants, but less suitable for those mutants with lower expression/activity. Table 5 shows $EC_{50}$ data in the second run of cAMP assays.

TABLE 4

EC$_{50}$ Data (high expression levels of D1R).

| Compound | EC$_{50}$ D1 WT [nM] | EC$_{50}$ (S188I mutant) [nM] | EC$_{50}$ (S202A mutant) [nM] | EC$_{50}$ (S198A mutant) [nM] | EC$_{50}$ (D103A mutant) [nM] |
|---|---|---|---|---|---|
| Example 27 | 3 | 12 | 5 | 18 | 102 |
| Example 25 | 6 | 40 | 7 | 36 | 188 |
| Dopamine | 58 | 95 | 3058 | 923 | >29,900 |
| Dihydrexidine | 9 | 6 | 189 | 208 | 1324 |
| SKF-38393 | 33 | 6 | 119 | 277 | >29,900 |
| SKF-77434 | 28 | 7 | 49 | 119 | >29,900 |

TABLE 5

EC$_{50}$ Data (lower expression levels of D1R).

| Compound | EC$_{50}$ D1 WT [nM] | EC$_{50}$ (S188I mutant) | EC$_{50}$ (Ser202A mutant) | EC$_{50}$ (Ser198A mutant) | EC$_{50}$ (Asp103A mutant) |
|---|---|---|---|---|---|
| Example 215 | 0.4 | 5 | 1 | 3 | 31 |
| Dopamine | 51 | 208 | 12709 | 1631 | >29,900 |
| Dihydrexidine | 7 | 6 | 527 | 349 | 1264 |
| SKF-38393 | 51 | 19 | 139 | >29,900 | >29,900 |
| SKF-77434 | 14 | 6 | 20 | >29,900 | >29,900 |

Results from both mutation runs revealed that many of the mutant receptors have weaker activity (higher EC$_{50}$ values) when compared to the WT D1, reflecting the loss of interaction between the ligand and the receptor with the mutated side chain. In an attempt to determine the side-chain contribution to activity, quantifications of the shift between the mutant receptor and the WT receptor, i.e., Fold Shift data were calculated according to the equation; Fold Shift=EC$_{50}$ (Mutant)/EC$_{50}$ (WT). Fold shift data are shown in Table 6.

In general, assays with most of the mutant D1 receptors provided values in the "kit-defined" linear range with the lower cell/well variant. However, S198A gave poor results for the lower cells/well run. A comparison of the average fold shifts for each tested mutant across both runs revealed that the fold shifts were more pronounced for the lower activity run by a factor of ~2.5. This factor was determined by regressing the average log(foldshift) values between runs for all mutants:

log(fold-shift_lower)=0.3968+1.023*log(fold-shift_higher). ($R^2$=0.92)

The intercept value of 0.3968 reflects the ~2.5× systematic difference between the runs.

Dopamine, another catechol-derivative full D1 agonist (Dihydrexidine), and two other catechol-derivative partial D1 agonist (SKF-38393 and SKF-77434) have fold shift less than about 4.0 with respect to 51881 mutant, indicating that they do not interact significantly with the Ser188 unit of D1R. In contrast, Examples 215 and 27 (full D1 agonists) and Example 25 (partial D1 agonist) have fold shift greater than about 7.0 with respect to 51881 mutant, indicating that they interact significantly with the Ser188 unit of D1R.

Dopamine and another catechol-derivative D1 full agonist (Dihydrexidine) have fold shift greater than about 70 with respect to S202A mutant, indicating that they interact significantly with the Ser202 unit of D1R. In contrast, Examples 215 and 27 (full D1 agonists) have fold shift less than about 4.0 with respect to S202A mutant, indicating that they do not interact significantly with the Ser202 unit of D1R.

Dopamine and 3 other catechol-derivative D1 agonists, as well as Examples 215 and 27 (full D1 agonists) and Example 25 (partial D1 agonist) have fold shift greater than about 7.0 with respect to D103A mutant, indicating that they interact significantly with the Asp103 unit of D1R. On average, the fold shift for the catechol-derivative agonist (greater than 100, 150, or 180) are much greater than those for Examples 215 and 27 (full D1 agonists) and Example 25 (partial D1 agonist), indicating the interactions between D1R and non-catechol derivative Examples 215, 27, and 25 are less strong than those between D1R and the catechol-derivative agonists.

Dopamine and 3 other catechol-derivative D1 agonists, as well as Examples 215 and 27 (full D1 agonists) and Example 25 (partial D1 agonist) have fold shift greater than about 7.0 with respect to S198A mutant, indicating that they interact significantly with the Ser198 unit of D1R. However, on average, the fold shift for the catechol-derivative full agonists (Dopamine and Dihydrexidine, both are greater than 25, 30, or 35) are greater than Examples 215 and 27 (full D1 agonists), indicating the interactions between D1R and non-catechol-derivative full agonist Examples 215, and 27 are less strong than those between D1R and the catechol-derivative full agonists.

The % intrinsic activity of each of the test compounds [i.e., the maximum percent efficacy (calculated by maximum cAMP concentration) in reference to Dopamine] was determined using cAMP data from a D1 cAMP HTRF assay as in Example BB.

TABLE 6

Fold-Shift Values and % intrinsic activity (intrinsic activity data: % activity comparing to Dopamine)

| Compound | % intrinsic activity | Fold Shift (S188I mutant) | Fold Shift (S202A mutant) | Fold Shift (S198A mutant) | Fold Shift (D103A mutant) |
|---|---|---|---|---|---|
| Example 215 | 101 | 11.6 | 2.3 | 7.0 | 72 |
| Example 27 | 109 | 8.9[a] | 3.7[a] | 13.4[a] | 76[a] |
| Example 25 | 74 | 15[a] | 2.6[a] | 13.4[a] | 70[a] |
| Dopamine | 100 | 4.0 | 249 | 36[a] | >586 |
| Dihydrexidine | 108 | 0.9 | 75 | 53[a] | 180 |
| SKF-38393 | 78.5 | 0.4 | 2.7 | 18.9[a] | >586 |
| SKF-77434 | 36.2 | 0.4 | 1.4 | 9.4[a] | >2135 |

[a]These fold shift value have been transformed using the equation: FoldShift = 2.234*(EC$_{50}$_Mutant/EC$_{50}$_WT). This correction was done in order to correct for differences in receptor density between two assay runs shown in Tables 4 and 5. Any other FoldShift refers to the shift in functional activity as defined: = EC$_{50}$ (Mutant)/EC$_{50}$ (WT).

Example DD

β-Arrestin Membrane Recruitment Assays and TIRF Microscopy

For all studies of β-arrestin, a stable U2OS cell line co-expressing human Dopamine D1(D1A) receptors and human β-arrestin2-green fluorescent fusion protein (GFP) was used. This cell line was obtained and licensed from Professor Marc G. Caron, Duke University, Durham, N.C., USA. The stable U2OS cell line provides a fluorescent biosensor of β-arrestin2-GFP that can be used to assess GPCR signaling and GPCR-mediated β-arrestin membrane recruitment using imaging-based methods such as fluorescence microscopy (U.S. Pat. Nos. 7,572,888 and 7,138,240) (9); this technology is currently marketed as the Transfluor Assay (Molecular Devices, USA). The U2OS cells were cultured under antibiotic selection in DMEM (Invitrogen) containing 25 mM glucose and 4 mM L-glutamine supplemented with 10% dialyzed fetal bovine serum, 200 mg/mL Geneticin, 100 mg/mL Zeocin, and 1000/mL penicillin/streptomycin (all from Invitrogen) and incubated at 37° C. in 5% carbon dioxide. Cells from passage four through ten were used in these experiments. Cells were grown in 35 mm glass bottomed imaging dishes (Mattek Corp). Cells were incubated for 1 h in serum free media (SFM) and subsequently treated for 10 minutes at 37° C. with 0.01% DMSO (control) or 1 µM of all test compounds dissolved in SFM followed by immediate fixation on ice with a 4% paraformaldehyde/1× phosphate buffered saline solution.

Total Internal Reflection Fluorescence Microscopy (TIRFM) was used. TIRFM is a microscopy technique that enables visualization of the plasma membrane and a narrow region just inside the cell, providing a means to visualize proteins at the plasma membrane of cells such as D1 receptors and recruited β-arrestin-GFP (see Yudowski G A, von Zastrow M. "Investigating G protein-coupled receptor endocytosis and trafficking by TIR-FM"; Methods in Molecular Biology. 2011; 756:325-32). All images were captured using a Zeiss PS.1 Elyra Superresoution fluorescence microscope equipped with TIRF module. Images of cells were obtained using TIRF and a 100× oil immersion objective and dedicated 488 nm excitation laser. Optimal exposure time and laser power was determined using Dopamine treated cells which exhibited maximal β-arrestin-GFP membrane signal and identical acquisition parameters were used for all cells and conditions. To quantify β-arrestin-GFP membrane recruitment, individual cells in microscopy images were identified and a polygon region of interest was traced for each cell using ImageJ, imaging analysis software (Schneider C A, Rasband W S, Eliceiri K W. "NIH Image to ImageJ: 25 years of image analysis". Nature Methods. 2012; 9(7):671-5). An intensity-based threshold was established by evaluating Dopamine treated cells which exhibited the maximal plasma membrane signal of β-arrestin-GFP. A range of values, 10, 30, 60, 90, etc. were tested and the lowest possible threshold, in this case 60, capable of identifying the individual β-arrestin-GFP puncta was selected for continued analysis. Sub-images were generated for all identified cells, and the total number of membrane β-arrestin-GFP puncta/cell, integrated intensity/cell, and total area/cell was established. Individual objects were filtered based on size. A minimum of 60 cells for each condition were analyzed across three independent cell preparations and experiments. The mean membrane β-arrestin-GFP intensity/cell and puncta area/cell were determined and statistical differences compared by a one-way ANOVA with Dunnett's post-test analysis using Graphpad Prism 5.02.

U2OS cells stably expressing human D1 receptors and human β-arrestin-GFP proteins were treated for 10 minutes with 0.01% DMSO in serum free media (control) or with 1 µM of a test compound).

Test compounds include Dopamine, Dihydrexidine, SKF-81297, SKF-38393, SKF-77434, Example 5 (partial agonist, 70% intrinsic activity at human D1R v. Dopamine), Example 9 (full agonist, 92% intrinsic activity at human D1R v. Dopamine), Example 13 (partial agonist, 58% intrinsic activity at human D1R v. Dopamine), and Example 25 (full agonist, 88% intrinsic activity at human D1R v. Dopamine). The % intrinsic activity of each of the test compounds [i.e., the maximum percent efficacy (calculated by maximum cAMP concentration) in reference to Dopamine] was determined using cAMP data from a D1 cAMP HTRF assay as in Example BB.

Cells were immediately fixed and β-arrestin-GFP located at the plasma membrane of cells was determined using Total Internal Reflection Fluorescence Microscopy (TIRFM).

Tables 7 and 8 list quantification of β-arrestin-GFP signal at the plasma membrane of cells using TIRFM to assess total intensity/cell and total area/cell; non-catechol-derivative D1 receptor agonists (Examples 5, 9, 13 and 25) showed significantly reduced plasma membrane β-arrestin-GFP total intensity and total area relative to Dopamine. All results are the mean±standard error averaged from 60 cells/condition obtained across three independent experiments (n=3). a, p<0.05 versus control; b, p<0.05 versus Dopamine.

TABLE 7

Membrane β-arrestin-GFP Total Intensity/cell

| Control/test compound | Membrane β-arrestin-GFP Total Intensity/cell Unit (arbitrary fluorescence units/cell) | % recruitment normalized to Dopamine |
|---|---|---|
| Control | 9 ± 6 [b] | 0.13 ± 0.08 |
| Dopamine | 7072 ± 966 [a] | 100 ± 14 |
| Dihydrexidine | 8969 ± 1130 [a] | 127 ± 16 |
| SKF-81297 | 7424 ± 1203 [a] | 105 ± 17 |
| SKF-38393 | 241 ± 99 [b] | 3.4 ± 1.4 |
| SKF-77434 | 35 ± 12 [b] | 0.50 ± 0.17 |
| Example 5 | 774 ± 205 [b] | 10.9 ± 2.9 |
| Example 9 | 940 ± 198 [b] | 13.3 ± 2.8 |
| Example 25 | 1801 ± 203 [b] | 25.5 ± 2.9 |
| Example 13 | 499 ± 101 [b] | 7.0 ± 1.4 |

TABLE 8

Membrane β-arrestin-GFP Total Area/cell

| Control/test compound | Membrane β-arrestin-GFP Total Area/cell Unit [µm] | % recruitment normalized to Dopamine |
|---|---|---|
| Control | ±0.08 [b] | 0.13 ± 0.10 |
| Dopamine | 79 ± 11 [a] | 100 ± 14 |
| Dihydrexidine | 92 ± 11 [a] | 116.4 ± 13.9 |
| SKF-81297 | 77 ± 11 [a] | 97.5 ± 13.9 |
| SKF-38393 | 6 ± 3 [b] | 7.6 ± 3.8 |
| SKF-77434 | 0.5 ± 0.2 [b] | 0.6 ± 0.2 |
| Example 5 | 10 ± 2 [b] | 12.6 ± 2.5 |
| Example 9 | 12 ± 2 [b] | 15.2 ± 2.5 |
| Example 25 | 24 ± 3 [b] | 30.3 ± 3.8 |
| Example 13 | 7 ± 1 [b] | 8.9 ± 1.3 |

As shown in Tables 7 and 8, Dopamine and two catechol-derivative full D1 agonists (Dihydrexidine and SKF-81297) recruited greater than about 95% β-arrestin-GFP to the plasma membrane relative to Dopamine (the result can also be observed qualitatively from representative TIRFM images of cells treated with these agonists). In contrast, either of Examples 9 and 25 (full non-catechol-derivative D1 agonists) recruited less than 60% (or 50%, or 40% or 30%) β-arrestin-GFP to the plasma membrane relative to Dopamine. Each of the partial D1 agonists tested (SKF-38393, SKF-77434, and Examples 5 and 13) recruited less than 60% (or 50%, or 40% or 30%) β-arrestin-GFP to the plasma membrane relative to Dopamine.

Example EE cAMP and Receptor Desensitization Assays

Primary striatal neurons were obtained from embryonic day 18 (E18) rats by standard neuronal isolation procedures and plated at a density of 35,000 cells/well in poly-ornithine/ laminin coated 96 well plates (BD Falcon). Striatal neurons were chosen because they express endogenous D1-like receptors and are a physiologically relevant tissue for examining neurotransmitter receptor desensitization in vitro. Neurons were cultured in neurobasal media supplemented with B27, 1× Glutamax and penicillin/streptomycin (100 U/mL) (all from Invitrogen) and incubated at 37° C. in 5% carbon dioxide for 14-16 days prior to assay. To assess D1R desensitization, neurons in wells were pretreated for 120 minutes with 0.1% DMSO in serum free media (Control/SFM) or 10 µM of a test compound dissolved in serum free neurobasal media. After the pretreatment, cells were washed twice at 5 minute intervals with 250 µl/well fresh neurobasal media. The ability of D1-like receptors to signal was then examined by treating cells for 30 minutes with 1 µM SKF-81297, a catechol derivative D1-like selective full agonist, in the presence of 500 µM isobutylmethylxanthine. The concentration of cAMP accumulated in each well was determined using the Cisbio HTRF cAMP dynamic range assay kit (Cisbio) according to the manufacturers' suggested protocol. The concentration of cAMP (nM) from treated wells was interpolated from a cAMP standard curve by non-linear regression least squares analysis using Graphpad Prism 5.02. The mean±standard error of the cAMP concentrations were calculated from results obtained across three independent experiments (n=3) each assayed in quadruplicate. The % desensitization was calculated as the percent decrease in cAMP relative to control. Statistical differences were compared by a one-way ANOVA with Dunnett's post-test analysis using Graphpad Prism 5.02.

All results are the mean±standard error from three independent experiments assayed in quadruplicate (n=3). *, p<0.05 versus control.

TABLE 9

| cAMP concentration v. Pretreatment of neurons with test compounds (in addition to Control and untreated neuron) | |
|---|---|
| Untreated/Control/Pretreated test compound | cAMP concentration Unit [nM] |
| Untreated | 4 ± 0.4 * |
| Control | 46 ± 4 |
| Dopamine | 20 ± 2 * |
| Dihydrexidine | 20 ± 2 * |
| SKF-81297 | 25 ± 2 * |
| SKF-38393 | 30 ± 3 * |
| SKF-77434 | 31 ± 3 * |
| Example 5 | 45 ± 3 |
| Example 9 | 39 ± 2 |
| Example 25 | 41 ± 2 |
| Example 13 | 41 ± 2 |

TABLE 10

| % Desensitization | |
|---|---|
| Control/Pretreated test compound | % Desensitization Unit (% decrease in cAMP v. Control) |
| Control | 0 ± 8 |
| Dopamine | 56 ± 4 * |
| Dihydrexidine | 56 ± 5 * |
| SKF-81297 | 46 ± 4 * |
| SKF-38393 | 34 ± 7 * |
| SKF-77434 | 32 ± 7 * |
| Example 5 | 2 ± 6 |
| Example 9 | 15 ± 5 |
| Example 25 | 10 ± 7 |
| Example 13 | 11 ± 4 |

As shown in Table 9, pretreatment of neurons with Dopamine, two catechol derivative full D1 agonists (Dihydrexidine and SKF-81297), and two catechol derivative partial D1 agonists (SKF-38393 and SKF-77434) significantly decreased D1R-mediated cAMP signaling. In contrast, pretreatments with non-catechol derivative D1 full agonists (Examples 9 and 25) and non-catechol derivative D1 partial agonists (Examples 5 and 13) did not significantly decrease D1R-mediated cAMP signaling (closer to Control).

As shown in Table 10, Dopamine, two catechol derivative full D1 agonists (Dihydrexidine and SKF-81297), and two catechol derivative partial D1 agonists (SKF-38393 and SKF-77434) significantly desensitized D1R receptors (decreased greater than about 30%, 40%, or 50% v. Control). In contrast, non-catechol derivative D1 full agonists (Examples 9 and 25) and non-catechol derivative D1 partial agonists (Examples 5 and 13) show decreased desensitization (only decreased less than about 25%, 20%, 18%, or 15% v. Control).

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:
1. A compound of Formula I:

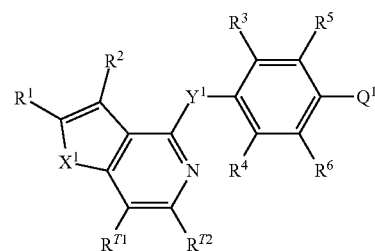

or an N-oxide thereof, or a pharmaceutically acceptable salt of said compound or said N-oxide, wherein:
$X^1$ is O;
$Y^1$ is O;
$Q^1$ is selected from 1H-pyrazolyl, 1H-imidazolyl, pyridinyl, pyrimidinyl, pyridazinyl, pyrazinyl, 3-oxo-2H-pyridazinyl, 1H-2-oxo-pyrimidinyl, 1H-2-oxo-pyrazinyl, 2,4(1H,3H)-dioxo-pyrimidinyl, 1H-2-oxo-pyridinyl, isoquinolinyl, 1H-imidazo[4,5-c]pyridinyl, imidazo[1,2-a]pyridinyl, imidazo[1,2-a]pyrimidinyl, [1,2,4]triazolo[4,3-b]pyridazinyl, and imidazo[1,2-a]pyrazinyl, wherein each of the selections is optionally substituted with 1, 2, 3, or 4 independently selected $R^7$;
$R^{T1}$ and $R^{T2}$ are each independently selected from the group consisting of H, $C_{1-3}$ alkyl, $C_{1-3}$ fluoroalkyl, cyclopropyl, fluorocyclopropyl, $C_{1-3}$ alkoxy, $C_{1-3}$ haloalkoxy, —C(=O)—O—($C_{1-3}$ alkyl), and —C(=O)OH;
$R^1$ is selected from the group consisting of H, F, —C(=O)OH, —C(=O)—O—($C_{1-3}$ alkyl), $C_{1-3}$ alkyl, $C_{1-3}$ fluoroalkyl, $C_{3-6}$ cycloalkyl, and $C_{3-6}$ fluorocycloalkyl, wherein said $C_{3-6}$ cycloalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy;

$R^2$ is selected from the group consisting of H, halogen, —CN, —OH, C(=O)OH, C(=O)—O—($C_{1-3}$ alkyl), $C_{1-3}$ alkoxy, $C_{1-3}$ haloalkoxy, —N($R^8$)($R^9$), $C_{1-3}$ alkyl, $C_{1-3}$ fluoroalkyl, $C_{3-6}$ cycloalkyl, $C_{3-6}$ fluorocycloalkyl, $C_{2-6}$ alkenyl, and $C_{2-6}$ alkynyl, wherein said $C_{3-6}$ cycloalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy;

$R^3$ and $R^4$ are each independently selected from the group consisting of H, $C_{1-6}$ alkyl, $C_{1-6}$ haloalkyl, $C_{1-6}$ alkoxy, $C_{1-6}$ haloalkoxy, —CN, $C_{3-6}$ cycloalkyl, —C(=O)OH, C(=O)—O—($C_{1-4}$ alkyl), and halogen, wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;

$R^5$ and $R^6$ are each independently selected from the group consisting of H, halogen, —OH, —$NO_2$, —CN, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —N($R^8$)($R^9$), —N($R^{10}$)(C(=O)$R^{11}$), —C(=O)—N($R^8$)($R^9$), —C(=O)—$R^{12}$, —C(=O)—$OR^{12}$, and —$OR^{13}$, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-3}$ alkyl, $C_{1-3}$ alkoxy, $C_{1-3}$ haloalkyl, $C_{1-3}$ haloalkoxy, $C_{3-6}$ cycloalkyl, —N($R^{14}$)($R^{15}$), —N($R^{16}$)(C(=O)$R^{17}$), —C(=O)—$OR^{18}$, —C(=O)H, —C(=O)$R^{18}$, —C(=O)N($R^{14}$)($R^{15}$), and —$OR^{19}$;

each $R^7$ is independently selected from the group consisting of halogen, —OH, —CN, —$NO_2$, oxo, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, cycloalkylalkyl, heterocycloalkylalkyl, arylalkyl, heteroarylalkyl, heteroarylalkenyl, —CH=N—O—($C_{1-3}$ alkyl), —N($R^{14}$)($R^{15}$), —N($R^{16}$)(C(=O)$R^{17}$), —S(=O)$_2$N($R^{14}$)($R^{15}$), —C(=O)N($R^{14}$)($R^{15}$), —C(=O)—$R^{12}$, —C(=O)—$OR^{18}$, and —$OR^{19}$, wherein each of said $C_{1-6}$ alkyl, $C_{3-7}$ cycloalkyl, cycloalkylalkyl, heterocycloalkylalkyl, arylalkyl, heteroarylalkyl, heteroarylalkenyl, $C_{6-10}$ aryl, heterocycloalkyl and heteroaryl is optionally substituted with 1, 2, 3, or 4 substituents each independently selected from the group consisting of halogen, OH, —CN, —$NO_2$, $C_{1-4}$ alkyl, $C_{1-4}$ hydroxylalkyl, $C_{1-4}$ alkoxy, —N($R^{14}$)($R^{15}$), —S—($C_{1-3}$ alkyl), —S(=O)$_2$—($C_{1-4}$ alkyl), aryloxy, arylalkyloxy optionally substituted with 1 or 2 $C_{1-4}$ alkyl, oxo, —C(=O)H, —C(=O)—$C_{1-4}$ alkyl, —C(=O)O—$C_{1-4}$ alkyl, —C(=O)$NH_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

$R^8$ and $R^9$ are each independently selected from the group consisting of H, $C_{1-6}$ alkyl, $C_{1-6}$ haloalkyl, $C_{3-10}$ cycloalkyl, a 4- to 10-membered heterocycloalkyl, cycloalkylalkyl, heterocycloalkylalkyl, arylalkyl, and heteroarylalkyl, wherein each of said $C_{1-6}$ alkyl, $C_{3-10}$ cycloalkyl, 4- to 10-membered heterocycloalkyl, cycloalkylalkyl, arylalkyl, and heteroarylalkyl is optionally substituted with 1, 2, 3, or 4 substituents each independently selected from the group consisting of —OH, —CN, $C_{1-3}$ alkyl, $C_{3-7}$ cycloalkyl, $C_{1-3}$ hydroxylalkyl, —S—$C_{1-3}$ alkyl, —C(=O)H, —C(=O)—$C_{1-3}$ alkyl, —C(=O)—O—$C_{1-3}$ alkyl, —C(=O)—$NH_2$, —C(=O)—N($C_{1-3}$ alkyl)$_2$, $C_{1-3}$ haloalkyl, $C_{1-3}$ alkoxy, and $C_{1-3}$ haloalkoxy;

or $R^8$ and $R^9$ together with the N atom to which they are attached form a 4- to 10-membered heterocycloalkyl or heteroaryl optionally substituted with 1, 2, 3, or 4 substituents each independently selected from the group consisting of halogen, —OH, oxo, —C(=O)H, —C(=O)OH, —C(=O)—$C_{1-3}$ alkyl, —C(=O)—$NH_2$, —C(=O)—N($C_{1-3}$ alkyl)$_2$, —CN, $C_{1-3}$ alkyl, $C_{1-3}$ alkoxy, $C_{1-3}$ hydroxylalkyl, $C_{1-3}$ haloalkyl, and $C_{1-3}$ haloalkoxy;

$R^{10}$ is selected from the group consisting of H, $C_{1-3}$ alkyl, and $C_{3-7}$ cycloalkyl;

$R^{11}$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, oxo, —S—$C_{1-3}$ alkyl, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{12}$ is H or is selected from the group consisting of $C_{1-10}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, —C(=O)OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{13}$ is selected from the group consisting of $C_{1-10}$ alkyl, $C_{1-6}$ haloalkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, 3, or 4 substituents each independently selected from the group consisting of halogen, —N($R^{14}$)($R^{15}$), —C(=O)N($R^{14}$)($R^{15}$), —N($R^{16}$)(C(=O)$R^{17}$), —C(=O)H, —C(=O)N($R^{16}$)($OR^{18}$), —C(=O)—$R^{18}$, —C(=O)—$OR^{18}$, —O—C(=O)$R^{18}$, —$CF_3$, —CN, —OH, —O—($C_{1-6}$ hydroxylalkyl), $C_{1-6}$ alkyl, $C_{1-6}$ hydroxylalkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{14}$ and $R^{15}$ are each independently selected from the group consisting of H, $C_{1-6}$ alkyl, $C_{2-6}$ alkenyl, $C_{3-10}$ cycloalkyl, a 4- to 14-membered heterocycloalkyl, cycloalkylalkyl, heterocycloalkylalkyl, arylalkyl, and heteroarylalkyl, wherein each of said $C_{1-6}$ alkyl, $C_{3-7}$ cycloalkyl, cycloalkylalkyl, arylalkyl, and heteroarylalkyl is optionally substituted with 1, 2, or 3 substituents each independently selected from the group consisting of —OH, —CN, oxo, —NHC(=O)—($C_{1-3}$ alkyl), —C(=O)N($C_{1-3}$ alkyl)$_2$, —O—($C_{1-6}$ hydroxylalkyl), —S(=O)$_2$—$C_{1-3}$ alkyl, —S—$C_{1-3}$ alkyl, $C_{1-3}$ alkyl, $C_{3-7}$ cycloalkyl, $C_{1-3}$ hydroxylalkyl, a 5- to 10-membered heteroaryl, $C_{1-3}$ alkoxy, $C_{1-3}$ haloalkyl, and $C_{1-3}$ haloalkoxy;

or $R^{14}$ and $R^{15}$ together with the N atom to which they are attached form a 4- to 10-membered heterocycloalkyl or 5- to 10-membered heteroaryl optionally substituted with 1, 2, or 3 substituents each independently selected from the group consisting of halogen, oxo, —OH, $C_{1-3}$ alkyl, $C_{1-3}$ alkoxy, $C_{1-3}$ haloalkyl, $C_{1-3}$ haloalkoxy, $C_{1-3}$ hydroxylalkyl, $C_{2-4}$ alkoxyalkyl, oxo, a 5- to 6-membered heteroaryl, —$NH_2$, —$N(C_{1-3}$ alkyl$)_2$, —$S(=O)_2$—$C_{1-3}$ alkyl, —S—$C_{1-3}$ alkyl, —C(=O)H, —C(=O)OH, —C(=O)$NH_2$, and —C(=O)—$C_{1-3}$ alkyl;

$R^{16}$ is selected from the group consisting of H, $C_{1-3}$ alkyl, and $C_{3-7}$ cycloalkyl;

$R^{17}$ is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{18}$ is H or is selected from the group consisting of $C_{1-6}$ alkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy;

$R^{19}$ is selected from the group consisting of $C_{1-6}$ alkyl, $C_{1-6}$ haloalkyl, $C_{3-7}$ cycloalkyl, a 4- to 14-membered heterocycloalkyl, $C_{6-10}$ aryl, a 5- to 10-membered heteroaryl, cycloalkylalkyl, heterocycloalkylalkyl, arylalkyl, and heteroarylalkyl, each optionally substituted with 1, 2, or 3 substituents each independently selected from the group consisting of halogen, —$N(R^{14})(R^{15})$, —C(=O)$N(R^{14})(R^{15})$, —$N(R^{18})(C(=O)R^{17})$, —C(=O)—$R^{18}$, —C(=O)—$OR^{18}$, —$CF_3$, —CN, —OH, $C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ alkoxy, and $C_{1-6}$ haloalkoxy; and $R^N$ is selected from the group consisting of H, $C_{1-6}$ alkyl, $C_{3-6}$ cycloalkyl, $C_{3-6}$ fluorocycloalkyl, heteroarylalkyl, and arylalkyl, wherein each of said $C_{3-6}$ cycloalkyl, heteroarylalkyl, and arylalkyl is optionally substituted with 1, 2, 3, 4, or 5 substituents each independently selected from halo, $C_{1-4}$ alkyl, $C_{1-4}$ haloalkyl, $C_{1-4}$ alkoxy, and $C_{1-4}$ haloalkoxy.

2. The compound of claim 1, or an N-oxide thereof or a pharmaceutically acceptable salt of said compound or said N-oxide, wherein $Q^1$ is selected from 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, wherein each of the selections is optionally substituted with 1, 2, 3, or 4 independently selected $R^7$.

3. The compound of claim 1, or an N-oxide thereof or a pharmaceutically acceptable salt of said compound or said N-oxide, wherein $Q^1$ is selected from:

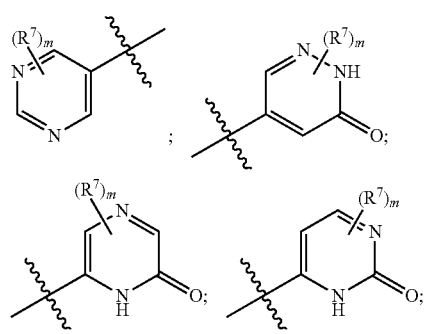

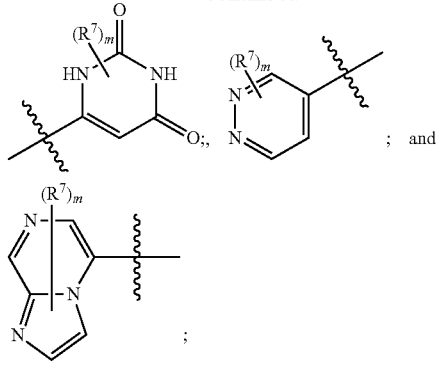

and
each m is independently 0, 1, 2, or 3.

4. The compound of claim 3, or an N-oxide thereof or a pharmaceutically acceptable salt of said compound or said N-oxide, wherein $R^{T1}$ and $R^{T2}$ are both H; $R^1$ is H; and $R^2$ is H, —CN, Br, $C_{1-3}$ alkyl, or cyclopropyl.

5. The compound of claim 4, or an N-oxide thereof or a pharmaceutically acceptable salt of said compound or said N-oxide, wherein $R^3$ and $R^4$ are each independently selected from the group consisting of H, F, Cl, and $C_{1-3}$ alkyl.

6. The compound of claim 5, or an N-oxide thereof or a pharmaceutically acceptable salt of said compound or said N-oxide, wherein one of $R^5$ and $R^6$ is H; and the other of $R^5$ and $R^6$ is selected from the group consisting of H, —OH, —CN, Cl, F, methyl, ethyl, $CF_3$, $CH_2F$, and —$OCH_3$.

7. The compound of claim 6, or an N-oxide thereof or a pharmaceutically acceptable salt of said compound or said N-oxide, wherein each $R^7$ is independently selected from the group consisting of $C_{1-4}$ alkyl, $C_{1-4}$ fluoroalkyl, oxo, —OH, $C_{1-4}$ alkoxy, and $C_{1-4}$ haloalkoxy; wherein the $C_{1-4}$ alkyl is optionally substituted with 1, 2, 3, 4, or 5 substituents each independently selected from halogen, OH, $C_{1-4}$ alkoxy, —$NH_2$, —NH($C_{1-4}$ alkyl), —N($C_{1-4}$ alkyl)$_2$, azetidin-1-yl, pyrrolidin-1-yl, and pyridin-1-yl.

8. The compound of claim 7, or an N-oxide thereof or a pharmaceutically acceptable salt of said compound or said N-oxide, wherein $Q^1$ is

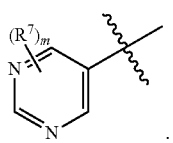

9. The compound of claim 7, or an N-oxide thereof or a pharmaceutically acceptable salt of said compound or said N-oxide, wherein $Q^1$ is

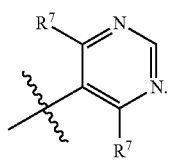

10. The compound of claim 9, or an N-oxide thereof or a pharmaceutically acceptable salt of said compound or said N-oxide, wherein:

$R^{T1}$ and $R^{T2}$ are both H;
$R^1$ is H;
$R^2$ is H or —CN;
$R^3$ and $R^4$ are both H; and
one of $R^5$ and $R^6$ is H, F, or methyl; and the other of $R^5$ and $R^6$ is selected from the group consisting of H, —OH, —CN, Cl, F, methyl, ethyl, $CF_3$, $CH_2F$, and —$OCH_3$.

11. The compound of claim 1, or an N-oxide thereof or a pharmaceutically acceptable salt of said compound or said N-oxide, wherein:
$Q^1$ is

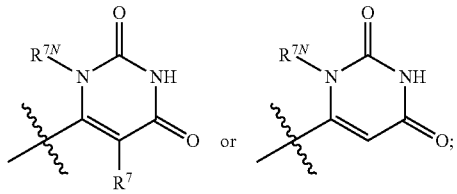

$R^7$ is H or $C_{1-3}$ alkyl;
$R^{7N}$ is $C_{1-3}$ alkyl optionally substituted with 1, 2, 3, 4, or 5 substituents each independent selected from halogen, OH, $C_{1-4}$ alkoxy, —$NH_2$, —NH($C_{1-4}$ alkyl), —N($C_{1-4}$ alkyl)$_2$, and —N($R^{14}$)($R^{15}$); and
$R^{14}$ and $R^{15}$, together with the N atom to which they are attached, form a 4- to 10-membered heterocycloalkyl optionally substituted with 1, 2, or 3 substituents each independently selected from the group consisting of halogen, oxo, —OH, $C_{1-4}$ alkyl, $C_{1-4}$ alkoxy, $C_{1-4}$ haloalkyl, $C_{1-4}$ haloalkoxy, and $C_{1-4}$ hydroxylalkyl.

12. The compound of claim 11, or an N-oxide thereof or a pharmaceutically acceptable salt of said compound or said N-oxide, wherein $R^7$ is methyl or ethyl; and $R^{7N}$ is $C_{1-3}$ alkyl optionally substituted with 1, 2, 3, 4, or 5 substituents each independent selected from halogen (e.g., F), OH, $C_{1-4}$ alkoxy, —$NH_2$, —NH($C_{1-4}$ alkyl), —N($C_{1-4}$ alkyl)$_2$, azetidin-1-yl, pyrrolidin-1-yl, and pyridin-1-yl.

13. The compound of claim 11, or an N-oxide thereof or a pharmaceutically acceptable salt of said compound or said N-oxide, wherein $R^7$ is methyl and $R^{7N}$ is methyl.

14. The compound of claim 12, or an N-oxide thereof or a pharmaceutically acceptable salt of said compound or said N-oxide, wherein:
$R^{T1}$ and $R^{T2}$ are both H;
$R^1$ is H;
$R^2$ is H or —CN;
$R^3$ and $R^4$ are both H; and
one of $R^5$ and $R^6$ is H, F, or methyl; and the other of $R^5$ and $R^6$ is selected from the group consisting of H, —OH, —CN, Cl, F, methyl, ethyl, $CF_3$, $CH_2F$, and —$OCH_3$.

15. The compound of claim 13, or an N-oxide thereof or a pharmaceutically acceptable salt of said compound or said N-oxide, wherein:
$R^{T1}$ and $R^{T2}$ are both H;
$R^1$ is H;
$R^2$ is H or —CN; and
$R^3$ and $R^4$ are both H; and
one of $R^5$ and $R^6$ is H, F, or methyl; and the other of $R^5$ and $R^6$ is selected from the group consisting of H, —OH, —CN, Cl, F, methyl, ethyl, $CF_3$, $CH_2F$, and —$OCH_3$.

16. The compound of claim 15, or an N-oxide thereof or a pharmaceutically acceptable salt of said compound or said N-oxide, wherein $Q^1$ is

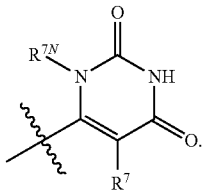

17. A compound of claim 1 selected from the group consisting of:
4-[4-(4,6-dimethylpyrimidin-5-yl)-3-methylphenoxy]furo[3,2-c]pyridine;
4-[4-(4,6-dimethylpyrimidin-5-yl)-3-(fluoromethyl)phenoxy]furo[3,2-c]pyridine;
4-[4-(4,6-dimethylpyrimidin-5-yl)-3-methylphenoxy]-3-methylfuro[3,2-c]pyridine;
4-[4-(1-methyl-1H-pyrazol-5-yl)-3-(trifluoromethyl)phenoxy]furo[3,2-c]pyridine;
(−)-6-[4-(furo[3,2-c]pyridin-4-yloxy)-2-methylphenyl]-1,5-dimethylpyrimidine-2,4(1H,3H)-dione; and
6-[4-(furo[3,2-c]pyridin-4-yloxy)phenyl]-1,5-dimethylpyrimidine-2,4(1H,3H)-dione, or an N-oxide thereof or a pharmaceutically acceptable salt of said compound or said N-oxide.

18. A pharmaceutical composition comprising a compound of claim 1 or an N-oxide thereof or a pharmaceutically acceptable salt of said compound or said N-oxide, and a pharmaceutically acceptable carrier.

* * * * *